US010584322B2

(12) United States Patent
Frisch et al.

(10) Patent No.: US 10,584,322 B2
(45) Date of Patent: Mar. 10, 2020

(54) PEPTIDE-MEDIATED DELIVERY OF RNA-GUIDED ENDONUCLEASE INTO CELLS

(71) Applicant: DUPONT US HOLDING, LLC, Wilmington, DE (US)

(72) Inventors: Ryan L Frisch, Newark, DE (US); Xiaochun Fan, West Chester, PA (US); Seung-Pyo Hong, Hockessin, DE (US); Ethel Noland Jackson, Greenville, DE (US)

(73) Assignee: DUPONT US HOLDING, LLC, Wilmington, DE (US)

( * ) Notice: Subject to any disclaimer, the term of this patent is extended or adjusted under 35 U.S.C. 154(b) by 0 days.

(21) Appl. No.: 16/218,808

(22) Filed: Dec. 13, 2018

(65) Prior Publication Data

US 2019/0100737 A1 Apr. 4, 2019

Related U.S. Application Data

(62) Division of application No. 15/523,741, filed as application No. PCT/US2015/058760 on Nov. 3, 2015, now Pat. No. 10,208,298.

(60) Provisional application No. 62/075,999, filed on Nov. 6, 2014.

(51) Int. Cl.

| | |
|---|---|
| ***C12N 9/22*** | (2006.01) |
| ***C12N 9/96*** | (2006.01) |
| ***C12N 15/10*** | (2006.01) |
| ***C12N 15/62*** | (2006.01) |
| ***C12N 15/86*** | (2006.01) |
| ***C12N 15/90*** | (2006.01) |

(52) U.S. Cl.

CPC ................ *C12N 9/22* (2013.01); *C12N 9/96* (2013.01); *C12N 15/102* (2013.01); *C12N 15/62* (2013.01); *C12N 15/86* (2013.01); *C12N 15/907* (2013.01); *C07K 2319/09* (2013.01); *C07K 2319/10* (2013.01); *C12N 2310/3513* (2013.01); *C12N 2750/14141* (2013.01)

(58) Field of Classification Search

CPC ........ C12N 9/22; C12N 15/102; C12N 15/70; C12N 15/10; C12N 2310/20

See application file for complete search history.

(56) References Cited

U.S. PATENT DOCUMENTS

| | | | |
|---|---|---|---|
| 5,990,275 | A | 11/1999 | Whitlow et al. |
| 8,580,922 | B2 | 11/2013 | Martini et al. |
| 8,642,744 | B2 | 2/2014 | Smart et al. |
| 8,828,690 | B2 | 9/2014 | Damude et al. |
| 9,526,784 | B2 | 12/2016 | Liu et al. |
| 2010/0192262 | A1 | 7/2010 | Krichevsky |
| 2011/0190813 | A1 | 8/2011 | Brownlee et al. |
| 2012/0042412 | A1 | 2/2012 | Albert et al. |
| 2014/0068797 | A1 | 3/2014 | Doudna et al. |
| 2014/0189896 | A1 | 7/2014 | Zhang et al. |

FOREIGN PATENT DOCUMENTS

| | | | |
|---|---|---|---|
| WO | 2013/176772 | A1 | 11/2013 |
| WO | 2014/065596 | A1 | 5/2014 |
| WO | 2014/089290 | A1 | 6/2014 |
| WO | 2014/165825 | A1 | 10/2014 |
| WO | 2015/026883 | A1 | 2/2015 |
| WO | 2015/086795 | A1 | 6/2015 |
| WO | 2016/025131 | A1 | 2/2016 |

OTHER PUBLICATIONS

Aguilera, Todd A. et al., Systemic in vivo distribution of activatable cell penetrating peptides is superior to cell penetrating peptides, Integr Biol, Jun. 2009, pp. 371-381, 1(5-6).

Anko, Maja et al., Influence of stearyl and triflouromethylquinoline modifications of the cell penetrating peptide TP10 on its interaction with a lipid membrane, Biochimica et Biophysica Acta 1818, 2012, pp. 915-924.

Austin, Christopher P. et al., The Knockout Mouse Project, Nat Genet, Sep. 2004, pp. 921-924, 36(9).

Bhaya, Devaki et al., CRISPR-Cas Systems in Bacteria and Archaea: Versatile Small RNAs for Adaptive Defense and Regulation, Annu. Rev. Genet., 2011, pp. 273-297, 45.

Bibikova, Marina et al., Stimulation of Homologous Recombination through Targeted Cleavage by Chimeric Nucleases, Molecular and Cellular Biology, Jan. 2011, pp. 289-297, vol. 21, No. 1.

Bibikova, Marina et al., Enhancing Gene Targeting with Designed Zinc Finger Nucleases, Science, May 2, 2003, p. 764, vol. 300.

Database WPI, Thomson Scientific, XP002753224, Shanghai Dida Biological Technology, Co., Feb. 4, 2015—Reference Not Included.

Deltcheva, Elitza et al., CRISPR RNA maturation by trans-encoded small RNA and host factor RNase III, Nature, Mar. 31, 2011, pp. 602-607, vol. 471 (7340).

DiCarlo, James E. et al., Genome engineering in *Saccharomyces cerevisiae*, Nucleic Acids Research, 2013, pp. 4336-4343—vol. 41, No. 7.

(Continued)

*Primary Examiner* — Karen Cochrane Carlson

(57) ABSTRACT

A composition is disclosed that comprises at least one protein component of an RNA-guided endonuclease (RGEN) and at least one cell-penetrating peptide (CPP), wherein the RGEN protein component and CPP are covalently or non-covalently linked to each other in an RGEN protein-CPP complex. The RGEN protein-CPP complex can traverse (i) a cell membrane, or (ii) a cell wall and cell membrane, of a cell. The RGEN protein component of an RGEN protein-CPP complex in certain embodiments can be associated with a suitable RNA component to provide an RGEN capable of specific DNA targeting. Further disclosed are compositions comprising at least one protein component of a guide polynucleotide/Cas endonuclease complex and at least one CPP, as well as methods of delivering RGEN proteins into microbial cells, as well as methods of targeting DNA with RGENs.

10 Claims, 10 Drawing Sheets

Figure 1:
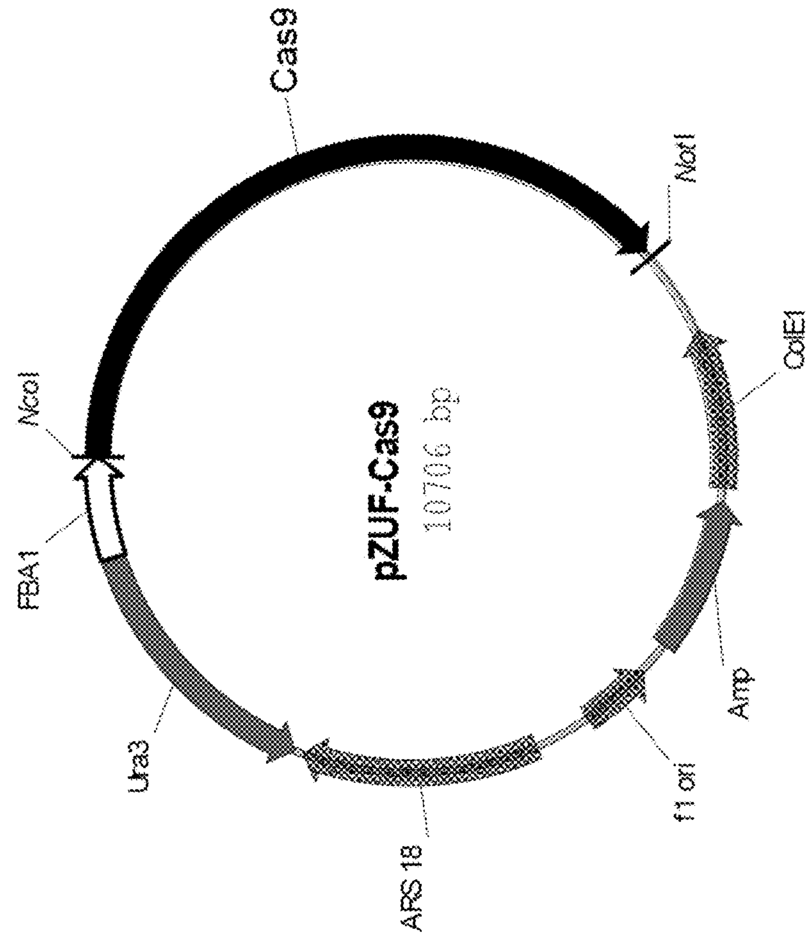

Specification includes a Sequence Listing.

(56) References Cited

OTHER PUBLICATIONS

Epinat, Jean-Charles et al., A novel engineered meganuclease induces homologous recombination in yeast and mammalian cells, Nucleic Acids Research, 2003, pp. 2952-2962, vol. 31, No. 11.
Gasiunas, Giedrius et al., Cas9-crRNA ribonucleoprotein complex mediates specific DNA cleavage for adaptive immunity in bacteria, PNAS, Sep. 4, 2012, E2579-E2586, 109.
Holm, Tina et al., Studying the uptake of cell-penetrating peptides, Nature Protocols, 2006, pp. 1001-1005, vol. 1, No. 2.
Horvath, Philippe et al., CRISPR/Cas, the Immune System of Bacteria and Archaea, Science, Jan. 8, 2010, pp. 167-170, vol. 327.
Hsu, Patrick D. et al., Development and Applications of CRISPR-Cas9 for Genome Engineering, Cell, Jun. 5, 2014, pp. 1262-1278, vol. 157.
Jiang, Wenyan et al., RNA-guided editing of bacterial genomes using CRISPR-Cas systems, Nature Biotechnology, Mar. 2013, pp. 233-239, vol. 31, No. 3.
Jinek, Martin et al., A Programmable Dual-RNA-Guided DNA Endonuclease in Adaptive Bacterial Immunity, Science, Aug. 17, 2012, pp. 816-821, vol. 337.
Karginov, Fedor V. et al., The CRISPR System: Small Rna-Guided Defense in Bacteria and Archaea, Molecular Cell, Jan. 15, 2010, pp. 7-19, vol. 37.
Liu, Min-Jie et al., A Gene Delivery Method Mediated by Three Arginine-rich Cell-penetrating Peptides in Plant Cells, Advanced Studies in Biology, 2013, pp. 71-88, vol. 5, No. 2.
Ma, Hongming et al., Pol III Promoters to Express Small RNAs: Delineation of Transcription Initiation, Molecular Therapy—Nucleic Acids, 2014, e161, 3.
Marchione, Roberta et al., ZEBRA cell-penetrating peptide as an efficient delivery system in Candida albicans, Biotechnol. J., 2014, pp. 1088-1094, vol. 9.
Miller, Jeffrey C. et al., A TALE nuclease architecture for efficient genome editing, Nature Biotechnology, Feb. 2011, pp. 143-148, vol. 29, No. 2.
Morris, May C. et al., A peptide carrier for the delivery of biologically active proteins into mammalian cells, Nat. Biotechnol, Dec. 2001, pp. 1173-1176, vol. 19.
Nekhotiaeva, Natalia et al., Cell entry and antimicrobial properties of eukaryotic cell-penetrating peptides, FASEB Journal, Feb. 1, 2004, pp. 394-396, vol. 18.
Ramakrishna, Suresh et al., Gene disruption by cell-penetrating peptide-mediated delivery of Cas9 protein and guide RNA, Genome Research, Apr. 2, 2014, pp. 1020-1027, vol. 24, No. 6.
Regberg, Jakob et al., Rational design of a series of novel amphipathic cell-penetrating peptides, International Journal of Pharmaceutics, 2014, pp. 111-116, vol. 464.
Rudin, Norah et al., Genetic and Physical Analysis of Double-Strand Break Repair and Recombination in *Saccharomyces cerevisiae*, Genetics, Jul. 1989, pp. 519-534, vol. 122.
Sapranauskas, Rimantas et al., The *Streptococcus thermophilus* CRISPR/Cas system provides immunity in *Escherichia coli*, Nucleic Acids Research, Aug. 3, 2011, pp. 9275-9282, vol. 39, No. 21.
Schmidt, Nathan et al., Arginine-rich cell-penetrating peptides, FEBS Letter, 2010, pp. 1806-1813, vol. 584.
Smith, Fatima et al., Nucleic Acids Research, 1995, pp. 5012-5019, vol. 23, No. 24.
Sternberg, Samuel H. et al., DNA interrogation by the CRISPR RNA-guided endonuclease Cas9, Nature, Mar. 6, 2014, pp. 62067, vol. 507 (7490).
Wender, Paul A., The design, synthesis, and evaluation of molecules that enable or enhance cellular uptake: Peptoid molecular transporters, PNAS, Nov. 21, 2000, pp. 13003-13008, vol. 97, No. 24.
Yandek, Lindsay E., Mechanism of the Cell-Penetrating Peptide Transportan 10 Permeation of Lipid Bilayers, Biophysical Journal, Apr. 2007, p. 2434-2444, vol. 92.
Zetsche, Bernd et al., Cpf1 Is a Single RNA-Guided Endonuclease of a Class 2 CRISPR-Cas System, Cell, Oct. 22, 2015, pp. 759-771, vol. 163.
International Search Report and Written Opinion—PCT/US2015/058760—dated Feb. 1, 2016.

PEPTIDE-MEDIATED DELIVERY OF RNA-GUIDED ENDONUCLEASE INTO CELLS

This application is a divisional of U.S. patent application Ser. No. 15/523,741 filed May 2, 2017, which is a national stage filing of PCT Application No. PCT/US15/58760 filed Nov. 3, 2015, which claims the benefit of U.S. Provisional Application No. 62/075,999, filed Nov. 6, 2014, which are each hereby incorporated herein in their entirety by reference.

FIELD OF INVENTION

The invention is in the field of molecular biology. Specifically, this invention pertains to delivery of protein components of RNA-guided endonucleases into cells using cell-penetrating peptides.

REFERENCE TO SEQUENCE LISTING SUBMITTED ELECTRONICALLY

The official copy of the sequence listing is submitted electronically via EFS-Web as an ASCII formatted sequence listing with a file named 20181212_CL6273PCD_SequenceListing_ST25.txt created Dec. 12, 2018, and having a size of 384 kilobytes and is filed concurrently with the specification. The sequence listing contained in this ASCII-formatted document is part of the specification and is herein incorporated by reference in its entirety.

BACKGROUND

A way to understand the function of a gene within an organism is to inhibit its expression. Inhibition of gene expression can be accomplished, for example, by interrupting or deleting the DNA sequence of the gene, resulting in "knock-out" of the gene (Austin et al., *Nat. Genetics* 36:921-924). Gene knock-outs mostly have been carried out through homologous recombination (HR), a technique applicable across a wide array of organisms from bacteria to mammals. Another way for studying gene function can be through genetic "knock-in", which is also usually performed by HR. HR for purposes of gene targeting (knock-out or knock-in) can employ the presence of an exogenously supplied DNA having homology with the target site ("donor DNA").

HR for gene targeting has been shown to be enhanced when the targeted DNA site contains a double-strand break (Rudin et al., *Genetics* 122:519-534; Smih et al., *Nucl. Acids Res.* 23:5012-5019). Strategies for introducing double-strand breaks to facilitate HR-mediated DNA targeting have therefore been developed. For example, zinc finger nucleases have been engineered to cleave specific DNA sites leading to enhanced levels of HR at the site when a donor DNA was present (Bibikova et al., *Science* 300:764; Bibikova et al., *Mol. Cell. Biol.* 21:289-297). Similarly, artificial meganucleases (homing endonucleases) and transcription activator-like effector (TALE) nucleases have also been developed for use in HR-mediated DNA targeting (Epinat et al., *Nucleic Acids Res.* 31: 2952-2962; Miller et al., *Nat. Biotech.* 29:143-148).

Loci encoding CRISPR (clustered regularly interspaced short palindromic repeats) DNA cleavage systems have been found exclusively in about 40% of bacterial genomes and most archaeal genomes (Horvath and Barrangou, *Science* 327:167-170; Karginov and Hannon, *Mol. Cell* 37:7-19). In particular, the CRISPR-associated (Cas) RNA-guided endonuclease (RGEN), Cas9, of the type II CRIPSR system has been developed as a means for introducing site-specific DNA strand breaks that stimulate HR with donor DNA (WO2015/026883, published Feb. 26, 2015). The sequence of the RNA component of Cas9 can be designed such that Cas9 recognizes and cleaves DNA containing (i) sequence complementary to a portion of the RNA component and (ii) a protospacer adjacent motif (PAM) sequence.

Native Cas9/RNA complexes comprise two RNA sequences, a CRISPR RNA (crRNA) and a trans-activating CRISPR RNA (tracrRNA). A crRNA contains, in the 5'-to-3' direction, a unique sequence complementary to a target DNA site and a portion of a sequence encoded by a repeat region of the CRISPR locus from which the crRNA was derived. A tracrRNA contains, in the 5'-to-3' direction, a sequence that anneals with the repeat region of crRNA and a stem loop-containing portion. Recent work has led to the development of guide RNAs (gRNA), which are chimeric sequences containing, in the 5'-to-3' direction, a crRNA linked to a tracrRNA (WO2015/026883, published Feb. 26, 2015).

Protein and RNA components for performing Cas9-mediated DNA targeting in a cell have been provided in some studies through recombinant DNA expression strategies. For example, Cas9 protein has been expressed in cells using nucleic acid-based expression systems. Methods of expressing RNA components such as gRNA in certain cell types have included using RNA polymerase III (Pol III) promoters, which allow for transcription of RNA with precisely defined, unmodified, 5'- and 3'-ends (DiCarlo et al., *Nucleic Acids Res.* 41: 4336-4343; Ma et al., *Mol. Ther. Nucleic Acids* 3:e161). These protein and RNA expression techniques have been applied in cells of several different species including maize and soybean (WO2015/026883, published Feb. 26, 2015), as well as humans, mouse, zebrafish, *Trichoderma* and *Saccharomyces cerevisiae.*

Despite these advances, other means of providing protein and RNA components in a cell, such as a microbial cell, to mediate Cas9-mediated DNA targeting are of interest.

SUMMARY OF INVENTION

In one embodiment, the invention concerns a composition comprising at least one protein component of an RNA-guided endonuclease (RGEN) and at least one cell-penetrating peptide (CPP), wherein the protein component and CPP are covalently, or non-covalently, linked to each other in an RGEN protein-CPP complex, and wherein the RGEN protein-CPP complex can traverse (i) a cell membrane, or (ii) a cell wall and cell membrane, of a microbial cell.

In a second embodiment, the protein component of the RGEN is associated with at least one RNA component that comprises a sequence complementary to a target site sequence on a chromosome or episome in the microbial cell, wherein the RGEN can bind to the target site sequence, and optionally cleave one or both DNA strands at the target site sequence. In a third embodiment, the RNA component comprises a guide RNA (gRNA) comprising a CRISPR RNA (crRNA) operably linked to a trans-activating CRISPR RNA (tracrRNA). In a fourth embodiment, the RGEN can cleave one or both DNA strands at the target site sequence.

In a fifth embodiment, the RGEN comprises a CRISPR-associated (Cas) protein-9 (Cas9) amino acid sequence.

In a sixth embodiment, the RGEN protein component and CPP are covalently linked.

In a seventh embodiment, the RGEN protein component and CPP are non-covalently linked.

In an eighth embodiment, the CPP is cationic or amphipathic.

In a ninth embodiment, the CPP comprises (i) a CPP from an Epstein-Barr virus Zebra trans-activator protein, (ii) a CPP having 6 or more contiguous arginine residues, (iii) a transportan-10 (TP10) CPP, or (iv) a CPP from a vascular endothelium cadherin protein.

In a tenth embodiment, the RGEN protein-CPP complex can traverse a cell wall and cell membrane of a microbial cell.

An eleventh embodiment concerns a microbial cell comprising a composition disclosed herein.

A twelfth embodiment concerns a method of delivering a protein component of an RNA-guided endonuclease (RGEN) into a microbial cell. This method comprises contacting a microbial cell with a composition comprising the RGEN protein component and at least one cell-penetrating peptide (CPP), wherein the RGEN protein component and CPP are covalently, or non-covalently, linked to each other in an RGEN protein-CPP complex. As a result of this contacting step, the RGEN protein-CPP complex can traverse (i) a cell membrane, or (ii) a cell wall and cell membrane, of the microbial cell, and thereby gain entry to the microbial cell.

In a thirteenth embodiment, with respect to the method, (i) the composition further comprises at least one RNA component that is associated with the protein component of the RGEN, or (ii) the microbial cell comprises the RNA component, wherein the RNA component associates with the protein component of the RGEN after the RGEN protein-CPP complex enters the microbial cell; wherein the RNA component in (i) or (ii) comprises a sequence complementary to a target site sequence on a chromosome or episome in the microbial cell, and wherein the RGEN can bind to the target site sequence, and optionally cleave one or both DNA strands at the target site sequence. In a fourteenth embodiment, the RGEN can cleave one or both DNA strands at the target site sequence. In a fifteenth embodiment, the microbial cell further comprises a donor polynucleotide comprising at least one sequence homologous to a sequence at or near the target site sequence, wherein the donor polynucleotide integrates at or near the target site sequence by homologous recombination.

A sixteenth embodiment concerns a polynucleotide sequence comprising a nucleotide sequence encoding an RGEN protein-CPP fusion protein that comprises a protein component of an RNA-guided endonuclease (RGEN) and at least one cell-penetrating peptide (CPP), wherein optionally, the nucleotide sequence is operably linked to a promoter sequence.

A seventeenth embodiment concerns a method of producing an RGEN protein-CPP fusion protein. This method comprises: (a) providing a polynucleotide sequence comprising a nucleotide sequence encoding an RGEN protein-CPP fusion protein that comprises a protein component of an RNA-guided endonuclease (RGEN) and at least one cell-penetrating peptide (CPP), wherein optionally, the nucleotide sequence is operably linked to a promoter sequence; (b) expressing the RGEN protein-CPP fusion protein from the polynucleotide sequence, thereby producing the RGEN protein-CPP fusion protein, wherein the expressing is optionally performed in a microbial cell; and (c) optionally, isolating the RGEN protein-CPP fusion protein produced in step (b).

An eighteenth embodiment concerns a composition comprising at least one protein component of a guide polynucleotide/Cas endonuclease complex and at least one cell-penetrating peptide (CPP), wherein the protein component and CPP are covalently, or non-covalently, linked to each other in a guide polynucleotide/Cas endonuclease-CPP complex, wherein the guide polynucleotide/Cas endonuclease-CPP complex can traverse (i) a cell membrane, or (ii) a cell wall and cell membrane, of a microbial cell.

A nineteenth embodiment concerns a method for modifying a target site in the genome of a microbial cell. This method comprises providing a guide polynucleotide, a cell-penetrating peptide (CPP) and a Cas endonuclease to a microbial cell, wherein the guide polynucleotide, Cas endonuclease and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of the microbial cell

BRIEF DESCRIPTION OF THE DRAWINGS AND SEQUENCES

FIG. 1: pZUFCas9 plasmid (SEQ ID NO:6) contains the *Yarrowia* codon-optimized Cas9 expression cassette set forth in SEQ ID NO:5. Origins of replication (ARS 18, f1 ori, ColE1) are in cross-hatch, and selectable markers (Ura3, Amp) are in grey. Refer to Example 1.

Figure 2A:
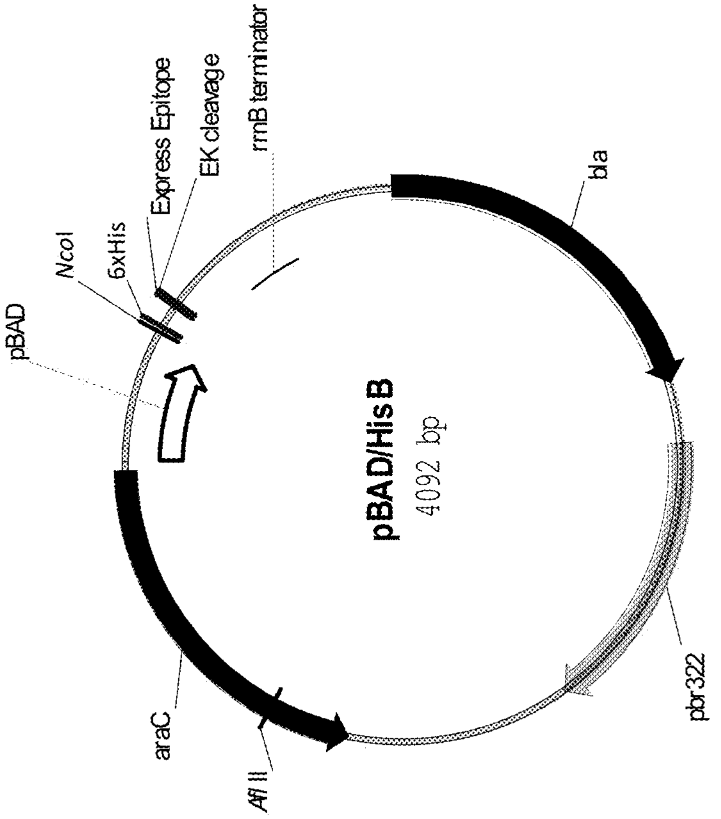

FIG. 2A: pBAD/HisB plasmid (SEQ ID NO:10) for expressing heterologous proteins in *E. coli*. pBAD promoter is in white. Origin of replication is in cross-hatch. Refer to Example 1.

Figure 2B:
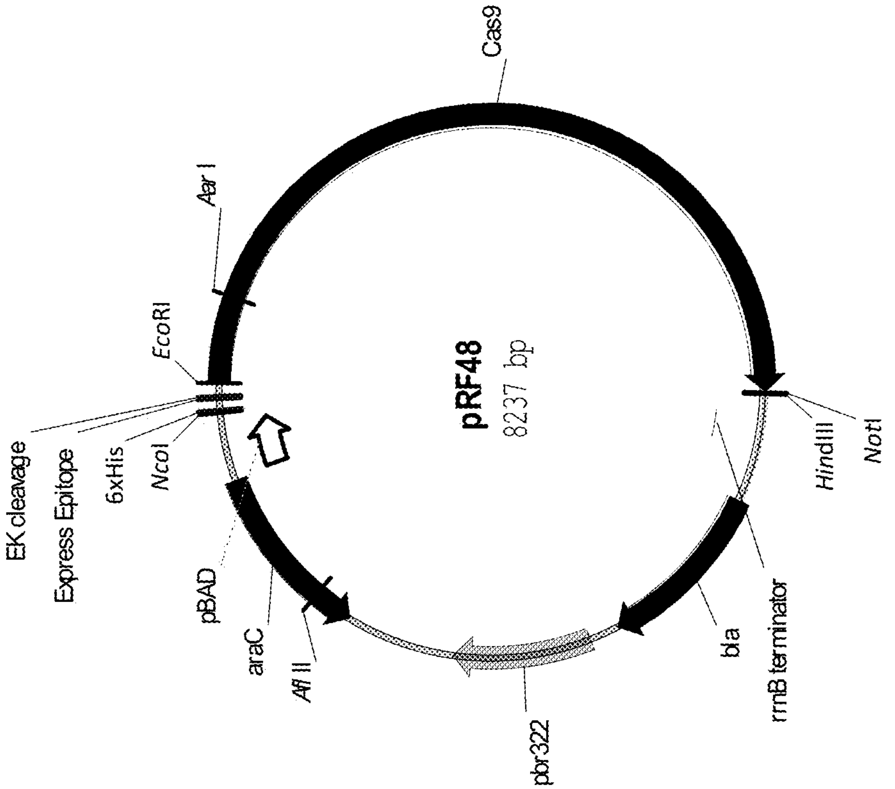

FIG. 2B: pRF48 plasmid (SEQ ID NO:11) for expressing Cas9-NLS ("Cas9" in figure) in *E. coli*. Origin of replication is in cross-hatch. Refer to Example 1.

Figure 3A:
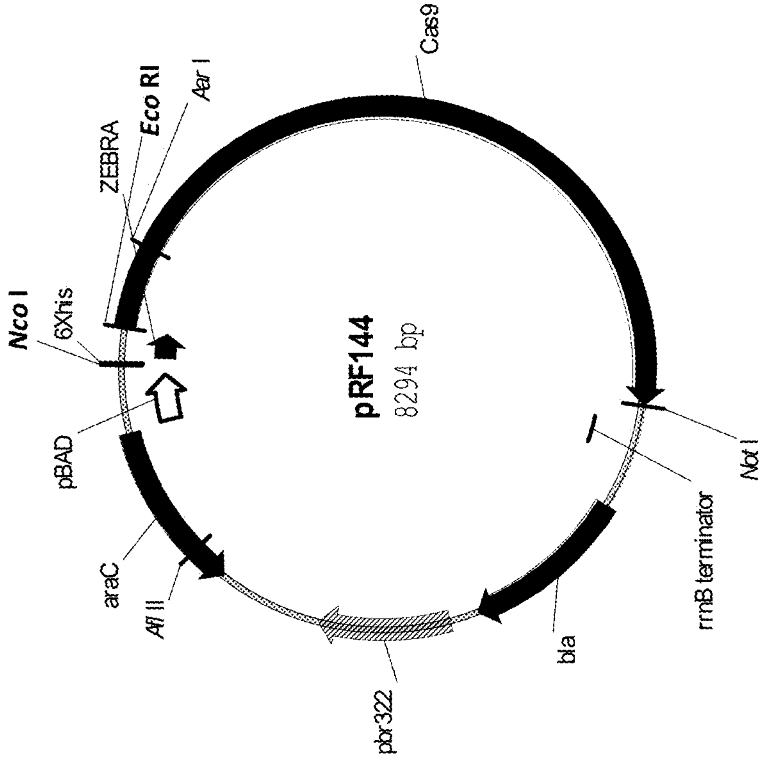

FIG. 3A: pRF144 plasmid (SEQ ID NO:20) for expressing 6×His-Zebra CPP-Cas9-NLS fusion in *E. coli*. Origin of replication is in cross-hatch. Refer to Example 1.

Figure 3B:
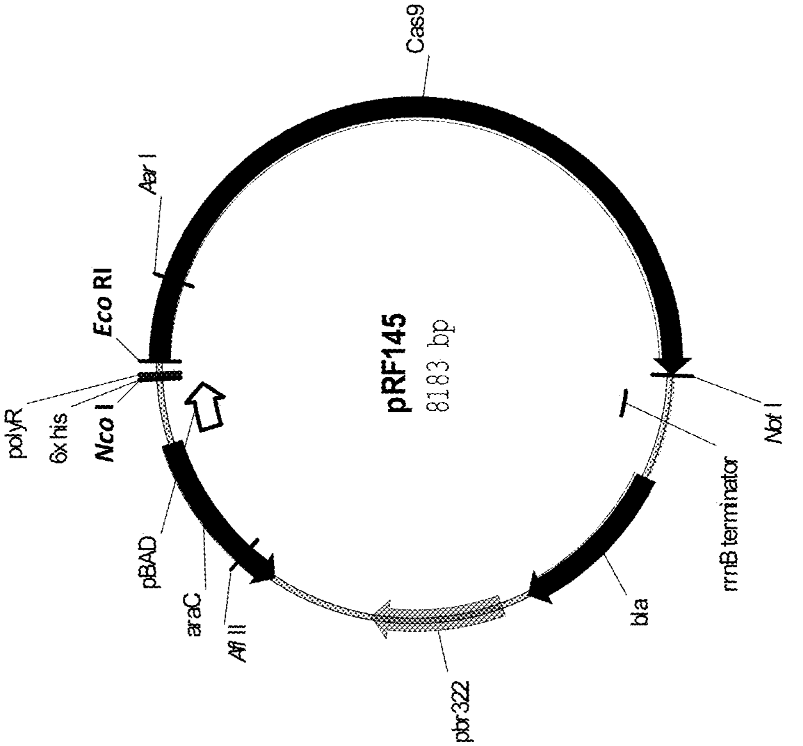

FIG. 3B: pRF145 plasmid (SEQ ID NO:21) for expressing 6×His-PolyR CPP-Cas9-NLS fusion in *E. coli*. Origin of replication is in cross-hatch. Refer to Example 1.

Figure 3D:
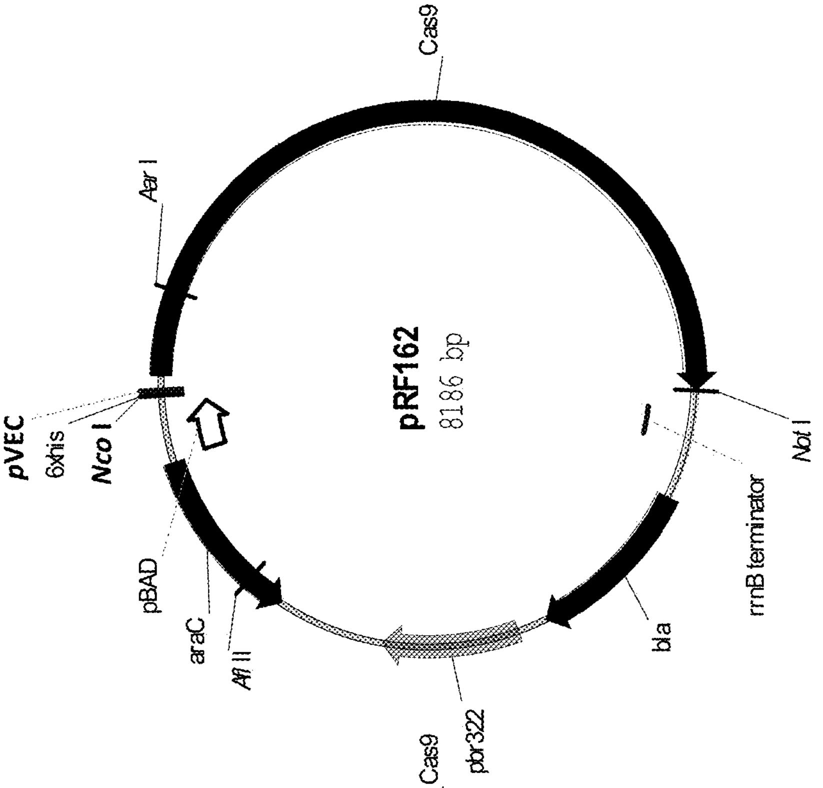
Figure 3C:
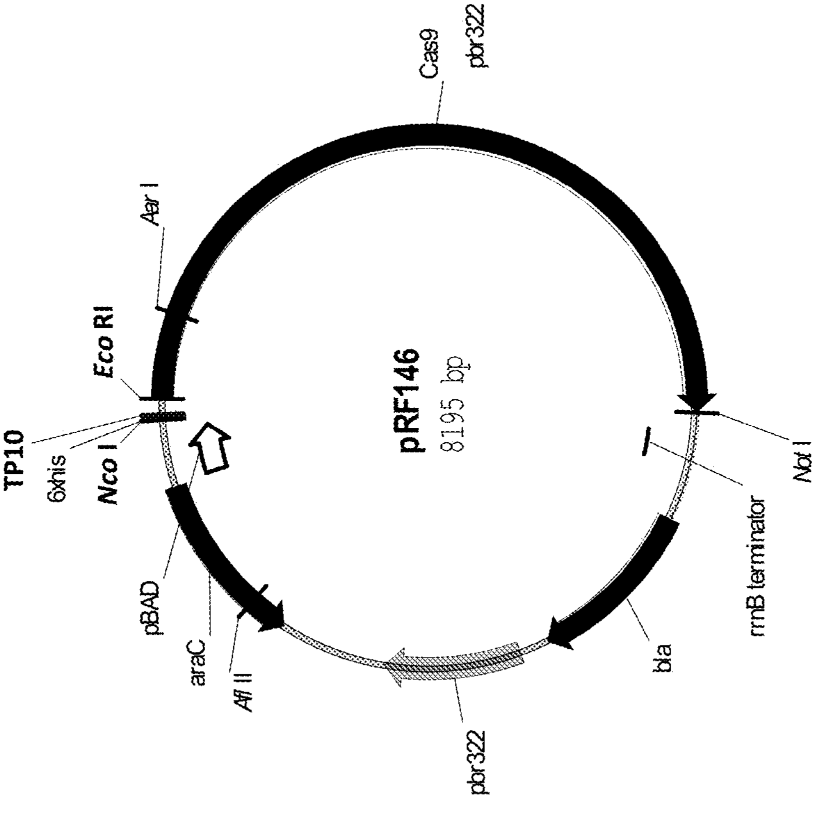

FIG. 3C: pRF146 plasmid (SEQ ID NO:22) for expressing 6×His-TP10 CPP-Cas9-NLS fusion in *E. coli*. Origin of replication is in cross-hatch. Refer to Example 1.

FIG. 3D: pRF162 plasmid (SEQ ID NO:23) for expressing 6×His-pVEC CPP-Cas9-NLS fusion in *E. coli*. Origin of replication is in cross-hatch. Refer to Example 1.

Figure 4:
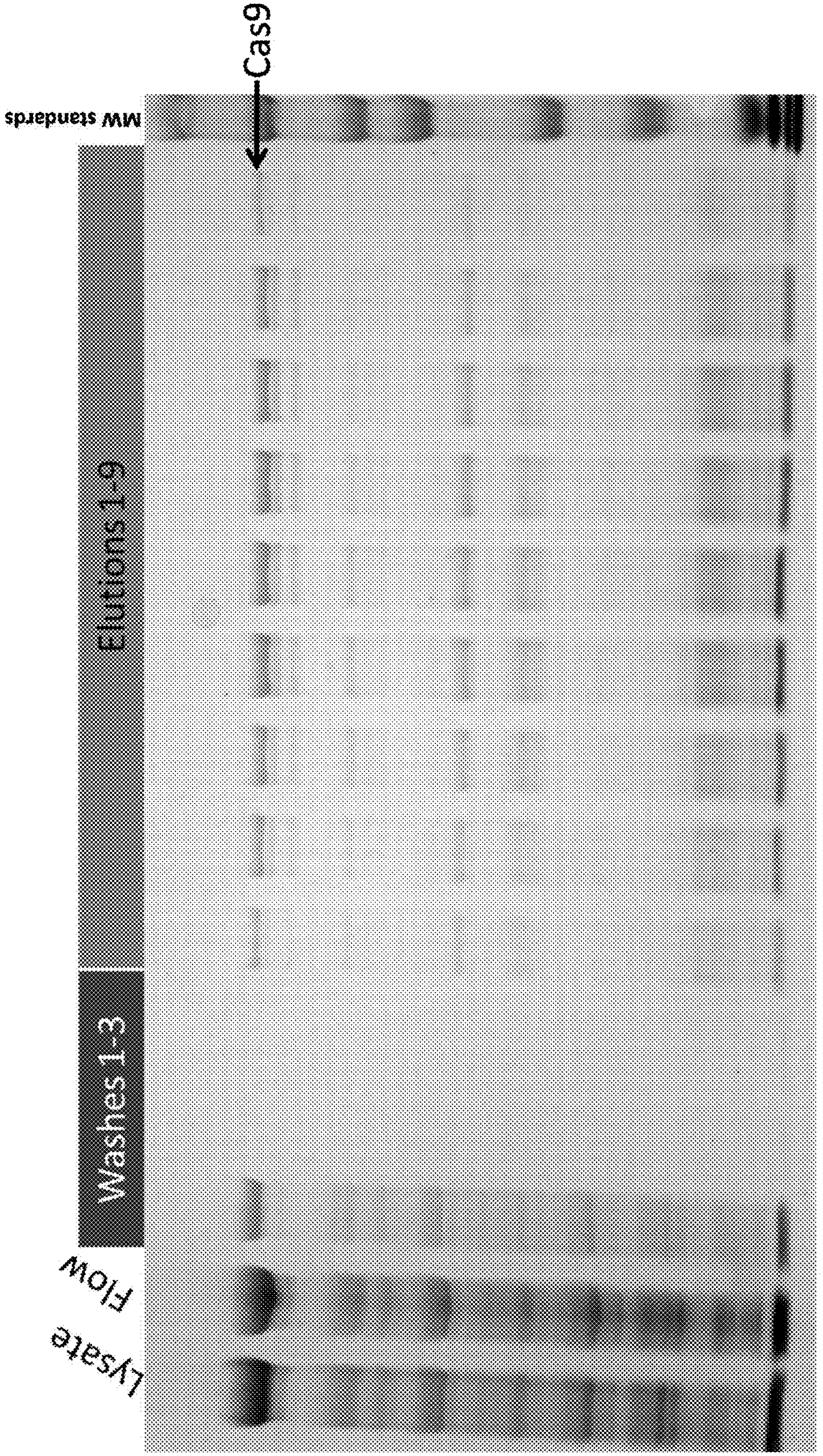

FIG. 4: SDS-PAGE separation of purification fractions of 6×His-Zebra-Cas9-NLS. Lysates, washes, elution fractions, and molecular weight standards are indicated. Refer to Example 1.

Figure 5:
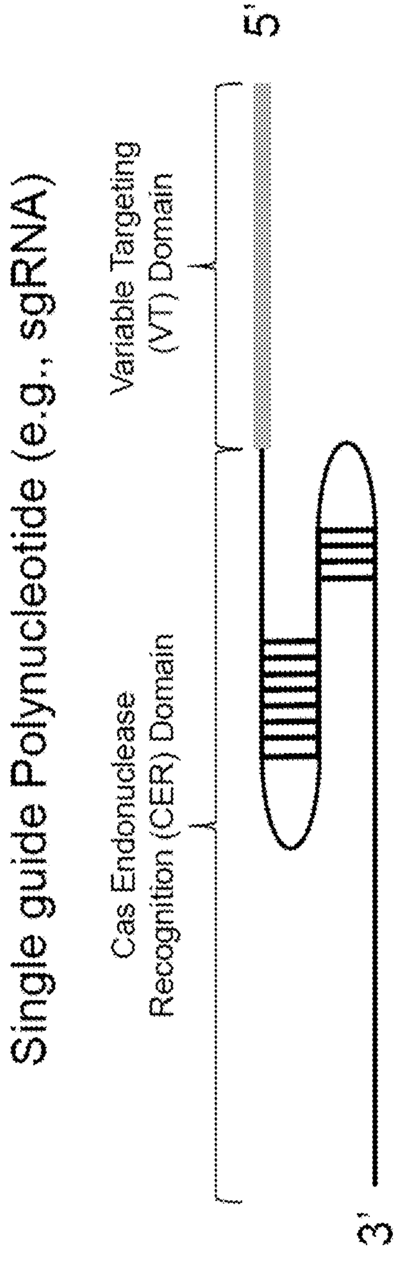

FIG. 5: A structural model of a single guide polynucleotide such as a single guide RNA (sgRNA). A variable targeting (VT) domain is shown in gray. A Cas9 endonuclease recognition (CER) domain is shown in black.

Figure 6:
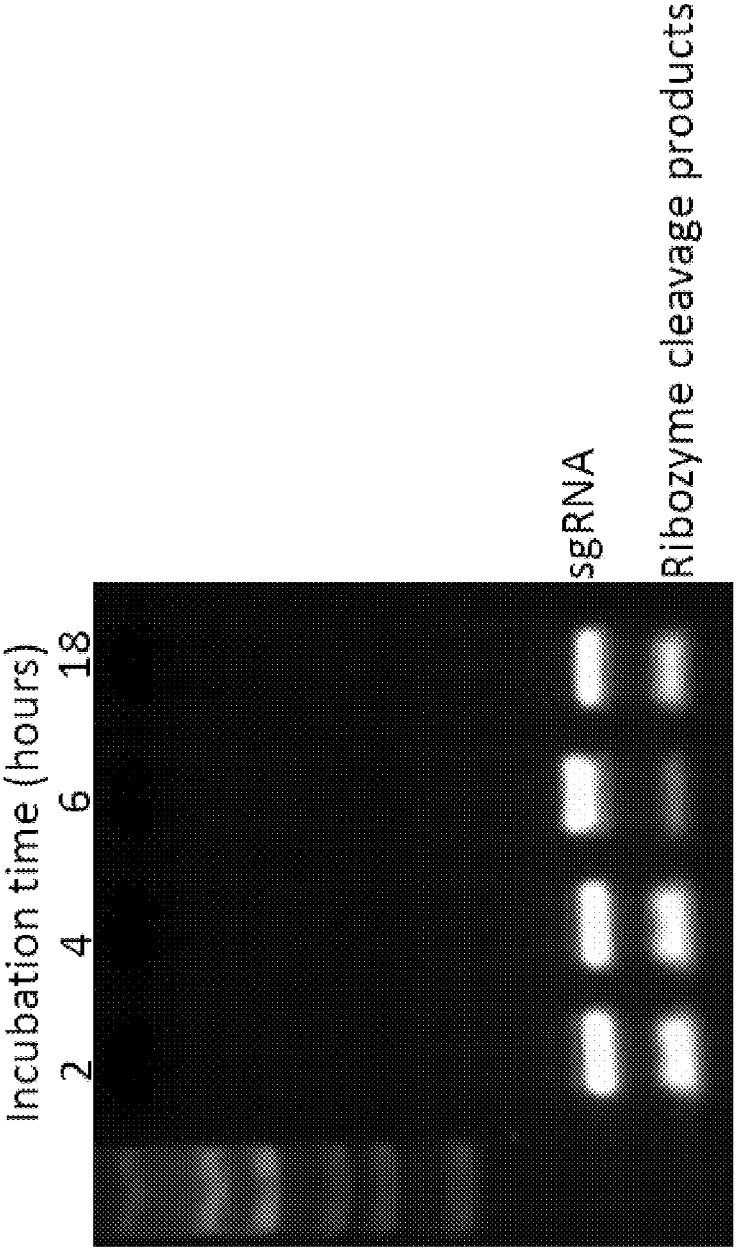

FIG. 6: In vitro transcription of RGR sgRNA (targeting Can1-1 locus) off of template derived from plasmid pRF46 (SEQ ID NO:30). In vitro transcription reactions incubated for 2, 4, 6 and 18 hours produced similar levels of sgRNA. Ribozyme autocatalytic cleavage products were also produced. Refer to Example 2.

Figure 7:
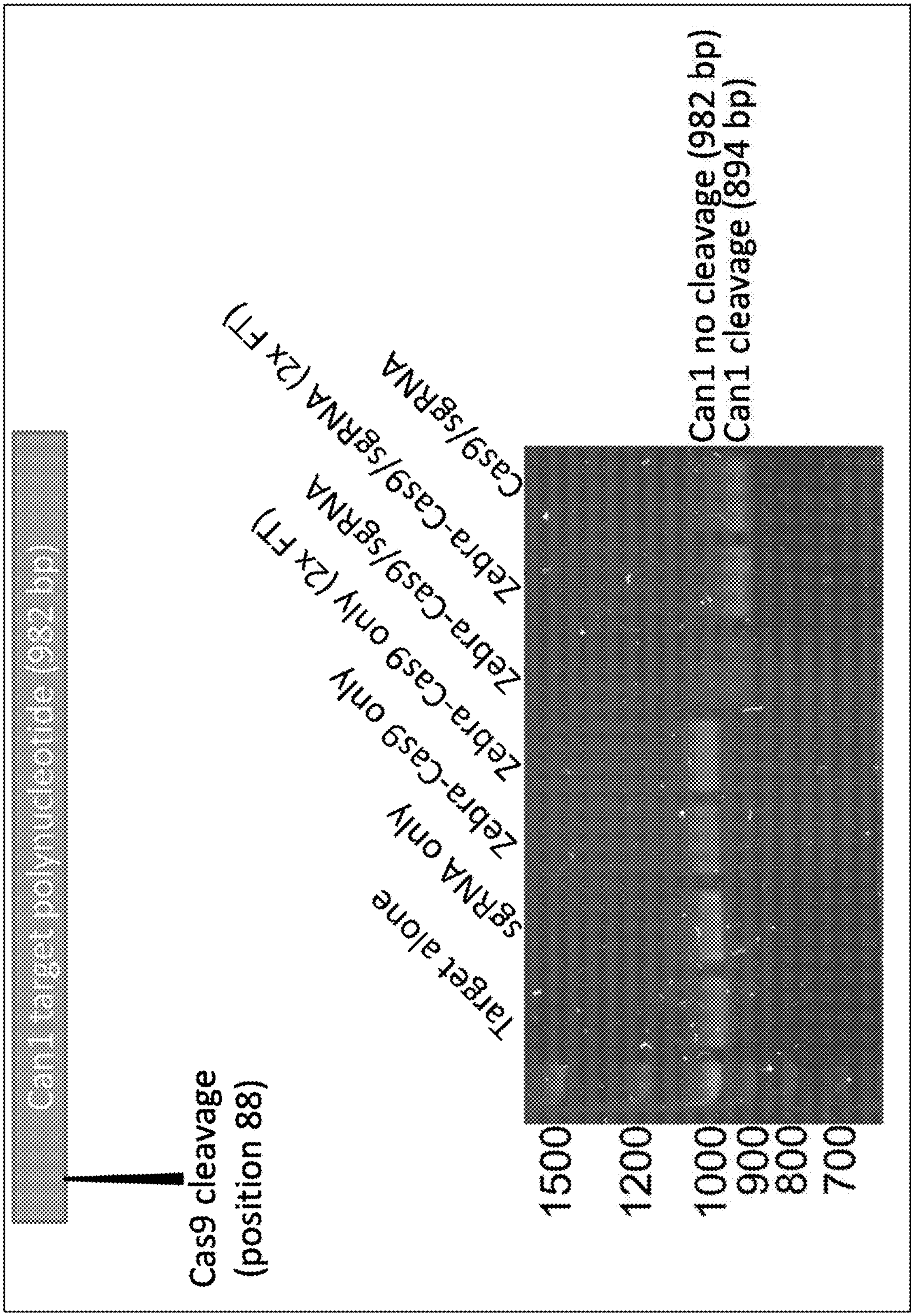

FIG. 7: In vitro cleavage assay using Zebra CPP-Cas9 complexed with sgRNA specific for Can1-1 target site. A DNA polynucleotide (982 bp) containing the Can1-1 target site was included in each reaction. Each reaction was electrophoretically resolved on a 1.2% gel. "Target only", "sgRNA only", "Zebra-Cas9 only", and "Zebra-Cas9 only (2×FT)" (FT, freeze-thaw) reactions did not cleave the target polynucleotide. "Zebra-Cas9/sgRNA", "Zebra-Cas9/sgRNA (2×FT)", and "Cas9/sgRNA" (wild type Cas9) reactions cleaved the target polynucleotide in a specific manner as indicated by the resulting cleavage products. Refer to Example 3.

Figure 8:
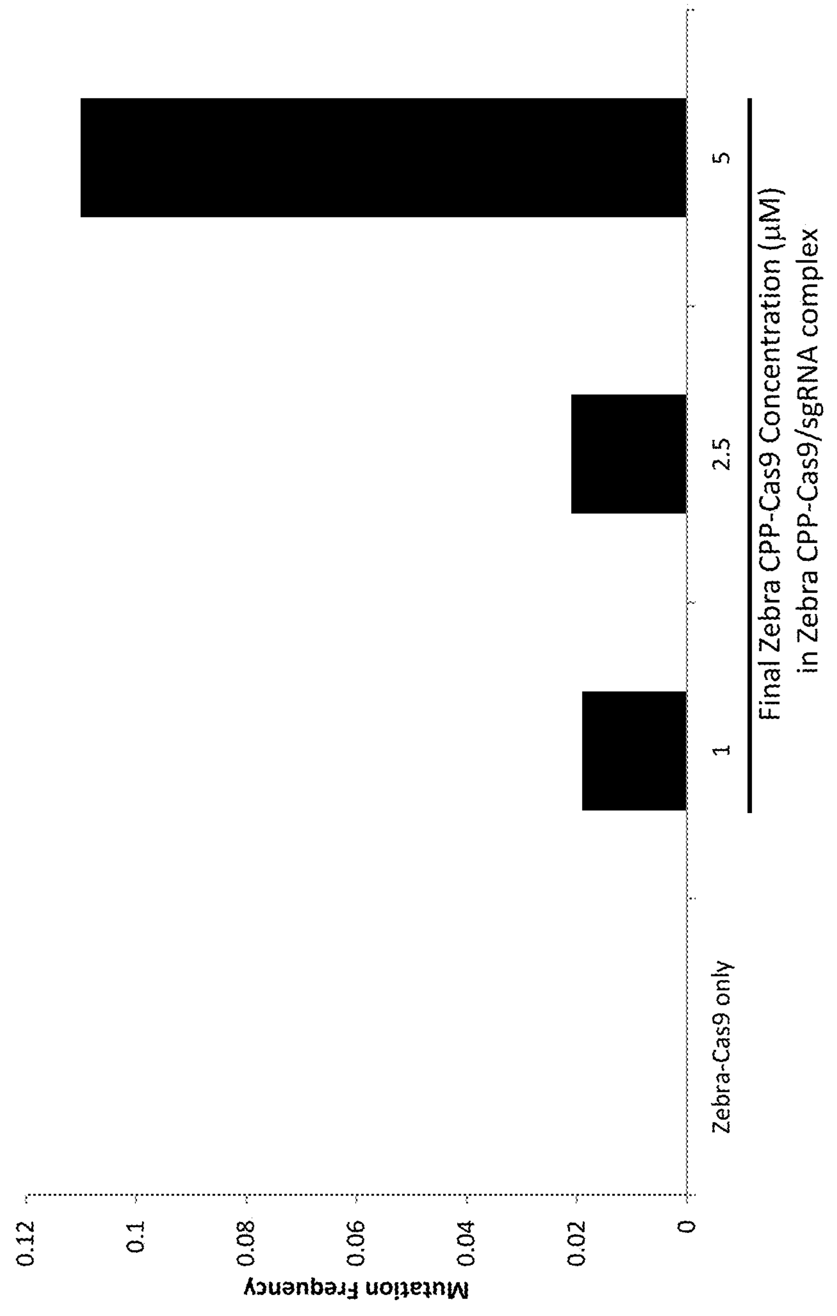

FIG. 8: Measuring the genome-targeting efficiency of Zebra CPP-Cas9 (not associated with sgRNA) and Zebra CPP-Cas9/gRNA complexes after contact thereof with *Yarrowia lipolytica* cells. The final concentration of Zebra-Cas9 used alone was 5 μM, while different final concentrations (1-5 μM) of Zebra CPP-Cas9 were used in the sgRNA complexes. Mutation frequency is reported as the proportion of yeast colonies (grown on non-selective medium after contacting cells with either Zebra CPP-Cas9 or Zebra CPP-Cas9/gRNA) that scored as resistant to canavanine upon transfer to canavanine-containing medium. Refer to Example 4.

Figure 9:
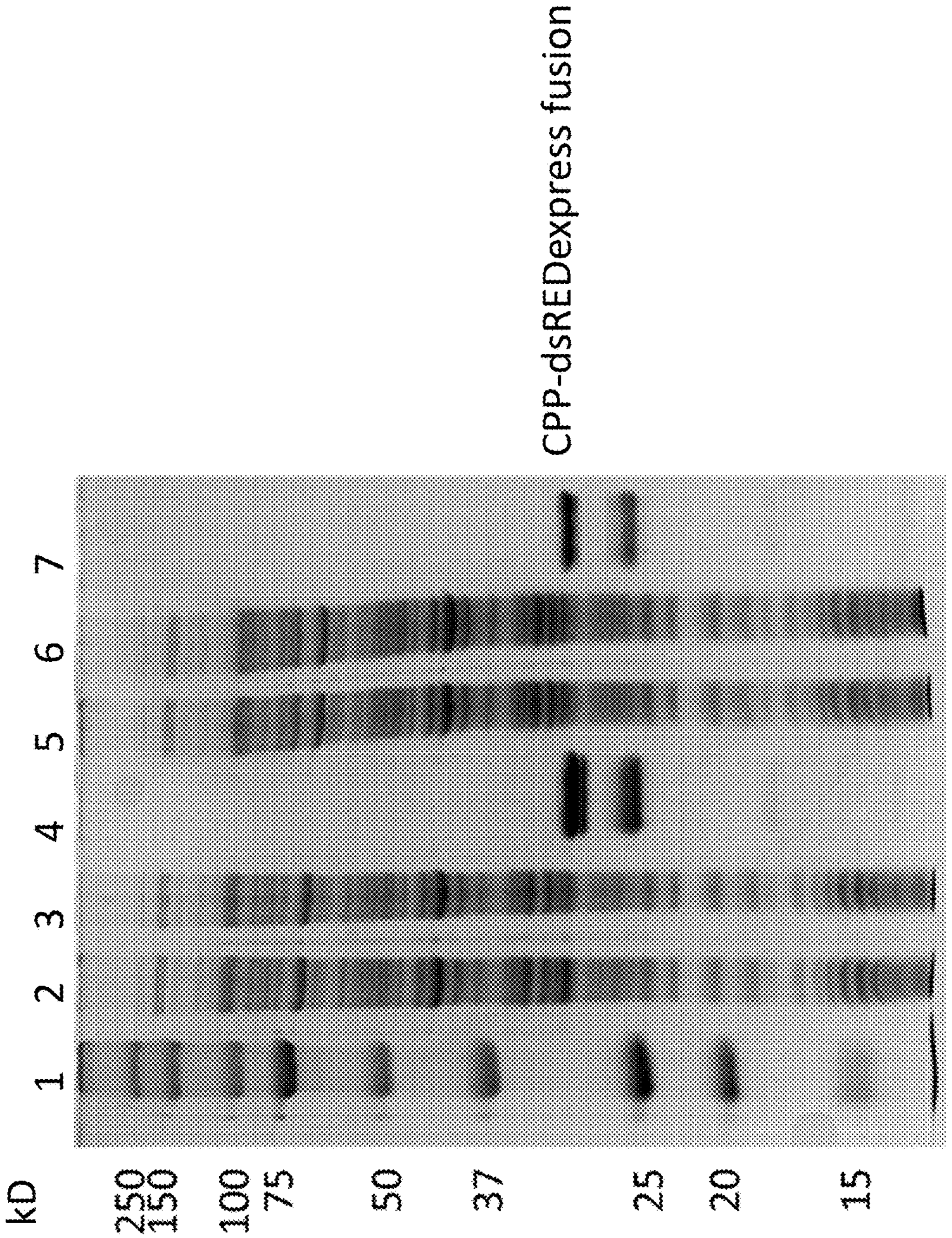

FIG. 9: Example of PAGE gel analysis of CPP-dsRED purification. 12.5% PAGE gel stained with Simply blue stain. Lane 1: Molecular weight standard, Lane 2: clarified cell extract tp10-dsREDexpress, Lane 3: clarified-cell extract post bead treatment tp10-dsREDexpress, lane 4: final protein solution tp10-dsREDexpress, Lane 5 clarified cell extract MPG-dsREDexpress, Lane 3: clarified-cell extract post bead treatment MPG-dsREDexpress, lane 4: final protein solution MPG-dsREDexpress.

TABLE 1

Summary of Nucleic Acid and Protein SEQ ID Numbers

| Description | Nucleic acid SEQ ID NO. | Protein SEQ ID NO. |
|---|---|---|
| *Streptococcus pyogenes* Cas9 open reading frame codon-optimized for expression in *Y. lipolytica*. | 1 (4107 bases) | |
| *Streptococcus pyogenes* Cas9 including C-terminal linker and SV40 NLS ("Cas9-NLS"); open reading frame codon-optimized for expression in *Y. lipolytica*. | 2 (4140 bases) | 3 (1379 aa) |
| *Y. lipolytica* FBA1 promoter. | 4 (543 bases) | |
| Cas9-NLS expression cassette (FBA1 promoter and Cas9-NLS open reading frame). | 5 (4683 bases) | |
| pZUFCas9plasmid. | 6 (10706 bases) | |
| Cas9-NLS forward PCR primer. | 7 (35 bases) | |
| Cas9-NLS reverse PCR primer. | 8 (31 bases) | |
| EcoRI-Cas9-NLS-HinDIII PCR product | 9 (4166 bases) | |
| pBAD/HisB plasmid | 10 (4092 bases) | |
| pRF48 plasmid | 11 (8237 bases) | |
| Zebra cell-penetrating peptide (CPP), from Epstein-Barr virus Zebra trans-activator protein | | 12 (54 aa) |
| pVEC CPP, from murine endothelial cadherin protein | | 13 (18 aa) |
| TP10 CPP, from neuropeptide galanin protein | | 14 (21 aa) |
| Poly-arginine (PolyR) CPP | | 15 (17 aa) |
| Ncol-6xHis-Zebra CPP-EcoRI | 16 (194 bases) | |
| Ncol-6xHis-pVEC CPP-EcoRI | 17 (86 bases) | |
| Ncol-6xHis-TP10 CPP-EcoRI | 18 (95 bases) | |
| Ncol-6xHis-PolyR CPP-EcoRI | 19 (83 bases) | |
| pRF144 plasmid, encoding Zebra CPP-Cas9 fusion protein | 20 (8294 bases) | |
| pRF145 plasmid, encoding PolyR CPP-Cas9 fusion protein | 21 (8183 bases) | |
| pRF146 plasmid, encoding TP10 CPP-Cas9 fusion protein | 22 (8195 bases) | |
| pRF162 plasmid, encoding pVEC CPP-Cas9 fusion protein | 23 (8186 bases) | |
| Cas9 endonuclease recognition (CER) domain of a gRNA. | 24 (80 bases) | |
| *Y. lipolytica* Can1-1 target site, or alternatively, DNA encoding Can1-1 variable target domain of a gRNA. | 25 (20 bases) | |
| Hammerhead (HH) ribozyme. | 26 (43 bases) | |
| HDV ribozyme. | 27 (68 bases) | |
| HH-sgRNA-HDV (RGR) pre-sgRNA expression cassette, or alternatively, "RGR" expression cassette (for targeting Can1-1 locus) | 28 (211 bases) | |

TABLE 1-continued

| Summary of Nucleic Acid and Protein SEQ ID Numbers | | |
|---|---|---|
| Description | Nucleic acid SEQ ID NO. | Protein SEQ ID NO. |
| T7 RNA polymerase promoter | 29 (20 bases) | |
| pRF46 plasmid | 30 (2875 bases) | |
| T7 forward primer | 31 (20 bases) | |
| gRNArev1 reverse primer | 32 (20 bases) | |
| IV-up primer | 33 (21 bases) | |
| IV-down primer | 34 (20 bases) | |
| Can1 cleavage assay DNA sequence | 35 (982 bases) | |
| RNA loop-forming sequence (GAAA). | 36 (4 bases) | |
| RNA loop-forming sequence (CAAA). | 37 (4 bases) | |
| RNA loop-forming sequence (AAAG). | 38 (4 bases) | |
| Zebra CPP-Cas9-NLS fusion protein | | 39 (1434 aa) |
| PolyR CPP-Cas9-NLS fusion protein | | 40 (1397 aa) |
| TP10 CPP-Cas9-NLS fusion protein | | 41 (1401 aa) |
| pVEC CPP-Cas9-NLS fusion protein | | 42 (1398 aa) |
| Example of a Cas9 target site: PAM sequence. | 43 (23 bases) | |
| PAM sequence NGG. | 44 (3 bases) | |
| PAM sequence NNAGAA. | 45 (6 bases) | |
| PAM sequence NNAGAAW. | 46 (7 bases) | |
| PAM sequence NGGNG. | 47 (5 bases) | |
| PAM sequence NNNNGATT. | 48 (8 bases) | |
| PAM sequence NAAAAC. | 49 (6 bases) | |
| PAM sequence NG. | 50 (2 bases) | |
| TracrRNA mate sequence example 1. | 51 (22 bases) | |
| TracrRNA mate sequence example 2. | 52 (15 bases) | |
| TracrRNA mate sequence example 3. | 53 (12 bases) | |
| TracrRNA mate sequence example 4. | 54 (13 bases) | |
| TracrRNA example 1. | 55 (60 bases) | |
| TracrRNA example 2. | 56 (45 bases) | |
| TracrRNA example 3. | 57 (32 bases) | |
| TracrRNA example 4. | 58 (85 bases) | |
| TracrRNA example 5. | 59 (77 bases) | |
| TracrRNA example 6. | 60 (65 bases) | |
| gRNA example 1. | 61 (131 bases) | |
| gRNA example 2. | 62 (117 bases) | |
| gRNA example 3. | 63 (104 bases) | |
| gRNA example 4. | 64 (99 bases) | |
| gRNA example 5. | 65 (81 bases) | |

TABLE 1-continued

| Summary of Nucleic Acid and Protein SEQ ID Numbers | | |
|---|---|---|
| Description | Nucleic acid SEQ ID NO. | Protein SEQ ID NO. |
| gRNAexample 6. | 66 (68 bases) | |
| gRNA example 7. | 67 (100 bases) | |
| Tat-derived CPP (GRKKRRQRRR) | | 68 (10 aa) |
| Tat-derived CPP (RKKRRQRRR) | | 69 (9 aa) |
| Tat-derived CPP (RKKRRQRR) | | 70 (8 aa) |
| Penetratin CPP (RQIKIWFQNRRMKWKK) | | 71 (16 aa) |
| Polyarginine CPP (THRLPRRRRRR) | | 72 (11 aa) |
| Polyarginine CPP (GGRRARRRRRR) | | 73 (11 aa) |
| pVEC CPP (shorter version), from murine endothelial cadherin protein | | 74 (17 aa) |
| CPP comprising $(KFF)_3K$ | | 75 (10 aa) |
| MAP peptide CPP | | 76 (18 aa) |
| CPP (RRQRRTSKLMKR) | | 77 (12 aa) |
| CPP (KALAWEAKLAKALAKALAKHLAKALAKALKCEA) | | 78 (33 aa) |
| Proline-rich CPP repeat VHLPPP | | 79 (6 aa) |
| Proline-rich CPP repeat VHRPPP | | 80 (6 aa) |
| MPG peptide CPP | | 81 (27 aa) |
| Pep-1 peptide CPP | | 82 (21 aa) |
| hCT CPP example 1 | | 83 (24 aa) |
| hCT CPP example 2 | | 84 (18 aa) |
| his tagged dsRED | | 85 |
| *E. coli* codon optimized dsRED | 86 | |
| pBAD/HisB | 87 | |
| pRF161 | 88 | |
| TAT | | 89 |
| TLM | | 90 |
| MPG1 | | 91 |
| pep1 | | 92 |
| CFFKDEL | | 93 |
| his-TAT *E. coli* optimized | 94 | |
| his-TLM *E. coli* optimized | 95 | |
| his-MPG1 *E. coli* optimized | 96 | |
| his-pep1 *E. coli* optimized | 97 | |
| his-CFFKDEL *E. coli* optimized | 98 | |
| pRF224 | 99 | |
| pRF214 | 100 | |
| pRF213 | 101 | |
| pRF217 | 102 | |
| pRF216 | 103 | |
| oligo 36 | 104 | |
| His-Zebra PCR | 105 | |
| His-tp10 PCR | 106 | |
| His-pVEC PCR | 107 | |
| pRF144 | 108 | |
| pRF162 | 109 | |
| pRF146 | 110 | |
| oligo 153 | 111 | |
| pRF186 | 112 | |
| pRF192 | 113 | |
| pRF190 | 114 | |
| his-CFFKDEL-Cas9 | | 115 |
| his-MPG1-Cas9 | | 116 |
| pRF48 | 117 | |
| pRF243 | 118 | |
| pRF238 | 119 | |
| galK gene | 120 | |
| galE gene | | 121 |

TABLE 1-continued

Summary of Nucleic Acid and Protein SEQ ID Numbers

| Description | Nucleic acid SEQ ID NO. | Protein SEQ ID NO. |
|---|---|---|
| galT gene | | 122 |
| CER domain I | 123 | |
| CER encoding DNA PCR | 124 | |
| pRF291 | 125 | |
| CER forward | 126 | |
| universal reverse | 127 | |
| universal forward T7 primer | 128 | |
| galK2-1 forward primer | 129 | |
| galK2-1 reverse primer | 130 | |
| galK2-1 sgRNA in vitro transcription template | 131 | |
| T7 promoter | 132 | |
| DNA encoding galK2-1 variable targeting domain | 133 | |
| galK2-1 target site | 134 | |
| galK2-1 sgRNA | 135 | |
| his-MPG1-dsREDexpress; | | 136 |
| pVEC-dsREDexpress | | 137 |
| CFFKDEL-dsREDexpress | | 138 |
| TLM-dsREDexpress | | 139 |
| Zebra-dsREDexpress | | 140 |
| pep1-dsREDexpress | | 141 |
| tp10-dsREDexpress | | 142 |
| Zebra-Cas9 | | 143 |
| pVEC-Cas9 | | 144 |

DETAILED DESCRIPTION OF THE INVENTION

The disclosures of all cited patent and non-patent literature are incorporated herein by reference in their entirety.

As used herein, the term "invention" or "disclosed invention" is not meant to be limiting, but applies generally to any of the inventions defined in the claims or described herein. These terms are used interchangeably herein.

The term "cell" herein refers to any type of cell such as a prokaryotic or eukaryotic cell. A eukaryotic cell has a nucleus and other membrane-enclosed structures (organelles), whereas a prokaryotic cell lacks a nucleus. A cell in certain embodiments can be a mammalian cell or non-mammalian cell. Non-mammalian cells can be eukaryotic or prokaryotic. For example, a non-mammalian cell herein can refer to a microbial cell or cell of a non-mammalian multicellular organism such as a plant, insect, nematode, avian species, amphibian, reptile, or fish.

A microbial cell herein can refer to a fungal cell (e.g., yeast cell), prokaryotic cell, protist cell (e.g., algal cell), euglenoid cell, stramenopile cell, or oomycete cell, for example. A prokaryotic cell herein can refer to a bacterial cell or archaeal cell, for example. Fungal cells (e.g., yeast cells), protist cells (e.g., algal cells), euglenoid cells, stramenopile cells, and oomycete cells represent examples of eukaryotic microbial cells. A eukaryotic microbial cell has a nucleus and other membrane-enclosed structures (organelles), whereas a prokaryotic cell lacks a nucleus.

The term "yeast" herein refers to fungal species that predominantly exist in unicellular form. Yeast can alternatively be referred to as "yeast cells". A yeast herein can be characterized as either a conventional yeast or non-conventional yeast, for example.

The term "conventional yeast" ("model yeast") herein generally refers to *Saccharomyces* or *Schizosaccharomyces* yeast species. Conventional yeast in certain embodiments are yeast that favor homologous recombination (HR) DNA repair processes over repair processes mediated by non-homologous end-joining (NHEJ).

The term "non-conventional yeast" herein refers to any yeast that is not a *Saccharomyces* or *Schizosaccharomyces* yeast species. Non-conventional yeast are described in *Non-Conventional Yeasts in Genetics, Biochemistry and Biotechnology: Practical Protocols* (K. Wolf, K. D. Breunig, G. Barth, Eds., Springer-Verlag, Berlin, Germany, 2003) and Spencer et al. (Appl. Microbiol. Biotechnol. 58:147-156), which are incorporated herein by reference. Non-conventional yeast in certain embodiments may additionally (or alternatively) be yeast that favor NHEJ DNA repair processes over repair processes mediated by HR. Definition of a non-conventional yeast along these lines—preference of NHEJ over HR—is further disclosed by Chen et al. (*PLoS ONE* 8:e57952), which is incorporated herein by reference. Preferred non-conventional yeast herein are those of the genus *Yarrowia* (e.g., *Yarrowia lipolytica*).

The term "plant" herein refers to whole plants, plant organs, plant tissues, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic plant material can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of a plant genome (chromosomal or extra-chromosomal) by conventional plant breeding methods, by a genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

A fertile plant is a plant that produces viable male and female gametes and is self-fertile. Such a self-fertile plant can produce a progeny plant without the contribution from any other plant of a gamete and the genetic material contained therein. Male-sterile plants include plants that do not produce male gametes that are viable or otherwise capable of fertilization. Female-sterile plants include plants that do not produce female gametes that are viable or otherwise capable of fertilization. It is recognized that male-sterile and female-sterile plants can be female-fertile and male-fertile, respectively. It is further recognized that a male-fertile (but female-sterile) plant can produce viable progeny when crossed with a female-fertile plant and that a female-fertile (but male-sterile) plant can produce viable progeny when crossed with a male-fertile plant.

The term "RNA-guided endonuclease" (RGEN) herein refers to a complex comprising at least one CRISPR (clustered regularly interspaced short palindromic repeats)-associated (Cas) protein and at least one RNA component. The terms "protein component of an RGEN" and "RGEN protein component" are used interchangeably herein and refer to a Cas protein, which is, or forms part of, the endonuclease component of an RGEN. A protein component in certain embodiments can be a complete endonuclease (e.g., Cas9); such a protein component can alternatively be referred to as "the endonuclease component" of an RGEN. An RGEN herein typically has specific DNA targeting activity, given its association with at least one RNA component.

Briefly, an RNA component of an RGEN contains sequence that is complementary to a DNA sequence in a target site sequence. Based on this complementarity, an RGEN can specifically recognize and cleave a particular DNA target site sequence. An RGEN herein can comprise Cas protein(s) and suitable RNA component(s) of any of the four known CRISPR systems (Horvath and Barrangou, *Science* 327:167-170) such as a type I, II, or III CRISPR system. An RGEN in preferred embodiments comprises a Cas9 endonuclease (CRISPR II system) and at least one RNA component (e.g., a crRNA and tracrRNA, or a gRNA).

The term "CRISPR" (clustered regularly interspaced short palindromic repeats) refers to certain genetic loci encoding factors of class I, II, or III DNA cleavage systems, for example, used by bacterial and archaeal cells to destroy foreign DNA (Horvath and Barrangou, *Science* 327:167-170). Components of CRISPR systems are taken advantage of herein in a heterologous manner for DNA targeting in cells.

The terms "type II CRISPR system" and "type II CRISPR-Cas system" are used interchangeably herein and refer to a DNA cleavage system utilizing a Cas9 endonuclease in complex with at least one RNA component. For example, a Cas9 can be in complex with a CRISPR RNA (crRNA) and a trans-activating CRISPR RNA (tracrRNA). In another example, a Cas9 can be in complex with a guide RNA. Thus, crRNA, tracrRNA, and guide RNA are non-limiting examples of RNA components herein.

The term CRISPR-associated ("Cas") endonuclease herein refers to a Cas protein encoded by a Cas gene. A Cas endonuclease, when in complex with a suitable RNA component, is capable of cleaving all or part of a specific DNA target sequence in certain embodiments. For example, it is can be capable of introducing a single- or double-strand break in a specific DNA target sequence; it can alternatively be characterized as being able to cleave one or both strands of a specific DNA target sequence. A Cas endonuclease can unwind the DNA duplex at the target sequence and cleaves at least one DNA strand, as mediated by recognition of the target sequence by a crRNA or guide RNA that is in complex with the Cas. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. A preferred Cas protein herein is Cas9.

Any guided endonuclease can be used in the methods disclosed herein. Such endonucleases include, but are not limited to Cas9 and Cpf1 endonucleases. Many endonucleases have been described to date that can recognize specific PAM sequences (see for example WO2016/186953, published on Nov. 14, 2016 and WO2016/186946 published on Nov. 14, 2016, and Zetsche B et al. 2015. Cell 163, 1013) and cleave the target DNA at a specific position. It is understood that based on the methods and embodiments described herein utilizing a guided Cas system, one can now tailor these methods such that they can utilize any guided endonuclease system.

"Cas9" (formerly referred to as Cas5, Csn1, or Csx12) herein refers to a Cas endonuclease of a type II CRISPR system that forms a complex with crRNA and tracrRNA, or with a guide RNA, for specifically recognizing and cleaving all or part of a DNA target sequence. Cas9 protein comprises an RuvC nuclease domain and an HNH (H—N—H) nuclease domain, each of which cleaves a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, *Cell* 157:1262-1278). "Apo-Cas9" refers to Cas9 that is not complexed with an RNA component. Apo-Cas9 can bind DNA, but does so in a non-specific manner, and cannot cleave DNA (Sternberg et al., *Nature* 507:62-67).

The term "RNA component" herein refers to an RNA component of an RGEN containing a ribonucleic acid sequence that is complementary to a strand of a DNA target sequence. This complementary sequence is referred to herein as a "guide sequence" or "variable targeting domain"

sequence (FIG. 5). Examples of suitable RNA components herein include crRNA and guide RNA. RNA components in certain embodiments (e.g., guide RNA alone, crRNA+tracrRNA) can render an RGEN competent for specific DNA targeting.

The term "CRISPR RNA" (crRNA) herein refers to an RNA sequence that can form a complex with one or more Cas proteins (e.g., Cas9) and provides DNA binding specificity to the complex. A crRNA provides DNA binding specificity since it contains "guide sequence" ("variable targeting domain" [VT]) that is complementary to a strand of a DNA target sequence. A crRNA further comprises a "repeat sequence" ("tracr RNA mate sequence") encoded by a repeat region of the CRISPR locus from which the crRNA was derived. A repeat sequence of a crRNA can anneal to sequence at the 5'-end of a tracrRNA. crRNA in native CRISPR systems is derived from a "pre-crRNA" transcribed from a CRISPR locus. A pre-crRNA comprises spacer regions and repeat regions; spacer regions contain unique sequence complementary to a DNA target site sequence. Pre-crRNA in native systems is processed to multiple different crRNAs, each with a guide sequence along with a portion of repeat sequence. CRISPR systems utilize crRNA, for example, for DNA targeting specificity.

The term "trans-activating CRISPR RNA" (tracrRNA) herein refers to a non-coding RNA used in type II CRISPR systems, and contains, in the 5'-to-3' direction, (i) a sequence that anneals with the repeat region of CRISPR type II crRNA and (ii) a stem loop-containing portion (Deltcheva et al., *Nature* 471:602-607).

The terms "guide RNA" (gRNA) and "single guide RNA" (sgRNA) are used interchangeably herein. A gRNA herein can refer to a chimeric sequence containing a crRNA operably linked to a tracrRNA. Alternatively, a gRNA can refer to a synthetic fusion of a crRNA and a tracrRNA, for example. A gRNA can also be characterized in terms of having a guide sequence (variable targeting domain) followed by a Cas endonuclease recognition (CER) domain. A CER domain can comprise a tracrRNA mate sequence followed by a tracrRNA sequence.

A "CRISPR DNA" (crDNA) can optionally be used instead of an RNA component. A crDNA has a DNA sequence corresponding to the sequence of a crRNA as disclosed herein. A crDNA can be used with a tracrRNA in a crDNA/tracrRNA complex, which in turn can be associated with an RGEN protein component. U.S. Appl. No. 61/953,090 discloses crDNA and the methods of its use in RGEN-mediated DNA targeting. It is contemplated that any disclosure herein regarding a crRNA can similarly apply to using a crDNA, accordingly. Thus, in embodiments herein incorporating a crDNA, an "RNA-guided endonuclease" (RGEN) could instead be referred to as a complex comprising at least one Cas protein and at least one crDNA.

As used herein, the term "guide polynucleotide", relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (an RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, Phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain ("crNucleotide") is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides).

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise an RNA sequence, a DNA sequence, or a, RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising an RNA sequence, a DNA sequence, or an RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides).

Thus, a guide polynucleotide and a type II Cas endonuclease in certain embodiments can form a complex with each other (referred to as a "guide polynucleotide/Cas endonuclease complex" or also referred to as "guide polynucleotide/Cas endonuclease system"), wherein the guide polynucleotide/Cas endonuclease complex can direct the Cas endonuclease to target a genomic target site in a cell (e.g., plant cell), optionally enabling the Cas endonuclease to introduce a single- or double-strand break into the genomic target site. A guide polynucleotide/Cas endonuclease complex can be linked to at least one CPP, wherein such complex is capable of binding to, and optionally creating a single- or double-strand break to, a target site of a cell (e.g., a plant cell).

The term "variable targeting domain" or "VT domain" is used interchangeably herein and refers to a nucleotide sequence that is complementary to one strand (nucleotide sequence) of a double strand DNA target site. The percent complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, an RNA sequence, a modified DNA sequence, a modified RNA sequence (see, e.g., modifications described herein), or any combination thereof.

The term "Cas endonuclease recognition domain" or "CER domain" of a guide polynucleotide is used interchangeably herein and relates to a nucleotide sequence (such as a second nucleotide sequence domain of a guide polynucleotide), that interacts with a Cas endonuclease polypeptide. A CER domain can be composed of a DNA sequence, an RNA sequence, a modified DNA sequence, a modified RNA sequence (see, e.g., modifications described herein), or any combination thereof.

The terms "target site", "target sequence", "target DNA", "DNA target sequence", "target locus", "protospacer" and the like are used interchangeably herein. A target site sequence refers to a polynucleotide sequence on a chromosome, episome, or any other DNA molecule in the genome of a cell to which an RGEN herein can recognize, bind to, and optionally nick or cleave. A target site can be (i) an endogenous/native site in the cell, (ii) heterologous to the cell and therefore not be naturally occurring in the genome, or (iii) found in a heterologous genomic location compared to where it natively occurs.

A target site sequence herein is at least 13 nucleotides in length and has a strand with sufficient complementarity to a guide sequence (of a crRNA or gRNA) to be capable of hybridizing with the guide sequence and direct sequence-specific binding of a Cas protein or Cas protein complex to the target sequence (if a suitable PAM is adjacent to the target sequence in certain embodiments). A cleavage/nick site (applicable with a endonucleolytic or nicking Cas) can be within the target sequence (e.g., using a Cas9) or a cleavage/nick site could be outside of the target sequence (e.g., using a Cas9 fused to a heterologous endonuclease domain such as one derived from a FokI enzyme). It is also possible for a target site sequence to be bound by an RGEN lacking cleavage or nicking activity.

An "artificial target site" or "artificial target sequence" herein refers to a target sequence that has been introduced into the genome of a cell. An artificial target sequence in some embodiments can be identical in sequence to a native target sequence in the genome of the cell, but be located at a different position (a heterologous position) in the genome, or it can different from the native target sequence if located at the same position in the genome of the cell.

An "episome" herein refers to a DNA molecule that can exist in a cell autonomously (can replicate and pass on to daughter cells) apart from the chromosomes of the cell. Episomal DNA can be either native or heterologous to a cell. Examples of native episomes herein include mitochondrial DNA (mtDNA) and chloroplast DNA. Examples of heterologous episomes herein include plasmids and yeast artificial chromosomes (YACs).

A "protospacer adjacent motif" (PAM) herein refers to a short sequence that is recognized by an RGEN herein. The sequence and length of a PAM herein can differ depending on the Cas protein or Cas protein complex used, but are typically 2, 3, 4, 5, 6, 7, or 8 nucleotides long, for example.

The terms "5'-cap" and "7-methylguanylate ($m^7G$) cap" are used interchangeably herein. A 7-methylguanylate residue is located on the 5' terminus of RNA transcribed by RNA polymerase II (Pol II) in eukaryotes. A capped RNA herein has a 5'-cap, whereas an uncapped RNA does not have such a cap.

The terminology "uncapped", "not having a 5'-cap", and the like are used interchangeably herein to refer to RNA lacking a 5'-cap and optionally having, for example, a 5'-hydroxyl group instead of a 5'-cap. Uncapped RNA can better accumulate in the nucleus following transcription, since 5'-capped RNA is subject to nuclear export.

The terms "ribozyme", "ribonucleic acid enzyme" and "self-cleaving ribozyme" are used interchangeably herein. A ribozyme refers to one or more RNA sequences that form secondary, tertiary, and/or quaternary structure(s) that can cleave RNA at a specific site, particularly at a cis-site relative to the ribozyme sequence (i.e., auto-catalytic, or self-cleaving). The general nature of ribozyme nucleolytic activity has been described (e.g., Lilley, *Biochem. Soc. Trans.* 39:641-646). A "hammerhead ribozyme" (HHR) herein may comprise a small catalytic RNA motif made up of three base-paired stems and a core of highly conserved, non-complementary nucleotides that are involved in catalysis. Pley et al. (*Nature* 372:68-74) and Hammann et al. (*RNA* 18:871-885), which are incorporated herein by reference, disclose hammerhead ribozyme structure and activity. A hammerhead ribozyme herein may comprise a "minimal hammerhead" sequence as disclosed by Scott et al. (*Cell* 81:991-1002, incorporated herein by reference), for example.

The terms "targeting", "gene targeting", "DNA targeting", "editing", "gene editing" and "DNA editing" are used interchangeably herein. DNA targeting herein may be the specific introduction of an indel, knock-out, or knock-in at a particular DNA sequence, such as in a chromosome or episome of a cell. In general, DNA targeting can be performed herein by cleaving one or both strands at a specific DNA sequence in a cell with a Cas protein associated with a suitable RNA component. Such DNA cleavage, if a double-strand break (DSB), can prompt NHEJ processes which can lead to indel formation at the target site. Also, regardless of whether the cleavage is a single-strand break (SSB) or DSB, HR processes can be prompted if a suitable donor DNA polynucleotide is provided at the DNA nick or cleavage site. Such an HR process can be used to introduce a knock-out or knock-in at the target site, depending on the sequence of the donor DNA polynucleotide. Alternatively, DNA targeting herein can refer to specific association of a Cas/RNA component complex herein to a target DNA sequence, where the Cas protein does or does not cut a DNA strand (depending on the status of the Cas protein's endonucleolytic domains).

The term "indel" herein refers to an insertion or deletion of a nucleotide base or bases in a target DNA sequence in a chromosome or episome. Such an insertion or deletion may be of 1, 2, 3, 4, 5, 6, 7, 8, 9, 10, or more bases, for example. An indel in certain embodiments can be even larger, at least about 20, 30, 40, 50, 60, 70, 80, 90, or 100 bases. If an indel is introduced within an open reading frame (ORF) of a gene, oftentimes the indel disrupts wild type expression of protein encoded by the ORF by creating a frameshift mutation.

The terms "knock-out", "gene knock-out" and "genetic knock-out" are used interchangeably herein. A knock-out represents a DNA sequence of a cell herein that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (by NHEJ, prompted by Cas-mediated cleavage), or by specific removal of sequence (by HR, prompted by Cas-mediated cleavage or nicking, when a suitable donor DNA polynucleotide is also used), that reduces or completely destroys the function of sequence at, adjoining, or near the targeting site. A knocked out DNA polynucleotide sequence herein can alternatively be characterized as being partially or totally disrupted or downregulated, for example.

The terms "knock-in", "gene knock-in" and "genetic knock-in" are used interchangeably herein. A knock-in represents the replacement or insertion of a DNA sequence at a specific DNA sequence in a cell by targeting with a Cas protein (by HR, prompted by Cas-mediated cleavage or nicking, when a suitable donor DNA polynucleotide is also used). Examples of knock-ins are a specific insertion of a heterologous amino acid coding sequence in a coding region of a gene, or a specific insertion of a transcriptional regulatory element in a genetic locus.

The terms "donor polynucleotide", "donor DNA", "targeting polynucleotide" and "targeting DNA" are used interchangeably herein. A donor polynucleotide refers to a DNA sequence that comprises at least one sequence that is homologous to a sequence at or near a DNA target site (e.g., a sequence specifically targeted by a Cas protein herein). A suitable donor polynucleotide is able to undergo HR with a DNA target site if the target site contains a SSB or DSB (such as can be introduced using certain Cas proteins herein associated with an appropriate RNA component). A "homologous sequence" within a donor polynucleotide herein can, for example, comprise or consist of a sequence of at least about 25 nucleotides, for example, having 100% identity with a sequence at or near a target site, or at least about 90%, 91%, 92%, 93%, 94%, 95%, 96%, 97%, 98%, or 99% A identity with a sequence at or near a target site.

In certain embodiments, a donor DNA polynucleotide can have two homologous sequences separated by a sequence (or base pair) that is heterologous to sequence at a target site. These two homologous sequences of such a donor polynucleotide can be referred to as "homology arms", which flank the heterologous sequence. HR between a target site and a donor polynucleotide with two homology arms typically results in the replacement of a sequence at the target site with the heterologous sequence of the donor polynucleotide (target site sequence located between DNA sequences homologous to the homology arms of the donor polynucleotide is replaced by the heterologous sequence of the donor polynucleotide). In a donor polynucleotide with two homology arms, the arms can be separated by 1 or more nucleotides (i.e., the heterologous sequence in the donor polynucleotide can be at least 1 nucleotide in length). Various HR procedures that can be performed in a cell herein are disclosed, for example, in *DNA Recombination: Methods and Protocols:* 1*st Edition* (H. Tsubouchi, Ed., Springer-Verlag, New York, 2011), which is incorporated herein by reference.

The terms "cell-penetrating peptide" (CPP) and "protein transduction domain" (PTD) are used interchangeably herein. A CPP refers to a peptide, typically of about 5-60 amino acid residues in length, that can facilitate cellular uptake of molecular cargo, particularly one or more RGEN protein components herein (e.g., Cas9 protein). Such protein cargo can be associated with one or more CPPs through covalent or non-covalent linkage. A CPP can also be characterized in certain embodiments as being able to facilitate the movement or traversal of molecular cargo across/through one or more of a lipid bilayer, micelle, cell membrane, organelle membrane, vesicle membrane, or cell wall. A CPP herein can be cationic, amphipathic, or hydrophobic in certain embodiments. Examples of CPPs useful herein, and further description of CPPs in general, are disclosed in Schmidt et al. (*FEBS Left.* 584:1806-1813), Holm et al. (*Nature Protocols* 1:1001-1005), Yandek et al. (*Biophys. J.* 92:2434-2444), Morris et al. (*Nat. Biotechnol.* 19:1173-1176), and U.S. Patent Appl. Publ. No. 2014/0068797, which are all incorporated herein by reference.

A "cationic", or "polycationic", CPP herein refers to a CPP having a high relative abundance (at least 60%) of positively charged amino acids such as lysine (K), arginine (R), and/or histidine (H).

An "amphipathic", or "amphiphilic", CPP herein refers to a CPP with an amino acid sequence containing an alternating pattern of polar/charged residues and non-polar, hydrophobic residues. An amphipathic CPP can alternatively be characterized as possessing both hydrophilic and lipophilic properties.

A "hydrophobic", or "lipophilic", CPP herein contains mostly, or only, non-polar residues with low net charge and/or hydrophobic amino acid groups.

The terms "covalently linked", "covalently attached", "covalently associated", "covalent linkage", "covalent interaction" and the like are used interchangeably herein. A covalent linkage herein can be via a peptide bond(s) or chemical crosslink(s), for example. A covalent linkage can be direct, for example, where there is a covalent link directly between (directly linking) an RGEN protein component and a CPP (e.g., there is a chemical bond [sharing of electrons] between an atom of an RGEN protein component and an atom of a CPP). A covalent linkage can alternatively be indirect, for example, where an RGEN protein component and a CPP are linked to each other through at least one intermediary factor. Such an intermediary factor, or group of intermediary factors that are themselves covalently linked together, is covalently linked to the RGEN protein component and CPP. Thus, an intermediary factor or group thereof can be characterized as being a bridge between an RGEN protein component and a CPP.

The terms "fusion protein", "protein fusion", "chimeric protein" and the like are used interchangeably herein. A fusion protein herein contains at least two different (heterologous) amino acid sequences linked together within a single polypeptide. Fusion proteins are typically produced by genetic engineering processes in which DNA sequences encoding different amino acid sequences are joined together to encode a single protein containing the different amino acid sequences. Examples of fusion proteins herein include RGEN protein-CPP fusions (RGEN protein amino acid sequence fused to one or more CPP amino acid sequences).

The terms "non-covalently linked", "non-covalently attached", "non-covalently associated", "non-covalent linkage", "non-covalent interaction" and the like are used interchangeably herein. A non-covalent linkage herein refers to an interaction between atoms in which electrons are not shared. This type of interaction is weaker than a covalent linkage. Hydrophobic interactions represent an example of a non-covalent linkage that may occur between an RGEN protein component and one or more CPPs. Other examples of non-covalent linkages that may apply herein include electrostatic forces (e.g., ionic, hydrogen bonding) and Van der Waals forces (London Dispersion forces).

An “RGEN protein-CPP complex” as used herein refers to a complex between a protein component of an RGEN and at least one CPP, where the RGEN and CPP interact via covalent or non-covalent linkage. Both RGEN and CPP components in this complex typically retain all of, or some of (e.g., at least 50%), their respective activity/function as disclosed herein. For example, in embodiment in which the RGEN protein component is Cas9, the Cas9 in a Cas9-CPP complex is capable of associating with a suitable RNA component (e.g., gRNA) and targeting the Cas9-CPP complex to a DNA target site in a cell.

The terms “traverse”, “travel through”, “cross through”, “goes across” and the like are used interchangeably herein.

The terms “cell membrane”, “plasma membrane”, and “cytoplasmic membrane” are used interchangeably herein and refer to a biological membrane that separates the interior of a cell from its exterior. A cell membrane typically comprises a phospholipid bilayer with proteins embedded therein. Among several other functions, a cell membrane can serve as an attachment surface for extracellular structures such as cell wall or glycocalyx structures. Detailed information regarding cell membrane lipid bilayers is provided in *Molecular Biology of the Cell.* 4*th Edition* (B. Alberts et al., Eds., Garland Science, New York, 2002), which is incorporated herein by reference.

The term “cell wall” herein refers to a tough, flexible (but sometimes fairly rigid) layer that surrounds some types of non-mammalian cells (e.g., bacteria, plants, algae, fungi such as yeast). It is located outside the cell membrane and provides structural support and protection to cells. A major function of a cell wall in certain embodiments is to help maintain cell osmotic pressure. Fungal cell (e.g., yeast cell) walls generally comprise chitin, and algal cells walls generally comprise glycoproteins and polysaccharides. Plant cell walls generally comprise mostly polysaccharides with lesser amounts of other components (e.g., phenolic esters, structural proteins). “Primary cell wall” and/or “secondary cell wall” may be used to characterize a plant cell wall, where the secondary wall is located inside the primary wall. Lignin is a major component of secondary walls. Bacterial cell walls generally comprise peptidoglycan as the main constituent. In certain aspects, such as in bacteria, a cell wall can further comprise at its outer layer a glycocalyx, which is generally a coat of polysaccharides.

The term “leucine zipper domain” herein refers to a dimerization domain characterized by the presence of a leucine residue every seventh residue in a stretch of approximately 35 residues. Leucine zipper domains form dimers held together by an alpha-helical coiled coil. A coiled coil has 3.5 residues per turn, which means that every seventh residue occupies an equivalent position with respect to the helix axis. The regular array of leucines inside the coiled coil stabilizes the structure by hydrophobic and Van der Waals interactions.

The terms “percent by volume”, “volume percent”, “vol %” and “v/v %” are used interchangeably herein. The percent by volume of a solute in a solution can be determined using the formula: [(volume of solute)/(volume of solution)]×100%.

The terms “percent by weight”, “weight percentage (wt %)” and “weight-weight percentage (% w/w)” are used interchangeably herein. Percent by weight refers to the percentage of a material on a mass basis as it is comprised in a composition, mixture, or solution.

The terms “polynucleotide”, “polynucleotide sequence”, and “nucleic acid sequence” are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof. Nucleotides (ribonucleotides or deoxyribonucleotides) can be referred to by a single letter designation as follows: “A” for adenylate or deoxyadenylate (for RNA or DNA, respectively), “C” for cytidylate or deoxycytidylate (for RNA or DNA, respectively), “G” for guanylate or deoxyguanylate (for RNA or DNA, respectively), “U” for uridylate (for RNA), “T” for deoxythymidylate (for DNA), “R” for purines (A or G), “Y” for pyrimidines (C or T), “K” for G or T, “H” for A or C or T, “I” for inosine, “W” for A or T, and “N” for any nucleotide (e.g., N can be A, C, T, or G, if referring to a DNA sequence; N can be A, C, U, or G, if referring to an RNA sequence). Any RNA sequence (e.g., crRNA, tracrRNA, gRNA) disclosed herein may be encoded by a suitable DNA sequence.

The term “isolated” as used herein refers to a polynucleotide or polypeptide molecule that has been completely or partially purified from its native source. In some instances, the isolated polynucleotide or polypeptide molecule is part of a greater composition, buffer system or reagent mix. For example, the isolated polynucleotide or polypeptide molecule can be comprised within a cell or organism in a heterologous manner. Compositions herein comprising a protein component of an RGEN and a cell-penetrating peptide can be considered isolated compositions. These compositions contain heterologous components and do not occur in nature.

The term “gene” as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA (e.g., a crRNA, tracrRNA, or gRNA herein). A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an “open reading frame” (ORF). A gene that is “native” or “endogenous” refers to a gene as found in nature with its own regulatory sequences; such a gene is located in its natural location in the genome of a host cell. A “chimeric” gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A “foreign” or “heterologous” gene refers to a gene that is introduced into the host organism by gene transfer. Foreign/heterologous genes can comprise native genes inserted into a non-native organism, native genes introduced into a new location within the native host, or chimeric genes. The polynucleotide sequences in certain embodiments disclosed herein are heterologous. A “transgene” is a gene that has been introduced into the genome by a gene delivery procedure (e.g., transformation). A “codon-optimized" open reading frame has its frequency of codon usage designed to mimic the frequency of preferred codon usage of the host cell.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that is made by using a guide polynucleotide/Cas endonuclease system as disclosed herein. A mutated plant is a plant comprising at least one mutated gene.

A "non-native" amino acid sequence or polynucleotide sequence comprised in a cell or organism herein does not occur in a native (natural) counterpart of such cell or organism.

"Regulatory sequences" as used herein refer to nucleotide sequences located upstream of a gene's transcription start site (e.g., promoter), 5' untranslated regions, and 3' non-coding regions, and which may influence the transcription, processing or stability, or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in a cell.

A plant promoter is a promoter capable of initiating transcription in a plant cell; for a review of plant promoters, see Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples, an inducible promoter may be used. Pathogen-inducible promoters induced following infection by a pathogen include, but are not limited to those regulating expression of PR proteins, SAR proteins, beta-1,3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112: 525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci.* USA 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean beta-phaseolin, napin, beta-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

The terms "3' non-coding sequence", "transcription terminator" and "terminator" as used herein refer to DNA sequences located downstream of a coding sequence. This includes polyadenylation recognition sequences and other sequences encoding regulatory signals capable of affecting mRNA processing or gene expression.

The term "cassette" as used herein refers to a promoter operably linked to a DNA sequence encoding a protein-coding RNA or non-protein-coding RNA. A cassette may optionally be operably linked to a 3' non-coding sequence.

The terms "upstream" and "downstream" as used herein with respect to polynucleotides refer to "5' of" and "3' of", respectively.

The term "expression" as used herein refers to (i) transcription of RNA (e.g., mRNA or a non-protein coding RNA such as crRNA, tracrRNA, or gRNA) from a coding region, or (ii) translation of a polypeptide from mRNA.

When used to describe the expression of a gene or polynucleotide sequence, the terms "down-regulation", "disruption", "inhibition", "inactivation", and "silencing" are used interchangeably herein to refer to instances when the transcription of the polynucleotide sequence is reduced or eliminated. This results in the reduction or elimination of RNA transcripts from the polynucleotide sequence, which results in a reduction or elimination of protein expression derived from the polynucleotide sequence (if the gene comprised an ORF). Alternatively, down-regulation can refer to instances where protein translation from transcripts produced by the polynucleotide sequence is reduced or eliminated. Alternatively still, down-regulation can refer to instances where a protein expressed by the polynucleotide sequence has reduced activity. The reduction in any of the above processes (transcription, translation, protein activity) in a cell can be by about 20%, 30%, 40%, 50%, 60%, 70%, 80%, 90%, 95%, or 100% relative to the transcription, translation, or protein activity of a suitable control cell. Down-regulation can be the result of a targeting event as disclosed herein (e.g., indel, knock-out), for example.

The terms "control cell" and "suitable control cell" are used interchangeably herein and may be referenced with respect to a cell in which a particular modification (e.g., over-expression of a polynucleotide, down-regulation of a polynucleotide) has been made (i.e., an "experimental cell"). A control cell may be any cell that does not have or does not express the particular modification of the experimental cell. Thus, a control cell may be an untransformed wild type cell or may be genetically transformed but does not express the genetic transformation. For example, a control cell may be a direct parent of the experimental cell, which direct parent cell does not have the particular modification that is in the experimental cell. Alternatively, a control cell may be a parent of the experimental cell that is removed by one or more generations. Alternatively still, a control cell may be a sibling of the experimental cell, which sibling does not comprise the particular modification that is present in the experimental cell.

The term "increased" as used herein may refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% A more than the quantity or activity for which the increased quantity or activity is being compared. The terms "increased", "elevated", "enhanced", "greater than", and "improved" are used interchangeably herein. The term "increased" can be used to characterize the expression of a polynucleotide encoding a protein, for example, where "increased expression" can also mean "over-expression".

The term "operably linked" as used herein refers to the association of two or more nucleic acid sequences such that that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences, for example. Also, for example, a crRNA can be operably linked (fused to) a tracrRNA herein such that the tracrRNA mate sequence of the crRNA anneals with 5' sequence of the tracrRNA. Such operable linkage may comprise a suitable loop-forming sequence such as GAAA (SEQ ID NO:36), CAAA (SEQ ID NO:37), or AAAG (SEQ ID NO:38). Also, for example, an RGEN can be operably linked (fused to) one or more CPPs.

The term "recombinant" as used herein refers to an artificial combination of two otherwise separated segments of sequence, e.g., by chemical synthesis or by the manipulation of isolated segments of nucleic acids by genetic engineering techniques.

Methods for preparing recombinant constructs/vectors herein (e.g., a DNA polynucleotide encoding an RNA component cassette herein, or a DNA polynucleotide encoding a Cas protein or Cas-CPP fusion protein herein) can follow standard recombinant DNA and molecular cloning techniques as described by J. Sambrook and D. Russell (*Molecular Cloning: A Laboratory Manual,* 3rd Edition, Cold Spring Harbor Laboratory Press, Cold Spring Harbor, N.Y., 2001); T. J. Silhavy et al. (*Experiments with Gene Fusions*, Cold Spring Harbor Laboratory Press, Cold Spring Harbor, N Y, 1984); and F. M. Ausubel et al. (*Short Protocols in Molecular Biology,* 5th Ed. Current Protocols, John Wiley and Sons, Inc., NY, 2002), for example.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules.

A "transgenic plant" herein includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. Transgenic plant material can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by genome editing procedures that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

A "phenotypic marker" is a screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT); DNA segments that encode products which are otherwise lacking in the recipient cell (e.g., tRNA genes, auxotrophic markers); DNA segments that encode products which can be readily identified (e.g., phenotypic markers such as beta-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph. D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

The terms "sequence identity" or "identity" as used herein with respect to polynucleotide or polypeptide sequences refer to the nucleic acid residues or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining percent complementarity of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Herein, a first sequence that is "complementary" to a second sequence can alternatively be referred to as being in the "antisense" orientation with the second sequence.

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence.

All the amino acid residues disclosed herein at each amino acid position of Cas9 proteins herein are examples. Given that certain amino acids share similar structural and/or charge features with each other (i.e., conserved), the amino acid at each position in a Cas9 can be as provided in the disclosed sequences or substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

Advances have been made in expressing protein and RNA components in cells for performing RGEN-mediated DNA targeting therein (e.g., WO2015/026883, published Feb. 26, 2015 and WO2016/025131, published Feb. 18, 2016). Such strategies typically have entailed recombinant DNA expression in the target cells. Additional means of providing protein and RNA components in a cell to mediate RGEN-mediated DNA targeting are of interest.

Embodiments of the disclosed invention concern a composition comprising at least one protein component of an RNA-guided endonuclease (RGEN) and at least one cell-penetrating peptide (CPP), wherein the RGEN protein component and CPP are covalently or non-covalently linked to each other in an RGEN protein-CPP complex. The RGEN protein-CPP complex can traverse (i) a cell membrane, or (ii) a cell wall and cell membrane, of a cell.

Significantly, certain embodiments of the disclosed invention can be used to deliver an RGEN already associated (pre-associated) with an RNA component into a cell. Such embodiments may avoid the need to deliver a DNA construct into cells for expressing an RGEN RNA component, thus averting any potentially unwanted effects of introducing exogenous DNA into cells. The disclosed invention is flexible, however, since in certain other embodiments an RNA component can be provided (e.g., expressed) in a cell into which an RGEN protein-CPP complex is being delivered. An RNA component provided in this manner can associate with an RGEN protein component after delivery/entry of the RGEN protein-CPP complex into the cell. Regardless of the mode of RNA component delivery, an RGEN protein-CPP complex herein is able to associate with an RNA component, forming an RGEN-CPP complex that can target a specific DNA sequence in the cell. Thus, the disclosed invention offers substantial flexibility for providing an RGEN in cells to perform RGEN-mediated DNA targeting.

Compositions disclosed in certain embodiments comprise at least one protein component of an RGEN. An RGEN herein refers to a complex comprising at least one Cas protein and at least one RNA component. Thus, an RGEN protein component can refer to a Cas protein such as Cas9. Examples of suitable Cas proteins include one or more Cas endonucleases of type I, II, or III CRISPR systems (Bhaya et al., *Annu. Rev. Genet.* 45:273-297, incorporated herein by reference). A type I CRISPR Cas protein can be a Cas3 or Cas4 protein, for example. A type II CRISPR Cas protein can be a Cas9 protein, for example. A type III CRISPR Cas protein can be a Cas10 protein, for example. A Cas9 protein is used in certain preferred embodiments. A Cas protein in certain embodiments may be a bacterial or archaeal protein. Type I-III CRISPR Cas proteins herein are typically prokaryotic in origin; type I and III Cas proteins can be derived from bacterial or archaeal species, whereas type II Cas proteins (i.e., a Cas9) can be derived from bacterial species, for example. In other embodiments, suitable Cas proteins include one or more of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof.

In other aspects of the disclosed invention, a Cas protein herein can be from any of the following genera: *Aeropyrum, Pyrobaculum, Sulfolobus, Archaeoglobus, Haloarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Streptococcus, Treponema, Francisella*, or *Thermotoga*. Alternatively, a Cas protein herein can be encoded, for example, by any of SEQ ID NOs:462-465, 467-472, 474-477, 479-487, 489-492, 494-497, 499-503, 505-508, 510-516, or 517-521 as disclosed in U.S. Appl. Publ. No. 2010/0093617, which is incorporated herein by reference.

An RGEN protein component can comprise a Cas9 amino acid sequence, for example. An RGEN comprising this type of protein component typically can be characterized as having Cas9 as the endonuclease component of the RGEN. The amino acid sequence of a Cas9 protein herein, as well as certain other Cas proteins herein, may be derived from a *Streptococcus* (e.g., *S. pyogenes, S. pneumoniae, S. thermophilus, S. agalactiae, S. parasanguinis, S. oralis, S. salivarius, S. macacae, S. dysgalactiae, S. anginosus, S. constellatus, S. pseudoporcinus, S. mutans*), *Listeria* (e.g., *L. innocua*), *Spiroplasma* (e.g., *S. apis, S. syrphidicola*), *Peptostreptococcaceae, Atopobium, Porphyromonas* (e.g., *P. catoniae*), *Prevotella* (e.g., *P. intermedia*), *Veillonella, Treponema* (e.g., *T. socranskii, T. denticola*), *Capnocytophaga, Finegoldia* (e.g., *F. magna*), *Coriobacteriaceae* (e.g., *C. bacterium*), *Olsenella* (e.g., *O. profusa*), *Haemophilus* (e.g., *H. sputorum, H. pittmaniae*), *Pasteurella* (e.g., *P. bettyae*), *Olivibacter* (e.g., *O. sitiensis*), *Epilithonimonas* (e.g., *E. tenax*), *Mesonia* (e.g., *M. mobilis*), *Lactobacillus, Bacillus* (e.g., *B. cereus*), *Aquimarina* (e.g., *A. muelleri*), *Chryseobacterium* (e.g., *C. palustre*), *Bacteroides* (e.g., *B. graminisolvens*), *Neisseria* (e.g., *N. meningitidis*), *Francisella* (e.g., *F. novicida*), or *Flavobacterium* (e.g., *F. frigidarium, F. soli*) species, for example. An *S. pyogenes* Cas9 is preferred in certain aspects herein. As another example, a Cas9 protein can be any of the Cas9 proteins disclosed in Chylinski et al. (*RNA Biology* 10:726-737), which is incorporated herein by reference.

Accordingly, the sequence of a Cas9 protein herein can comprise, for example, any of the Cas9 amino acid sequences disclosed in GenBank Accession Nos. G3ECR1 (*S. thermophilus*), WP_026709422, WP_027202655, WP_027318179, WP_027347504, WP_027376815, WP_027414302, WP_027821588, WP_027886314, WP_027963583, WP_028123848, WP_028298935, Q03JI6 (*S. thermophilus*), EGP66723, EGS38969, EGV05092, EHI65578 (*S. pseudoporcinus*), EIC75614 (*S. oralis*), EID22027 (*S. constellatus*), EIJ69711, EJP22331 (*S. oralis*), EJP26004 (*S. anginosus*), EJP30321, EPZ44001 (*S. pyogenes*), EPZ46028 (*S. pyogenes*), EQL78043 (*S. pyogenes*), EQL78548 (*S. pyogenes*), ERL10511, ERL12345, ERL19088 (*S. pyogenes*), ESA57807 (*S. pyogenes*), ESA59254 (*S. pyogenes*), ESU85303 (*S. pyogenes*), ETS96804, UC75522, EGR87316 (*S. dysgalactiae*), EGS33732, EGV01468 (*S. oralis*), EHJ52063 (*S. macacae*), EID26207 (*S. oralis*), EID33364, EIG27013 (*S. parasanguinis*), EJF37476, EJ019166 (*Streptococcus* sp. BS35b), EJU16049, EJU32481, YP_006298249, ERF61304, ERK04546, ETJ95568 (*S. agalactiae*), TS89875, ETS90967 (*Streptococcus* sp. SR4), ETS92439, EUB27844 (*Streptococcus* sp. BS21), AFJ08616, EUC82735 (*Streptococcus* sp. CM6), EWC92088, EWC94390, EJP25691, YP_008027038, YP_008868573, AGM26527, AHK22391, AHB36273, Q927P4, G3ECR1, or Q99ZW2 (*S. pyogenes*), which are incorporated by reference. A variant of any of these Cas9 protein sequences may be used, but should have specific binding activity, and optionally cleavage or nicking activity, toward DNA when associated with an RNA component herein. Such a variant may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the reference Cas9.

Alternatively, a Cas9 protein herein can be encoded by any of SEQ ID NOs:462 (*S. thermophilus*), 474 (*S. thermophilus*), 489 (*S. agalactiae*), 494 (*S. agalactiae*), 499 (*S. mutans*), 505 (*S. pyogenes*), or 518 (*S. pyogenes*) as disclosed in U.S. Appl. Publ. No. 2010/0093617 (incorporated herein by reference), for example. Alternatively still, a Cas9 protein herein can comprise the amino acid sequence of SEQ ID NO:3, or residues 1-1368, 2-1368, or 2-1379, of SEQ ID NO:3, for example. Alternatively still, a Cas9 protein may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% A identical to any of the foregoing amino acid sequences, for example. Such a variant Cas9 protein should have specific binding activity, and optionally cleavage or nicking activity, toward DNA when associated with an RNA component herein.

The origin of a Cas protein used herein (e.g., Cas9) may be from the same species from which the RNA component (s) is derived, or it can be from a different species. For example, an RGEN comprising a Cas9 protein derived from a *Streptococcus* species (e.g., *S. pyogenes* or *S. thermophilus*) may be complexed with at least one RNA component having a sequence (e.g., crRNA repeat sequence, tracrRNA sequence) derived from the same *Streptococcus* species. Alternatively, the origin of a Cas protein used herein (e.g., Cas9) may be from a different species from which the RNA component(s) is derived (the Cas protein and RNA component(s) may be heterologous to each other); such heterologous Cas/RNA component RGENs should have DNA targeting activity.

Determining binding activity and/or endonucleolytic activity of a Cas protein herein toward a specific target DNA sequence may be assessed by any suitable assay known in the art, such as disclosed in U.S. Pat. No. 8,697,359, which is disclosed herein by reference. A determination can be made, for example, by expressing a Cas protein and suitable RNA component in a cell, and then examining the predicted DNA target site for the presence of an indel (a Cas protein in this particular assay would typically have complete endonucleolytic activity [double-strand cleaving activity]). Examining for the presence of an alteration/modification (e.g., indel) at the predicted target site could be done via a DNA sequencing method or by inferring alteration/modification formation by assaying for loss of function of the target sequence, for example. In another example, Cas protein activity can be determined by expressing a Cas protein and suitable RNA component in a cell that has been provided a donor DNA comprising a sequence homologous to a sequence in at or near the target site. The presence of donor DNA sequence at the target site (such as would be predicted by successful HR between the donor and target sequences) would indicate that targeting occurred. In still another example, Cas protein activity can be determined using an in vitro assay in which a Cas protein and suitable RNA component are mixed together along with a DNA polynucleotide containing a suitable target sequence. This assay can be used to detect binding (e.g., gel-shift) by Cas proteins lacking cleavage activity, or cleavage by Cas proteins that are endonucleolytically competent.

A Cas protein herein such as a Cas9 can further comprise a heterologous nuclear localization sequence (NLS) in certain aspects. A heterologous NLS amino acid sequence herein may be of sufficient strength to drive accumulation of a Cas protein, or Cas protein-CPP complex, in a detectable amount in the nucleus of a cell herein, for example. An NLS may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NLS may be operably linked to the N-terminus or C-terminus of a Cas protein herein, for example. Two or more NLS sequences can be linked to a Cas protein, for example, such as on both the N- and C-termini of a Cas protein. Non-limiting examples of suitable NLS sequences herein include those disclosed in U.S. Pat. Nos. 6,660,830 and 7,309,576 (e.g., Table 1 therein), which are both incorporated herein by reference. Another example of an NLS useful herein includes amino acid residues 1373-1379 of SEQ ID NO:3. A Cas protein as disclosed herein can be fused with a CPP (an example of a Cas protein covalently linked to a CPP), for example. It would be understood that such a Cas-CPP fusion protein can also comprise an NLS as described above. It would also be understood that, in embodiments in which a Cas protein is fused with an amino acid sequence targeting a different organelle (e.g., mitochondria), such a Cas protein typically would not contain an NLS.

In certain embodiments, a Cas protein and its respective RNA component (e.g., crRNA) that directs DNA-specific targeting by the Cas protein can be heterologous to a cell, in particular a non-prokaryotic cell. The heterologous nature of these RGEN components is due to that Cas proteins and their respective RNA components are only known to exist in prokaryotes (bacteria and archaea).

In some embodiments, a Cas protein is part of a fusion protein comprising one or more heterologous protein domains (e.g., 1, 2, 3, or more domains in addition to the Cas protein). These embodiments can encompass a Cas protein that is covalently linked to a CPP and one or more additional heterologous amino acid sequences, for example. Other embodiments can encompass a Cas protein that is covalently linked to one or more additional heterologous amino acid sequences not including a CPP, for example (a CPP would be non-covalently linked to a Cas fusion protein in such embodiments). A fusion protein comprising a Cas protein may comprise any additional protein sequence, and optionally a linker sequence between any two domains, such as between Cas and a first heterologous domain. Examples of protein domains that may be fused to a Cas protein herein include, without limitation, epitope tags (e.g., histidine [His, poly-histidine], V5, FLAG, influenza hemagglutinin [HA], myc, VSV-G, thioredoxin [Trx]), reporters (e.g., glutathione-5-transferase [GST], horseradish peroxidase [HRP], chloramphenicol acetyltransferase [CAT], beta-galactosidase, beta-glucuronidase [GUS], luciferase, green fluorescent protein [GFP], HcRed, DsRed, cyan fluorescent protein [CFP], yellow fluorescent protein [YFP], blue fluorescent protein [BFP]), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas protein in other embodiments may be in fusion with a protein that binds DNA molecules or other molecules, such as maltose binding protein (MBP), S-tag, Lex A DNA binding domain (DBD), GAL4A DNA binding domain, and herpes simplex virus (HSV) VP16. Additional domains that may be part of a fusion protein comprising a Cas protein herein are disclosed in U.S. Patent Appl. Publ. No. 2011/0059502, which is incorporated herein by reference. In certain embodiments in which a Cas protein is fused to a heterologous protein (e.g., a transcription factor), the Cas protein has DNA recognition and binding activity (when in complex with a suitable RNA component herein), but no DNA nicking or cleavage activity. A Cas protein as disclosed herein can be fused with a CPP (an example of a Cas protein covalently linked to a CPP), for example. It would be understood that such a Cas-CPP fusion protein can also be fused with one or more heterologous domains as described above, if desired.

Other examples of heterologous domains that can be linked to a Cas protein herein include amino acid sequences targeting the protein to a particular organelle (i.e., localization signal). Examples of organelles that can be targeted include mitochondria and chloroplasts. Typically, such targeting domains are used instead of an NLS when targeting extra-nuclear DNA sites. A mitochondrial targeting sequence (MTS) can be situated at or near the N-terminus of a Cas protein, for example. MTS examples are disclosed in U.S. Patent Appl. Publ. Nos. 2007/0011759 and 2014/0135275, which are incorporated herein by reference. A chloroplast targeting sequence can be as disclosed in U.S. Patent Appl. Publ. No. 2010/0192262 or 2012/0042412, for example, which are incorporated herein by reference.

The protein component of an RGEN can be associated with at least one RNA component (thereby constituting a complete RGEN) that comprises a sequence complementary to a target site sequence on a chromosome or episome in a cell, for example. The RGEN in such embodiments can bind to the target site sequence, and optionally cleave one or both DNA strands at the target site sequence. An RGEN can cleave one or both strands of a DNA target sequence, for example. An RGEN can cleave both strands of a DNA target sequence in another example. It would be understood that in all these embodiments, an RGEN protein component can be covalently or non-covalently linked to at least one CPP in an RGEN protein-CPP complex. The association of an RGEN protein-CPP complex with an RNA component herein can be characterized as forming an RGEN-CPP complex. Any disclosure herein regarding an RGEN can likewise apply to the RGEN component of an RGEN-CPP complex, unless otherwise noted.

An RGEN herein that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas9 protein disclosed herein), or a variant thereof retaining some or all activity in each endonuclease domain of the Cas protein, is a suitable example of an RGEN that can cleave both strands of a DNA target sequence. A Cas9 protein comprising functional RuvC and HNH nuclease domains is an example of a Cas protein that can cleave both strands of a DNA target sequence. An RGEN herein that can cleave both strands of a DNA target sequence typically cuts both strands at the same position such that blunt-ends (i.e., no nucleotide overhangs) are formed at the cut site.

An RGEN herein that can cleave one strand of a DNA target sequence can be characterized herein as having nickase activity (e.g., partial cleaving capability). A Cas nickase (e.g., Cas9 nickase) herein typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain.

Non-limiting examples of Cas9 nickases suitable for use herein are disclosed by Gasiunas et al. (*Proc. Natl. Acad. Sci. U.S.A.* 109:E2579-E2586), Jinek et al. (Science 337:816-821), Sapranauskas et al. (*Nucleic Acids Res.* 39:9275-9282) and in U.S. Patent Appl. Publ. No. 2014/0189896, which are incorporated herein by reference. For example, a Cas9 nickase herein can comprise an *S. thermophilus* Cas9 having an Asp-31 substitution (e.g., Asp-31-Ala) (an example of a mutant RuvC domain), or a His-865 substitution (e.g., His-865-Ala), Asn-882 substitution (e.g., Asn-882-Ala), or Asn-891 substitution (e.g., Asn-891-Ala) (examples of mutant HNH domains). Also for example, a Cas9 nickase herein can comprise an *S. pyogenes* Cas9 having an Asp-10 substitution (e.g., Asp-10-Ala), Glu-762 substitution (e.g., Glu-762-Ala), or Asp-986 substitution (e.g., Asp-986-Ala) (examples of mutant RuvC domains), or a His-840 substitution (e.g., His-840-Ala), Asn-854 substitution (e.g., Asn-854-Ala), or Asn-863 substitution (e.g., Asn-863-Ala) (examples of mutant HNH domains). Regarding *S. pyogenes* Cas9, the three RuvC subdomains are generally located at amino acid residues 1-59, 718-769 and 909-1098, respectively, and the HNH domain is located at amino acid residues 775-908 (Nishimasu et al., *Cell* 156:935-949).

A Cas9 nickase herein can be used for various purposes in cells, if desired. For example, a Cas9 nickase can be used to stimulate HR at or near a DNA target site sequence with a suitable donor polynucleotide. Since nicked DNA is not a substrate for NHEJ processes, but is recognized by HR processes, nicking DNA at a specific target site should render the site more receptive to HR with a suitable donor polynucleotide.

As another example, a pair of Cas9 nickases can be used to increase the specificity of DNA targeting. In general, this can be done by providing two Cas9 nickases that, by virtue of being associated with RNA components with different guide sequences, target and nick nearby DNA sequences on opposite strands in the region for desired targeting. Such nearby cleavage of each DNA strand creates a DSB (i.e., a DSB with single-stranded overhangs), which is then recognized as a substrate for NHEJ (leading to indel formation) or HR (leading to recombination with a suitable donor polynucleotide, if provided). Each nick in these embodiments can be at least about 5, 10, 15, 20, 30, 40, 50, 60, 70, 80, 90, or 100 (or any integer between 5 and 100) bases apart from each other, for example. One or two Cas9 nickase proteins herein can be used in a Cas9 nickase pair as described above. For example, a Cas9 nickase with a mutant RuvC domain, but functioning HNH domain (i.e., Cas9 $HNH^+/RuvC^-$), could be used (e.g., *S. pyogenes* Cas9 $HNH^+/RuvC^-$). Each Cas9 nickase (e.g., Cas9 $HNH^+/RuvC^-$) would be directed to specific DNA sites nearby each other (up to 100 base pairs apart) by using suitable RNA components herein with guide RNA sequences targeting each nickase to each specific DNA site.

An RGEN in certain embodiments can bind to a DNA target site sequence, but does not cleave any strand at the target site sequence. Such an RGEN may comprise a Cas protein in which all of its nuclease domains are mutant, dysfunctional. For example, a Cas9 protein herein that can bind to a DNA target site sequence, but does not cleave any strand at the target site sequence, may comprise both a mutant, dysfunctional RuvC domain and a mutant, dysfunctional HNH domain. Non-limiting examples of such a Cas9 protein comprise any of the RuvC and HNH nuclease domain mutations disclosed above (e.g., an *S. pyogenes* Cas9 with an Asp-10 substitution such as Asp-10-Ala and a His-840 substitution such as His-840-Ala). A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein). For example, a Cas9 comprising an *S. pyogenes* Cas9 with an Asp-10 substitution (e.g., Asp-10-Ala) and a His-840 substitution (e.g., His-840-Ala) can be fused to a VP16 or VP64 transcriptional activator domain. The guide sequence used in the RNA component of such an RGEN would be complementary to a DNA sequence in a gene promoter or other regulatory element (e.g., intron), for example.

An RGEN herein can bind to a target site sequence, and optionally cleave one or both strands of the target site sequence, in a chromosome, episome, or any other DNA molecule in the genome of a cell. This recognition and binding of a target sequence is specific, given that an RNA component of the RGEN comprises a sequence (guide sequence) that is complementary to a strand of the target sequence. A target site in certain embodiments can be unique (i.e., there is a single occurrence of the target site sequence in the subject genome).

The length of a target sequence herein can be at least 13, 14, 15, 16, 17, 18, 19, 20, 21, 22, 23, 24, 25, 26, 27, 28, 29, or 30 nucleotides; between 13-30 nucleotides; between 17-25 nucleotides; or between 17-20 nucleotides, for example. This length can include or exclude a PAM sequence. Also, a strand of a target sequence herein has sufficient complementarity with a guide sequence (of a crRNA or gRNA) to hybridize with the guide sequence and direct sequence-specific binding of a Cas protein or Cas protein complex to the target sequence (if a suitable PAM is adjacent to the target sequence, see below). The degree of complementarity between a guide sequence and a strand of its corresponding DNA target sequence is at least about 90%, 91%, 92%, 93%, 94%, 95%, 96%, 97%, 98%, 99%, or 100%, for example. A target site herein may be located in a sequence encoding a gene product (e.g., a protein or an RNA) or a non-coding sequence (e.g., a regulatory sequence or a "junk" sequence), for example.

A PAM (protospacer-adjacent motif) sequence may be adjacent to the target site sequence. A PAM sequence is a short DNA sequence recognized by an RGEN herein. The associated PAM and first 11 nucleotides of a DNA target sequence are likely important to Cas9/gRNA targeting and cleavage (Jiang et al., *Nat. Biotech.* 31:233-239). The length of a PAM sequence herein can vary depending on the Cas protein or Cas protein complex used, but is typically 2, 3, 4, 5, 6, 7, or 8 nucleotides long, for example. A PAM sequence is immediately downstream from, or within 2, or 3 nucleotides downstream of, a target site sequence that is complementary to the strand in the target site that is in turn complementary to an RNA component guide sequence, for example. In embodiments herein in which an RGEN is an endonucleolytically active Cas9 protein complexed with an RNA component, Cas9 binds to the target sequence as directed by the RNA component and cleaves both strands immediately 5' of the third nucleotide position upstream of the PAM sequence. Consider the following example of a target site:PAM sequence:

(SEQ ID NO: 43)
5'-NNNNNNNNNNNNNNNNNNNNXGG-3'.

N can be A, C, T, or G, and X can be A, C, T, or G in this example sequence (X can also be referred to as $N_{PAM}$). The PAM sequence in this example is XGG (underlined). A suitable Cas9/RNA component complex would cleave this target immediately 5' of the double-underlined N. The string of N's in SEQ ID NO:43) represents target sequence that is at least about 90%, 91%, 92%, 93%, 94%, 95%, 96%, 97%, 98%, 99%, or 100% identical, for example, with a guide sequence in an RNA component herein (where any T's of the DNA target sequence would align with any U's of the RNA guide sequence). A guide sequence of an RNA component of a Cas9 complex, in recognizing and binding at this target sequence (which is representative of target sites herein), would anneal with the complement sequence of the string of N's; the percent complementarity between a guide sequence and the target site complement is at least about 90%, 91%, 92%, 93%, 94%, 95%, 96%, 97%, 98%, 99%, or 100%, for example. If a Cas9 nickase is used to target SEQ ID NO:43) in a genome, the nickase would nick immediately 5' of the double-underlined N or at the same position of the complementary strand, depending on which endonuclease domain in the nickase is dysfunctional. If a Cas9 having no nucleolytic activity (both RuvC and HNH domains dysfunctional) is used to target SEQ ID NO:43 in a genome, it would recognize and bind the target sequence, but not make any cuts to the sequence.

A PAM herein is typically selected in view of the type of RGEN being employed. A PAM sequence herein may be one recognized by an RGEN comprising a Cas, such as Cas9, derived from any of the species disclosed herein from which a Cas can be derived, for example. In certain embodiments, the PAM sequence may be one recognized by an RGEN comprising a Cas9 derived from *S. pyogenes, S. thermophilus, S. agalactiae, N. meningitidis, T. denticola*, or *F. novicida*. For example, a suitable Cas9 derived from *S. pyogenes* could be used to target genomic sequences having a PAM sequence of NGG (SEQ ID NO:44; N can be A, C, T, or G). As other examples, a suitable Cas9 could be derived from any of the following species when targeting DNA sequences having the following PAM sequences: *S. thermophilus* (NNAGAA [SEQ ID NO:45]), *S. agalactiae* (NGG [SEQ ID NO:44]), NNAGAAW [SEQ ID NO:46, W is A or T], NGGNG [SEQ ID NO:47]), *N. meningitidis* (NNNNGATT [SEQ ID NO:48]), *T. denticola* (NAAAAC [SEQ ID NO:49]), or *F. novicida* (NG [SEQ ID NO:50]) (where N's in all these particular PAM sequences are A, C, T, or G). Other examples of Cas9/PAMs useful herein include those disclosed in Shah et al. (*RNA Biology* 10:891-899) and Esvelt et al. (*Nature Methods* 10:1116-1121), which are incorporated herein by reference. Examples of target sequences herein follow SEQ ID NO:43, but with the 'XGG' PAM replaced by any one of the foregoing PAMs.

An RNA component herein can comprise a sequence complementary to a target site sequence in a chromosome or episome in a cell. An RGEN can specifically bind to a target site sequence, and optionally cleave one or both strands of the target site sequence, based on this sequence complementary. Thus, the complementary sequence of an RNA component in certain embodiments of the disclosed invention can also be referred to as a guide sequence or variable targeting domain.

The guide sequence of an RNA component (e.g., crRNA or gRNA) herein can be at least 13, 14, 15, 16, 17, 18, 19, 20, 21, 22, 23, 24, 25, 26, 27, 28, 29, or 30 ribonucleotides in length; between 13-30 ribonucleotides in length; between 17-25 ribonucleotides in length; or between 17-20 ribonucleotides in length, for example. In general, a guide sequence herein has sufficient complementarity with a strand of a target DNA sequence to hybridize with the target sequence and direct sequence-specific binding of a Cas protein or Cas protein complex to the target sequence (if a suitable PAM is adjacent to the target sequence). The degree of complementarity between a guide sequence and its corresponding DNA target sequence is at least about 90%, 91%, 92%, 93%, 94%, 95%, 96%, 97%, 98%, 99%, or 100%, for example. The guide sequence can be engineered accordingly to target an RGEN to a DNA target sequence in a cell.

An RNA component herein can comprise a crRNA, for example, which comprises a guide sequence and a repeat (tracrRNA mate) sequence. The guide sequence is typically located at or near (within 1, 2, 3, 4, 5, 6, 7, 8, 9, 10 or more bases) the 5' end of the crRNA. Downstream the guide sequence of a crRNA is a "repeat" or "tracrRNA mate" sequence that is complementary to, and can hybridize with, sequence at the 5' end of a tracrRNA. Guide and tracrRNA mate sequences can be immediately adjacent, or separated by 1, 2, 3, 4 or more bases, for example. A tracrRNA mate sequence has, for example, at least 50%, 60%, 70%, 80%, 90%, 95%, 96%, 97%, 98%, 99%, 99%, or 100% sequence complementarity to the 5' end of a tracrRNA. In general, degree of complementarity can be with reference to the optimal alignment of the tracrRNA mate sequence and 5' end of the tracrRNA sequence, along the length of the shorter of the two sequences. The length of a tracrRNA mate sequence herein can be at least 8, 9, 10, 11, 12, 13, 14, 15, 16, 17, or 18 ribonucleotides in length, for example, and hybridizes with sequence of the same or similar length (e.g., plus or minus 1, 2, 3, 4, or 5 bases) at the 5' end of a tracrRNA. Suitable examples of tracrRNA mate sequences herein comprise SEQ ID NO:51 (guuuuuguacucucaagauuua), SEQ ID NO:52 (guuuuuguacucuca), SEQ ID NO:53 (guuuuagagcua), or SEQ ID NO:54 (guuuuagagcuag), or variants thereof that (i) have at least about 90%, 91%, 92%, 93%, 94%, 95%, 96%, 97%, 98%, or 99% sequence identity and (ii) can anneal with the 5'-end sequence of a tracrRNA. The length of a crRNA herein can be at least about 18, 20, 22, 24, 26, 28, 30, 32, 34, 36, 38, 40, 42, 44, 46, or 48 ribonucleotides; or about 18-48 ribonucleotides; or about 25-50 ribonucleotides, for example.

A tracrRNA can be included along with a crRNA in embodiments in which a Cas9 protein of a type II CRISPR system is comprised in the RGEN. A tracrRNA herein comprises in 5'-to-3' direction (i) a sequence that anneals with the repeat region (tracrRNA mate sequence) of crRNA and (ii) a stem loop-containing portion. The length of a sequence of (i) can be the same as, or similar with (e.g., plus or minus 1, 2, 3, 4, or 5 bases), any of the tracrRNA mate sequence lengths disclosed above, for example. The total length of a tracrRNA herein (i.e., sequence components [i] and [ii]) can be at least about 30, 35, 40, 45, 50, 55, 60, 65, 70, 75, 80, 85, or 90 (or any integer between 30 and 90) ribonucleotides, for example. A tracrRNA may further include 1, 2, 3, 4, 5, or more uracil residues at the 3'-end, which may be present by virtue of expressing the tracrRNA with a transcription terminator sequence.

A tracrRNA herein can be derived from any of the bacterial species listed above from which a Cas9 sequence can be derived, for example. Examples of suitable tracrRNA sequences include those disclosed in U.S. Pat. No. 8,697,359 and Chylinski et al. (*RNA Biology* 10:726-737), which are incorporated herein by reference. A preferred tracrRNA herein can be derived from a *Streptococcus* species tracrRNA (e.g., *S. pyogenes, S. thermophilus*). Other suitable examples of tracrRNAs herein may comprise:

```
SEQ ID NO: 55:
uagcaaguuaaaauaaggcuaguccguuaucaacuugaaaaaguggcacc
gagucggugc,

SEQ ID NO: 56:
uagcaaguuaaaauaaggcuaguccguuaucaacuugaaaaagug,
or

SEQ ID NO: 57:
uagcaaguuaaaauaaggcuaguccguuauca,
```

which are derived from *S. pyogenes* tracrRNA. Other suitable examples of tracrRNAs herein may comprise:

```
SEQ ID NO: 58:
uaaaucuugcagaagcuacaaagauaaggcuucaugccgaaaucaacacc
cugucauuuuauggcaggguguuuucguuauuuaa,

SEQ ID NO: 59:
ugcagaagcuacaaagauaaggcuucaugccgaaaucaacacccugucau
uuuauggcaggguguuuucguuauuua,
or

SEQ ID NO: 60:
ugcagaagcuacaaagauaaggcuucaugccgaaaucaacacccugucau
uuuauggcagggugu,
```

which are derived from *S. thermophilus* tracrRNA.

Still other examples of tracrRNAs herein are variants of these tracrRNA SEQ ID NOs that (i) have at least about 80%, 85%, 90, 91, 92, 93, 94, 95, 96, 97, 98, or 99% sequence identity therewith and (ii) can function as a tracrRNA (e.g., 5'-end sequence can anneal to tracrRNA mate sequence of a crRNA, sequence downstream from the 5'-end sequence can form one or more hairpins, variant tracrRNA can form complex with a Cas9 protein).

An RNA component of an RGEN disclosed herein (or said another way, an RNA component that may be associated with an RGEN protein component) can comprise, for example, a guide RNA (gRNA) comprising a crRNA operably linked to, or fused to, a tracrRNA. The crRNA component of a gRNA in certain preferred embodiments is upstream of the tracrRNA component (i.e., such a gRNA comprises, in 5'-to-3' direction, a crRNA operably linked to a tracrRNA). Any crRNA and/or tracrRNA (and/or portion thereof, such as a crRNA repeat sequence, tracrRNA mate sequence, or tracrRNA 5'-end sequence) as disclosed herein (e.g., above embodiments) can be comprised in a gRNA, for example.

The tracrRNA mate sequence of the crRNA component of a gRNA herein should be able to anneal with the 5'-end of the tracrRNA component, thereby forming a hairpin structure. Any of the above disclosures regarding lengths of, and percent complementarity between, tracrRNA mate sequences (of crRNA component) and 5'-end sequences (of tracrRNA component) can characterize the crRNA and tracrRNA components of a gRNA, for example. To facilitate this annealing, the operable linkage or fusion of the crRNA and tracrRNA components preferably comprises a suitable loop-forming ribonucleotide sequence (i.e., a loop-forming sequence may link the crRNA and tracrRNA components together, forming the gRNA). Suitable examples of RNA loop-forming sequences include GAAA (SEQ ID NO:36), CAAA (SEQ ID NO:37) and AAAG (SEQ ID NO:38). However, longer or shorter loop sequences may be used, as may alternative loop sequences. A loop sequence preferably comprises a ribonucleotide triplet (e.g., AAA) and an additional ribonucleotide (e.g., C or G) at either end of the triplet.

A gRNA herein forms a hairpin ("first hairpin") with annealing of its tracrRNA mate sequence (of the crRNA component) and tracrRNA 5'-end sequence portions. One or more (e.g., 1, 2, 3, or 4) additional hairpin structures can form downstream from this first hairpin, depending on the sequence of the tracrRNA component of the gRNA. A gRNA may therefore have up to five hairpin structures, for example. A gRNA may further include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more residues following the end of the gRNA sequence, which may be present by virtue of expressing the gRNA with a transcription terminator sequence, for example. These additional residues can be all U residues, or at least 90%, 91%, 92%, 93%, 94%, 95%, 96%, 97%, 98%, or 99% U residues, for example, depending on the choice of terminator sequence.

Non-limiting examples of suitable gRNAs useful in the disclosed invention may comprise:

```
SEQ ID NO: 61:
NNNNNNNNNNNNNNNNNNNNguuuuuguacucucaagauuuaGAAAuaaa
ucuugcagaagcuacaaagauaaggcuucaugccgaaaucaacacccugu
cauuuuauggcaggguguuuucguuauuuaa,

SEQ ID NO: 62:
NNNNNNNNNNNNNNNNNNNNguuuuuguacucucaGAAAugcagaagcua
caaagauaaggcuucaugccgaaaucaacacccugucauuuuauggcagg
guguuuucguuauuuaa,

SEQ ID NO: 63:
NNNNNNNNNNNNNNNNNNNNguuuuuguacucucaGAAAugcagaagcua
caaagauaaggcuucaugccgaaaucaacacccugucauuuuauggcagg
gugu,

SEQ ID NO: 64:
NNNNNNNNNNNNNNNNNNNNguuuuuguacucucaGAAAuagcaaguuaa
aauaaggcuaguccguuaucaacuugaaaaaguggcaccgagucggugc,
```

-continued

```
SEQ ID NO: 65:
NNNNNNNNNNNNNNNNNNNNguuuuagagcuaGAAAuagcaaguuaaaau
aaggcuaguccguuaucaacuugaaaaagug,

SEQ ID NO: 66:
NNNNNNNNNNNNNNNNNNNNguuuuagagcuaGAAAuagcaaguuaaaau
aaggcuaguccguuauca,
or

SEQ ID NO: 67:
NNNNNNNNNNNNNNNNNNNNguuuuagagcuaGAAAuagcaaguuaaaau
aaggcuaguccguuaucaacuugaaaaaguggcaccgagucggugcuuuu.
```

In each of SEQ ID NOs:61-67, the single-underlined sequence represents a crRNA portion of the gRNA. Each "N" represents a ribonucleotide base (A, U, G, or C) of a suitable guide sequence. The first block of lower case letters represents tracrRNA mate sequence. The second block of lower case letters represents a tracrRNA portion of the gRNA. The double-underlined sequence approximates that portion of tracrRNA sequence that anneals with the tracrRNA mate sequence to form a first hairpin. A loop sequence (GAAA, SEQ ID NO:36) is shown in capital letters, which operably links the crRNA and tracrRNA portions of each gRNA. Other examples of gRNAs herein include variants of the foregoing gRNAs that (i) have at least about 80%, 85%, 90, 91, 92, 93, 94, 95, 96, 97, 98, or 99% sequence identity (excluding guide sequence in this calculation) with these sequences, and (ii) can function as a gRNA that specifically targets a Cas9 protein to bind with, and optionally nick or cleave, a target DNA sequence.

A gRNA herein can also be characterized in terms of having a guide sequence (VT domain) followed by a Cas endonuclease recognition (CER) domain. A CER domain comprises a tracrRNA mate sequence followed by a tracrRNA sequence. Examples of CER domains useful herein include those comprised in SEQ ID NOs:61-67 above (the CER domain in each is the sequence following the N's of the VT domain). Another suitable example of a CER domain is SEQ ID NO:24 (see Examples), which comprises in 5'-to-3' direction the tracrRNA mate sequence of SEQ ID NO:53, the loop-forming sequence of SEQ ID NO:36 (GAAA), and the tracrRNA sequence of SEQ ID N0:55.

An RNA component of an RGEN optionally does not have a 5'-cap (7-methylguanylate [$m^7G$] cap) (i.e., such an RNA component does not have an $m^7G$ cap at its 5'-terminus). An RNA component herein can have, for example, a 5'-hydroxyl group instead of a 5'-cap. Alternatively, an RNA component herein can have, for example, a 5' phosphate instead of a 5'-cap. It is believed that an RNA component in these embodiments can better accumulate in the nucleus (such as after its transcription in the nucleus, or after its RGEN-mediated import into the nucleus, depending on how the RNA component is provided herein), since 5'-capped RNA (i.e., RNA having 5' $m^7G$ cap) is subject to nuclear export. Preferred examples of uncapped RNA components herein include suitable gRNAs, crRNAs, and/or tracrRNAs. In certain embodiments, an RNA component herein lacks a 5'-cap, and optionally has a 5'-hydroxyl group instead, by virtue of RNA autoprocessing by a ribozyme sequence at the 5'-end of a precursor of the RNA component (i.e., a precursor RNA comprising a ribozyme sequence upstream of an RNA component such as a gRNA undergoes ribozyme-mediated autoprocessing to remove the ribozyme sequence, thereby leaving the downstream RNA component without a 5'-cap). In certain other embodiments, an RNA component herein is not produced by transcription from an RNA polymerase III (Pol III) promoter.

A cell-penetrating peptide (CPP) herein can be about 5-30, 5-25, 5-20, 10-30, 10-25, or 10-20 amino acid residues in length, for example. As other examples, a CPP can be about 5, 6, 7, 8, 9, 10, 11, 12, 13, 14, 15, 16, 17, 18, 19, 20, 21, 22, 23, 24, 25, 26, 27, 28, 29, or 30 amino acid residues in length. Yet in further aspects herein, a CPP can be up to about 35, 40, 45, 50, 55, or 60 amino acid residues in length.

A CPP disclosed herein can be cationic or amphipathic, for example. A cationic CPP herein typically comprises at least about 60% positively charged amino acids such as lysine (K), arginine (R), and/or histidine (H). Alternatively, a cationic CPP can comprise, for example, at least 60%, 65%, 70%, 75%, 80%, 85%, 90%, or 95% positively charged amino acids (e.g., R residues; K residues; K and R residues; K, R and H residues). A cationic CPP can be characterized as being arginine-rich (e.g., comprising at least 70% or 80% R residues) or lysine-rich (e.g., comprising at least 70% or 80% L residues) in certain embodiments. Examples of cationic CPPs useful herein are disclosed in Schmidt et al. (*FEBS Lett.* 584:1806-1813) and Wender et al. (polylysine; *Proc. Natl. Acad. Sci. USA* 97:13003-13008), which are incorporated herein by reference. Other examples of cationic CPPs comprise GRKKRRQRRR (SEQ ID NO:68), RKKRRQRRR (SEQ ID NO:69), or RKKRRQRR (SEQ ID NO:70), which were originally derived from HIV Tat protein, and penetratin (RQIKIWFQNRRMKWKK, SEQ ID NO:71), which was originally derived for the Antennapedia homeodomain protein of *Drosophila.*

Another example of a cationic CPP comprises a polyarginine sequence having a number of contiguous arginines sufficient to direct entry of the CPP and its cargo (e.g., RGEN protein component or RGEN) into a cell. The number of contiguous arginine residues in such a polyarginine sequence can be at least 3, 4, 5, 6, 7, 8, 9, 10, or 10-50 arginines, for instance. In certain aspects herein, a CPP can have 6 or more contiguous arginine residues (e.g., 6-7, 6-8, 6-9, or 6-10 arginine residues). “PolyR” (GGGGRRRRRRRRRLLLL, SEQ ID NO:15) can be comprised in a polyarginine CPP, if desired. Other polyarginine CPP examples comprise THRLPRRRRRR (SEQ ID NO:72) or GGRRARRRRRR (SEQ ID NO:73). In some embodiments, a CPP is an activatable CPP (“ACPP”) (Aguilera et al., *Integr Biol.* (*Camb*) 1:371-381; incorporated herein by reference). ACPPs typically comprise a polycationic CPP (e.g., nine contiguous arginines) connected via a cleavable linker to a matching polyanion (e.g., nine contiguous glutamates), which reduces the net charge to nearly zero and thereby inhibits CPP adhesion and uptake into cells. Upon cleavage of the linker, the polyanion is released, locally unmasking the polycation portion and its inherent adhesiveness, thereby allowing CPP cell entry. Another example herein is a polylysine CPP; any of the above embodiments of polyarginine, but in which R is replaced with K, are examples of polylysine CPPs herein.

An amphipathic CPP herein comprises an amino acid sequence containing an alternating pattern of polar/charged residues and non-polar, hydrophobic residues. The following CPPs are believed to be amphipathic, and are useful in certain aspects (regardless of whether amphipathic terminology perfectly applies): a CPP comprising transportan-10 (TP10) peptide (e.g., AGYLLGKINLKACAACAKKIL, SEQ ID NO:14); a CPP from a vascular endothelium cadherin protein, such as a CPP comprising a pVEC peptide (e.g., LIILRRRIRKQAHAHSK, SEQ ID NO:74; LLIILRRRIRKQAHAHSK, SEQ ID NO:13); a CPP from an Epstein-Barr virus Zebra trans-activator protein, such as a CPP comprising a Zebra peptide (e.g., ECDSELEIKRYKRVRVASRKCRAKFKQLLQHYREVAAAKSSENDRLRLLLKQMC, SEQ ID NO:12); a CPP comprising a $(KFF)_3K$ peptide (e.g., KFFKFFKFFK, SEQ ID NO:75); a CPP comprising a MAP peptide (KLALKLALKALKAALKLA, SEQ ID NO:76); a CPP comprising RRQRRTSKLMKR (SEQ ID NO:77); a CPP comprising KALAWEAKLAKALAKALAKHLAKALAKALKCEA (SEQ ID NO:78). Other amphipathic CPPs suitable herein include proline-rich CPPs, such as those comprising at least 3, 4, 5, 6, 7, or 8 repeats of VHLPPP (SEQ ID NO:79) or VRLPPP (SEQ ID NO:80).

As other examples, a CPP herein may comprise an MPG peptide (e.g., GALFLGFLGAAGSTMGAWSQPKSKRKV, SEQ ID NO:81); a Pep-1 peptide (e.g., KETVWVETVWVTEWSQPKKKRKV, SEQ ID NO:82); or a CPP from a human calcitonin protein, such as an hCT peptide (e.g., LGTYTQDFNKFHTFPQTAIGVGAP, SEQ ID NO:83; CGNLSTCMLGTYTQDFNK, SEQ ID NO:84). Still other examples of CPPs herein include those disclosed in Regberg et al. (*Int. J. Pharm.* 464:111-116), which is incorporated herein by reference.

A CPP suitable herein can alternatively comprise an amino acid sequence that is at least 90%, 91%, 92%, 93%, 94%, 95%, 96%, 97%, 98%, or 99% identical to any of the CPP amino acid sequences disclosed herein, for example. Such a variant CPP protein should have CPP activity, such as the ability to mediate cellular uptake of molecular cargo (e.g., an amino acid sequence comprising one or more RGEN protein components [e.g., Cas9], or an amino acid sequence comprising one or more RGEN protein components [e.g., Cas9] associated with an RNA component). Testing the activity of a variant CPP can be done any number of ways, such as by covalently linking it with a fluorescent protein (e.g., GFP) and measuring the degree of fluorescence emitted from a cell contacted with a the CPP-fluorescent protein complex.

A CPP herein can be modified, if desired, to render it even more capable of carrying RGEN protein cargo from outside a cell to inside a cell. For example, a CPP can be modified to have a lipid group at either its N- or C-terminus. Suitable lipid groups herein include acyl groups such as stearyl and myristyl groups. Other examples of lipid groups are acyl groups with 8, 9, 10, 11, 12, 13, 14, 15, 16, 17, or 18 carbons. Conditions for modifying peptides with lipid groups useful herein are disclosed in Regberg et al. (*Int. J. Pharm.* 464:111-116) and Anko et al. (*Biochim. Biophys. Acta—Biomembranes* 1818:915-924) for example, which are incorporated herein by reference.

An RGEN protein component and at least one CPP herein can be covalently linked to each other in an RGEN protein-CPP complex in certain aspects herein. For example, an RGEN protein component and at least one CPP can be fused together in a single amino acid sequence (i.e., an RGEN protein component and at least one CPP can be comprised within a fusion protein). Thus, an example of covalent linkage herein can be via a peptide bond in which the amino acid sequence of an RGEN protein component is fused with the amino acid sequence of a CPP, such that both these amino acid sequences are contained in a single amino acid sequence. Such a fusion protein (or “chimeric protein”), can be characterized as an RGEN protein-CPP fusion herein. In those embodiments in which an RNA component is associated with an RGEN protein component, such a fusion protein can be characterized as an RGEN-CPP fusion.

One or more CPPs can be located at the N-terminus or C-terminus of an RGEN protein-CPP fusion, for example.

Alternatively, one or more CPPs can be located at both the N- and C-termini of an RGEN protein-CPP fusion. Alternatively still, one or more CPPs can be located within the amino acid sequence of an RGEN protein-CPP fusion. Embodiments herein comprising more than one CPP can comprise at least 2, 3, 4, 5, 6, 7, 8, 9, 10, 11, 12, 13, 14, 15, 16, 17, 18, 19, or 20 CPPs, or 5-10, 5-20, or 10-20 CPPs. The CPPs fused to the RGEN protein component can be the same or different (e.g., 2, 3, 4, or more different types of CPPs). One or more CPPs can be fused directly to the amino acid sequence of an RGEN protein, and/or can be fused to a heterologous domain(s) (e.g., NLS or other organelle-targeting sequence such as an MTS) that is fused with an RGEN protein.

A fusion between a CPP and an RGEN protein component herein can be direct (i.e., CPP amino acid sequence is directly linked to RGEN amino acid sequence by a peptide bond). Alternatively, a fusion between a CPP and an RGEN protein component can be via an intermediary amino acid sequence (this is an example of a CPP and RGEN protein component being indirectly linked). Examples of an intermediary amino acid sequence include suitable linker sequences comprising at least 1, 2, 3, 4, 5, 6, 7, 8, 9, 10, 11, 12, 13, 14, 15, 16, 17, 18, 19, 20, 30, 40, 50, 60, 70, 80, 90, or 100 amino acid residues such as glycine, serine, alanine and/or proline. Suitable amino acid linkers are disclosed in U.S. Pat. Nos. 8,828,690, 8,580,922 and 5,990,275, for example, which are incorporated herein by reference. Other examples of intermediary amino acid sequences can comprise one or more other types of proteins and/or domains. For example, a marker protein (e.g., a fluorescent protein such as any of those disclosed herein) can be comprised in an intermediary amino acid sequence.

A composition comprising a covalent complex of an RGEN protein component and at least one CPP, such as in a fusion protein, can be used with any cell type disclosed herein. Optionally, however, this composition can be used with non-mammalian cells such as yeast, fungi, and plants, but excludes use on mammalian cells.

Examples of RGEN protein-CPP fusion proteins herein can comprise SEQ ID NO:39 (Zebra CPP-Cas9-NLS fusion protein), 40 (PolyR CPP-Cas9-NLS fusion protein), 41 (TP10 CPP-Cas9-NLS fusion protein), or 42 (pVEC CPP-Cas9-NLS fusion protein). SEQ ID NOs:39-42 are examples of Cas9-CPP fusion proteins. Other examples of RGEN protein-CPP fusion proteins comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of SEQ ID NOs:39-42. Such a variant fusion protein should have (i) a CPP domain that can mediate cellular uptake of the fusion protein, and (ii) a Cas9 protein with specific binding activity, and optionally cleavage or nicking activity, toward DNA when associated with an RNA component. SEQ ID NO:39, 40, 41 and 42 comprise Zebra CPP (SEQ ID NO:12), PolyR CPP (SEQ ID NO:15), TP10 CPP (SEQ ID NO:14) and pVEC CPP (SEQ ID NO:13), respectively, operably linked to Cas9 (*S. pyogenes*)-NLS protein (residues 2-1379 of SEQ ID NO:3).

In certain embodiments, the protein component of a guide polynucleotide/Cas endonuclease system can be fused to a CPP, wherein the CPP comprises:

(i) a CPP from an Epstein-Barr virus Zebra trans-activator protein, (ii) a CPP having 6 or more contiguous arginine residues, (iii) a transportan-10 (TP10) CPP, (iv) a CPP from a vascular endothelium cadherin protein, or (vi) a CPP selected from the group consisting of a synthetic non-arginine CPP, a histidine-rich nona-arginine CPP and a Pas nona-arginine CPP. Examples of synthetic nona-arginine, histidine-rich nona-arginine, and Pas nona-arginine CPPs are disclosed in, for example, Liu et al. (*Advanced Studies in Biology* 5(2):71-88, HIKARI Ltd), which is incorporated herein by reference.

Another example of how an RGEN protein component and at least one CPP can be covalently linked is via crosslinking (chemical crosslinking). Thus, an example of an RGEN protein-CPP complex herein can comprise an RGEN protein crosslinked to at least one CPP. Crosslinking herein refers to a process of chemically joining two or more molecules (an RGEN protein component and at least one CPP, in this case) by a covalent bond(s). Crosslinking can be performed using any number of processes known in the art, such as those disclosed in U.S. Patent Appl. Publ. No. 2011/0190813, U.S. Pat. No. 8,642,744, and *Bioconjugate Techniques, 2nd Edition* (G. T. Hermanson, Academic Press, 2008), which are all incorporated herein by reference.

Typically, a CPP can be modified and/or synthesized to contain a suitable protein linking group at its N-terminus, C-terminus, and/or an amino acid side group, for the purpose of crosslinking the CPP to an RGEN protein component. A "protein linking group" refers to a group that is capable of reacting directly, either spontaneously or after activation (e.g., light), with an accessible side chain functional group of an RGEN protein component under suitable conditions (e.g., aqueous conditions) to produce a covalently link the CPP to the RGEN protein. A protein linking group may react with the side chain functional groups of a Lys, Cys, Ser, Thr, Tyr, His, or Arg amino acid residue in an RGEN protein, for example, to produce a covalent linkage to the protein. Either a homobifunctional (e.g., capable of linking amine to amine) or heterobifunctional (e.g., capable of linking amine to thiol) protein linking group can be used, for example. A protein linking group on a CPP can also react with a terminal group (e.g., N-terminus) of an RGEN protein in certain embodiments. Suitable protein linking groups herein include amino-reactive (e.g., NHS ester or imidoester), thiol (sulfhydryl)-reactive (e.g., a maleimide such as BMOE, BMB, or BMH), hydroxyl-reactive, imidazolyl-reactive, or guanidinyl-reactive groups. Exemplary protein linking groups include active esters (e.g., an amino-reactive NHS ester), and thiol-reactive maleimide or iodoacetamide groups. Further exemplary protein linking groups useful herein and methods of using them are described in *Bioconjugate Techniques, 2nd Edition* (G. T. Hermanson, Academic Press, 2008), for example.

A protein linking group herein typically can produce a link between a CPP and an RGEN protein with a backbone of 20 atoms or less in length. For example, such a link can be between 1 and 20 atoms in length, or about 1, 2, 3, 4, 5, 6, 8, 10, 12, 14, 16, 18 or 20 carbon atoms in length. A link may be linear, branched, cyclic or a single atom in certain embodiments. In certain cases, one, two, three, four or five or more carbon atoms of a linker backbone may be substituted with a sulfur, nitrogen or oxygen heteroatom. The bonds between backbone atoms may be saturated or unsaturated (usually not more than one, two, or three unsaturated bonds in the linker backbone). A linker may include, without limitation, an oligo(ethylene glycol); ether; thioether; tertiary amine; or alkyl group, which may be straight or branched (e.g., methyl, ethyl, n-propyl, iso-propyl, n-butyl, n-pentyl, t-butyl). As other examples, a linker backbone may include a cyclic group such as an aryl, a heterocycle, or a cycloalkyl group, where 2 or more atoms (e.g., 2, 3 or 4 atoms) of the cyclic group are included in the backbone.

More than one type of CPP (e.g., 2, 3, 4, or more different types of CPPs) can be crosslinked to an RGEN protein component in certain embodiments. The ratio (molar ratio) of CPP(s) to RGEN protein that can be used when cross-linking can be at least about 1:1, 2:1, 3:1, 4:1, 5:1, 6:1, 7:1, 8:1, 9:1, 10:1 15:1, 20:1, 30:1, 40:1, or 50:1, for example. In other aspects, the average number of CPPs crosslinked to an RGEN protein may be at least 1, 2, 3, 4, 5, 6, 7, 8, 9, 10, 11, 12, 13, 14, 15, 16, 17, 18, 19, 20, 21, 22, 23, 24, or 25, or at least 5-10, 5-15, 5-20, or 5-25.

An RGEN protein component and at least one CPP can be crosslinked into a complex further comprising one or more other proteins/peptides/domains, if desired. Such other elements can optionally be used to bridge an RGEN protein component with a CPP, and may include any of the intermediary amino acid sequences described above.

An RGEN protein component and at least one CPP herein can be non-covalently linked to each other in an RGEN protein-CPP complex in certain aspects herein. Though not intending to be held to any particular theory or mechanism, it is contemplated that a non-covalent linkage between an RGEN protein component and at least one CPP can be due to electrostatic, Van der Waals, and/or hydrophobic forces. In those embodiments in which an RNA component is associated with an RGEN protein component, such embodiments can be characterized as comprising an RGEN that is non-covalently linked to at least one CPP in an RGEN-CPP complex. A composition comprising an RGEN protein component and CPP that are non-covalently linked can optionally be characterized as a mixture of these components.

In certain embodiments, an RGEN protein component is non-covalently linked to at least one CPP with an amino acid sequence consisting of the CPP amino acid sequence only. Such a CPP, while not having any "non-CPP" amino acid sequence, can optionally comprise a modification such as a lipid group as disclosed herein.

Alternatively, a CPP that is non-covalently linked to an RGEN protein component may be comprised in a fusion protein having both CPP amino acid sequence and one or more heterologous amino acid sequences (non-RGEN protein sequences). A heterologous sequence in such embodiments can be that of a domain or a protein (e.g., a fluorescent protein such as any of those disclosed herein, or any domain/protein listed in the above disclosure regarding Cas fusions). Another example is fusing a dimerization domain to a CPP, which dimerization domain is able to bind to a dimerization domain linked or fused to an RGEN protein component.

Leucine zipper domains are examples of dimerization domains herein. Leucine zipper domains can represent those from natural proteins known to contain such domains (e.g., transcription factors), or can be synthetically designed. A leucine zipper domain linked to a CPP can associate ("zip together") with a leucine zipper domain of an RGEN protein component, thereby linking the CPP and RGEN protein component in a non-covalent complex. A pair of leucine zipper domains for non-covalently linking a CPP and an RGEN protein component can be the same (such a domain pair forms a homodimeric leucine zipper) or different (such a domain pair forms a heterodimeric leucine zipper). Examples of leucine zipper domains include those disclosed in U.S. Patent Appl. Publ. Nos. 2003/0108869 and 2004/0147721. In certain aspects, a homodimeric leucine zipper can be formed using a leucine zipper domain from a GCN4 transcription factor, while in other aspects a heterodimeric leucine zipper can be formed using leucine zipper domains from fos and jun transcription factors, respectively.

A non-covalent complex of an RGEN protein component and at least one CPP can further comprise one or more other proteins/peptides/domains, if desired. Such other elements can optionally be used to bridge an RGEN protein component with a CPP, and may include any of the intermediary amino acid sequences described above.

More than one type of CPP (e.g., 2, 3, 4, or more different types of CPPs) can be non-covalently linked to an RGEN protein component in certain embodiments. The ratio (molar ratio) of CPP(s) to RGEN protein that can be used to prepare such a complex can be at least about 1:1, 2:1, 3:1, 4:1, 5:1, 6:1, 7:1, 8:1, 9:1, 10:1 15:1, 20:1, 30:1, 40:1, or 50:1, for example. In other aspects, the average number of CPPs non-covalently linked to an RGEN protein may be at least 1, 2, 3, 4, 5, 6, 7, 8, 9, 10, 11, 12, 13, 14, 15, 16, 17, 18, 19, 20, 21, 22, 23, 24, or 25, or at least 5-10, 5-15, 5-20, or 5-25.

In certain embodiments, a non-covalent complex of an RGEN protein component and at least one CPP can be prepared by mixing an appropriate amount of each component (e.g., such as to obtain a ratio of CPP to RGEN protein disclosed above) in an aqueous medium. A suitable aqueous medium can comprise a buffer solution such as PBS or a serum-free medium such as DMEM, for example. The mixture can be incubated for about 30, 60, 90, or 120 minutes at a temperature of about 4 to 45° C., for example, to allow formation of a non-covalent RGEN protein-CPP complex. A suitable volume (e.g., a minimum volume that adequately covers/immerses cells being treated) of this solution comprising the complex can be applied to a cell in a cell type-appropriate manner. In embodiments in which an RNA component is associated with an RGEN protein component, such formation of an RGEN can comprise adding an RNA component before, at the same time of, or after incubating a CPP with the RGEN protein component.

A composition comprising a non-covalent complex of an RGEN protein component and at least one CPP can be used with any cell type disclosed herein. Optionally, however, this composition can be used with non-mammalian cells such as yeast, fungi, and plants, but excludes use on mammalian cells.

An RGEN protein-CPP complex, as it may exist in a composition before application to cells can be at least about 30%, 40%, 50%, 60%, 65%, 70%, 75%, 80%, 85%, 90%, 95%, 98%, or 99% pure, for example. Such purity can be on a protein basis in certain embodiments. As an example, if the purity of a complex is at least 80%, this would mean that at least 80% of all the protein in a composition is constituted by the complex. Complex purity alternatively can take into account not only purity on a protein basis, but also in account of other biomolecules (e.g., lipids, saccharides, and/or nucleic acids). As an example, if the purity of a complex is at least 80%, this could mean that at least 80% of all the biomolecules in the composition herein is constituted by the complex. In certain embodiments, compounds such as carbohydrates, salts, and/or lipids and the like do not affect the determination of percent purity herein. All these disclosures regarding purity can also apply to an RGEN-CPP complex (i.e., RGEN protein component of complex is associated with an RNA component).

A composition herein is preferably aqueous, wherein the solvent in which an RGEN protein-CPP complex or RGEN-CPP complex is dissolved is at least about 70, 75, 80, 85, 90, 95, 98, or 99 wt % water. The concentration of a complex in a composition can be at least about 0.5, 1.0, 1.5, 2.0, 2.5, 3.0, 3.5, 4.0, 4.5, 5.0, 6.0, 7.0, 8.0, 9.0 or 10.0 μM, or about 0.5 to 5.0 μM, 0.5 to 2.5 μM, 1.0 to 5.0 μM, 1.0 to 2.5 μM, or 2.5 to 5.0 μM, for example. It would be understood that such compositions can be in a liquid state.

The pH of a composition in certain embodiments can be between about 4.0 to about 10.0. Alternatively, the pH can be about 4.0, 4.5, 5.0, 5.5, 6.0, 6.5, 7.0, 7.5, 8.0, 8.5, 9.0, 9.5 or 10.0. pH can be adjusted or controlled by the addition or incorporation of a suitable buffer, including but not limited to: HEPES, phosphate (e.g., PBS), Tris, Tris-HCl, citrate, or a combination thereof. Buffer concentration in a composition herein can be from 0 mM to about 100 mM, or about 10, 20, or 50 mM, for example. A HEPES buffer (e.g., ~25 mM HEPES, such as 25 mM HEPES/KOH pH 7.5, 200 mM KCl, 20% glycerol, 1 mM DTT) can be used in certain aspects.

A composition herein can optionally comprise other components in addition to an RGEN protein-CPP complex or RGEN-CPP complex. For example, the composition can comprise one or more salts such as a sodium salt (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in a composition herein, for example. A salt can be present at a wt % of about 0.01 to about 10.00 (or any hundredth increment between 0.01 and 10.00), for example.

An RGEN protein-CPP complex herein can traverse (i) a cell membrane, or (ii) a cell wall and cell membrane, of a cell. In those embodiments in which an RGEN protein component is associated with an RNA component (thereby constituting a complete RGEN), an RGEN-CPP complex similarly has this cell membrane/cell wall-traversing ability. Either an RGEN protein-CPP complex or an RGEN-CPP complex can traverse a cell wall and cell membrane in certain aspects herein.

An RGEN protein-CPP or RGEN-CPP complex herein can optionally traverse a cell wall that comprises a glycocalyx (capsule). These embodiments typically are with regard to prokaryotic cells (e.g., bacteria), some of which may have a glycocalyx depending on species type and growth conditions.

Though not intending to be held to any particular theory or mechanism, it is believed that a CPP herein may deliver an RGEN protein component into a cell via an endocytic process. Examples of such a process might include macropinocytosis, clathrin-mediated endocytosis, caveolae/lipid raft-mediated endocytosis, and/or receptor mediated endocytosis mechanisms (e.g., scavenger receptor-mediated uptake, proteoglycan-mediated uptake).

Once an RGEN protein-CPP or RGEN-CPP complex is inside a cell, it can traverse an organelle membrane such as a nuclear membrane or mitochondrial membrane, for example. This ability depends on, in certain embodiments, the presence of at least one organelle-targeting sequence (e.g., NLS, MTS) being included with the RGEN protein. Still, in other embodiments, the ability to traverse an organelle membrane such as a nuclear membrane or mitochondrial membrane does not depend on the presence of an organelle-targeting sequence (i.e., a CPP[s] in such embodiments may be responsible for allowing RGEN traversal into an organelle such as the nucleus or mitochondria).

A cell herein can be a mammalian cell or a non-mammalian cell, the latter of which is used in certain preferred embodiments. In certain other aspects, a cell herein can be as it exists (i) in an organism/tissue in vivo, (ii) in a tissue or group of cells ex vivo, or (iii) in an in vitro state.

A microbial cell herein can be as it exists in an isolated state (e.g., in vitro cells, cultured cells) or a non-isolated state.

A microbial cell in certain embodiments is a fungal cell such as a yeast cell. A yeast in certain aspects herein can be one that reproduces asexually (anamorphic) or sexually (teleomorphic). While yeast herein typically exist in unicellular form, certain types of these yeast may optionally be able to form pseudohyphae (strings of connected budding cells). In still further aspects, a yeast may be haploid or diploid, and/or may have the ability to exist in either of these ploidy forms.

Examples of yeast herein include conventional yeast and non-conventional yeast. Conventional yeast in certain embodiments are yeast that favor homologous recombination (HR) DNA repair processes over repair processes mediated by non-homologous end-joining (NHEJ). Examples of conventional yeast herein include species of the genera *Saccharomyces* (e.g., *S. cerevisiae*, which is also known as budding yeast, baker's yeast, and/or brewer's yeast; *S. bayanus; S. boulardii; S. bulderi; S. cariocanus; S. cariocus; S. chevalieri; S. dairenensis; S. ellipsoideus; S. eubayanus; S. exiguus; S. florentinus; S. kluyveri; S. martiniae; S. monacensis; S. norbensis; S. paradoxus; S. pastorianus; S. spencerorum; S. turicensis; S. unisporus; S. uvarum; S. zonatus*) and *Schizosaccharomyces* (e.g., *S. pombe*, which is also known as fission yeast; *S. cryophilus; S. japonicus; S. octosporus*).

A non-conventional yeast herein is not a conventional yeast such as a *Saccharomyces* (e.g., *S. cerevisiae*) or *Schizosaccharomyces* (e.g., *S. pombe*) species. Non-conventional yeast in certain embodiments can be yeast that favor NHEJ DNA repair processes over repair processes mediated by HR. Conventional yeasts such as *S. cerevisiae* and *S. pombe* typically exhibit specific integration of donor DNA with short flanking homology arms (30-50 bp) with efficiencies routinely over 70%, whereas non-conventional yeasts such as *Pichia pastoris, Pichia stipitis, Hansenula polymorpha, Yarrowia lipolytica* and *Kluyveromyces lactis* usually show specific integration with similarly structured donor DNA at efficiencies of less than 1% (Chen et al., *PLoS ONE* 8:e57952). Thus, a preference for HR processes can be gauged, for example, by transforming yeast with a suitable donor DNA and determining the degree to which it is specifically recombined with a genomic site predicted to be targeted by the donor DNA. A preference for NHEJ (or low preference for HR), for example, would be manifest if such an assay yielded a high degree of random integration of the donor DNA in the yeast genome. Assays for determining the rate of specific (HR-mediated) and/or random (NHEJ-mediated) integration of DNA in yeast are known in the art (e.g., Ferreira and Cooper, *Genes Dev.* 18:2249-2254; Corrigan et al., *PLoS ONE* 8:e69628; Weaver et al., *Proc. Natl. Acad. Sci. U.S.A.* 78:6354-6358; Keeney and Boeke, *Genetics* 136:849-856).

Given their low level of HR activity, non-conventional yeast herein can (i) exhibit a rate of specific targeting by a suitable donor DNA having 30-50 bp flanking homology arms of less than about 1%, 2%, 3%, 4%, 5%, 6%, 7%, or 8%, for example, and/or (ii) exhibit a rate of random integration of the foregoing donor DNA of more than about 65%, 66%, 67%, 68%, 69%, 70%, 71%, 72%, 73%, 74%, or 75%, for example. These rates of (i) specific targeting and/or (ii) random integration of a suitable donor DNA can characterize a non-conventional yeast as it exists before being provided an RGEN as disclosed herein. An aim for providing an RGEN to a non-conventional yeast in certain embodiments is to create site-specific DNA single-strand breaks (SSB) or double-strand breaks (DSB) for biasing the yeast toward HR at the specific site. Thus, providing a suitable RGEN in a non-conventional yeast typically should allow the yeast to exhibit an increased rate of HR with a particular donor DNA. Such an increased rate can be at least about 2-, 3-, 4-, 5-, 6-, 7-, 8-, 9-, or 10-fold higher than the rate of HR in a suitable control (e.g., same non-conventional yeast transformed with the same donor DNA, but lacking a suitable RGEN).

A non-conventional yeast herein can be cultivated following any means known in the art, such as described in *Non-Conventional Yeasts in Genetics, Biochemistry and Biotechnology: Practical Protocols* (K. Wolf, K. D. Breunig, G. Barth, Eds., Springer-Verlag, Berlin, Germany, 2003), *Yeasts in Natural and Artificial Habitats* (J. F. T. Spencer, D. M. Spencer, Eds., Springer-Verlag, Berlin, Germany, 1997), and/or *Yeast Biotechnology: Diversity and Applications* (T. Satyanarayana, G. Kunze, Eds., Springer, 2009), all of which are incorporated herein by reference.

Non-limiting examples of non-conventional yeast herein include yeasts of the following genera: *Yarrowia, Pichia, Schwanniomyces, Kluyveromyces, Arxula, Trichosporon, Candida, Ustilago, Torulopsis, Zygosaccharomyces, Trigonopsis, Cryptococcus, Rhodotorula, Phaffia, Sporobolomyces, Pachysolen*, and *Moniliella*. A suitable example of a *Yarrowia* species is *Y. lipolytica*. Suitable examples of *Pichia* species include *P. pastoris, P. methanolica, P. stipitis, P. anomala* and *P. angusta*. Suitable examples of *Schwanniomyces* species include *S. castellii, S. alluvius, S. hominis, S. occidentalis, S. capriottii, S. etchellsii, S. polymorphus, S. pseudopolymorphus, S. vanrijiae* and *S. yamadae*. Suitable examples of *Kluyveromyces* species include *K. lactis, K. marxianus, K. fragilis, K. drosophilarum, K. thermotolerans, K. phaseolosporus, K. vanudenii, K. waltii, K. africanus* and *K. polysporus*. Suitable examples of Arxula species include *A. adeninivorans* and *A. terrestre*. Suitable examples of *Trichosporon* species include *T. cutaneum, T. capitatum, T. inkin* and *T. beemeri*. Suitable examples of *Candida* species include *C. albicans, C. ascalaphidarum, C. amphixiae, C. antarctica, C. apicola, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogii, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis* and *C. zemplinina*. Suitable examples of *Ustilago* species include *U. avenae, U. esculenta, U. hordei, U. maydis, U. nuda* and *U. tritici*. Suitable examples of *Torulopsis* species include *T. geochares, T. azyma, T. glabrata* and *T. candida*. Suitable examples of *Zygosaccharomyces* species include *Z. bairn, Z. bisporus, Z. cidri, Z. fermentati, Z. florentinus, Z. kombuchaensis, Z. lentus, Z. meffis, Z. microeffipsoides, Z. mrakii, Z. pseudorouxii* and *Z. rouxii*. Suitable examples of Trigonopsis species include *T. variabilis*. Suitable examples of *Cryptococcus* species include *C. laurentii, C. albidus, C. neoformans, C. gattii, C. uniguttulatus, C. adeliensis, C. aerius, C. albidosimilis, C. antarcticus, C. aquaticus, C. ater, C. bhutanensis, C. consortionis, C. curvatus, C. phenolicus, C. skinneri, C. terreus* and *C. vishniacci*. Suitable examples of *Rhodotorula* species include *R. acheniorum, R. tula, R. acuta, R. americana, R. araucariae, R. arctica, R. armeniaca, R. aurantiaca, R. auriculariae, R. bacarum, R. benthica, R. biourgei, R. bogoriensis, R. bronchialis, R. buffonii, R. calyptogenae, R. chungnamensis, R. cladiensis, R. coraffina, R. cresolica, R. crocea, R. cycloclastica, R. dairenensis, R. diffluens, R. evergladiensis, R. ferulica, R. foliorum, R. fragaria, R. fujisanensis, R. futronensis, R. gelatinosa, R. glacialis, R. glutinis, R. gracilis, R. graminis, R. grinbergsii, R. himalayensis, R. hinnulea, R. histolytica, R. hylophila, R. incarnata, R. ingeniosa, R. javanica, R. koishikawensis, R. lactosa, R. lamellibrachiae, R. laryngis, R. lignophila, R. lini, R. longissima, R. ludwigii, R. lysinophila, R. marina, R. martyniae-fragantis, R. matritensis, R. meli, R. minuta, R. mucilaginosa, R. nitens, R. nothofagi, R. oryzae, R. pacifica, R. pallida, R. peneaus, R. philyla, R. phylloplana, R. pilatii, R. pilimanae, R. pinicola, R. plicata, R. polymorpha, R. psychrophenolica, R. psychrophila, R. pustula, R. retinophila, R. rosacea, R. rosulata, R. rubefaciens, R. rubella, R. rubescens, R. rubra, R. rubrorugosa, R. rufula, R. rutila, R. sanguines, R. sanniei, R. sartoryi, R. silvestris, R. simplex, R. sinensis, R. slooffiae, R. sonckii, R. straminea, R. subericola, R. suganii, R. taiwanensis, R. taiwaniana, R. terpenoidalis, R. terrea, R. texensis, R. tokyoensis, R. ulzamae, R. vaniffica, R. vuilleminii, R. yarrowii, R. yunnanensis* and *R. zsoltii*. Suitable examples of *Phaffia* species include *P. rhodozyma*. Suitable examples of Sporobolomyces species include *S. alborubescens, S. bannaensis, S. beijingensis, S. bischofiae, S. clavatus, S. coprosmae, S. coprosmicola, S. coraffinus, S. dimmenae, S. dracophylli, S. elongatus, S. gracilis, S. inositophilus, S. johnsonii, S. koalae, S. magnisporus, S. novozealandicus, S. odorus, S. patagonicus, S. productus, S. roseus, S. sasicola, S. shibatanus, S. singularis, S. subbrunneus, S. symmetricus, S. syzygii, S. taupoensis, S. tsugae, S. xanthus* and *S. yunnanensis*. Suitable examples of *Pachysolen* and *Moniliella* species include *P. tannophilus* and *M. poffinis*, respectively. Still other examples of non-conventional yeasts herein include *Pseudozyma* species (e.g., *S. antarctica*), *Thodotorula* species (e.g., *T. bogoriensis*), *Wickerhamiella* species (e.g., *W. domercqiae*), and *Starmerella* species (e.g., *S. bombicola*).

*Yarrowia lipolytica* is preferred in certain embodiments disclosed herein. Examples of suitable *Y. lipolytica* include the following isolates available from the American Type Culture Collection (ATCC, Manassas, Va.): strain designations ATCC #20362, #8862, #8661, #8662, #9773, #15586, #16617, #16618, #18942, #18943, #18944, #18945, #20114, #20177, #20182, #20225, #20226, #20228, #20327, #20255, #20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #34922, #38295, #42281, #44601, #46025, #46026, #46027, #46028,

#46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, and/or #201847.

A fungal cell herein can be a yeast (e.g., as described above) or of any other fungal type such as a filamentous fungus. For instance, a fungus herein can be a Basidiomycetes, Zygomycetes, Chytridiomycetes, or Ascomycetes fungus. Examples of filamentous fungi herein include those of the genera *Trichoderma, Chrysosporium, Thielavia, Neurospora* (e.g., *N. crassa, N. sitophila*), *Cryphonectria* (e.g., *C. parasitica*), *Aureobasidium* (e.g., *A. pullulans*), *Filibasidium, Piromyces, Cryplococcus, Acremonium, Tolypocladium, Scytalidium, Schizophyllum, Sporotrichum, Penicillium* (e.g., P. bilaiae, P. camemberti, *P. candidum, P. chrysogenum, P. expansum, P. funiculosum, P. glaucum, P. marneffei, P. roqueforti, P. verrucosum, P. viridicatum*), *Gibberella* (e.g., *G. acuminata, G. avenacea, G. baccata, G. circinata, G. cyanogena, G. fujikuroi, G. intricans, G. pulicaris, G. stilboides, G. tricincta, G. zeae*), *Myceliophthora, Mucor* (e.g., *M. rouxii, M. circinelloides*), *Aspergillus* (e.g., *A. niger, A. oryzae, A. nidulans, A. flavus, A. lentulus, A. terreus, A. clavatus, A. fumigatus*), *Fusarium* (e.g., *F. graminearum, F. oxysporum, F. bubigenum, F. solani, F. oxysporum, F. verticillioides, F. proliferatum, F. venenatum*), and *Humicola*, and anamorphs and teleomorphs thereof. The genus and species of fungi herein can be defined, if desired, by morphology as disclosed in Barnett and Hunter (*Illustrated Genera of Imperfect Fungi, 3rd Edition*, Burgess Publishing Company, 1972). A fungus can optionally be characterized as a pest/pathogen of a plant or animal (e.g., human) in certain embodiments.

*Trichoderma* species in certain aspects herein include *T. aggressivum, T. amazonicum, T. asperellum, T. atroviride, T. aureoviride, T. austrokoningii, T. brevicompactum, T. candidum, T. caribbaeum, T. catoptron, T. cremeum, T. ceramicum, T. cerinum, T. chlorosporum, T. chromospermum, T. cinnamomeum, T. citrinoviride, T. crassum, T. cremeum, T. dingleyeae, T. dorotheae, T. effusum, T. erinaceum, T. estonicum, T. fertile, T. gelatinosus, T. ghanense, T. hamatum, T. harzianum, T. helicum, T. intricatum, T. konilangbra, T. koningii, T. koningiopsis, T. longibrachiatum, T. longipile, T. minutisporum, T. oblongisporum, T. ovalisporum, T. petersenii, T. phyllostahydis, T. piluliferum, T. pleuroticola, T. pleurotum, T. polysporum, T. pseudokoningii, T. pubescens, T. reesei, T. rogersonii, T. rossicum, T. satumisporum, T. sinensis, T. sinuosum, T. spirale, T. stramineum, T. strigosum, T. stromaticum, T. surrotundum, T. taiwanense, T. thailandicum, T. thelephoricolum, T. theobromicola, T. tomentosum, T. velutinum, T. virens, T. viride* and *T. viridescens*. A *Trichoderma* species herein can be cultivated and/or manipulated as described in *Trichoderma: Biology and Applications* (P. K. Mukherjee et al., Eds., CABI, Oxfordshire, U K, 2013), for example, which is incorporated herein by reference.

A microbial cell in certain embodiments is an algal cell. For example, an algal cell can be from any of the following: Chlorophyta (green algae), Rhodophyta (red algae), Phaeophyceae (brown algae), Bacillariophycaeae (diatoms), and Dinoflagellata (dinoflagellates). An algal cell can be of a microalgae (e.g., phytoplankton, microphytes, or planktonic algae) or macroalgae (kelp, seaweed) in other aspects. As further examples, an algal cell herein can be a *Porphyra* (purple laver), *Palmaria* species such as *P. palmata* (dulse), *Arthrospira* species such as *A. platensis* (*spirulina*), *Chlorella* (e.g., *C. protothecoides*), a *Chondrus* species such as *C. crispus* (Irish moss), *Aphanizomenon, Sargassum, Cochayuyo, Botryococcus* (e.g., *B. braunii*), *Dunaliella* (e.g., *D. tertiolecta*), *Gracilaria, Pleurochrysis* (e.g., *P. carterae*), *Ankistrodesmus, Cyclotella, Hantzschia, Nannochloris, Nannochloropsis, Nitzschia, Phaeodactylum* (e.g., *P. tricomutum*), *Scenedesmus, Stichococcus, Tetraselmis* (e.g., *T. suecica*), *Thalassiosira* (e.g., *T. pseudonana*), *Crypthecodinium* (e.g., *C. cohnii*), *Neochloris* (e.g., *N. oleoabundans*), or *Schiochytrium*. An algal species herein can be cultivated and/or manipulated as described in Thompson (*Algal Cell Culture. Encyclopedia of Life Support System* (*EOLSS*), *Biotechnology Vol* 1, available at eolss.net/sample-chapters internet site), for example, which is incorporated herein by reference.

In one embodiment, the method comprises a method of delivering a protein component of an RNA-guided endonuclease (RGEN) into a microbial cell, said method comprising: contacting the microbial cell with a composition comprising the protein component of the RNA-guided endonuclease (RGEN) and at least one cell-penetrating peptide (CPP), wherein said protein component and CPP are covalently, or non-covalently, linked to each other in an RGEN protein-CPP complex, wherein said RGEN protein-CPP complex traverses (i) a cell membrane, or (ii) a cell wall and cell membrane, of the cell, thereby entering the microbial cell. Microbial cells useful for the methods and composition described herein include cells selected from *Phytophtora* species such as *Phytophtora capsici* (Lamour et al. 2012. The oomycete broad-host-range pathogen *Phytophthora capsici*. Mol. Plant Pathol. May 13(4): 329-337), *Zymoseptoria* species such as *Septoria tritici* (Testa et al. 2015. Overview of genomic and bioinformatics resources for *Zymoseptoria tritici*. Fungal Genet. Biol. June 79:13-16) and *Botrytis* species such as *Botrytis cinerea* (Hahn M. 2014. The rising threat of fungicide resistance in plant pathogenic fungi: *Botrytis* as a case study. J. Chem. Biol 7:133-141).

A protist cell herein can be selected from the class Ciliata (e.g., the genera *Tetrahymena, Paramecium, Colpidium, Colpoda, Glaucoma, Platyophrya, Vorticella, Potomacus, Pseudocohnilembus, Euplotes, Engelmaniella*, and *Stylonichia*), the subphylum Mastigophora (*flagellates*), the class Phytomastigophorea (e.g., the genera *Euglena, Astasia, Haematococcus*, and *Crypthecodinium*), the class Zoomastigophorea, the superclass Rhizopoda, the class Lobosea (e.g., the genus Amoeba), and the class Eumycetozoea (e.g., the genera *Dictyostelium* and Physarum), for example. Certain protist species herein can be cultivated and/or manipulated as described in *ATCC® Protistology Culture Guide: tips and techniques for propagating protozoa and algae* (2013, available at American Type Culture Collection internet site), for example, which is incorporated herein by reference. A protist can optionally be characterized as a pest/pathogen of a plant or animal (e.g., human) in certain embodiments.

A bacterial cell in certain embodiments can be those in the form of cocci, bacilli, spirochetes, spheroplasts, protoplasts, etc. Other non-limiting examples of bacteria include those that are Gram-negative and Gram-positive. Still other non-limiting examples of bacteria include those of the genera *Salmonella* (e.g., *S. typhi, S. enteritidis*), *Shigella* (e.g., *S. dysenteriae*), *Escherichia* (e.g., *E. coli*), *Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus* (e.g., *S. aureus, S. epidermidis*), *Vibrio* (e.g., *V. cholerae*), *Aeromonas, Plessiomonas, Haemophilus* (e.g.,

*H. influenzae*), *Actinobacillus, Pasteurella, Mycoplasma* (e.g., *M. pneumonia*), *Ureaplasma, Rickettsia, Coxiella, Rochalimaea, Ehrlichia, Streptococcus* (e.g., *S. pyogenes, S. mutans, S. pneumoniae*), *Enterococcus* (e.g., *E. faecalis*), *Aerococcus, Gemella, Lactococcus* (e.g., *L. lactis*), *Leuconostoc* (e.g., *L. mesenteroides*), *Pedicoccus, Bacillus* (e.g., *B. cereus, B. subtilis, B. thuringiensis*), *Corynebacterium* (e.g., *C. diphtheriae*), *Arcanobacterium, Actinomyces, Rhodococcus, Listeria* (e.g., *L. monocytogenes*), *Erysipelothrix, Gardnerella, Neisseria* (e.g., *N. meningitidis, N. gonorrhoeae*), *Campylobacter, Arcobacter, Wolinella, Helicobacter* (e.g., *H. pylori*), *Achromobacter, Acinetobacter, Agrobacterium* (e.g., *A. tumefaciens*), *Alcaligenes, Chryseomonas, Comamonas, Eikenella, Flavimonas, Flavobacterium, Moraxella, Oligella, Pseudomonas* (e.g., *P. aeruginosa*), *Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus* (e.g., *L. lactis, L. acidophilus*), *Rothia, Clostridium* (e.g., *C. botulinum, C. perfringens*), *Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium* (e.g., *M. tuberculosis, M. bovis, M. leprae*), *Treponema, Borrelia* (e.g., *B. burgdorferi*), *Leptospira*, and *Chlamydiae*. A bacteria can optionally be characterized as a pest/pathogen of a plant or animal (e.g., human) in certain embodiments. Bacteria can be comprised in a mixed microbial population (e.g., containing other bacteria, or containing yeast and/or other bacteria) in certain embodiments.

An archaeal cell in certain embodiments can be from any Archaeal phylum, such as Euryarchaeota, Crenarchaeota, Nanoarchaeota, Korarchaeota, Aigarchaeota, or Thaumarchaeota. Archaeal cells herein can be extremophilic (e.g., able to grow and/or thrive in physically or geochemically extreme conditions that are detrimental to most life), for example. Some examples of extremophilic archaea include those that are thermophilic (e.g., can grow at temperatures between 45-122° C.), hyperthermophilic (e.g., can grow at temperatures between 80-122° C.), acidophilic (e.g., can grow at pH levels of 3 or below), alkaliphilic (e.g., can grow at pH levels of 9 or above), and/or halophilic (e.g., can grow in high salt concentrations [e.g., 20-30% NaCl]). Examples of archaeal species include those of the genera *Halobacterium* (e.g., *H. volcanii*), *Sulfolobus* (e.g., *S. solfataricus, S. acidocaldarius*), *Thermococcus* (e.g., T. *alcaliphilus, T. celer, T. chitonophagus, T. gammatolerans, T. hydrothermalis, T. kodakarensis, T. litoralis, T. peptonophilus, T. profundus, T. stetteri*), *Methanocaldococcus* (e.g., *M. thermolithotrophicus, M. jannaschii*), *Methanococcus* (e.g., *M. maripaludis*), *Methanothermobacter* (e.g., *M. marburgensis, M. thermautotrophicus*), *Archaeoglobus* (e.g., *A. fulgidus*), *Nitrosopumilus* (e.g., *N. maritimus*), *Metallosphaera* (e.g., *M. sedula*), *Ferroplasma, Thermoplasma, Methanobrevibacter* (e.g., *M. smithii*), and *Methanosphaera* (e.g., *M. stadtmanae*).

Examples of insect cells herein include *Spodoptera frugiperda* cells, *Trichoplusia ni* cells, *Bombyx mori* cells and the like. *S. frugiperda* cells include Sf9 and Sf21, for instance. *T. ni* ovary cells include HIGH FIVE cells (alias BTI-TN-5B1-4, manufactured by Invitrogen), for example. *B. mori* cells include N4, for example. Certain insect cells herein can be cultivated and/or manipulated as described in *Growth and Maintenance of Insect cell lines* (2010, Invitrogen, Manual part no. 25-0127, MAN0000030), for example, which is incorporated herein by reference. In other aspects, an insect cell can be a cell of a plant pest/pathogen such as an armyworm, black cutworm, corn earworm, corn flea beetle, corn leaf aphid, corn root aphid, European corn borer, fall armyworm, granulate cutworm, Japanese beetle, lesser cornstalk borer, maize billbug, melanotus *communis*, seedcorn maggot, sod webworms, sorghum midge, sorghum webworm, southern corn billbug, southern corn rootworm, southern cornstalk borer, southern potato wireworm, spider mite, stalk borer, sugarcane beetle, tobacco wireworm, white grub, aphid, boll weevil, bollworm complex, cabbage looper, tarnished plant bug, thrip, two spotted spider mite, yellow striped armyworm, alfalfa weevil, clover leaf weevil, clover root curculio, fall armyworm, grasshopper, meadow spittlebug, pea aphid, potato leafhopper, sod webworm, variegated cutworm, lesser cornstalk borer, tobacco thrip, wireworm, cereal leaf beetle, chinch bug, English grain aphid, greenbug, hessian fly, bean leaf beetle, beet armyworm, blister beetle, grape *colaspis*, green cloverworm, Mexican bean beetle, soybean looper, soybean stem borer, stink bug, three-cornered alfalfa hopper, velvetbean caterpillar, budworm, cabbage looper, cutworm, green june beetle, green peach aphid, hornworm, potato tuberworm, southern mole cricket, suckfly, tobacco flea beetle, vegetable weevil, or whitefringed beetle. Alternatively, an insect cell can be a cell of a pest/pathogen of an animal (e.g., human).

A nematode cell, for example, can be of a nematode from any of the following genera: *Meloidogyne* (root-knot nematode), *Pratylenchus* (lesion nematode), *Heterodera* (cyst nematode), *Globodera* (cyst nematode), *Ditylenchus* (stem and bulb nematode), *Tylenchulus* (citrus nematode), *Xiphinema* (dagger nematode), *Radopholus* (burrowing nematode), *Rotylenchulus* (reniform nematode), *Helicotylenchus* (spiral nematode), or *Belonolaimus* (sting nematode). A nematode can optionally be characterized as a pest/pathogen of a plant or animal (e.g., human) in certain embodiments. A nematode can be *C. elegans* in other aspects.

A fish cell herein can be any of those as disclosed in U.S. Pat. Nos. 7,408,095 and 7,217,564, and *Tissue Culture of Fish Cell Lines* (T. Ott, NWFHS Laboratory Procedures Manual—Second Edition, Chapter 10, 2004), for example, which are incorporated herein by reference. These references also disclose information regarding cultivating and/or manipulating fish cells. Non-limiting examples of fish cells can be from a teleost such as zebrafish, medaka, Giant *rerio*, or puffer fish.

A plant cell herein can be, for example, a monocot plant cell or dicot plant cell. Examples of monocot plants herein include corn (*Zea mays*), rice (*Oryza sativa*), rye (*Secale cereale*), sorghum (*Sorghum bicolor, Sorghum vulgare*), millet (e.g., pearl millet, *Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas comosus*), banana (Musa spp.), palm, ornamentals, and turfgrasses. Examples of dicot plants herein include soybean (*Glycine max*), canola (*Brassica napus* and *B. campestris*), alfalfa (*Medicago sativa*), tobacco (*Nicotiana tabacum*), *Arabidopsis* (*A. thaliana*), sunflower (*Helianthus annuus*), cotton (*Gossypium arboreum*), peanut (*Arachis hypogaea*), tomato (*Solanum lycopersicum*), and potato (*Solanum tuberosum*). A plant cell may be from any part of a plant and/or from any stage of plant development.

Plant cells herein may be grown or regenerated into plants using conventional conditions, see for example, McCormick et al., (1986) *Plant Cell Rep* 5:81-4. Regenerated plants may then be grown, and either pollinated with the same strain or with a different strain, and resulting progeny having the desired characteristic (e.g., alteration) and/or comprising an introduced polynucleotide or polypeptide identified. Two or more generations may be grown to ensure that an alteration is stably maintained and inherited, and seeds harvested.

Mammalian cells in certain embodiments can be human, non-human primate (e.g., monkey, ape), rodent (e.g., mouse, rat, hamster, guinea pig), rabbit, dog, cat, cow, pig, horse, goat, or sheep cells. Other examples of mammalian cells herein include primary epithelial cells (e.g., keratinocytes, cervical epithelial cells, bronchial epithelial cells, tracheal epithelial cells, kidney epithelial cells, retinal epithelial cells); established cell lines (e.g., 293 embryonic kidney cells, HeLa cervical epithelial cells, PER-C6 retinal cells, MDBK, CRFK, MDCK, CHO, BeWo, Chang cells, Detroit 562, Hep-2, KB, LS 180, LS 174T, NCI-H-548, RPMI 2650, SW-13, T24, WI-28 VA13, 2RA, WISH, BS-C-I, LLC-MK2, Clone M-3, RAG, TCMK-1, LLC-PK1, PK-15, GH1, GH3, L2, LLC-RC 256, MH1C1, XC, MDOK, VSW, TH-I, B1 cells); any epithelial, mesenchymal (e.g., fibroblast), neural, or muscular cell from any tissue or organ (e.g., skin, heart; liver; kidney; colon; intestine; esophagus; stomach; neural tissue such as brain or spinal cord; lung; vascular tissue; lymphoid tissue such as lymph gland, adenoid, tonsil, bone marrow, or blood; spleen); and fibroblast or fibroblast-like cell lines (e.g., TRG-2, IMR-33, Don cells, GHK-21, citrullinemia cells, Dempsey cells, Detroit 551, Detroit 510, Detroit 525, Detroit 529, Detroit 532, Detroit 539, Detroit 548, Detroit 573, HEL 299, IMR-90, MRC-5, WI-38, WI-26, MiCl1, CV-1, COS-1, COS-3, COS-7, Vero, DBS-FrhL-2, BALB/3T3, F9, SV-T2, M-MSV-BALB/3T3, K-BALB, BLO-11, NOR-10, C3H/IOTI/2, HSDM1C3, KLN205, McCoy cells, Mouse L cells, SCC-PSA1, Swiss/3T3 cells, Indian muntjac cells, SIRC, Jensen cells). Methods of culturing and manipulating mammalian cells lines are known in the art.

In certain embodiments, a microbial cell can be of any pathogen and/or pest of an animal or plant. Examples of such pathogens/pests include various types of bacteria, fungi, yeast, protists, nematodes, and insects. Those skilled in the art would recognize examples of such pathogens/pests disclosed above.

As described herein (see Example 10), cell-penetrating peptides were able to deliver cargo to different eukaryotic species including *Phytophthora capsici, Septoria tritici*, and *Botrytis cinerea.*

In one embodiment, the method described herein is a method of delivering a protein component of an RNA-guided endonuclease (RGEN) into a microbial cell selected from the group consisting of *Phytophthora capsici, Septoria tritici*, and *Botrytis cinerea*, said method comprising: contacting the microbial cell with a composition comprising the protein component of the RNA-guided endonuclease (RGEN) and at least one cell-penetrating peptide (CPP), wherein said protein component and CPP are covalently, or non-covalently, linked to each other in an RGEN protein-CPP complex, wherein said RGEN protein-CPP complex traverses (i) a cell membrane, or (ii) a cell wall and cell membrane, of the cell, thereby entering the microbial cell.

A composition in certain embodiments herein can comprise at least one protein component of a guide polynucleotide/Cas endonuclease complex and at least one cell-penetrating peptide (CPP), wherein the protein component and CPP are covalently, or non-covalently, linked to each other in a polynucleotide/endonuclease protein-CPP complex, and wherein the polynucleotide/endonuclease protein-CPP complex can traverse (i) a cell membrane, or (ii) a cell wall and cell membrane, of a cell (such as a microbial cell). The guide polynucleotide and Cas endonuclease are capable of forming a complex, referred to as a "guide polynucleotide/Cas endonuclease complex", that enables the Cas endonuclease to introduce a double-strand break at a DNA target site.

The disclosed invention also concerns a method of delivering a protein component of an RNA-guided endonuclease (RGEN) into a cell (such as a microbial cell). This method comprises contacting a cell with a composition comprising the RGEN protein component and at least one cell-penetrating peptide (CPP), wherein the RGEN protein component and CPP are covalently, or non-covalently, linked to each other in an RGEN protein-CPP complex. As a result of this contacting step, the RGEN protein-CPP complex can traverse (i) a cell membrane, or (ii) a cell wall and cell membrane, of the cell, and thereby gain entry to the cell. In certain embodiments in which an RGEN protein component is associated with an RNA component (thereby forming an RGEN), the disclosed method is directed to delivering an RGEN-CPP complex into a cell. Additionally, since an RGEN can be used in RGEN-mediated DNA targeting in certain embodiments, this method can optionally be characterized as a method of targeting DNA in a cell.

This method can be practiced using any of the above-disclosed embodiments or below Examples regarding each of the method features (e.g., cell type, RGEN protein component, CPP, organelle-targeting sequence, etc.), for example. Thus, any of the features disclosed above or in the Examples, or any combination of these features, can be used appropriately to characterize embodiments of a delivery method herein. The following delivery method features are examples.

Embodiments of a delivery method herein comprise contacting a cell (such as a microbial cell) with a composition comprising an RGEN protein-CPP complex. It is believed that such contacting results in interaction of the complex with the outer surface of the cell (e.g., cell membrane, cell wall), thereby allowing the CPP component of the complex to initiate traversal of the complex across (i) a cell membrane, or (ii) a cell wall and cell membrane.

Contacting a composition comprising an RGEN protein-CPP complex with a cell (such as a microbial cell) can be done at a temperature that allows the complex to enter the cell. Such contacting can be done at any temperature between about 4 and 45° C., for example. The contacting temperature can be about 4, 15, 20, 30, 37, or 42° C. in non-limiting embodiments. The same temperature or temperature range can be maintained during the contacting step, or modified appropriately (e.g., two or more different temperatures).

Contacting a composition comprising an RGEN protein-CPP complex with a cell can be done for an amount of time that is adequate for allowing the complex to enter the cell. For example, cells can be incubated with an RGEN protein-CPP complex for at least about 15, 30, 45, 60, 75, 90, 105, 120, 135, 150, 165, 180, 240, 300, 360, 420, 480, 540, 600, 660, or 720 minutes.

The milieu (e.g., buffer, water and salt concentrations, pH, purity of RGEN protein-CPP complex) in which the contacting is performed may be any of those conditions disclosed above regarding a composition comprising an RGEN protein-CPP complex. For example, cells can be incubated with a complex in a HEPES buffer (e.g., ~25 mM HEPES, such as 25 mM HEPES/KOH pH 7.5, 200 mM KCl, 20% glycerol, 1 mM DTT) or PBS (e.g., 1×PBS, pH 7).

One or more cells (such as microbial cells) may be contacted with a composition comprising an RGEN protein-CPP complex. A cell herein may be as it exists (i) in an organism/tissue in vivo, (ii) in a tissue or group of cells ex vivo, or (iii) in an in vitro state (e.g., cultured cells).

Entry of an RGEN protein-CPP complex into a cell herein typically refers to when a complex has completely traversed (i) a cell membrane, or (ii) a cell wall and cell membrane, and is comprised within at least the cell cytoplasm. Though not intending to be held to any particular theory or mechanism, it is believed that an RGEN protein-CPP complex held together by non-covalent linkage either remains in a complete or partial complex, or the RGEN protein component separates from the CPP component(s) of the complex, after the RGEN protein-CPP complex gains cell entry. In either case, the RGEN protein component is able to associate with a suitable RNA component herein; such association can occur in the cytoplasm, nucleus, or mitochondria, for example. This capability likewise applies to an RGEN protein-CPP complex held together by covalent linkage.

In certain embodiments of an RGEN protein delivery method, a composition herein further comprises at least one RNA component that is associated with the RGEN protein component of the RGEN protein-CPP complex (i.e., the composition comprises an RGEN-CPP complex). The RNA component in this embodiment can be as disclosed herein, comprising a sequence complementary to a target site sequence on a chromosome or episome in the microbial cell. The RGEN can bind to the target site sequence, and optionally cleave one or both DNA strands at the target site sequence. Such an embodiment can also be characterized as a method of delivering an RGEN-CPP complex into a microbial cell, or alternatively as a method of delivering an RNA into a microbial cell.

An RNA component (e.g., gRNA) for use in this embodiment can be prepared using any number of means known in the art. For example, an in vitro transcription process can be used to prepare an RNA component herein. Bacterial RNA polymerases (e.g., T7, T3, SP6) can be used to transcribe an RNA component from a suitable DNA construct encoding the RNA component in certain non-limiting embodiments. An RNA component may be processed to at least about 70%, 80%, 90%, or 95% purity with respect to other biomolecules (e.g., protein, saccharides, lipids), if desired.

To prepare a composition comprising an RNA component and an RGEN protein-CPP complex, the RNA component can be dissolved in a composition in which an RGEN protein-CPP complex is already dissolved, or vice versa (or these components can be dissolved at the same time). A molar ratio of RNA component to RGEN protein-CPP complex of at least about 0.5:1, 1.0:1, 1.5:1, 2.0:1, 2.5:1, 3.0:1, 3.5:1, or 4.0:1, for example, can be used when mixing these elements together. In certain aspects, the molar ratio of RNA component to RGEN protein-CPP complex can be about 3.0:1, or can range from about 2.5:1 to 3.5:1, 2.75:1 to 3.25:1, or 2.9:1 to 3.1:1. In these and other aspects, the concentration of an RGEN protein-CPP complex with which an RNA component is mixed can be at least about 0.5, 1.0, 1.5, 2.0, 2.5, 3.0, 3.5, 4.0, 4.5, 5.0, 6.0, 7.0, 8.0, 9.0 or 10.0 μM, or about 0.5 to 5.0 μM, 0.5 to 2.5 μM, 1.0 to 5.0 μM, 1.0 to 2.5 μM, or 2.5 to 5.0 μM. The amount of time allowed for RNA association with an RGEN protein-CPP complex to form an RGEN-CPP complex can be at least about 1, 2, 3, 4, 5, 6, 7, 8, 9, 10, 15, 20, 25, 30, 45, or 60 minutes, for example. Other conditions (e.g., temperature, buffer, water and salt concentrations, pH, purity of RGEN protein-CPP complex) in which an RNA component can be associated with an RGEN protein-CPP complex may be any of those conditions disclosed above regarding (i) a composition comprising an RGEN protein-CPP complex, or (ii) contacting an RGEN protein-CPP complex with a cell. For example, an RNA component such as a gRNA can be contacted with an RGEN protein-CPP complex in a HEPES buffer (e.g., ~25 mM HEPES, such as 25 mM HEPES/KOH pH 7.5, 200 mM KCl, 20% glycerol, 1 mM DTT), or PBS (e.g., 1×PBS, pH 7), at room temperature (e.g., about 20-25° C.) for about 15 minutes. In those embodiments in which an RGEN protein-CPP complex is held together by non-covalent linkage, association of an RNA component to an RGEN protein can comprise adding an RNA component before, at the same time of, or after incubating a CPP with the RGEN protein component.

After associating an RNA component with an RGEN protein-CPP complex the resulting composition comprising an RGEN-CPP complex (e.g., CPP-Cas9/gRNA) can be immediately contacted with cells, for example. Contact can be made in the milieu in which the RNA component and RGEN protein-CPP complex were associated (e.g., see above), for example. A composition comprising an RGEN-CPP complex can be stored at about room temperature, 4° C., or frozen (e.g., −20 or −80° C.) for later use, if desired. RGEN-CPP complex stability, and/or ability to enter cells and effect DNA targeting, can remain unchanged, or can have at least about 50%, 60%, 70%, 80%, 90%, or 95% of either respective activity, even if the complex is in a composition that has been through one, two, or more freeze-thaw cycles.

A composition comprising an RGEN protein-CPP complex or RGEN-CPP complex, for contacting with a cell, may optionally comprise one or more volume exclusion agents, which are contemplated to enhance contact points between the cell and complexes. Examples of suitable volume exclusion agents herein include glycerol and polyethylene glycol (PEG). Other examples include anionic polymer such as polyacrylate, polymethylacrylate, or anionic polysaccharidic polymers (e.g., dextran sulfate). Still other examples of volume exclusion agents are disclosed in U.S. Pat. No. 4,886,741, which is incorporated herein by reference.

In certain embodiments of an RGEN protein delivery method, a cell (such as a microbial cell) comprises an RNA component that associates with an RGEN protein component of an RGEN protein-CPP complex after the RGEN protein-CPP complex enters the cell (i.e., thereby forming an RGEN-CPP complex in the cell). The RNA component in this embodiment can be as disclosed herein, comprising a sequence complementary to a target site sequence on a chromosome or episome in the cell. The RGEN can bind to the target site sequence, and optionally cleave one or both DNA strands at the target site sequence.

One or more RNA components herein can be stably or transiently expressed in a cell (such as a microbial cell) to which an RGEN protein-CPP complex is introduced, for example. As examples of transient expression, an RGEN protein-CPP complex can be (i) delivered into a cell that has previously been modified to transiently express an RNA component, (ii) co-delivered into a cell with an RNA component, or (iii) delivered into a cell after which the cell is modified for transient RNA component expression.

A DNA polynucleotide sequence comprising (i) a promoter operably linked to (ii) a nucleotide sequence encoding an RNA component can typically be used for stable and/or transient RNA component expression herein. Such a polynucleotide sequence can be comprised within a plasmid, yeast artificial chromosome (YAC), cosmid, phagemid, bacterial artificial chromosome (BAC), virus, or linear DNA (e.g., linear PCR product), for example, or any other type of vector or construct useful for transferring a polynucleotide sequence into a cell. This polynucleotide sequence can be capable of existing transiently (i.e., not integrated into the genome) or stably (i.e., integrated into the genome) in a cell. Also, this polynucleotide sequence can comprise, or lack, one or more suitable marker sequences (e.g., selection or phenotype marker).

A suitable promoter comprised in a polynucleotide sequence for expressing an RNA component herein can be constitutive or inducible, for example. A promoter in certain aspects can comprise a strong promoter, which is a promoter that can direct a relatively large number of productive initiations per unit time, and/or is a promoter driving a higher transcription level than the average transcription level of the genes in a cell comprising the strong promoter.

Examples of strong promoters useful in certain aspects herein (e.g., fungal and/or yeast cells) herein include those disclosed in U.S. Patent Appl. Publ. Nos. 2012/0252079 (DGAT2), 2012/0252093 (EL1), 2013/0089910 (ALK2), 2013/0089911 (SPS19), 2006/0019297 (GPD and GPM), 2011/0059496 (GPD and GPM), 2005/0130280 (FBA, FBAIN, FBAINm), 2006/0057690 (GPAT) and 2010/0068789 (YAT1), which are incorporated herein by reference. Other examples of strong promoters include those listed in Table 2, which also may be useful in fungal and/or yeast cells, for example.

TABLE 2

Strong Promoters

| Promoter Name | Native Gene | Reference[a] |
|---|---|---|
| XPR2 | alkaline extracellular protease | U.S. Pat. No. 4937189; EP220864 |
| TEF | translation elongation factor EF1-α (tef) | U.S. Pat. No. 6265185 |
| GPD, GPM | glyceraldehyde-3-phosphate-dehydrogenase (gpd), phosphoglycerate mutase (gpm) | U.S. Pat. Nos. 7259255 and 7459546 |
| GPDIN | glyceraldehyde-3-phosphate-dehydrogenase (gpd) | U.S. Pat. No. 7459546 |
| GPM/FBAIN | chimeric phospho-glycerate mutase (gpm)/fructose-bisphosphate aldolase (fba1) | U.S. Pat. No. 7202356 |
| FBA, FBAIN, FBAINm | fructose-bisphosphate aldolase (fba1) | U.S. Pat. No. 7202356 |
| GPAT | glycerol-3-phosphate O-acyltransferase (gpat) | U.S. Pat. No. 7264949 |
| YAT1 | ammonium transporter enzyme (yat1) | U.S. Pat. Appl. Publ. No. 2006/0094102 |
| EXP1 | export protein | U.S. Pat. No. 7932077 |

[a]Each reference in this table is incorporated herein by reference.

Other examples of strong promoters useful in certain embodiments herein include PGK1, ADH1, TDH3, TEF1, PHO5, LEU2, and GAL1 promoters, as well as strong yeast promoters disclosed in Velculescu et al. (*Cell* 88:243-251), which is incorporated herein by reference.

A promoter for stable and/or transient expression of an RNA component herein can be an RNA polymerase II (Pol II) promoter, for example. It is believed that all the above-listed strong promoters are examples of suitable Pol II promoters. Transcription from a Pol II promoter may involve formation of an RNA polymerase II complex of at least about 12 proteins (e.g., RPB1-RPN12 proteins), for example. RNA transcribed from a Pol II promoter herein typically is 5'-capped (e.g., contains an $m^7G$ group at the 5'-end) and/or has a polyadenylate (polyA) tail, for example. Means for removing a 5'-cap and/or polyA tail from an RNA component can be employed, if desired, when expressing an RNA component from a Pol II promoter. Suitable means for effectively removing a 5'-cap and/or polyA tail from a Pol II-transcribed RNA component herein include appropriate use of one or more ribozymes (see below), group 1 self-splicing introns, and group 2 self-splicing introns, for example.

Alternatively, a promoter for stable and/or transient expression of an RNA component herein can be an RNA polymerase III (Pol III) promoter, for example. Such a promoter typically allows for expressing an RNA component with defined 5'- and 3'-ends, since initiation and termination of transcription with an RNA polymerase III can be controlled. Examples of Pol III promoters useful herein include U6 and H1 promoters. Other suitable Pol III promoters are disclosed in U.S. Appl. Publ. No. 2010/0160416, for example, which is incorporated herein by reference.

One or more ribozyme sequences may be used to create defined 5' and/or 3' transcript ends, such as in those embodiments in which a Pol II promoter is used for expressing an RNA component in a cell. For example, a nucleotide sequence herein encoding an RNA component may further encode a ribozyme that is upstream of the sequence encoding the RNA component. Thus, a cell in certain embodiments further comprises a DNA polynucleotide sequence comprising (i) a promoter operably linked to (ii) a nucleotide sequence encoding, in 5'-to-3' direction, a ribozyme and an RNA component. Transcripts expressed from such a polynucleotide sequence autocatalytically remove the ribozyme sequence to yield an RNA with a defined 5'-end (without a 5'-cap) but which comprises the RNA component sequence. This "autoprocessed" RNA can comprise a crRNA or gRNA, for example, and can complex with an RGEN protein component such as a Cas9, thereby forming an RGEN.

A ribozyme herein can be a hammerhead (HH) ribozyme, hepatitis delta virus (HDV) ribozyme, group I intron ribozyme, RnaseP ribozyme, or hairpin ribozyme, for example. Other non-limiting examples of ribozymes herein include Varkud satellite (VS) ribozymes, glucosamine-6-phosphate activated ribozymes (glmS), and CPEB3 ribozymes. Lilley (*Biochem. Soc. Trans.* 39:641-646) discloses information pertaining to ribozyme structure and activity. Examples of ribozymes that should be suitable for use herein include ribozymes disclosed in EP0707638 and U.S. Pat. Nos. 6,063,566, 5,580,967, 5,616,459, and 5,688,670, which are incorporated herein by reference. Further information regarding using ribozymes to express RNA components with defined 5' and/or 3' ends is disclosed in WO2016/025131, published Feb. 18, 2016.

In certain embodiments, a DNA polynucleotide comprising a cassette for expressing an RNA component comprises a suitable transcription termination sequence downstream of the RNA component sequence. Examples of transcription termination sequences useful herein are disclosed in U.S. Pat. Appl. Publ. No. 2014/0186906, which is herein incorporated by reference. Such embodiments typically comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more residues following the end of the RNA component sequence, depending on the choice of terminator sequence. These additional residues can be all U residues, or at least 90%, 91%, 92%, 93%, 94%, 95%, 96%, 97%, 98%, or 99% A U residues, for example, depending on the choice of terminator sequence. Alternatively, a ribozyme sequence (e.g., hammerhead or HDV ribozyme) can be 3' of (e.g., 1, 2, 3, 4, 5, 6, 7, 8, 9, 10 or more nucleotides downstream) the RNA component sequence, for example. A 3' ribozyme sequence can be positioned accordingly such that it cleaves itself from the RNA component sequence; such cleavage would render a transcript ending exactly at the end of the RNA component sequence, or with 1, 2, 3, 4, 5, 6, 7, 8, 9, 10, 11, 12, 13, 14, 15, or more residues following the end of the RNA component sequence, for example.

An RNA component in other examples can be provided in the nucleus and/or cytoplasm of a cell into which an RGEN protein-CPP complex is delivered. For example, an RNA component expressed from a Pol II promoter without use of a 5'-located ribozyme sequence can be expected to exist in both the nucleus and cytoplasm. An RNA component expressed from any type of promoter (e.g. Pol II or III promoter) and using a 5'-located ribozyme sequence can be expected to exist mostly in the nucleus in other embodiments. An RNA component expressed from a Pol III promoter in certain aspects can be expected to exist mostly in the nucleus. In certain aspects, an RNA component is uncapped (e.g., by virtue of being expressed from a Pol III promoter, and/or by ribozyme autoprocessing) and typically is located in the nucleus, while in other aspects is capped and located in nuclear and cytoplasmic locations. In general, the RGEN protein component of an RGEN protein-CPP complex, once delivered into a cell, can associate with an RNA component (thereby forming an RGEN) in the cytoplasm and/or nucleus (depending on RNA component location). Such association in the nucleus is generally due to the ability of an RGEN protein component herein to localize to the nucleus as directed by an NLS.

An RGEN herein is useful for RGEN-mediated DNA targeting. Any of the above embodiments regarding delivering an RGEN protein component into a cell can be applied to a DNA targeting method. For example, an RGEN protein-CPP complex can be contacted with at least one RNA component outside of a microbial cell to form an RGEN-CPP complex for delivery into a cell for DNA targeting therein. As another example, an RGEN protein-CPP complex, after its delivery into a microbial cell, can be contacted with at least one RNA component inside a microbial cell to form an RGEN-CPP complex therein that can then mediate DNA targeting. The following disclosure regarding targeting methods refers to an "RGEN", as opposed to referring to an "RGEN-CPP complex". It would be understood that, depending on whether a covalent or non-covalent RGEN-CPP complex is used in an RGEN delivery method herein (and depending on how strong a non-covalent linkage is in embodiments employing a non-covalent RGEN-CPP complex), reference to an RGEN below refers to such an RGEN-CPP complex, accordingly.

An RGEN herein that can cleave one or both DNA strands of a DNA target sequence can be used in a DNA targeting method, for example. Such DNA targeting methods can involve HR-mediated DNA targeting if a suitable donor DNA is provided in the method. Thus, in certain embodiments, a microbial cell in a targeting method herein can comprise a donor polynucleotide comprising at least one sequence homologous to a sequence at or near a target site sequence (a sequence specifically targeted by an RGEN herein). Such embodiments can optionally be characterized in that the targeting method further comprises a step of providing a suitable donor polynucleotide to the microbial cell.

A donor polynucleotide herein can undergo HR with a sequence at or near a DNA target site if the target site contains a SSB or DSB (such as can be introduced using an RGEN herein). A "homologous sequence" within a donor polynucleotide herein can, for example, comprise or consist of a sequence of at least about 25, 50, 75, 100, 150, 200, 300, 400, 500, 600, 700, 800, 900, 1000, 2000, 3000, 4000, 5000, 6000, 7000, 8000, 9000 or 10000 nucleotides, or about 50-500, 50-550, 50-600, 50-650, or 50-700 nucleotides, that have 100% identity with a sequence at or near the target site sequence, or at least about 90%, 91%, 92%, 93%, 94%, 95%, 96%, 97%, 98%, or 99% identity with a sequence at or near the target site sequence, for example.

A donor polynucleotide herein can have two homologous sequences (homology arms), for example, separated by a sequence that is heterologous to sequence at or near a target site sequence. HR between such a donor polynucleotide and a target site sequence typically results in the replacement of a sequence at the target site with the heterologous sequence of the donor polynucleotide (i.e., a target site sequence located between target site sequences homologous to the homology arms of the donor polynucleotide is replaced by the heterologous sequence of the donor polynucleotide). In a donor polynucleotide with two homology arms, the arms can be separated by at least about 1, 2, 3, 4, 5, 10, 20, 30, 40, 50, 75, 100, 250, 500, 1000, 2500, 5000, 10000, 15000, 20000, 25000, or 30000 nucleotides (i.e., the heterologous sequence in the donor polynucleotide can be at least about 1, 2, 3, 4, 5, 10, 20, 30, 40, 50, 75, 100, 250, 500, 1000, 2500, 5000, 10000, 15000, 20000, 25000, or 30000 nucleotides in length), for example. The length (e.g., any of the lengths disclosed above for a homologous sequence) of each homology arm may be the same or different. The percent identity (e.g., any of the % identities disclosed above for a homologous sequence) of each arm with respective homologous sequences at or near the target site can be the same or different.

A DNA sequence at or near (alternatively, in the locality or proximity of) the target site sequence that is homologous to a corresponding homologous sequence in a donor polynucleotide can be within about 1, 2, 3, 4, 5, 6, 7, 8, 9, 10, 15, 20, 25, 30, 35, 40, 45, 50, 60, 70, 80, 90, 100, 150, 200, 250, 300, 450, 500, 750, 1000, 2000, 3000, 4000, 5000, 6000, 7000, 8000, 9000, 10000, 20000, 30000, 40000, 50000, or 60000 (or any integer between 1 and 60000) nucleotides (e.g., about 1-1000, 100-1000, 500-1000, 1-500, or 100-500 nucleotides), for example, from the predicted RGEN cut site (DSB or nick) in the target sequence. These nucleotide distances can be marked from the cut site to the first nucleotide of the homologous sequence, going either in the upstream or downstream direction from the cut site. For example, a sequence near a target sequence that is homologous to a corresponding sequence in a donor polynucleotide can start at 500 nucleotide base pairs downstream the predicted RGEN cut site in a target sequence. In embodiments herein employing a donor polynucleotide with two homology arms (e.g., first and second homology arms separated by a heterologous sequence), a homologous sequence (corresponding in homology with the first homology arm of a donor) can be upstream the predicted RGEN cut site, and a homologous sequence (corresponding in homology with the second homology arm of a donor) can be downstream the predicted RGEN cut site, for example. The nucleotide distances of each of these upstream and downstream homologous sequences from the predicted cut site can be the same or different, and can be any of the nucleotide distances disclosed above, for example. For instance, the 3' end of a homologous sequence (corresponding in homology with the first homology arm of a donor) may be located 600 nucleotide base pairs upstream a predicted RGEN cut site, and the 5' end of a homologous sequence (corresponding in homology with the second homology arm of a donor) may be located 400 nucleotide base pairs downstream the predicted RGEN cut site.

A donor polynucleotide in various aspects can be delivered into a cell (such as a microbial cell) at or near (e.g., within 1, 2, 3 or more hours) the time when an RGEN protein-CPP complex is delivered into the cell. Such delivery can be via by any means known in the art suitable for the particular type of cell being used. These techniques include transformation (e.g., lithium acetate transformation [*Methods in Enzymology,* 194:186-187]), transfection, biolistic impact, electroporation, and microinjection, for example. As examples, U.S. Pat. Nos. 4,880,741 and 5,071,764, and Chen et al. (*Appl. Microbiol. Biotechnol.* 48:232-235), which are incorporated herein by reference, describe DNA transfer techniques for *Y. lipolytica*. Examples of delivery modes useful in plants include *Agrobacterium*-mediated transformation and biolistic particle bombardment.

An RGEN that cleaves one or both DNA strands of a DNA target sequence can be used to create an indel in other non-limiting embodiments of DNA targeting herein. A method of forming an indel in a cell can be performed as disclosed above for HR-mediated targeting, but without further providing a donor DNA polynucleotide that could undergo HR at or near the target DNA site (i.e., NHEJ is induced in this method). Examples of indels that can be created are disclosed herein. The size of an indel may be 1, 2, 3, 4, 5, 6, 7, 8, 9, 10, or more bases, for example. An indel in certain embodiments can be even larger such as at least about 20, 30, 40, 50, 60, 70, 80, 90, 100, 110, 120, 130, 140, or 150 bases. In still other embodiments, insertions or deletions can be at least about 500, 750, 1000, or 1500 bases. When attempting to create an indel in certain embodiments, a single base substitution may instead be formed in a target site sequence. Thus, a targeting method herein can be performed for the purpose of creating single base substitution, for example.

In certain embodiments of a targeting method herein aimed at indel formation, the frequency of indel formation in a non-conventional yeast (e.g., *Y. lipolytica*) is significantly higher than what would be observed using the same or similar targeting strategy in a conventional yeast such as *S. cerevisiae*. For example, while the frequency of indel formation in a conventional yeast may be about 0.0001 to 0.001 (DiCarlo et al., *Nucleic Acids Res.* 41:4336-4343), the frequency in a non-conventional yeast herein may be at least about 0.05, 0.10, 0.15, 0.20, 0.25, 0.30, 0.35, 0.40, 0.45, 0.50, 0.55, 0.60, 0.65, 0.70, 0.75, or 0.80. Thus, the frequency of indel formation in a non-conventional yeast herein may be at least about 50, 100, 250, 500, 750, 1000, 2000, 4000, or 8000 times higher, for example, than what would be observed using the same or similar RGEN-mediated targeting strategy in a conventional yeast.

A targeting method in certain embodiments can be performed to disrupt one or more DNA polynucleotide sequences encoding a protein or a non-coding RNA. An example of such a sequence that can be targeted for disruption is one encoding a marker (i.e., a marker gene). Non-limiting examples of markers herein include screenable markers and selectable markers. A screenable marker herein can be one that renders a cell visually different under appropriate conditions. Examples of screenable markers include polynucleotides encoding beta-glucuronidase (GUS), beta-galactosidase (lacZ), and fluorescent proteins (e.g., GFP, RFP, YFP, BFP). A selectable marker herein can be one that renders a cell resistant to a selective agent or selective environment. Examples of selectable markers are auxotrophic markers such as HIS3, LEU2, TRP1, MET15, or URA3, which allow cells such as yeast cells to survive in the absence of exogenously provided histidine, leucine, tryptophan, methionine, or uracil, respectively. Other examples of selectable markers are antibiotic- or antifungal-resistance markers such as those rendering a cell resistant to ampicillin, chloramphenicol, hygromycin B, nourseothricin, phleomycin, puromycin, or neomycin (e.g., G418). Examples of these methods can optionally be characterized as marker recycling methods.

At least one purpose for disrupting a marker in certain embodiments can be for marker recycling. Marker recycling is a process, for example, comprising (i) transforming a cell with a marker and heterologous DNA sequence, (ii) selecting a transformed cell comprising the marker and the heterologous DNA sequence (where a marker-selectable cell typically has a higher chance of containing the heterologous DNA sequence), (iii) disrupting the marker, and then repeating steps (i)-(iii) as many times as necessary (using the same [or different] marker, but each cycle using a different heterologous DNA sequence) to transform cells with multiple heterologous DNA sequences. One or more heterologous sequences in this process may comprise the marker itself in the form of a donor polynucleotide (e.g., marker flanked by homology arms for targeting a particular locus). Examples of marker recycling processes herein include those using URA3 as a marker, such as in certain methods employing a yeast (e.g., a non-conventional yeast such as *Y. lipolytica*).

An RGEN herein that can bind to a DNA target site sequence, but does not cleave any strand at the target site sequence, can be used in a DNA targeting method in other embodiments. Any RGEN disclosed herein that has only dysfunctional nuclease domains, but retains specific DNA-binding activity, can be used in this type of targeting method.

In certain embodiments of DNA targeting with an RGEN having no functional nuclease domains, an RGEN can bind to a target site and modulate transcription of a polynucleotide sequence (i.e., gene transcription). Typically, an RGEN is targeted to a regulatory sequence such as a promoter (e.g., within 1-1000, 1-500, 1-250, 1-125, or 1-50 bases upstream a transcription start site), a sequence encoding a 5'-untranslated RNA sequence, or an intron (e.g., first intron) to effect transcriptional modulation of a polynucleotide sequence.

As a non-limiting example, an RGEN linked or fused to a repressor transcription factor or repressor domain thereof can be used to repress, or silence, expression of one or more polynucleotide sequences. An RGEN in certain alternative embodiments can, by itself (without a repressor or domain thereof), inhibit gene expression; such an RGEN can be targeted such that it inhibits binding and/or movement of RNA transcriptional machinery necessary for transcription. A method incorporating any repressing RGEN can optionally be characterized as a gene silencing or transcriptional silencing method. The level of transcriptional down-regulation in a silencing method can be about 100% (gene completely silenced), or at least about 30% (gene moderately silenced), 40%, 50%, 60%, 70%, 80%, 90%, or 95% (gene substantially silenced), for example, compared to the transcription level before application of a repressing RGEN.

An RGEN linked or fused to an activator transcription factor or activator domain thereof can be used to upregulate expression of one or more polynucleotide sequences. A method incorporating such an activating RGEN can optionally be characterized as a transcriptional up-regulation or activation method. The level of transcriptional up-regulation in such a method can be at least about 25%, 50%, 75%, 100%, 250%, 500%, or 1000%, for example, compared to the transcription level before application of an activating RGEN.

In certain embodiment, an RGEN that can bind to a DNA target site sequence, but preferably does not cleave any strand at the target site sequence, can be used as a diagnostic tool (e.g., probe for detecting a DNA sequence). An RGEN protein component in DNA probe can be linked to a reporter agent such as a reporter protein (e.g., fluorescent protein such as GFP), for example. Specific DNA binding of the RGEN-reporter protein, as specified by the RNA component of the RGEN, can be incorporated in a detection system accordingly, taking advantage of the activity of the reporter agent. Flow cytometry (e.g., flow-activated cell sorting [FACS]) and fluorescence in situ hybridization (FISH) are examples of suitable detection systems herein that use a fluorescent reporter.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide an RGEN to a unique DNA target site. For example, two or more different RNA components can be used to prepare a mix of RGEN-CPP complexes in vitro (e.g., following a procedure disclosed herein for associating an RNA component with an RGEN protein-CPP complex), which mix is then contacted with a cell.

Another aspect of multiplex targeting herein can comprise providing two or more different RNA components in a cell which associate with the RGEN protein components of RGEN protein-CPP complexes that have traversed into the cell. Such a method can comprise, for example, providing to the cell (i) individual DNA polynucleotides, each of which express a particular RNA component that, and/or (ii) at least one DNA polynucleotide encoding two or more RNA components (e.g., see below disclosure regarding tandem ribozyme-RNA component cassettes).

A multiplex method can optionally target DNA sites very close to the same sequence (e.g., a promoter or open reading frame, and/or sites that are distant from each other (e.g., in different genes and/or chromosomes). A multiplex method in other embodiments can be performed with (for HR) or without (for NHEJ leading to indel and/or base substitution) suitable donor DNA polynucleotides, depending on the desired outcome of the targeting (if an endonuclease- or nickase-competent RGEN is used). In still other embodiments, a multiplex method can be performed with a repressing or activating RGEN as disclosed herein. For example, multiple repressing RGENs can be provided that down-regulate a set of genes, such as genes involved in a particular metabolic pathway.

A multiplex method in certain embodiments can comprise providing to a cell a DNA polynucleotide comprising (i) a promoter operably linked to (ii) a sequence comprising more than one ribozyme-RNA component cassettes (i.e., tandem cassettes). A transcript expressed from such a DNA polynucleotide can have, for example, 2, 3, 4, 5, 6, 7, 8, 9, 10, or more cassettes. A 3' ribozyme sequence can optionally be included following all or some RNA component sequences to allow cleavage and separation of the RNA component from downstream transcript sequence (i.e., tandem cassettes may comprise one or more ribozyme-RNA component-ribozyme cassettes). A DNA polynucleotide herein for expressing tandem ribozyme-RNA component-ribozyme cassettes can be designed such that there are about 10, 20, 30, 40, 50, 60, 70, 80, 90, 100, or more nucleotides between each cassette (e.g., non-coding spacer sequence). The distances between each cassette may be the same or different.

Any construct or vector comprising a DNA polynucleotide encoding an RNA component described herein can be introduced into a cell by any means known in the art suitable for the particular type of cell being used. For example, any of the means disclosed above for delivering a donor DNA into a cell can be employed.

Certain embodiments herein concern a method of modifying or altering a target site in the genome of a microbial cell, wherein the method comprises contacting the microbial cell with a guide polynucleotide and Cas endonuclease covalently or non-covalently linked to a CPP, wherein the guide polynucleotide and CPP-Cas endonuclease are capable of forming a complex that enables the Cas endonuclease to introduce a double-strand break at the target site in the genome of the microbial cell. The modification or alteration of the target site can include (i) a replacement of at least one nucleotide, (ii) a deletion of at least one nucleotide, (iii) an insertion of at least one nucleotide, or (iv) any combination of (i)-(iii).

Certain embodiments herein concern a polynucleotide sequence comprising a nucleotide sequence encoding a fusion protein that comprises a protein component of an RNA-guided endonuclease (RGEN) and at least one cell-penetrating peptide (CPP). Any fusion protein as disclosed herein, for example, can be encoded by the nucleotide sequence. The nucleotide sequence may optionally be in operable linkage with a promoter sequence. Certain embodiments include, for example, a polynucleotide (e.g., vector or construct) comprising at least one open reading frame encoding any RGEN protein-CPP fusion disclosed herein. Such a coding region can optionally be operably linked to a promoter sequence suitable for expressing an RGEN protein-CPP fusion in a cell (e.g., bacteria cell; eukaryotic cell such as a yeast, insect, or mammalian cell) or in an in vitro protein expression system, for example. Examples of a vector or construct include circular (e.g., plasmid) and non-circular (e.g., linear DNA such as an amplified DNA sequence) polynucleotide molecules.

Certain embodiments herein concern a method of producing an RGEN protein-CPP fusion protein comprising the steps of: providing a polynucleotide sequence having a nucleotide sequence encoding the RGEN protein-CPP fusion protein, and expressing the RGEN protein-CPP fusion protein from the polynucleotide sequence, thereby producing the RGEN protein-CPP fusion protein. The expression step in such a method can optionally be performed in a cell (e.g., bacteria cell such as *E. coli*; eukaryotic cell such as a yeast [e.g., *S. cerevisiae*], insect, or mammalian cell). Alternatively, expression of an RGEN protein-CPP fusion protein can be performed in an in vitro protein expression system (e.g., cell-free protein expression systems such as those employing rabbit reticulocyte lysate or wheat germ extract). Also, the RGEN protein-CPP fusion protein produced in the expression step can optionally be isolated. Such isolation can be performed in a manner that produces a composition having any of the above-disclosed features (e.g., purity, pH, buffer, and/or salt level), for example.

Non-limiting examples of compositions and methods disclosed herein include:

1. A composition comprising at least one protein component of an RNA-guided endonuclease (RGEN) and at least one cell-penetrating peptide (CPP), wherein the protein component and CPP are covalently, or non-covalently, linked to each other in an RGEN protein-CPP complex, and wherein the RGEN protein-CPP complex can traverse (i) a cell membrane, or (ii) a cell wall and cell membrane, of a cell.
2. The composition of embodiment 1, wherein the protein component of the RGEN is associated with at least one RNA component that comprises a sequence complementary to a target site sequence on a chromosome or episome in the cell, wherein the RGEN can bind to the target site sequence, and optionally cleave one or both DNA strands at the target site sequence.
3. The composition of embodiment 2, wherein the RNA component comprises a guide RNA (gRNA) comprising a CRISPR RNA (crRNA) operably linked to a trans-activating CRISPR RNA (tracrRNA).
4. The composition of embodiment 2, wherein the RGEN can cleave one or both DNA strands at the target site sequence.
5. The composition of embodiment 1, wherein the RGEN comprises a CRISPR-associated (Cas) protein-9 (Cas9) amino acid sequence.
6. The composition of embodiment 1, wherein the RGEN protein component and CPP are covalently linked.
7 The composition of embodiment 1, wherein the RGEN protein component and CPP are non-covalently linked.
8. The composition of embodiment 1, wherein the CPP is cationic or amphipathic.
9. The composition of embodiment 1, wherein the CPP comprises:
   (i) a CPP from an Epstein-Barr virus Zebra trans-activator protein,
   (ii) a CPP having 6 or more contiguous arginine residues,
   (iii) a transportan-10 (TP10) CPP, or
   (iv) a CPP from a vascular endothelium cadherin protein.
10. The composition of embodiment 1, wherein the RGEN protein-CPP complex can traverse a cell wall and cell membrane of a cell.
11. A cell comprising the composition according to embodiment 1.
12. A method of delivering a protein component of an RNA-guided endonuclease (RGEN) into a cell, the method comprising:
   contacting the cell with a composition comprising the protein component of the RNA-guided endonuclease (RGEN) and at least one cell-penetrating peptide (CPP),
   wherein the protein component and CPP are covalently, or non-covalently, linked to each other in an RGEN protein-CPP complex,
   wherein the RGEN protein-CPP complex traverses (i) a cell membrane, or (ii) a cell wall and cell membrane, of the cell, thereby entering the cell.
13. The method of embodiment 12, wherein:
   (i) the composition further comprises at least one RNA component that is associated with the protein component of the RGEN; or
   (ii) the cell comprises the RNA component, wherein the RNA component associates with the protein component of the RGEN after the RGEN protein-CPP complex enters the cell;
   wherein the RNA component comprises a sequence complementary to a target site sequence on a chromosome or episome in the cell, wherein the RGEN can bind to the target site sequence, and optionally cleave one or both DNA strands at the target site sequence.
14. The method of embodiment 13, wherein the RGEN can cleave one or both DNA strands at the target site sequence.
15. The method of embodiment 14, wherein the cell further comprises a donor polynucleotide comprising at least one sequence homologous to a sequence at or near the target site sequence.
16. The method of embodiment 12, wherein the cell is a non-mammalian cell.
17. A composition comprising at least one protein component of a guide polynucleotide/Cas endonuclease complex and at least one cell-penetrating peptide (CPP), wherein the protein component and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of a cell, wherein the cell is optionally a plant cell.
18. The composition of embodiment 17, wherein the Cas endonuclease is a plant-optimized Cas9 endonuclease.
19. The composition of embodiment 17, wherein the guide polynucleotide comprises
   (i) a first nucleotide sequence domain that is complementary to a nucleotide sequence in a target DNA, and
   (ii) a second nucleotide sequence domain that interacts with a Cas endonuclease,
   wherein the first nucleotide sequence domain and the second nucleotide sequence domain are composed of deoxyribonucleic acids (DNA), ribonucleic acids (RNA), or a combination thereof.
20. The composition of embodiment 17, wherein the guide polynucleotide/Cas endonuclease-CPP complex can traverse the cell wall of a plant cell.
21. The composition of embodiment 17, wherein the CPP comprises:
   (i) a CPP from an Epstein-Barr virus Zebra trans-activator protein,
   (ii) a CPP having 6 or more contiguous arginine residues,
   (iii) a transportan-10 (TP10) CPP,
   (iv) a CPP from a vascular endothelium cadherin protein, or
   (vi) a CPP selected from the group consisting of a synthetic nona-arginine CPP, a histidine-rich nona-arginine CPP, and a Pas nona-arginine CPP.
22. The composition of embodiment 20, wherein the plant cell is a monocot or a dicot cell.
23. The composition of embodiment 22, wherein the monocot is selected from the group consisting of maize, rice, sorghum, rye, barley, wheat, millet, oats, sugarcane, turfgrass, and switchgrass.
24. The composition of embodiment 22, wherein the dicot is selected from the group consisting of soybean, canola, alfalfa, sunflower, cotton, tobacco, peanut, potato, tobacco, *Arabidopsis*, and safflower.
25. A method for modifying a target site in the genome of a cell, the method comprising providing a guide polynucleotide, a cell-penetrating peptide (CPP) and a Cas endonuclease to the cell, wherein the guide polynucleotide, Cas endonuclease and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of a cell, wherein the cell is optionally a plant cell.

26. The method of embodiment 25, further comprising identifying at least one plant cell that has a modification at the target site, wherein the modification at the target site is selected from the group consisting of (i) a replacement of at least one nucleotide, (ii) a deletion of at least one nucleotide, (iii) an insertion of at least one nucleotide, and (iv) any combination of (i)-(iii).

27. The method of embodiment 25, wherein the plant cell is a monocot or dicot cell.

28. A composition comprising at least one protein component of an RNA-guided endonuclease (RGEN) and at least one cell-penetrating peptide (CPP), wherein the protein component and CPP are covalently, or non-covalently, linked to each other in an RGEN protein-CPP complex, and wherein the RGEN protein-CPP complex can traverse (i) a cell membrane, or (ii) a cell wall and cell membrane, of a microbial cell.

29. The composition of embodiment 28, wherein the protein component of the RGEN is associated with at least one RNA component that comprises a sequence complementary to a target site sequence on a chromosome or episome in the microbial cell, wherein the RGEN can bind to the target site sequence, and optionally cleave one or both DNA strands at the target site sequence.

30. The composition of embodiment 28, wherein the RGEN protein-CPP complex can traverse a cell wall and cell membrane of a microbial cell.

31. A microbial cell comprising the composition according to embodiment 28.

32. A method of delivering a protein component of an RNA-guided endonuclease (RGEN) into a microbial cell, the method comprising: contacting the microbial cell with a composition comprising the protein component of the RNA-guided endonuclease (RGEN) and at least one cell-penetrating peptide (CPP), wherein the protein component and CPP are covalently, or non-covalently, linked to each other in an RGEN protein-CPP complex, wherein the RGEN protein-CPP complex traverses (i) a cell membrane, or (ii) a cell wall and cell membrane, of the microbial cell, thereby entering the microbial cell.

33. The method of embodiment 32, wherein:
   (i) the composition further comprises at least one RNA component that is associated with the protein component of the RGEN; or
   (ii) the microbial cell comprises the RNA component, wherein the RNA component associates with the protein component of the RGEN after the RGEN protein-CPP complex enters the microbial cell;
   wherein the RNA component comprises a sequence complementary to a target site sequence on a chromosome or episome in the microbial cell, wherein the RGEN can bind to the target site sequence, and optionally cleave one or both DNA strands at the target site sequence.

34. The method of embodiment 33, wherein the RGEN can cleave one or both DNA strands at the target site sequence.

34. The method of embodiment 34, wherein the microbial cell further comprises a donor polynucleotide comprising at least one sequence homologous to a sequence at or near the target site sequence.

36. The method of embodiment 32, wherein the microbial cell is a yeast cell.

37. A composition comprising at least one protein component of a guide polynucleotide/Cas endonuclease complex and at least one cell-penetrating peptide (CPP), wherein the protein component and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of a microbial cell.

38. The composition of embodiment 37, wherein the guide polynucleotide/Cas endonuclease-CPP complex can traverse the cell wall of the microbial cell.

39. A method for modifying a target site in the genome of a microbial cell, the method comprising providing a guide polynucleotide, a cell-penetrating peptide (CPP) and a Cas endonuclease to the microbial cell, wherein the guide polynucleotide, Cas endonuclease and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of a microbial cell.

23. The method of embodiment 39, further comprising identifying at least one microbial cell that has a modification at the target site, wherein the modification at the target site is selected from the group consisting of (i) a replacement of at least one nucleotide, (ii) a deletion of at least one nucleotide, (iii) an insertion of at least one nucleotide, and (iv) any combination of (i)-(iii).

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Vectors for Expressing a Cas9-CPP (Cell-Penetrating Peptide) Fusion Protein in *E. coli*

In this example, vectors designed for inducible expression of translational fusion proteins comprising Cas9 protein and a cell-penetrating peptide (CPP) were produced and tested for expression in *E. coli*. Cas9-CPP fusion proteins were shown to express in *E. coli* as expected, and subsequently purified.

The open reading frame of the Cas9 gene from *Streptococcus pyogenes* M1 GAS (SF370) was codon-optimized for expression in *Yarrowia* per standard techniques, yielding SEQ ID NO:1. DNA sequence encoding a simian virus 40 (SV40) monopartite nuclear localization signal (NLS) plus a short linker (4 amino acids) was incorporated after the last sense codon of SEQ ID NO:1 to render SEQ ID NO:2. SEQ ID NO:2 encodes the amino acid sequence shown in SEQ ID NO:3. The last seven amino acids of SEQ ID NO:3 encode the added NLS, whereas residues at positions 1369-1372 of SEQ ID NO:3 encode the added linker. The *Yarrowia* codon-optimized Cas9-NLS sequence (SEQ ID NO:2) was linked to a *Yarrowia* constitutive promoter, FBA1 (SEQ ID NO:4), by standard molecular biology techniques. A *Yarrowia* codon-optimized Cas9 expression cassette containing the constitutive FBA1 promoter, *Yarrowia* codon-optimized Cas9, and the SV40 NLS is set forth in SEQ ID NO:5. This Cas9 expression cassette (SEQ ID NO:5) was cloned into the plasmid pZUF rendering construct pZUFCas9 (FIG. 1, SEQ ID NO:6).

The *Yarrowia* codon-optimized Cas9-NLS sequence was PCR-amplified from pZUFCas9 (SEQ ID NO:6) using standard molecular biology techniques. Primers for the PCR reaction were SEQ ID NO:7 (Forward) and SEQ ID NO:8 (Reverse), which added a 5' EcoRI site and 3' HindIII site, respectively, to the amplified DNA product. The added 5' EcoRI site replaced the ATG start codon of the Cas9-NLS open reading frame (ORF) in the amplified product. The amplified product (SEQ ID NO:9) was digested with EcoRI and HindIII, and then purified using Zymoclean™ and concentrator columns (Zymo Research, Irvine, Calif.). The purified DNA fragment was cloned into the EcoRI and HindIII sites of plasmid pBAD/HisB from Life Technologies (Carlsbad, Calif.) (FIG. 2A, SEQ ID NO:10) to create plasmid construct pRF48 (FIG. 2B, SEQ ID NO:11). Plasmid pRF48 is capable of expressing, in *E. coli*, a Cas9-NLS comprising a hexahistidine (6×His) tag at its N-terminus.

To fuse a cell-penetrating peptide (CPP) sequence to Cas9-NLS, individual DNA polynucleotide sequences were prepared, each codon-optimized for expression in *E. coli* and comprising sequence encoding a 6×His tag linked to a particular CPP amino acid sequence: Zebra peptide (ECDSELEIKRYKRVRVASRKCRAKFKQLLQHYREVAAAKSSENDRLRLLLKQMC, SEQ ID NO:12), from the Epstein-Barr virus Zebra trans-activator protein; pVEC peptide (LLIILRRRIRKQAHAHSK, SEQ ID NO:13), from a murine endothelial cadherin protein; TP10 peptide (AGYLLGKINLKACAACAKKIL, SEQ ID NO:14), from a neuropeptide galanin protein; and synthetic arginine-rich "PolyR" peptide (GGGGRRRRRRRRRLLLL, SEQ ID NO:15). Each DNA polynucleotide sequence included a 5'-end NcoI restriction site and a 3'-end EcoRI site to create cloning sequences structured as follows: NcoI-6×His-CPP-EcoRI (SEQ ID NO:16-19). Each of SEQ ID NOs:16-19 was individually cloned into the NcoI and EcoRI sites of pRF48, thereby creating plasmid constructs capable of expressing certain 6×His-CPP-Cas9-NLS fusion proteins in *E. coli*. In particular, plasmid construct pRF144 (FIG. 3A, SEQ ID NO:20) was prepared for expressing a 6×His-Zebra CPP-Cas9-NLS fusion; plasmid construct pRF145 (FIG. 3B, SEQ ID NO:21) was prepared for expressing a 6×His-PolyR CPP-Cas9-NLS fusion; plasmid construct pRF146 (FIG. 3C, SEQ ID NO:22) was prepared for expressing a 6×His-TP10 CPP-Cas9-NLS fusion, and plasmid construct pRF162 (FIG. 3D, SEQ ID NO:23) was prepared for expressing a 6×His-pVEC CPP-Cas9-NLS fusion.

Each of plasmids pRF48, pRF144, pRF145, pRF146 and pRF162 was individually transformed into TOP10 competent cells (Life Technologies). Cells were grown overnight at 37° C. with shaking (220 rpm) in L broth (Miller) containing 0.4% (w/v) glucose and 100 μg/mL ampicillin. Each preculture was diluted 1:100 in 2×YT medium containing 100 μg/mL ampicillin and further grown at 37° C. with shaking (220 rpm). When cultures reached an $OD_{600}$ of about 0.5, protein expression from each plasmid was induced by adding L-arabinose to a final concentration of 0.2% (w/v). The cultures were grown for an additional 18 hours at 18° C. with shaking (200 rpm). Cells were pelleted at 5000×g for 15 minutes at 4° C. Medium was disposed of and cell pellets were frozen at −80° C. for at least 4 hours. Cell pellets were thawed for 15 minutes on ice and resuspended in 15 mL of lysis buffer (20 mM tris pH 7.5, 500 mM NaCl, 1 mM $MgCl_2$, 10 mM imidazole, 120 units/mL DNaseI, 1 mM PMSF, 1 mM DTT) per liter of original culture. Cells were lysed by passage twice through a large French pressure cell at 16000 psi. Cell debris was pelleted at 20000×g for 30 minutes at 4° C. Supernatants were transferred to a 50-mL conical tubes, to which 2 ml of a 50% slurry of Ni-NTA resin (Qiagen) was added for binding the 6×His Tag of each expressed fusion protein. Each tube was slowly rotated at 4° C. for 1 hour and then applied to an empty gravity column through which the supernatant was allowed to flow. Flow-through sample (75 μL) was taken, added to 25 μL of 4×-reduced Laemmeli buffer, and stored on ice. The resin was washed four times in each column with 5 ml of wash buffer (20 mM tris pH 7.5, 500 mM NaCl, 10 mM imidazole, 1 mM PMSF, 1 mM DTT). A sample (75 μL) was taken from each wash, added to 25 μL of 4×-reduced Laemmeli buffer, and stored on ice. 1-ml aliquots of elution buffer (20 mM Tris pH 7.5, 500 mM NaCl, 1 mM $MgCl_2$, 500 mM imidazole, 1 mM PMSF, 1 mM DTT) were applied to the resin in each column and allowed to incubate for 10 minutes. Protein elution was monitored by absorbance at 280 nm. A sample (75 μL) was taken from each elution, added to 25 μL of 4×-reduced Laemmeli buffer, and stored on ice. For each plasmid expression experiment, fractions containing eluted protein from the column were combined, loaded into 10000 MWCO dialysis membrane, and dialyzed against dialysis buffer (25 mM HEPES/KOH pH 7.5, 200 mM KCl, 20% glycerol, 1 mM DTT) at 4° C. for at least 14 hours. The protein concentration of each dialysate was determined using the Bradford assay and absorbance at 565 nm. Purified protein was split into two aliquots, one of which was frozen at −80° C. and the other stored on ice at 4° C. Samples taken during the column purification process for each plasmid expression experiment were heated at 95° C. for 5 minutes and loaded onto an 8% (w/v) tris-glycine polyacrylamide resolving gel with a 4% (w/v) stacking gel. Proteins were electrophoretically separated at 200 volts for 30 minutes and stained with Coomassie blue. The gel for the 6×His-Zebra-Cas9-NLS purification process is shown in FIG. 4 as an example.

Thus, four different CPP-Cas9 fusion proteins were expressed and isolated. These fusion proteins represent examples of RGEN protein-CPP complexes herein.

Example 2

Expressing Short Guide RNA (sgRNA) by In Vitro Transcription

In this example, a DNA sequence was designed that encodes an sgRNA fused to ribozymes at its 5'- and 3'-ends (referred to as "RGR"), respectively. The RGR sequence allowed for in vitro transcription by T7 RNA polymerase of an sgRNA with precisely defined ends.

FIG. 5 illustrates an sgRNA molecule, which is a single RNA molecule containing two regions, a variable targeting domain (VT) (guide sequence) and Cas endonuclease recognition (CER) domain (SEQ ID NO:24 represents an example of a CER). The VT region can be a 20mer of RNA polynucleotide that has identity to a targeted nucleic acid molecule, for example. The VT domain specifies a target site for cleavage in the target site that lies 5' of a PAM motif. The CER domain interacts with Cas9 protein and allows the VT domain to interact and direct the Cas9 protein cleavage (Jinek et al., *Science* 337:816-821). Both VT and CER domains are required for the function of an sgRNA.

The addition of 5' HammerHead (HH) and 3' Hepatitis Delta Virus (HDV) ribozymes to an sgRNA sequence allows expression of the sgRNA from any promoter without consideration for certain transcriptional requirements of some RNA polymerases (e.g., T7 RNA polymerase requires one transcribed G residue directly after initiation of transcription, but works best with three transcribed G residues). When such sgRNA is expressed, the ribozymes present in the pre-sgRNA transcript autocleave, thereby separating from the transcript leaving an unmodified sgRNA.

A DNA sequence encoding an sgRNA that targets the Can1-1 locus (SEQ ID NO:25) in *Yarrowia lipolytica* was prepared; this sgRNA comprises SEQ ID NO:24 as its CER domain. The sgRNA-encoding sequence was linked at its 5'-end to sequence encoding an HH ribozyme (SEQ ID NO:26) and at its 3'-end to a sequence encoding an HDV ribozyme (SEQ ID NO:27), such that the first 6 bases of the HH ribozyme were a reverse compliment to the first 6 bases of the VT region of the sgRNA. This particular RGR sgRNA is encoded by SEQ ID NO:28. The RGR sgRNA of SEQ ID NO:28 was then linked to a T7 RNA polymerase promoter (SEQ ID NO:29) via standard molecular biology techniques to create plasmid pRF46 (SEQ ID NO:30).

T7-RGR sgRNA-encoding sequence was PCR-amplified from plasmid pRF46 (SEQ ID NO:30) using standard techniques. Primers for the PCR reaction were SEQ ID NO:31 (T7 forward primer) and SEQ ID NO:32 (gRNArev1 reverse primer). The PCR product was purified by ethanol precipitation and resuspended in $ddH_2O$; this DNA was used as template in an in vitro transcription reaction. Template DNA was added to a final concentration of 150 nM in 20-μL in vitro transcription reactions (MEGAshortscript™ T7 Kit, Life Technologies). Reactions were allowed to proceed for various times (2 hours, 4 hours, 6 hours, and overnight) to determine suitable conditions for in vitro transcription (FIG. 6). The reactions were then treated with 10 units of DNaseI for 15 minutes at 37° C. to remove template DNA. RNA was precipitated using ethanol and standard protocols. Each 20-μl in vitro transcription reaction produced between 60 and 100 μg of RNA.

Thus, sgRNA with defined 5'- and 3'-ends was synthesized in vitro. As demonstrated in Example 3 below, in vitro transcribed sgRNA can be associated with a Cas9-CPP fusion protein to form an RGEN-CPP complex.

Example 3

Specific In Vitro Cleavage of Target DNA Sequence Using Cas9-CPP Fusion Protein Complexed with sgRNA In this example, the targeting endonuclease function of Zebra CPP-Cas9 fusion protein (comprising SEQ ID NO:39) in complex with an sgRNA was tested to confirm that fusion with a CPP does not hinder Cas9 endonuclease activity.

An in vitro Can1 cleavage assay DNA polynucleotide (SEQ ID NO:35) containing the Can1-1 target sequence of SEQ ID NO:25 was PCR-amplified from *Y. lipolytica* cells (ATCC 20362) and purified using standard techniques. Primers for the PCR reaction were SEQ ID NO:33 (IV-up forward primer) and SEQ ID NO:34 (IV-down reverse primer).

Purified Zebra CPP-Cas9 fusion protein (600 ng, prepared in Example 1), sgRNA targeting the Can1-1 target site (250 ng, prepared in Example 2), NEBuffer 3.1 (New England BioLabs, Ipswich, Mass.), and Can1 cleavage assay DNA (150 ng, SEQ ID NO:35) were mixed in a 10-μL reaction (volume brought up to final volume with $ddH_2O$). As negative controls, reactions lacking either Zebra CPP-Cas9 fusion protein or sgRNA were also prepared. As a positive control, wild type Cas9 protein (PNA Bio, Thousand Oaks, Calif.) was used in a reaction instead of Zebra CPP-Cas9. The reactions were incubated at 37° C. for 60 minutes. RNaseI (4 μg) was then added to each reaction and incubated at 37° C. for 15 minutes to degrade the sgRNA. Stop solution (1 μL; 30% [w/v] glycerol, 1.2% [w/v] SDS, 250 mM EDTA, pH 8.0) was added to terminate the reactions, which were then further incubated for 15 minutes at 37° C. Each reaction was loaded onto a 1.2% FlashGel™ (Lonza, Basel, Switzerland) and electrophoresed for 10 minutes at 200 volts (FIG. 7). The target DNA cleavage pattern rendered by Zebra CPP-Cas9 was consistent with the cleavage pattern rendered by wild type Cas9 (FIG. 7), thereby indicating that Zebra CPP-Cas9 functions normally in vitro. Furthermore, this activity was not inhibited using Zebra CPP-Cas9/sgRNA that had been subjected to two freeze-thaw cycles.

Thus, a CPP-Cas9 fusion protein complexed with a suitable sgRNA (i.e., an example of an RGEN-CPP complex) had specific DNA cleavage activity. This activity was shown to be similar with the activity of a wild type Cas9-sgRNA complex, thereby indicating that CPP fusion does not inhibit Cas9-sgRNA endonucleolytic function. While the CPP-Cas9 fusion protein in this example comprised SEQ ID NO:39 (Zebra CPP-Cas9), it is contemplated that a CPP-Cas9 fusion protein comprising SEQ ID NO:40, 41, or 42, for example, also has cleavage activity when associated with a suitable sgRNA as an RNA component.

Example 4

Delivery of a CPP-Cas9/sgRNA Complex into Yeast Cells and Cleavage of Target DNA Therein In this example, Zebra CPP-Cas9 fusion protein (comprising SEQ ID NO:39) in complex with an sgRNA (Zebra CPP-Cas9/sgRNA) was tested for the ability to enter yeast cells after simple contact with the cells. Zebra CPP-Cas9/sgRNA specific for Can1-1 was able to enter cells and cleave the Can1 gene, thereby rendering cells to be canavanine-resistant.

*Y. lipolytica* yeast cells (ATCC 20362) were grown in YPD (2% glucose, 2% peptone, 1% yeast extract) liquid medium at 30° C. with shaking (220 rpm) to $OD_{600}=0.5$ (approximately $5\times10^6$ cells per mL of culture). Purified Zebra CPP-Cas9 fusion protein (prepared in Example 1) and sgRNA targeting the Can1-1 target site (prepared in Example 2) were mixed in a 1:3 molar ratio, respectively, in the dialysis buffer used in Example 1 and pre-incubated at room temperature for 15 minutes to allow the sgRNA to associate with the Zebra CPP-Cas9. $5\times10^5$ *Y. lipolytica* cells were mixed into the Zebra CPP-Cas9/sgRNA preparation such that the final concentration of Zebra CPP-Cas9 was 1 μM, 2.5 μM, or 5 μM. Cells were also mixed with 5 μM final concentration Zebra CPP-Cas9 alone (no sgRNA as RNA component) as a negative control. All the cell-Cas9 preparations were incubated at 30° C. with shaking (220 rpm) for 2 hours. The cells were then serially diluted 1000- and 10000-fold. Each serial dilution (100 μL) was plated onto complete medium lacking arginine (CM-Arg) and allowed to recover for 48 hours at 30° C.

Colonies of the $10^{-3}$-dilution plates were counted to determine the total number of cells plated. Colonies were transferred to CM-Arg plates with canavanine (60 μg/mL) via replica-plating technique. Colonies were allowed to grow at 30° C. for 48 hours. The number of canavanine-resistant colonies were scored and divided by the total number of colonies (from plates without canavanine) to determine a mutation frequency for each case. Contacting cells with Zebra CPP-Cas9/sgRNA complexes yielded colonies that were resistant to canavanine at frequencies of about 2% to 10% of the total colonies (FIG. 8). This canavanine-resistance is expected to be due to loss of Can1 gene function by indel formation at/near the predicted Cas9 cleavage site in the Can1 gene coding sequence. However, contacting cells with Zebra CPP-Cas9 alone (no sgRNA) did not yield canavanine-resistant colonies (FIG. 8), indicating that canavanine-resistance in the experimental cells was dependent on sgRNA-based specificity given to CPP-Cas9 protein. Given the nature of yeast cells, the CPP-Cas9/sgRNA complexes likely had to traverse both cell wall and cell membrane structures to mediate specific DNA targeting.

Thus, a CPP-Cas9 fusion protein complexed with a suitable sgRNA (i.e., an example of an RGEN-CPP complex) is able to enter yeast cells (traverse cell wall and cell membrane) and target a specific DNA sequence therein. While the CPP-Cas9 fusion protein in this example comprised SEQ ID NO:39 (Zebra CPP-Cas9), it is contemplated that a CPP-Cas9 fusion protein comprising SEQ ID NO: 40, 41, or 42, for example, also has cell-entry activity, and specific DNA targeting activity in cells, when associated with a suitable sgRNA as an RNA component.

Example 5

CPP-Facilitated Cas9/sgRNA Complex Delivery into Plant Cells and Cleavage of Target DNA Therein CPP-facilitated protein delivery into soybean cells can be tested by incubating soybean callus cells with DS-RED fluorescent proteins fused to CPPs. Fluorescent signals are expected in CPP-DS-RED treatments, but not in controls incubated with DS-RED proteins only. Various CPPs can be tested in this manner to help identify the most effective CPPs for plant cell penetration and delivery of protein cargo. Some examples of CPPs that can be tested include:

(i) a CPP from an Epstein-Barr virus Zebra trans-activator protein, (ii) a CPP having 6 or more contiguous arginine residues, (iii) a transportan-10 (TP10) CPP, (iv) a CPP from a vascular endothelium cadherin protein, or (vi) a CPP selected from the group consisting of a synthetic nona-arginine CPP, a histidine-rich nona-arginine CPP and a Pas nona-arginine CPP. Examples of a synthetic nona-arginine CPP, a histidine-rich nona-arginine CPP and a Pas nona-arginine CPP are disclosed in, for example, Liu et al. (*Advanced Studies in Biology* 5(2):71-88, HIKARI Ltd).

In vitro translated Cas9 proteins and synthetic sgRNA can be mixed with CPPs, by themselves or in a fusion (e.g., CPP-DS-RED above), and incubated with soybean callus to test if Cas9/sgRNA can be transported into the cells. Once in the cells, the Cas9/sgRNA complex can recognize a genomic target specified by the sgRNA targeting sequence to make DNA double strand breaks (DSBs). Spontaneous repair of the DSBs by cell machinery can result in mutations through non-homologous end joining (NHEJ), or gene integration through homologous recombination if appropriate donor DNA is present. CPPs can also be covalently linked to Cas9 proteins for potentially better efficiency. The success of CPP-Cas9/sgRNA delivery into soybean cells, and thus the transfer of the CPP-Cas endonuclease complex across a plant cell wall and plant cell membrane, can be verified by the detection of mutations or gene integrations at the specific target site by PCR analysis, for example.

Example 6

Expression and Purification of CPP-dsREDexpress Proteins from *E. coli* Cells To rapidly assess the ability of a given cell-penetrating peptide to enter a specific cell type CPP fusions to the dsREDexpress protein (SEQ ID NO: 85) were created, expressed in *E. coli* cells, and purified. The CPP-dsREDexpress protein fusions are a tool that allows rapid assessment of cargo delivery into a given cell type by a given CPP. This allows selection of a species, cell type, or strain specific CPP molecule to maximize delivery of cargo in a rapid and high-throughput manner by assessing cellular fluorescence by microscopic or flow cytometric analysis.

An *E. coli* codon optimized dsREDexpress gene (SEQ ID NO: 86) was synthesized (IDT DNA) and cloned into the NcoI/HinDIII sites of pBAD/HisB (SEQ ID NO: 87) creating pRF161 (SEQ ID NO: 88). The *E. coli* codon optimized dsREDexpress contained an internal EcoRI site such that digestion of the plasmid with NcoI/EcoRI would allow replacement of the his tag with various his tag-CPP sequences to create his tag-CPP-dsREDexpress fusion expression plasmids. Various his-tag-CPP fusions; TAT (SEQ ID NO: 89), TLM (SEQ ID NO: 90), MPG1 (SEQ ID NO: 91), pe μl (SEQ ID NO: 92), and CFFKDEL (SEQ ID NO: 93); were codon optimized for *E. coli* and flanked with in frame 5' NcoI and 3' EcoRI sites (SEQ ID NO: 94-98 respectively) and cloned using standard techniques into the NcoI/EcoRI sites of pRF161 (SEQ ID NO: 88) replacing the his tag sequence with the corresponding his tag-CPP fusion and generating plasmids pRF224 (his-TAT-dsREDexpress SEQ ID NO: 99), pRF214 (his-TLM-dsREDexpress SEQ ID NO: 100), pRF213 (his-MPG1-dsREDexpress SEQ ID NO: 101), pRF217 (his-pep1-dsREDexpress SEQ ID NO: 102), pRF216 (his-CFFKDEL-dsREDexpress SEQ ID NO: 103). Sequences of the inserted fragments were verified using standard sequencing techniques and oligo 36 (SEQ ID NO: 104).

*E. coli* codon optimized His-Zebra (SEQ ID NO: 105), His-tp10 (SEQ ID NO: 106), and His-pVEC (SEQ ID NO: 107) were PCR amplified from pRF144 (SEQ ID NO 108), pRF162 (SEQ ID NO 109), and pRF146 (SEQ ID NO: 110) respectively using oligo 36 (SEQ ID NO: 104) and oligo 153 (SEQ ID NO: 111) with standard PCR techniques. PCR fragments were cloned into the NcoI/EcoRI sites of pRF161 (SEQ ID NO: 88) creating plasmids pRF186 (his-Zebra-dsREDexpress SEQ ID NO:112), pRF192 (his-tp10-dsREDexpress SEQ ID NO: 113), and pRF190 (his-pVEC-dsREDexpress SEQ ID NO: 114). Sequences were verified using oligo 36 (SEQ ID NO: 104).

His tagged CPP-dsREDexpress fusion proteins were expressed using standard techniques. In brief, cells were precultured in either 10 ml ZYM-505 (1% N-Z amine, 0.5% yeast extract, 5% glycerol, 1.0% dextrose, 25 mM $Na_2HPO_4$, 25 mM $KH_2PO_4$, 50 mM $NH_4Cl$, 5 mM $Na_2SO_4$, 1× trace metals (Teknova), $5\times10^{-5}$% Thiamine, 2 mM $MgCl_2$, 100 μg/ml Ampicillin) or lysogeny broth (1% Tryptone, 0.5% yeast extract, 1% sodium chloride, 100 μg/ml Ampicillin, 0.4% dextrose) in 125 ml flasks for 12-16 hours at 37° C. and 220 RPM. Precultures were diluted 1:1000 (ZYM-505) in 500 ml ZYM-5052 (1% N-Z amine, 0.5% yeast extract, 5% glycerol, 0.5% dextrose, 2% L-arabinose, 25 mM $Na_2HPO_4$, 25 mM $KH_2PO_4$, 50 mM $NH_4Cl$, 5 mM $Na_2SO_4$, 1× trace metals (Teknova), $5\times10^{-5}$% Thiamine, 2 mM $MgCl_2$, 100 μg/ml Ampicillin) or 1:100 (Lysis broth) in 500 ml 2×YT (1.6% Tryptone, 1% Yeast extract, 0.5% NaCl, 100 μg/ml ampicillin) and grown at 37° C. 220 RPM in 2.9 L Fernbach flasks to $OD_{600}$~0.5. L-arabinose was added to a final concentration of 0.1% to 2×YT cultures and all cultures were shifted to 18° C. 220 R\PM for 20-30 hours for protein expression. Cells were harvested at 5000 RPM for 10 minutes, spent medium was discarded and cell pellets frozen at −80° C.

Cell pellets were thawed and resuspended in Denaturing lysis buffer (50 mM Tris pH8.0, 150 mM NaCl, 8M Urea, 20 mM Imidazole) and lysed via passage through a French pressure cell at 16,000 PSI twice. Solid precipitates were removed from the supernatant by centrifugation at 10,000 g 4° C. for 15 minutes. 20 μl of clarified extract was mixed with 20 μl of 2× Laemmli buffer (4% SDS, 20% Glycerol, 100 mM DTT, 0.004% bromophenol blue, 125 mM Tris pH 6.8), heated to 95° C. for 5 minutes and frozen at −20° C. to save for analysis. Clarified extract was mixed with 6 ml of 50% (v/v) Nickel-NTA-agarose slurry for 1 hour at room temperature. Beads were pelleted from mixture at 2000 RPM for 5 minutes. Supernatant was removed and a 20 μl sample was taken as for the clarified extract. The pelleted beads were resuspended in 10 ml of denaturing lysis buffer and applied to a gravity flow chromatography column. The liquid was allowed to flow out leaving a bed of packed beads. The bed was washed with a series washes using different ratios of wash buffer 1 (50 mM Tris pH8.0, 150 mM NaCl, 8M Urea, 20 mM Imidazole) and wash buffer 2 (50 mM Tris pH 8.0, 500 mM NaCl, 20 mM Imidazole) to step down the concentration of the denaturant (urea) and step up the concentration of NaCl and allow the protein to refold on the column. In brief the column was washed with (Buffer 1: Buffer 2): 10 ml of 1:0 (8M urea 150 mM NaCl), 10 ml of 7:1 (7M Urea, 194 mM NaCl), 10 ml of 3:1 (6M Urea, 238 mM NaCl) 10 ml of 5:3 (5M Urea, 281 mM NaCl), 10 ml of 1:1 (4M Urea, 325 mM NaCl), 20 ml of 3:5 (3M Urea, 369 mM NaCl), 20 ml of 1:3 (2M Urea, 413 mM NaCl), 20 ml of 3:13 (1.5M Urea, 434 mM NaCl), 20 ml of 1:5 (1M urea, 456 mM NaCl), 20 ml of 1:15 (0.5M Urea, 478 mM NaCl), and 30 ml of 0:1 (0M Urea, 500 mM NaCl). Protein was eluted in native elution buffer (50 mM Tris pH8.0, 500 mM NaCl, 10% Glycerol, 500 mM Imidazole) in 10×1 ml fractions. Fractions containing the eluted dsREDexpress or CPP-dsREDexpress protein were red in color. Red fractions were combined and dialyzed in 10,000 MWCO regenerated cellulose dialysis membrane against 1000 volumes of dialysis buffer (50 mM Tris pH 8.0, 10% glycerol) overnight at room temperature. Protein solution was removed from dialysis membrane and filter sterilized using a 0.22 μM Tuffryn® membrane. 20 μl of protein solution was processed as for the clarified cell extract.

Samples taken during the purification in Laemmli buffer were heated to 95° C. for 5 minutes and loaded onto a 12.5% PAGE gel. The gel was run at 200 volts constant for 1 hour and stained using simply blue stain. An example of a representative PAGE gel for the purification of CPP-dsREDexpress tagged proteins is shown in FIG. 9. Total protein concentration for each purified protein was determined using Pierce™ Coomassie Plus assay with bovine serum albumin as a standard. The concentration of each purified CPP-dsREDexpress fusion is given in Table 3.

TABLE 3

Concentration of purified dsREDexpress protein fusions.

| Protein | mg/ml | μM |
|---|---|---|
| dsREDexpress (SEQ ID NO: 700) | 3.8 | 137 |
| MPG1-dsREDexpress (SEQ ID NO: 751) | 0.5 | 17 |
| pVEC-dsREDexpress (SEQ ID NO: 752) | 2.0 | 68 |
| CFFKDEL-dsREDexpress (SEQ ID NO: 753) | 1.5 | 54 |
| TLM-dsREDexpress (SEQ ID NO: 754) | 2.5 | 86 |
| Zebra-dsREDexpress (SEQ ID NO: 755) | 0.5 | 18 |
| pep1-dsREDexpress (SEQ ID NO: 756) | 0.3 | 10 |
| tp10-dsREDexpress (SEQ ID NO: 757) | 0.9 | 33 |

Example 7

Expression and Purification of Additional CPP-Cas9 Proteins from *E. coli* Cells The delivery of Cas9 into different cell types may require Cas9 tagged with different CPP molecules. In order to isolate various CPP-Cas9 fusion proteins different CPPs were fused to Cas9 in an *E. coli* expression vector. These proteins were expressed and purified from *E. coli* cells for use in CPP mediated delivery of Cas9/sgRNA ribonucleoprotein complex to cells.

In order to make His-CFFKDEL-Cas9 (SEQ ID NO: 115) and His-MPG1-Cas9 (SEQ ID NO: 116) fusion expression cassettes the NcoI/EcoRI fragments of pRF216 (CFFKDEL SEQ ID NO: 103) or pRF213 (MPG1 SEQ ID NO: 101) were cloned into the same sites of the Cas9 protein expression plasmid pRF48 (SEQ ID NO: 117) using standard techniques generating plasmids pRF243 (his-CFFKDEL-Cas9 SEQ ID NO: 118) and pRF238 (his-MPG1-Cas9, SEQ ID NO: 119) respectively. Correct construction of the MPG1-Cas9 or CFFKDEL-Cas9 fusion cassettes was confirmed via Sanger sequencing with oligo 36 (SEQ ID NO: 104).

His tagged CPP-Cas9 fusion proteins were expressed using standard techniques. In brief, cells were precultured in either 10 ml ZYM-505 (1% N-Z amine, 0.5% yeast extract, 5% glycerol, 1.0% dextrose, 25 mM $Na_2HPO_4$, 25 mM $KH_2PO_4$, 50 mM $NH_4Cl$, 5 mM $Na_2SO_4$, 1× trace metals (Teknova), 5x10-5% Thiamine, 2 mM $MgCl_2$, 100 μg/ml Ampicillin) or lysogeny broth (1% Tryptone, 0.5% yeast extract, 1% sodium chloride, 100 μg/ml Ampicillin, 0.4% dextrose) in 125 ml flasks for 12-16 hours at 37° C. and 220 RPM. Precultures were diluted 1:1000 (ZYM-505) in 500 ml ZYM-5052 (1% N-Z amine, 0.5% yeast extract, 5% glycerol, 0.5% dextrose, 2% L-arabinose, 25 mM $Na_2HPO_4$, 25 mM $KH_2PO_4$, 50 mM $NH_4Cl$, 5 mM $Na_2SO_4$, 1× trace metals (Teknova), 5x10-5% Thiamine, 2 mM $MgCl_2$, 100 μg/ml Ampicillin) or 1:100 (Lysis broth) in 500 ml 2×YT (1.6% Tryptone, 1% Yeast extract, 0.5% NaCl, 100 μg/ml ampicillin) and grown at 37° C. 220 RPM in 2.9 L Fernbach flasks to $OD_{600}$~0.5. L-arabinose was added to a final concentration of 0.1% to 2×YT cultures and all cultures were shifted to 18° C. 220 R\PM for 20-30 hours for protein expression. Cells were harvested at 5000 RPM for 10 minutes, spent medium was discarded and cell pellets frozen at −80° C. Proteins were purified as described in Example 1. The final concentrations of the purified CPP-Cas9 proteins as determined by Coomasie Plus assay (Pierce™) are listed in Table 4.

TABLE 4

| Concentration of purified CPP-Cas9 proteins. | | |
|---|---|---|
| Protein | mg/ml | μM |
| Zebra-Cas9 (SEQ ID NO: 758) | 1.5 | 9 |
| CFFKDEL-Cas9 (SEQ ID NO: 730) | 4.6 | 28 |
| MPG1-Cas9 (SEQ ID NO: 731) | 3.8 | 23 |
| pVEC-Cas9 (SEQ ID NO: 759) | 2.5 | 15 |

Example 8

CPP-Cas9/gRNA Mediated Gene Targeting in *E. coli* Cells

This example demonstrates the treatment of *Escherichia coli* cells with CPP-Cas9/sgRNA ribonucleoprotein complexes with sgRNAs targeting the galK gene of *E. coli*. The entry of the CPP-Cas9/sgRNA into the cell allows targeting and cleavage to occur within the galK gene leading to gene inactivation by error-prone DNA repair mechanisms which can be phenotypically monitored as resistance to galactose. This method depends on delivery of Cas9/sgRNA cargo to the cells via CPP-mediated delivery.

The galK gene of *E. coli* (SEQ ID NO: 120) is responsible for a galactose sensitive phenotype seen in galE mutants in the presence of the sugar galactose. As galactose enters the cell it is phosphorylated by galactokinase, the product of the galK gene (SEQ ID NO: 120). Galactose phosphate is toxic to the cell. In wild-type cells the galactose phosphate is further metabolized by the products of the gale (SEQ ID NO: 121) and galT (SEQ ID NO: 122) genes and used as a carbon source. In galE or galT loss-of-function mutants galactose phosphate accumulates leading to cell death. Therefore, loss of function mutations in the galK gene can be selected in the background of a galE mutant as allowing colony formation in the presence of galactose.

In order to produce sgRNA (SEQ ID NO: 135) targeting the galK gene (SEQ ID NO: 120) at the galK2-1 target site (SEQ ID NO: 134) an in vitro transcription template (SEQ ID NO: 131) was produced. First a PCR product of the DNA encoding the CER domain (SEQ ID NO: 123) was amplified from pRF291 (SEQ ID NO: 125) using CER forward (SEQ ID NO: 126) and universal reverse primers (SEQ ID NO: 127) in a standard PCR reaction (SEQ ID NO: 124). The CER encoding PCR product (SEQ ID NO: 124) was purified using Zymo™ clean and concentrate 25 columns and eluted in 35 μl of $ddH_2O$. Amplification of the sgRNA in vitro transcription template used a multiplex PCR containing 4 primers, a universal forward primer containing the T7 promoter (SEQ ID NO: 128), a target specific forward primer containing some of the T7 promoter and some of the target site (SEQ ID NO: 129), a target reverse primer containing some of the target site and overlap with the CER domain (SEQ ID NO: 130), and the universal reverse primer (SEQ ID NO: 127). A PCR reaction was run using Phusion flash master mix containing 15 nM CER domain PCR product (SEQ ID NO: 124), 1 μM each the universal forward (SEQ ID NO: 128) and reverse primers (SEQ ID NO: 127) and 300 nM each target forward (SEQ ID NO: 129) and target reverse (SEQ ID NO: 130) primers. The PCR reaction was cycled as for a standard reaction. sgRNA in vitro transcription template (SEQ ID NO: 131) was purified using Zymo clean and concentrate 25 columns and eluted in 35 μl of $ddH_2O$. The sgRNA in vitro transcription template (SEQ ID NO: 131) contained the T7 promoter (SEQ ID NO: 132), the DNA encoding the galK2-1 variable targeting domain (SEQ ID NO: 133), and the DNA encoding the CER domain (SEQ ID NO: 125) The in vitro transcription reaction to create the galK2-1 sgRNA (SEQ ID NO: 135) was performed as described in Example 2.

CPP delivery of Cas9/sgRNA nucleoprotein complexes was performed by growing a strain of *E. coli* deleted for galE in lysogeny broth (1% Tryptone, 0.5% Yeast Extract, 1% NACl) overnight at 37° C., 220 RPM. The culture was diluted 1:100 in fresh lysogeny broth and grown at 37° C., 220 RPM for 2 hours to obtain cells in exponential growth phase. CPP-Cas9 (pvEC-Cas9 (SEQ ID NO: 144), Zebra-Cas9 (SEQ ID NO: 143), MPG1-Cas9 (SEQ ID NO: 116), CFFKDEL-Cas9 (SEQ ID NO: 115)) were incubated at 10 μM final concentration either in the presence or absence of 10 μM galK2-1 sgRNA (SEQ ID NO: 135) in a 50 μl volume for 30 minutes at room temperature. For the treatment 1.2 ml of cells were pelleted at 3000 RPM for 3 minutes, supernatant was discarded and cells were resuspended in 600 μl of LB containing 2× nuclease buffer (200 mM NaCl, 100 mM Tris-HCl, 20 mM $MgCl_2$, 200 μg/ml BSA pH 7.9). 50 μl of the cell suspension was mixed with each reaction as well as gRNA only control and no treatment. Samples were incubated at 37° C., 220 RPM for 4 hours. 100 μl of $10^{-3}$, $10^{-4}$, and $10^{-5}$ dilutions of the samples were plated on lysogeny broth plates to obtain a viable cell count at the end of the treatment, the remainder of the reaction was plated onto lysogeny broth plates and incubated overnight at 37° C. Viable cells were counted from the $10^{-5}$ dilution to determine the number of viable colony forming units (CFU) plated on the sample lysogeny broth plate. The sample plates were replica plated via standard techniques to minimal A medium (1 g/L $(NH_4)_2SO_4$, 4.5 g/L $KH_2PO_4$, 10.5 g/L $K_2HPO_4$, 0.5 g/L sodium Citrate.$2H_2O$, 1 mM $MgSO_4.7H_2O$, $5\times10^{-5}$% Thiamine) solidified with 1.5% (w/v) Bacto agar containing 0.2% (w/v) glycerol and 0.2% (w/v) galactose as carbon sources. The plates were incubated at 37° C. for 24 hours and then scored for formation of colonies. Each CFU from a galE strain on a plate containing galactose represents a gene inactivation event of the galK gene. The results of the replica plating are shown in Table 5.

TABLE 5

Frequency of galK gene inactivation in galE mutant *E. coli* cells treated with CPP-Cas9/sgRNA.

| Cas9 protein | sgRNA | CFU on galactose | CFU plated on galactose | Frequency of $Gal^R$ CFU | Fold Frequency $Gal^R$/ untreated $Gal^R$ frequency |
|---|---|---|---|---|---|
| None | None | 21 | $1.65 \times 10^8$ | $1.27 \times 10^{-7}$ | 1.00 |
| pVEC-Cas9 | None | 21 | $1.18 \times 10^8$ | $1.78 \times 10^{-7}$ | 1.39 |
| pVEC-Cas9 | galK2-1 | 15 | $1.23 \times 10^8$ | $1.22 \times 10^{-7}$ | 0.96 |
| MPG1-Cas9 | None | 22 | $1.34 \times 10^8$ | $1.65 \times 10^{-7}$ | 1.29 |
| MPG1-Cas9 | galK2-1 | 16 | $1.11 \times 10^8$ | $1.44 \times 10^{-7}$ | 1.13 |
| Zebra-Cas9 | None | 29 | $1.89 \times 10^8$ | $1.53 \times 10^{-7}$ | 1.20 |
| Zebra-Cas9 | galK2-1 | 25 | $8.88 \times 10^7$ | $2.82 \times 10^{-7}$ | 2.21 |
| CFFKDEL-Cas9 | None | 29 | $1.24 \times 10^8$ | $2.34 \times 10^{-7}$ | 1.84 |

TABLE 5-continued

Frequency of galK gene inactivation in galE mutant *E. coli* cells treated with CPP-Cas9/sgRNA.

| Cas9 protein | sgRNA | CFU on galactose | CFU plated on galactose | Frequency of $Gal^R$ CFU | Fold Frequency $Gal^R$/ untreated $Gal^R$ frequency |
|---|---|---|---|---|---|
| CFFKDEL-Cas9 | galK2-1 | 63 | $1.24 \times 10^8$ | $5.10 \times 10^{-7}$ | 4.00 |
| None | galK2-1 | 31 | $1.42 \times 10^8$ | $2.19 \times 10^{-7}$ | 1.72 |

The treatment of *E. coli* cells with CPP-Cas9/sgRNA ribonucleoprotein complexes in some cases enhanced the frequency of galK inactivation around 4 fold over the background of untreated cells. This enhancement was not seen in cells treated with only CPP-Cas9 or sgRNA only suggesting that the increased inactivation of the galK gene was due to the CPP-Cas9/sgRNA ribonucleoprotein entering the cell and making DNA double-stranded breaks at the galK2-1 target site within the galK gene.

Example 9

Delivery of CPP-dsREDexpress Protein to Archeal Cells

In order to test the delivery of cargo using cell-penetrating peptides to Archeal cells and determine candidate CPPs that cross the archeal cell wall which includes elements that are similar to bacterial and eukaryotic cell walls (eg. phospholipids) and membranes and elements that are distinctly archeal (eg. S-layer) archeal cells were treated with CPP-dsREDexpress protein fusions. The CPPs identified in this screen could be used to deliver other cargo (eg. Cas9/sgRNA ribonucleoprotein complex) to Archeal cells.

The archeon *Halobacterium salinarum* ATCC19700 was grown on medium 213 (250 g/L NaCl, 10 g/L $MgSO_4.7H_2O$, 5 g/L KCl, 0.2 g/L $CaCl_2.6H_2O$, 10 g/L Yeast extract, 2.5 g/L Tryptone) solidified with 1.5% Bacto agar at 37° C. until colonies formed (4 days). A single colony was used to inoculate 50 ml of medium 213 in a 250 ml flask. The culture was grown at 37° C. 220 RPM until the $OD_{600}$ reached approximately 0.5 indicating exponential growth phase. 100 μl of cells were mixed with either No protein, 5 μM dsREDexpress (SEQ ID NO: 85), 5 μM MPG1-dsREDexpress (SEQ ID NO: 136), 5 μM pVEC-dsREDexpress (SEQ ID NO: 137), 5 μM CFFKDEL-dsREDexpress (SEQ ID NO: 138), 5 μM TLM-dsREDexpress (SEQ ID NO: 139), 5 μM pep1-dsREDexpress (SEQ ID NO: 141), or 5 μM tp10 dsRED-express (SEQ ID NO: 142) in a 24 well block. Mixtures were incubated for 4 hours at 37° C. 220 RPM. Cells were washed twice with medium 213 lacking tryptone and yeast extract and resuspended in 100 μl of medium 213 lacking tryptone and yeast extract. Cells were analyzed for fluorescence in the red channel of an Accuri C5 flow cytometer to determine which CPP tags had delivered the dsREDexpress cargo to *H. salinarum* cells. The untreated cells were used to create an analysis gate for the flow cytometry data between non-red and red cells such that the gate created a false positive frequency of 0.2% of the untreated cells falling in the red gate (Table 6).

TABLE 6

CPP delivery of dsREDexpress to *H. salinarum*.

| Treatment | Percent of population in red cell gate ± standard deviation[1] | Fold increase in red population over dsREDexpress alone |
|---|---|---|
| No dsREDexpress | 0.21 ± 0.06 | 0.73 |
| dsREDexpress | 0.29 ± 0.21 | 1.00 |
| MPG1-dsREDexpress | 0.37 ± 0.08 | 1.27 |
| pVEC-dsREDexpress | 16.87 ± 9.90 | 57.50 |
| CFFKDEL-dsREDexpress | 0.33 ± 0.14 | 1.14 |
| TLM-dsREDexpress | 2.03 ± 1.02 | 6.93 |
| pep1-dsREDexpress | 0.36 ± 0.18 | 1.23 |
| tp10-dsREDexpress | 0.91 ± 0.27 | 3.09 |

[1]Data represents three replicates ± standard deviation.

The delivery of the dsREDexpress cargo into archeal cells demonstrates that at least three of the cell-penetrating peptides (pVEC, TLM, tp10) are capable of delivering a protein cargo to the archeal cells with an efficiency as high as more than 50 fold that of the delivery of the dsREDexpress protein alone suggesting that these three CPP motifs can be used to deliver other cargo to archeal cells (eg. Cas9 ribonucleoprotein complex). Additionally the CPP motifs deliver cargo to as much 16% of the entire cell population suggesting that deliver of cargo by CPP to archeal cells is an efficient process.

Example 10

Delivery of CPP-dsREDexpress Protein to Eukaryotic Cells

To test the ability of cell-penetrating peptides to deliver cargo to different eukaryotic species a panel of three species, *Phytophthora capsici* (Oomycete), *Septori tritici* (True Fungus), and *Botrytis cinerea* (True Fungus) was treated with various CPP-dsREDexpress fusions. The delivery of dsREDexpress cargo was monitored for various CPP moieties by FACS analysis to determine the percentage of cells to which the cargo was delivered. CPPs that are capable of delivering the dsREDexpress cargo to these cells which suggests that the CPPs would be capable of delivering other cargos to these classes of eukaryotic cells (eg. Cas9/sgRNA ribonucleoprotein complex).

*P. capsici* was grown on V8 medium (20% V8 juice, 4.5 g/L $CaCO_3$) solidified with 1.8% Bacto Agar at 23° C. in the dark for 3 days. The plate was then placed in the light at 23° C. for an additional 7 days. Plates were chilled at 4° C. for 30 minutes. Water was placed on the plate to just cover the surface and allowed to incubate for 30 minutes at room temperature. Liquid was removed to harvest zoospores. Zoospores were confirmed via microscopic analysis. An equal volume of 2× encystment medium (40 g/L Tryptone, 10 g/L Yeast extract, 200 ml/L 10×SOC salts [5.84 g/L NaCl, 1.86 g/L KCl, 20.3 g/L $MgCl_2.6H_2O$, 24.6 g/L $MgSO_4.7H_2O$, 36 g/L Dextrose], 36.4 g/L Sorbitol, 1.47 g/L $CaCl_2.2H_2O$) was added to the zoospores and gently mixed. Zoospores in enzystment medium were incubated for 20 minutes at room temperature. Encystment was confirmed microscopically. Spores were pelleted and resuspended in an equal volume of YMA medium (2 g/L Yeast extract, 4 g/L Malt extract) and counted using a hemocytometer. Zoospores were diluted to $3\times10^7$ spores/ml in YMA. 100 μl of Zoospores in YMA were mixed with various dsREDexpress fusion proteins (New example 5, table N1) to a final concentration of 5 μM protein. Mixtures were incubated at 25° C. 400 RPM for 2 hours. Cells were washed twice with phosphate buffered saline (PBS) (8 g/L NaCl, 0.2 g/L KCl, 1.44 g/L $Na_2HPO_4.2H_2O$, 0.24 g/L $KH_2PO_4$ pH 6.8) and resuspended in a final volume of 200 µl PBS. Uptake of dsREDexpress fusion proteins was monitored using flow cytometry as for *Halobacterium salinarium* (Example 9). The percent of cells to which the cargo was successfully delivered was determined by drawing an arbitrary gate in the dsREDexpress treated cells such that 0.1% of the population scored as a false positive red event (1:1000 cells). The results of this treatment can be seen in Table 7. pVEC, pep1, and tp10 produce 5.8, 5.5, and 1.8 fold more red cells than the dsREDexpress treated cells alone suggesting that these CPP moieties might be candidates for delivering other cargo to Oomycetes (eg. Cas9/sgRNA ribonucleoprotein complex)

TABLE 7

CPP delivery of dsREDexpress to *Phytophora capsici.*

| Treatment | Percent of population in red cell gate ± standard deviation[1] | Fold increase in red population over dsREDexpress alone |
|---|---|---|
| dsREDexpress | 0.10 ± 0.03 | 1.00 |
| pVEC-dsREDexpress | 0.56 ± 0.16 | 5.79 |
| CFFKDEL-dsREDexpress | 0.01 ± 0.01 | 0.07 |
| TLM-dsREDexpress | 0.00 ± 0.00 | 0.00 |
| pep1-dsREDexpress | 0.53 ± 0.29 | 5.52 |
| Tp10-dsREDexpress | 0.17 ± 0.14 | 1.76 |
| MPG-dsREDexpress | 0.00 ± 0.00 | 0.00 |
| Zebra-dsREDexpress | 0.03 ± 0.05 | 0.34 |

[1]Data represents three biological replicates ± standard deviation

*B. cinerea* was grown on PDA medium (24 g/L potato dextrose broth) solidified with 1.8% Bacto agar in the dark for 5 to 10 days. Conidia were harvested in water with a sterile plastic spreader and filtered through 2 layers of cheesecloth. Conidia were counted on a hemocytometer and diluted to $3\times10^7$ conidia per ml in YMA medium. 100 µl of conidia in YMA were mixed with various dsREDexpress fusion proteins (New example 5, table N1) to a final concentration of 5 µM protein. Mixtures were incubated at 25° C. 400 RPM for 2 hours. Cells were washed twice with phosphate buffered saline (PBS) (8 g/L NaCl, 0.2 g/L KCl, 1.44 g/L $Na_2HPO_4.2H_2O$, 0.24 g/L $KH_2PO_4$ pH 6.8) and resuspended in a final volume of 200 µl PBS. Uptake of dsREDexpress fusion proteins was monitored using flow cytometry as for *Halobacterium salinarium* (Example 8). The percent of cells to which the cargo was successfully delivered was determined by drawing an arbitrary gate in the dsREDexpress treated cells such that 0.1% of the population scored as a false positive red event (1:1000 cells). The results of this treatment can be seen in Table 8.

TABLE 8

CPP delivery of dsREDexpress to *Botrytis cinerea*

| Treatment | Percent of population in red cell gate ± standard deviation[1] | Fold increase in red population over dsREDexpress alone |
|---|---|---|
| dsREDexpress | 0.12 ± 0.04 | 1.00 |
| pVEC-dsREDexpress | 0.08 ± 0.10 | 0.68 |
| CFFKDEL-dsREDexpress | 0.03 ± 0.01 | 0.22 |
| TLM-dsREDexpress | 0.01 ± 0.01 | 0.05 |
| pep1-dsREDexpress | 0.01 ± 0.01 | 0.05 |
| Tp10-dsREDexpress | 0.03 ± 0.02 | 0.24 |
| MPG-dsREDexpress | 0.01 ± 0.02 | 0.11 |
| Zebra-dsREDexpress | 0.01 ± 0.02 | 0.11 |

[1]Data represents three biological replicates ± standard deviation

*S. tritici* was grown on YMA medium solidified with 1.8% Bacto agar at 23° C. in light. Conidia were harvested after 5 to 10 days with a sterile plastic spreader and water. Conidia was counted on a hemocytometer and diluted to $3\times10^7$ conidia in YMA medium. 100 µl of conidia in YMA were mixed with various dsREDexpress fusion proteins (New example 5, table N1) to a final concentration of 5 µM protein. Mixtures were incubated at 25° C. 400 RPM for 2 hours. Cells were washed twice with phosphate buffered saline (PBS) (8 g/L NaCl, 0.2 g/L KCl, 1.44 g/L $Na_2HPO_4.2H_2O$, 0.24 g/L $KH_2PO_4$ pH 6.8) and resuspended in a final volume of 200 µl PBS. Uptake of dsREDexpress fusion proteins was monitored using flow cytometry as for *Halobacterium salinarium* (Example 9). The percent of cells to which the cargo was successfully delivered was determined by drawing an arbitrary gate in the dsREDexpress treated cells such that 0.1% of the population scored as a false positive red event (1:1000 cells). The results of this treatment can be seen in Table 9. pVEC, TLM, pep1, and tp10 increased the delivery of dsREDexpress 25, 4, 3, and 5 fold respectively compared to dsREDexpress alone. This suggests that these CPPs would be good candidates for the delivery of other cargo to True fungi (eg. Cas9/sgRNA ribonucleoprotein complex).

TABLE 9

CPP delivery of dsREDexpress to *Septoria tritici*

| Treatment | Percent of population in red cell gate ± standard deviation[1] | Fold increase in red population over dsREDexpress alone |
|---|---|---|
| dsREDexpress | 0.12 ± 0.03 | 1.00 |
| pVEC-dsREDexpress | 3.02 ± 0.91 | 25.2 |
| CFFKDEL-dsREDexpress | 0.00 ± 0.01 | 0.03 |
| TLM-dsREDexpress | 0.48 ± 0.14 | 4.03 |
| pep1-dsREDexpress | 0.37 ± 0.21 | 3.06 |
| Tp10-dsREDexpress | 0.71 ± 0.69 | 5.94 |
| MPG-dsREDexpress | 0.14 ± 0.05 | 1.17 |
| Zebra-dsREDexpress | 0.00 ± 0.00 | 0.00 |

[1]Data represents three biological replicates ± standard deviation

Example 11

Delivery of Seven CPPs-dsRED and Two CPPs-tagRFP into Seven Gut Bacteria

In this example, the efficiency of CPPs in delivering two cargo proteins, dsRED and tag RFP, into 7 gut bacterial species (whose beneficial effects on host physiology have been demonstrated) was tested.

Bacterial cells were grown in appropriate media (see Table 10) overnight at 37° C. in a rotary shaker at 150 rpm in an anaerobic tent (80% $N_2$, 15% $CO_2$, and 5% $H_2$). For the assay, $1\times10^8$ bacterial cells were mixed with a final concentration of 5 uM of CPPs-dsRED and CPPs-tagRFP proteins in a 96 well plate, followed by two hours outgrowth at 37° C. To measure the dsRED and RFP fluorescence signals in cells, bacterial cells were harvested by centrifugation (3,500×g, 4° C., 20 min) and washed twice in phosphate buffered saline (100 ul per well). Fluorescence intensities were quantitated with Tecan Spark 10M plate reader (Tecan, Männedorf, Switzerland) equipped with 554 nm excitation and 586 nm emission filters with 10 nm bandwidth. Raw fluorescence values were subtracted from that of the untreated cells (background). The fluorescence intensity values of 7000 as a minimum cutoff was taken for delivery of CPPs inside the cells.

TABLE 10

Culture medium of 7 bacterial species

| Bacteria | Phylum | Culture medium |
|---|---|---|
| *Bacteroides thetaiotaomicron* | Bacteroidetes | Brain and Heart Infusion supplemented with 10% bovine blood (Blood BHI) |
| *Eubacterium hallii* | Firmicutes | Blood BHI |
| *Faecalibacterium prausnitzii* | Firmicutes | Blood BHI |
| *Blautia hydrogenotrophica* | Firmicutes | YCFA |
| *Bacteroides fragilis* | Bacteroidetes | Blood BHI |
| *Prevotella histicola* | Bacteroidetes | Blood BHI |
| *Clostridium scindens* | Firmicutes | YCFA |

As shown in Table 11, these results indicate that five CPPs including MPG, pVEC, TLM, ZEBRA, and pep1 were effectively delivered into the anaerobic gut bacteria belonging to the phyla Firmicutes and Bacteroidetes, thereby indicating that the CPP's can traverse through the cell membrane of these (Table 9).

TABLE 11

Differential delivery efficiencies of CPPs in different bacterial strains as demonstrated by the fluorescence intensity above the cutoff value of 7000

| | MPG-1-dsRED | pVEC-dsRED | TLM-dsRED | ZEBRA-dsRED | pep1-dsRED |
|---|---|---|---|---|---|
| *Bacteroides thetaiotaomicron* | — | — | — | 10230 | 16657 |
| *Eubacterium hallii* | 10015 | 17156 | — | 16894 | 7004 |
| *Faecalibacterium prausnitzii* | — | 40525 | 14998 | 17014 | 12696 |
| *Blautia hydrogenotrophica* | — | 11770 | 14612 | 9623 | — |
| *Bacteroides fragilis* | — | 14783 | — | 15026 | — |
| *Prevotella histicola* | — | — | — | 22416 | — |
| *Clostridium scindens* | — | 17677 | 32492 | — | — |

What is claimed is:

1. A method for modifying a target site in the genome of a microbial cell, the method comprising providing a guide polynucleotide, a cell-penetrating peptide (CPP) and a Cas endonuclease to the microbial cell, wherein said guide polynucleotide, Cas endonuclease and CPP are covalently, or non-covalently, linked to each other in a guide polynucleotide/Cas endonuclease-CPP complex, and wherein said guide polynucleotide/Cas endonuclease-CPP complex can traverse (i) a cell membrane, or (ii) a cell wall and cell membrane, of the microbial cell, wherein the guide polynucleotide and CPP-Cas endonuclease are capable of forming a complex that enables the Cas endonuclease to introduce a double-strand break at the target site in the genome of the microbial cell.

2. The method of claim 1, wherein the modifying at said target site includes (i) a replacement of at least one nucleotide, (ii) a deletion of at least one nucleotide, (iii) an insertion of at least one nucleotide, or (iv) any combination of (i)-(iii).

3. The method of claim 1, further comprising identifying at least one microbial cell that has a modification at the target site, wherein the modification at the target site is selected from the group consisting of (i) a replacement of at least one nucleotide, (ii) a deletion of at least one nucleotide, (iii) an insertion of at least one nucleotide, and (iv) any combination of (i)-(iii).

4. The method of claim 1, wherein the microbial cell further comprises a donor polynucleotide comprising at least one sequence homologous to a sequence at or near the target site sequence, and wherein the donor polynucleotide integrates at or near the target site sequence by homologous recombination.

5. The method of claim 1 wherein said Cas endonuclease and CPP are covalently linked to each other.

6. The method of claim 1, wherein said Cas endonuclease and CPP are non-covalently linked to each other.

7. The method of claim 1, wherein the guide polynucleotide comprises (i) a first nucleotide sequence domain that is complementary to a nucleotide sequence in said target site, and (ii) a second nucleotide sequence domain that interacts with a Cas endonuclease, wherein the first nucleotide sequence domain and the second nucleotide sequence domain are composed of deoxyribonucleic acids (DNA), ribonucleic acids (RNA), or a combination thereof.

8. The method of any preceding claims, wherein the guide polynucleotide is composed of ribonucleic acids (RNA).

9. The method of claim 1, wherein the guide polynucleotide/Cas endonuclease-CPP complex is a RNA-guided endonuclease (RGEN)-CPP complex.

10. The method of claim 9, wherein the RGEN comprises a CRISPR-associated (Cas) protein-9 (Cas9) amino acid sequence.

* * * * *

SEQUENCE LISTING

```
<160> NUMBER OF SEQ ID NOS: 144

<210> SEQ ID NO 1
<211> LENGTH: 4107
<212> TYPE: DNA
<213> ORGANISM: artificial sequence
<220> FEATURE:
<223> OTHER INFORMATION: S. pyogenes Cas9

<400> SEQUENCE: 1

atggacaaga aatactccat cggcctggac attggaacca actctgtcgg ctgggctgtc      60

atcaccgacg agtacaaggt gccctccaag aaattcaagg tcctcggaaa caccgatcga     120

cactccatca agaaaaacct cattggtgcc ctgttgttcg attctggcga gactgccgaa     180

gctaccagac tcaagcgaac tgctcggcga cgttacaccc gacggaagaa ccgaatctgc     240

tacctgcagg agatcttttc caacgagatg gccaaggtgg acgattcgtt ctttcatcga     300

ctggaggaat ccttcctcgt cgaggaagac aagaaacacg agcgtcatcc catctttggc     360

aacattgtgg acgaggttgc ttaccacgag aagtatccta ccatctacca cctgcgaaag     420

aaactcgtcg attccaccga caaggcggat ctcagactta tctacctcgc tctggcacac     480

atgatcaagt ttcgaggtca tttcctcatc gagggcgatc tcaatcccga caacagcgat     540

gtggacaagc tgttcattca gctcgttcag acctacaacc agctgttcga ggaaaacccc     600

atcaatgcct ccggagtcga tgcaaaggcc atcttgtctg ctcgactctc gaagagcaga     660

cgactggaga acctcattgc ccaacttcct ggcgagaaaa agaacggact gtttggcaac     720

ctcattgccc tttctcttgg tctcacaccc aacttcaagt ccaacttcga tctggcggag     780

gacgccaagc tccagctgtc caaggacacc tacgacgatg acctcgacaa cctgcttgca     840

cagattggcg atcagtacgc cgacctgttt ctcgctgcca agaacctttc ggatgctatt     900

ctcttgtctg acattctgcg agtcaacacc gagatcacaa aggctcccct ttctgcctcc     960
```

```
atgatcaagc gatacgacga gcaccatcag gatctcacac tgctcaaggc tcttgtccga   1020
cagcaactgc ccgagaagta caaggagatc tttttcgatc agtcgaagaa cggctacgct   1080
ggatacatcg acggcggagc ctctcaggaa gagttctaca agttcatcaa gccaattctc   1140
gagaagatgg acggaaccga ggaactgctt gtcaagctca atcgagagga tctgcttcgg   1200
aagcaacgaa ccttcgacaa cggcagcatt cctcatcaga tccacctcgg tgagctgcac   1260
gccattcttc gacgtcagga agacttctac ccctttctca aggacaaccg agagaagatc   1320
gagaagattc ttacctttcg aatcccctac tatgttggtc ctcttgccag aggaaactct   1380
cgatttgctt ggatgactcg aaagtccgag gaaaccatca ctccctggaa cttcgaggaa   1440
gtcgtggaca agggtgcctc tgcacagtcc ttcatcgagc gaatgaccaa cttcgacaag   1500
aatctgccca acgagaaggt tcttcccaag cattcgctgc tctacgagta ctttacagtc   1560
tacaacgaac tcaccaaagt caagtacgtt accgagggaa tgcgaaagcc tgccttcttg   1620
tctggcgaac agaagaaagc cattgtcgat ctcctgttca agaccaaccg aaaggtcact   1680
gttaagcagc tcaaggagga ctacttcaag aaaatcgagt gtttcgacag cgtcgagatt   1740
tccggagttg aggaccgatt caacgcctct ttgggcacct atcacgatct gctcaagatt   1800
atcaaggaca aggattttct cgacaacgag gaaaacgagg acattctgga ggacatcgtg   1860
ctcactctta ccctgttcga agatcgggag atgatcgagg aacgactcaa gacatacgct   1920
cacctgttcg acgacaaggt catgaaacaa ctcaagcgac gtagatacac cggctgggga   1980
agactttcgc gaaagctcat caacggcatc agagacaagc agtccggaaa gaccattctg   2040
gactttctca agtccgatgg ctttgccaac cgaaacttca tgcagctcat tcacgacgat   2100
tctcttacct tcaaggagga catccagaag gcacaagtgt ccggtcaggg cgacagcttg   2160
cacgaacata ttgccaacct ggctggttcg ccagccatca agaaaggcat tctccagact   2220
gtcaaggttg tcgacgagct ggtgaaggtc atgggacgtc acaagcccga gaacattgtg   2280
atcgagatgg ccagagagaa ccagacaact caaaagggtc agaaaaactc gcgagagcgg   2340
atgaagcgaa tcgaggaagg catcaaggag ctgggatccc agattctcaa ggagcatccc   2400
gtcgagaaca ctcaactgca gaacgagaag ctgtatctct actatctgca gaatggtcga   2460
gacatgtacg tggatcagga actggacatc aatcgtctca gcgactacga tgtggaccac   2520
attgtccctc aatcctttct caaggacgat tctatcgaca acaaggtcct tacacgatcc   2580
gacaagaaca gaggcaagtc ggacaacgtt cccagcgaag aggtggtcaa aaagatgaag   2640
aactactggc gacagctgct caacgccaag ctcattaccc agcgaaagtt cgacaatctt   2700
accaaggccg agcgaggcgg tctgtccgag ctcgacaagg ctggcttcat caagcgtcaa   2760
ctcgtcgaga ccagacagat cacaaagcac gtcgcacaga ttctcgattc tcggatgaac   2820
accaagtacg acgagaacga caagctcatc cgagaggtca aggtgattac tctcaagtcc   2880
aaactggtct ccgatttccg aaaggacttt cagttctaca aggtgcgaga gatcaacaat   2940
taccaccatg cccacgatgc ttacctcaac gccgtcgttg gcactgcgct catcaagaaa   3000
taccccaagc tcgaaagcga gttcgtttac ggcgattaca aggtctacga cgttcgaaag   3060
atgattgcca agtccgaaca ggagattggc aaggctactg ccaagtactt cttttactcc   3120
aacatcatga actttttcaa gaccgagatc accttggcca acggagagat tcgaaagaga   3180
ccacttatcg agaccaacgg cgaaactgga gagatcgtgt gggacaaggg tcgagacttt   3240
gcaaccgtgc gaaaggttct gtcgatgcct caggtcaaca tcgtcaagaa aaccgaggtt   3300
cagactggcg gattctccaa ggagtcgatt ctgcccaagc gaaactccga caagctcatc   3360
```

```
gctcgaaaga aagactggga tcccaagaaa tacggtggct tcgattctcc taccgtcgcc   3420

tattccgtgc ttgtcgttgc gaaggtcgag aagggcaagt ccaaaaagct caagtccgtc   3480

aaggagctgc tcggaattac catcatggag cgatcgagct tcgagaagaa tcccatcgac   3540

ttcttggaag ccaagggtta caaggaggtc aagaaagacc tcattatcaa gctgcccaag   3600

tactctctgt tcgaactgga gaacggtcga aagcgtatgc tcgcctccgc tggcgagctg   3660

cagaagggaa acgagcttgc cttgccttcg aagtacgtca actttctcta tctggcttct   3720

cactacgaga agctcaaggg ttctcccgag gacaacgaac agaagcaact cttcgttgag   3780

cagcacaaac attacctcga cgagattatc gagcagattt ccgagttttc gaagcgagtc   3840

atcctggctg atgccaactt ggacaaggtg ctctctgcct acaacaagca tcgggacaaa   3900

cccattcgag aacaggcgga gaacatcatt cacctgttta ctcttaccaa cctgggtgct   3960

cctgcagctt tcaagtactt cgataccact atcgaccgaa agcggtacac atccaccaag   4020

gaggttctcg atgccaccct gattcaccag tccatcactg gcctgtacga gacccgaatc   4080

gacctgtctc agcttggtgg cgactaa                                       4107


<210> SEQ ID NO 2
<211> LENGTH: 4140
<212> TYPE: DNA
<213> ORGANISM: artificial sequence
<220> FEATURE:
<223> OTHER INFORMATION: S. pyogenes Cas9 with NLS

<400> SEQUENCE: 2

atggacaaga aatactccat cggcctggac attggaacca actctgtcgg ctgggctgtc     60

atcaccgacg agtacaaggt gccctccaag aaattcaagg tcctcggaaa caccgatcga    120

cactccatca agaaaaacct cattggtgcc ctgttgttcg attctggcga gactgccgaa    180

gctaccagac tcaagcgaac tgctcggcga cgttacaccc gacggaagaa ccgaatctgc    240

tacctgcagg agatcttttc caacgagatg gccaaggtgg acgattcgtt ctttcatcga    300

ctggaggaat ccttcctcgt cgaggaagac aagaaacacg agcgtcatcc catctttggc    360

aacattgtgg acgaggttgc ttaccacgag aagtatccta ccatctacca cctgcgaaag    420

aaactcgtcg attccaccga caaggcggat ctcagactta tctacctcgc tctggcacac    480

atgatcaagt ttcgaggtca tttcctcatc gagggcgatc tcaatcccga caacagcgat    540

gtggacaagc tgttcattca gctcgttcag acctacaacc agctgttcga ggaaaacccc    600

atcaatgcct ccggagtcga tgcaaaggcc atcttgtctg ctcgactctc gaagagcaga    660

cgactggaga acctcattgc ccaacttcct ggcgagaaaa agaacggact gtttggcaac    720

ctcattgccc tttctcttgg tctcacaccc aacttcaagt ccaacttcga tctggcggag    780

gacgccaagc tccagctgtc caaggacacc tacgacgatg acctcgacaa cctgcttgca    840

cagattggcg atcagtacgc cgacctgttt ctcgctgcca agaacctttc ggatgctatt    900

ctcttgtctg acattctgcg agtcaacacc gagatcacaa aggctcccct ttctgcctcc    960

atgatcaagc gatacgacga gcaccatcag gatctcacac tgctcaaggc tcttgtccga   1020

cagcaactgc ccgagaagta caaggagatc tttttcgatc agtcgaagaa cggctacgct   1080

ggatacatcg acggcggagc ctctcaggaa gagttctaca agttcatcaa gccaattctc   1140

gagaagatgg acggaaccga ggaactgctt gtcaagctca atcgagagga tctgcttcgg   1200

aagcaacgaa ccttcgacaa cggcagcatt cctcatcaga tccacctcgg tgagctgcac   1260
```

-continued

```
gccattcttc gacgtcagga agacttctac ccctttctca aggacaaccg agagaagatc   1320
gagaagattc ttacctttcg aatcccctac tatgttggtc ctcttgccag aggaaactct   1380
cgatttgctt ggatgactcg aaagtccgag gaaaccatca ctccctggaa cttcgaggaa   1440
gtcgtggaca agggtgcctc tgcacagtcc ttcatcgagc gaatgaccaa cttcgacaag   1500
aatctgccca acgagaaggt tcttcccaag cattcgctgc tctacgagta ctttacagtc   1560
tacaacgaac tcaccaaagt caagtacgtt accgagggaa tgcgaaagcc tgccttcttg   1620
tctggcgaac agaagaaagc cattgtcgat ctcctgttca agaccaaccg aaaggtcact   1680
gttaagcagc tcaaggagga ctacttcaag aaaatcgagt gtttcgacag cgtcgagatt   1740
tccggagttg aggaccgatt caacgcctct ttgggcacct atcacgatct gctcaagatt   1800
atcaaggaca aggattttct cgacaacgag gaaaacgagg acattctgga ggacatcgtg   1860
ctcactctta ccctgttcga agatcgggag atgatcgagg aacgactcaa gacatacgct   1920
cacctgttcg acgacaaggt catgaaacaa ctcaagcgac gtagatacac cggctgggga   1980
agactttcgc gaaagctcat caacggcatc agagacaagc agtccggaaa gaccattctg   2040
gactttctca agtccgatgg ctttgccaac cgaaacttca tgcagctcat tcacgacgat   2100
tctcttacct tcaaggagga catccagaag gcacaagtgt ccggtcaggg cgacagcttg   2160
cacgaacata ttgccaacct ggctggttcg ccagccatca agaaaggcat tctccagact   2220
gtcaaggttg tcgacgagct ggtgaaggtc atgggacgtc acaagcccga gaacattgtg   2280
atcgagatgg ccagagagaa ccagacaact caaaagggtc agaaaaactc gcgagagcgg   2340
atgaagcgaa tcgaggaagg catcaaggag ctgggatccc agattctcaa ggagcatccc   2400
gtcgagaaca ctcaactgca gaacgagaag ctgtatctct actatctgca gaatggtcga   2460
gacatgtacg tggatcagga actggacatc aatcgtctca gcgactacga tgtggaccac   2520
attgtccctc aatcctttct caaggacgat tctatcgaca acaaggtcct tacacgatcc   2580
gacaagaaca gaggcaagtc ggacaacgtt cccagcgaag aggtggtcaa aaagatgaag   2640
aactactggc gacagctgct caacgccaag ctcattaccc agcgaaagtt cgacaatctt   2700
accaaggccg agcgaggcgg tctgtccgag ctcgacaagg ctggcttcat caagcgtcaa   2760
ctcgtcgaga ccagacagat cacaaagcac gtcgcacaga ttctcgattc tcggatgaac   2820
accaagtacg acgagaacga caagctcatc cgagaggtca aggtgattac tctcaagtcc   2880
aaactggtct ccgatttccg aaaggacttt cagttctaca aggtgcgaga gatcaacaat   2940
taccaccatg cccacgatgc ttacctcaac gccgtcgttg gcactgcgct catcaagaaa   3000
taccccaagc tcgaaagcga gttcgtttac ggcgattaca aggtctacga cgttcgaaag   3060
atgattgcca agtccgaaca ggagattggc aaggctactg ccaagtactt cttttactcc   3120
aacatcatga actttttcaa gaccgagatc accttggcca acggagagat tcgaaagaga   3180
ccacttatcg agaccaacgg cgaaactgga gagatcgtgt gggacaaggg tcgagacttt   3240
gcaaccgtgc gaaaggttct gtcgatgcct caggtcaaca tcgtcaagaa aaccgaggtt   3300
cagactggcg gattctccaa ggagtcgatt ctgcccaagc gaaactccga caagctcatc   3360
gctcgaaaga aagactggga tcccaagaaa tacggtggct tcgattctcc taccgtcgcc   3420
tattccgtgc ttgtcgttgc gaaggtcgag aagggcaagt ccaaaaagct caagtccgtc   3480
aaggagctgc tcggaattac catcatggag cgatcgagct tcgagaagaa tcccatcgac   3540
ttcttggaag ccaagggtta caaggaggtc aagaaagacc tcattatcaa gctgcccaag   3600
tactctctgt tcgaactgga gaacggtcga aagcgtatgc tcgcctccgc tggcgagctg   3660
```

cagaagggaa acgagcttgc cttgccttcg aagtacgtca actttctcta tctggcttct 3720
cactacgaga agctcaaggg ttctcccgag gacaacgaac agaagcaact cttcgttgag 3780
cagcacaaac attacctcga cgagattatc gagcagattt ccgagttttc gaagcgagtc 3840
atcctggctg atgccaactt ggacaaggtg ctctctgcct acaacaagca tcgggacaaa 3900
cccattcgag aacaggcgga gaacatcatt cacctgttta ctcttaccaa cctgggtgct 3960
cctgcagctt tcaagtactt cgataccact atcgaccgaa agcggtacac atccaccaag 4020
gaggttctcg atgccaccct gattcaccag tccatcactg gcctgtacga gacccgaatc 4080
gacctgtctc agcttggtgg cgactccaga gccgatccca agaaaaagcg aaaggtctaa 4140

<210> SEQ ID NO 3
<211> LENGTH: 1379
<212> TYPE: PRT
<213> ORGANISM: artificial sequence
<220> FEATURE:
<223> OTHER INFORMATION: S. pyogenes Cas9 with NLS

<400> SEQUENCE: 3

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp

-continued

```
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700
```

-continued

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110
```

```
Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

Ser Arg  Ala Asp Pro Lys Lys  Lys Arg Lys Val
    1370                 1375
```

<210> SEQ ID NO 4
<211> LENGTH: 543
<212> TYPE: DNA
<213> ORGANISM: Yarrowia lipolytica

<400> SEQUENCE: 4

```
tcgacgttta aaccatcatc taagggcctc aaaactacct cggaactgct gcgctgatct     60

ggacaccaca gaggttccga gcactttagg ttgcaccaaa tgtcccacca ggtgcaggca    120

gaaaacgctg gaacagcgtg tacagtttgt cttaacaaaa agtgagggcg ctgaggtcga    180

gcagggtggt gtgacttgtt atagccttta gagctgcgaa agcgcgtatg gatttggctc    240

atcaggccag attgagggtc tgtggacaca tgtcatgtta gtgtacttca atcgccccct    300

ggatatagcc ccgacaatag gccgtggcct cattttttg ccttccgcac atttccattg    360

ctcggtaccc acaccttgct tctcctgcac ttgccaacct taatactggt ttacattgac    420

caacatctta caagcggggg gcttgtctag ggtatatata aacagtggct ctcccaatcg    480

gttgccagtc tcttttttcc tttctttccc cacagattcg aaatctaaac tacacatcac    540
```

acc 543

<210> SEQ ID NO 5
<211> LENGTH: 4683
<212> TYPE: DNA
<213> ORGANISM: artificial sequence
<220> FEATURE:
<223> OTHER INFORMATION: Cas9-NLS expression cassette (FBA1 promoter and Cas9-NLS open reading frame)

<400> SEQUENCE: 5
tcgacgttta aaccatcatc taagggcctc aaaactacct cggaactgct gcgctgatct 60
ggacaccaca gaggttccga gcactttagg ttgcaccaaa tgtcccacca ggtgcaggca 120
gaaaacgctg gaacagcgtg tacagtttgt cttaacaaaa agtgagggcg ctgaggtcga 180
gcagggtggt gtgacttgtt atagccttta gagctgcgaa agcgcgtatg gatttggctc 240
atcaggccag attgagggtc tgtggacaca tgtcatgtta gtgtacttca atcgccccct 300
ggatatagcc ccgacaatag gccgtggcct cattttttg ccttccgcac atttccattg 360
ctcggtaccc acaccttgct tctcctgcac ttgccaacct taatactggt ttacattgac 420
caacatctta caagcggggg gcttgtctag ggtatatata aacagtggct ctcccaatcg 480
gttgccagtc tcttttttcc tttctttccc cacagattcg aaatctaaac tacacatcac 540
accatggaca agaaatactc catcggcctg gacattggaa ccaactctgt cggctgggct 600
gtcatcaccg acgagtacaa ggtgccctcc aagaaattca aggtcctcgg aaacaccgat 660
cgacactcca tcaagaaaaa cctcattggt gccctgttgt tcgattctgg cgagactgcc 720
gaagctacca gactcaagcg aactgctcgg cgacgttaca cccgacggaa gaaccgaatc 780
tgctacctgc aggagatctt ttccaacgag atggccaagg tggacgattc gttctttcat 840
cgactggagg aatccttcct cgtcgaggaa gacaagaaac acgagcgtca tcccatcttt 900
ggcaacattg tggacgaggt tgcttaccac gagaagtatc ctaccatcta ccacctgcga 960
aagaaactcg tcgattccac cgacaaggcg gatctcagac ttatctacct cgctctggca 1020
cacatgatca agtttcgagg tcatttcctc atcgagggcg atctcaatcc cgacaacagc 1080
gatgtggaca agctgttcat tcagctcgtt cagacctaca accagctgtt cgaggaaaac 1140
cccatcaatg cctccggagt cgatgcaaag gccatcttgt ctgctcgact ctcgaagagc 1200
agacgactgg agaacctcat tgcccaactt cctggcgaga aaaagaacgg actgtttggc 1260
aacctcattg ccctttctct tggtctcaca cccaacttca agtccaactt cgatctggcg 1320
gaggacgcca agctccagct gtccaaggac acctacgacg atgacctcga caacctgctt 1380
gcacagattg gcgatcagta cgccgacctg tttctcgctg ccaagaacct ttcggatgct 1440
attctcttgt ctgacattct gcgagtcaac accgagatca caaaggctcc cctttctgcc 1500
tccatgatca agcgatacga cgagcaccat caggatctca cactgctcaa ggctcttgtc 1560
cgacagcaac tgcccgagaa gtacaaggag atcttttttcg atcagtcgaa gaacggctac 1620
gctggataca tcgacggcgg agcctctcag gaagagttct acaagttcat caagccaatt 1680
ctcgagaaga tggacggaac cgaggaactg cttgtcaagc tcaatcgaga ggatctgctt 1740
cggaagcaac gaaccttcga caacggcagc attcctcatc agatccacct cggtgagctg 1800
cacgccattc ttcgacgtca ggaagacttc taccccttttc tcaaggacaa ccgagagaag 1860
atcgagaaga ttcttacctt tcgaatcccc tactatgttg gtcctcttgc cagaggaaac 1920
tctcgatttg cttggatgac tcgaaagtcc gaggaaacca tcactccctg gaacttcgag 1980

-continued

```
gaagtcgtgg acaagggtgc ctctgcacag tccttcatcg agcgaatgac caacttcgac   2040
aagaatctgc ccaacgagaa ggttcttccc aagcattcgc tgctctacga gtactttaca   2100
gtctacaacg aactcaccaa agtcaagtac gttaccgagg gaatgcgaaa gcctgccttc   2160
ttgtctggcg aacagaagaa agccattgtc gatctcctgt tcaagaccaa ccgaaaggtc   2220
actgttaagc agctcaagga ggactacttc aagaaaatcg agtgtttcga cagcgtcgag   2280
atttccggag ttgaggaccg attcaacgcc tctttgggca cctatcacga tctgctcaag   2340
attatcaagg acaaggattt tctcgacaac gaggaaaacg aggacattct ggaggacatc   2400
gtgctcactc ttaccctgtt cgaagatcgg gagatgatcg aggaacgact caagacatac   2460
gctcacctgt tcgacgacaa ggtcatgaaa caactcaagc gacgtagata caccggctgg   2520
ggaagacttt cgcgaaagct catcaacggc atcagagaca agcagtccgg aaagaccatt   2580
ctggactttc tcaagtccga tggctttgcc aaccgaaact tcatgcagct cattcacgac   2640
gattctctta ccttcaagga ggacatccag aaggcacaag tgtccggtca gggcgacagc   2700
ttgcacgaac atattgccaa cctggctggt tcgccagcca tcaagaaagg cattctccag   2760
actgtcaagg ttgtcgacga gctggtgaag gtcatgggac gtcacaagcc cgagaacatt   2820
gtgatcgaga tggccagaga gaaccagaca actcaaaagg gtcagaaaaa ctcgcgagag   2880
cggatgaagc gaatcgagga aggcatcaag gagctgggat cccagattct caaggagcat   2940
cccgtcgaga acactcaact gcagaacgag aagctgtatc tctactatct gcagaatggt   3000
cgagacatgt acgtggatca ggaactggac atcaatcgtc tcagcgacta cgatgtggac   3060
cacattgtcc ctcaatcctt tctcaaggac gattctatcg acaacaaggt ccttacacga   3120
tccgacaaga acagaggcaa gtcggacaac gttcccagcg aagaggtggt caaaaagatg   3180
aagaactact ggcgacagct gctcaacgcc aagctcatta cccagcgaaa gttcgacaat   3240
cttaccaagg ccgagcgagg cggtctgtcc gagctcgaca aggctggctt catcaagcgt   3300
caactcgtcg agaccagaca gatcacaaag cacgtcgcac agattctcga ttctcggatg   3360
aacaccaagt acgacgagaa cgacaagctc atccgagagg tcaaggtgat tactctcaag   3420
tccaaactgg tctccgattt ccgaaaggac tttcagttct acaaggtgcg agagatcaac   3480
aattaccacc atgcccacga tgcttacctc aacgccgtcg ttggcactgc gctcatcaag   3540
aaatacccca agctcgaaag cgagttcgtt tacggcgatt acaaggtcta cgacgttcga   3600
aagatgattg ccaagtccga acaggagatt ggcaaggcta ctgccaagta cttcttttac   3660
tccaacatca tgaacttttt caagaccgag atcaccttgg ccaacggaga gattcgaaag   3720
agaccactta tcgagaccaa cggcgaaact ggagagatcg tgtgggacaa gggtcgagac   3780
tttgcaaccg tgcgaaaggt tctgtcgatg cctcaggtca acatcgtcaa gaaaaccgag   3840
gttcagactg gcggattctc caaggagtcg attctgccca agcgaaactc cgacaagctc   3900
atcgctcgaa agaaagactg ggatcccaag aaatacggtg gcttcgattc tcctaccgtc   3960
gcctattccg tgcttgtcgt tgcgaaggtc gagaagggca agtccaaaaa gctcaagtcc   4020
gtcaaggagc tgctcggaat taccatcatg gagcgatcga gcttcgagaa gaatcccatc   4080
gacttcttgg aagccaaggg ttacaaggag gtcaagaaag acctcattat caagctgccc   4140
aagtactctc tgttcgaact ggagaacggt cgaaagcgta tgctcgcctc cgctggcgag   4200
ctgcagaagg gaaacgagct tgccttgcct tcgaagtacg tcaactttct ctatctggct   4260
tctcactacg agaagctcaa gggttctccc gaggacaacg aacagaagca actcttcgtt   4320
```

gagcagcaca aacattacct cgacgagatt atcgagcaga tttccgagtt ttcgaagcga 4380
gtcatcctgg ctgatgccaa cttggacaag gtgctctctg cctacaacaa gcatcgggac 4440
aaacccattc gagaacaggc ggagaacatc attcacctgt ttactcttac caacctgggt 4500
gctcctgcag ctttcaagta cttcgatacc actatcgacc gaaagcggta cacatccacc 4560
aaggaggttc tcgatgccac cctgattcac cagtccatca ctggcctgta cgagacccga 4620
atcgacctgt ctcagcttgg tggcgactcc agagccgatc ccaagaaaaa gcgaaaggtc 4680
taa 4683

<210> SEQ ID NO 6
<211> LENGTH: 10706
<212> TYPE: DNA
<213> ORGANISM: artificial sequence
<220> FEATURE:
<223> OTHER INFORMATION: pZUFCas9 plasmid

<400> SEQUENCE: 6
catggacaag aaatactcca tcggcctgga cattggaacc aactctgtcg gctgggctgt 60
catcaccgac gagtacaagg tgccctccaa gaaattcaag gtcctcggaa acaccgatcg 120
acactccatc aagaaaaacc tcattggtgc cctgttgttc gattctggcg agactgccga 180
agctaccaga ctcaagcgaa ctgctcggcg acgttacacc cgacggaaga accgaatctg 240
ctacctgcag gagatctttt ccaacgagat ggccaaggtg gacgattcgt tctttcatcg 300
actggaggaa tccttcctcg tcgaggaaga caagaaacac gagcgtcatc ccatctttgg 360
caacattgtg gacgaggttg cttaccacga gaagtatcct accatctacc acctgcgaaa 420
gaaactcgtc gattccaccg acaaggcgga tctcagactt atctacctcg ctctggcaca 480
catgatcaag tttcgaggtc atttcctcat cgagggcgat ctcaatcccg acaacagcga 540
tgtggacaag ctgttcattc agctcgttca gacctacaac cagctgttcg aggaaaaccc 600
catcaatgcc tccggagtcg atgcaaaggc catcttgtct gctcgactct cgaagagcag 660
acgactggag aacctcattg cccaacttcc tggcgagaaa aagaacggac tgtttggcaa 720
cctcattgcc ctttctcttg gtctcacacc caacttcaag tccaacttcg atctggcgga 780
ggacgccaag ctccagctgt ccaaggacac ctacgacgat gacctcgaca acctgcttgc 840
acagattggc gatcagtacg ccgacctgtt tctcgctgcc aagaaccttt cggatgctat 900
tctcttgtct gacattctgc gagtcaacac cgagatcaca aaggctcccc tttctgcctc 960
catgatcaag cgatacgacg agcaccatca ggatctcaca ctgctcaagg ctcttgtccg 1020
acagcaactg cccgagaagt acaaggagat ctttttcgat cagtcgaaga acggctacgc 1080
tggatacatc gacggcggag cctctcagga agagttctac aagttcatca agccaattct 1140
cgagaagatg gacggaaccg aggaactgct tgtcaagctc aatcgagagg atctgcttcg 1200
gaagcaacga accttcgaca acggcagcat tcctcatcag atccacctcg gtgagctgca 1260
cgccattctt cgacgtcagg aagacttcta cccctttctc aaggacaacc gagagaagat 1320
cgagaagatt cttacctttc gaatccccta ctatgttggt cctcttgcca gaggaaactc 1380
tcgatttgct tggatgactc gaaagtccga ggaaaccatc actccctgga acttcgagga 1440
agtcgtggac aagggtgcct ctgcacagtc cttcatcgag cgaatgacca acttcgacaa 1500
gaatctgccc aacgagaagg ttcttcccaa gcattcgctg ctctacgagt actttacagt 1560
ctacaacgaa ctcaccaaag tcaagtacgt taccgaggga atgcgaaagc ctgccttctt 1620
gtctggcgaa cagaagaaag ccattgtcga tctcctgttc aagaccaacc gaaaggtcac 1680

```
tgttaagcag ctcaaggagg actacttcaa gaaaatcgag tgtttcgaca gcgtcgagat   1740
ttccggagtt gaggaccgat tcaacgcctc tttgggcacc tatcacgatc tgctcaagat   1800
tatcaaggac aaggattttc tcgacaacga ggaaaacgag gacattctgg aggacatcgt   1860
gctcactctt accctgttcg aagatcggga gatgatcgag gaacgactca agacatacgc   1920
tcacctgttc gacgacaagg tcatgaaaca actcaagcga cgtagataca ccggctgggg   1980
aagactttcg cgaaagctca tcaacggcat cagagacaag cagtccggaa agaccattct   2040
ggactttctc aagtccgatg gctttgccaa ccgaaacttc atgcagctca ttcacgacga   2100
ttctcttacc ttcaaggagg acatccagaa ggcacaagtg tccggtcagg gcgacagctt   2160
gcacgaacat attgccaacc tggctggttc gccagccatc aagaaaggca ttctccagac   2220
tgtcaaggtt gtcgacgagc tggtgaaggt catgggacgt cacaagcccg agaacattgt   2280
gatcgagatg gccagagaga accagacaac tcaaaagggt cagaaaaact cgcgagagcg   2340
gatgaagcga atcgaggaag gcatcaagga gctgggatcc cagattctca aggagcatcc   2400
cgtcgagaac actcaactgc agaacgagaa gctgtatctc tactatctgc agaatggtcg   2460
agacatgtac gtggatcagg aactggacat caatcgtctc agcgactacg atgtggacca   2520
cattgtccct caatcctttc tcaaggacga ttctatcgac aacaaggtcc ttacacgatc   2580
cgacaagaac agaggcaagt cggacaacgt tcccagcgaa gaggtggtca aaaagatgaa   2640
gaactactgg cgacagctgc tcaacgccaa gctcattacc cagcgaaagt tcgacaatct   2700
taccaaggcc gagcgaggcg gtctgtccga gctcgacaag gctggcttca tcaagcgtca   2760
actcgtcgag accagacaga tcacaaagca cgtcgcacag attctcgatt ctcggatgaa   2820
caccaagtac gacgagaacg acaagctcat ccgagaggtc aaggtgatta ctctcaagtc   2880
caaactggtc tccgatttcc gaaaggactt tcagttctac aaggtgcgag agatcaacaa   2940
ttaccaccat gcccacgatg cttacctcaa cgccgtcgtt ggcactgcgc tcatcaagaa   3000
ataccccaag ctcgaaagcg agttcgttta cggcgattac aaggtctacg acgttcgaaa   3060
gatgattgcc aagtccgaac aggagattgg caaggctact gccaagtact tcttttactc   3120
caacatcatg aactttttca agaccgagat caccttggcc aacggagaga ttcgaaagag   3180
accacttatc gagaccaacg gcgaaactgg agagatcgtg tgggacaagg gtcgagactt   3240
tgcaaccgtg cgaaaggttc tgtcgatgcc tcaggtcaac atcgtcaaga aaaccgaggt   3300
tcagactggc ggattctcca aggagtcgat tctgcccaag cgaaactccg acaagctcat   3360
cgctcgaaag aaagactggg atcccaagaa atacggtggc ttcgattctc ctaccgtcgc   3420
ctattccgtg cttgtcgttg cgaaggtcga gaagggcaag tccaaaaagc tcaagtccgt   3480
caaggagctg ctcggaatta ccatcatgga gcgatcgagc ttcgagaaga atcccatcga   3540
cttcttggaa gccaagggtt acaaggaggt caagaaagac ctcattatca agctgcccaa   3600
gtactctctg ttcgaactgg agaacggtcg aaagcgtatg ctcgcctccg ctggcgagct   3660
gcagaaggga aacgagcttg ccttgccttc gaagtacgtc aactttctct atctggcttc   3720
tcactacgag aagctcaagg gttctcccga ggacaacgaa cagaagcaac tcttcgttga   3780
gcagcacaaa cattacctcg acgagattat cgagcagatt tccgagtttt cgaagcgagt   3840
catcctggct gatgccaact tggacaaggt gctctctgcc tacaacaagc atcgggacaa   3900
acccattcga gaacaggcgg agaacatcat tcacctgttt actcttacca acctgggtgc   3960
tcctgcagct ttcaagtact tcgataccac tatcgaccga aagcggtaca catccaccaa   4020
```

-continued

```
ggaggttctc gatgccaccc tgattcacca gtccatcact ggcctgtacg agacccgaat   4080
cgacctgtct cagcttggtg gcgactccag agccgatccc aagaaaaagc gaaaggtcta   4140
agcggccgca agtgtggatg gggaagtgag tgcccggttc tgtgtgcaca attggcaatc   4200
caagatggat ggattcaaca cagggatata gcgagctacg tggtggtgcg aggatatagc   4260
aacggatatt tatgtttgac acttgagaat gtacgataca agcactgtcc aagtacaata   4320
ctaaacatac tgtacatact catactcgta cccgggcaac ggtttcactt gagtgcagtg   4380
gctagtgctc ttactcgtac agtgtgcaat actgcgtatc atagtctttg atgtatatcg   4440
tattcattca tgttagttgc gtacgagccg gaagcataaa gtgtaaagcc tggggtgcct   4500
aatgagtgag ctaactcaca ttaattgcgt tgcgctcact gcccgctttc cagtcgggaa   4560
acctgtcgtg ccagctgcat taatgaatcg gccaacgcgc ggggagaggc ggtttgcgta   4620
ttgggcgctc ttccgcttcc tcgctcactg actcgctgcg ctcggtcgtt cggctgcggc   4680
gagcggtatc agctcactca aaggcggtaa tacggttatc cacagaatca ggggataacg   4740
caggaaagaa catgtgagca aaaggccagc aaaaggccag gaaccgtaaa aaggccgcgt   4800
tgctggcgtt tttccatagg ctccgccccc ctgacgagca tcacaaaaat cgacgctcaa   4860
gtcagaggtg gcgaaacccg acaggactat aaagatacca ggcgtttccc cctggaagct   4920
ccctcgtgcg ctctcctgtt ccgaccctgc cgcttaccgg atacctgtcc gcctttctcc   4980
cttcgggaag cgtggcgctt tctcatagct cacgctgtag gtatctcagt tcggtgtagg   5040
tcgttcgctc caagctgggc tgtgtgcacg aaccccccgt tcagcccgac cgctgcgcct   5100
tatccggtaa ctatcgtctt gagtccaacc cggtaagaca cgacttatcg ccactggcag   5160
cagccactgg taacaggatt agcagagcga ggtatgtagg cggtgctaca gagttcttga   5220
agtggtggcc taactacggc tacactagaa ggacagtatt tggtatctgc gctctgctga   5280
agccagttac cttcggaaaa agagttggta gctcttgatc cggcaaacaa accaccgctg   5340
gtagcggtgg tttttttgtt tgcaagcagc agattacgcg cagaaaaaaa ggatctcaag   5400
aagatccttt gatcttttct acggggtctg acgctcagtg gaacgaaaac tcacgttaag   5460
ggattttggt catgagatta tcaaaaagga tcttcaccta gatcctttta aattaaaaat   5520
gaagttttaa atcaatctaa agtatatatg agtaaacttg gtctgacagt taccaatgct   5580
taatcagtga ggcacctatc tcagcgatct gtctatttcg ttcatccata gttgcctgac   5640
tccccgtcgt gtagataact acgatacggg agggcttacc atctggcccc agtgctgcaa   5700
tgataccgcg agacccacgc tcaccggctc cagatttatc agcaataaac cagccagccg   5760
gaagggccga gcgcagaagt ggtcctgcaa ctttatccgc ctccatccag tctattaatt   5820
gttgccggga agctagagta agtagttcgc cagttaatag tttgcgcaac gttgttgcca   5880
ttgctacagg catcgtggtg tcacgctcgt cgtttggtat ggcttcattc agctccggtt   5940
cccaacgatc aaggcgagtt acatgatccc ccatgttgtg caaaaaagcg gttagctcct   6000
tcggtcctcc gatcgttgtc agaagtaagt tggccgcagt gttatcactc atggttatgg   6060
cagcactgca taattctctt actgtcatgc catccgtaag atgcttttct gtgactggtg   6120
agtactcaac caagtcattc tgagaatagt gtatgcggcg accgagttgc tcttgcccgg   6180
cgtcaatacg ggataatacc gcgccacata gcagaacttt aaaagtgctc atcattggaa   6240
aacgttcttc ggggcgaaaa ctctcaagga tcttaccgct gttgagatcc agttcgatgt   6300
aacccactcg tgcacccaac tgatcttcag catcttttac tttcaccagc gtttctgggt   6360
gagcaaaaac aggaaggcaa aatgccgcaa aaaagggaat aagggcgaca cggaaatgtt   6420
```

```
gaatactcat actcttcctt tttcaatatt attgaagcat ttatcagggt tattgtctca   6480
tgagcggata catatttgaa tgtatttaga aaaataaaca aataggggtt ccgcgcacat   6540
ttccccgaaa agtgccacct gacgcgccct gtagcggcgc attaagcgcg gcgggtgtgg   6600
tggttacgcg cagcgtgacc gctacacttg ccagcgccct agcgcccgct cctttcgctt   6660
tcttcccttc ctttctcgcc acgttcgccg gctttccccg tcaagctcta aatcgggggc   6720
tccctttagg gttccgattt agtgctttac ggcacctcga ccccaaaaaa cttgattagg   6780
gtgatggttc acgtagtggg ccatcgccct gatagacggt ttttcgccct ttgacgttgg   6840
agtccacgtt ctttaatagt ggactcttgt tccaaactgg aacaacactc aaccctatct   6900
cggtctattc ttttgattta taagggattt tgccgatttc ggcctattgg ttaaaaaatg   6960
agctgattta acaaaaattt aacgcgaatt ttaacaaaat attaacgctt acaatttcca   7020
ttcgccattc aggctgcgca actgttggga agggcgatcg gtgcgggcct cttcgctatt   7080
acgccagctg gcgaaagggg gatgtgctgc aaggcgatta agttgggtaa cgccagggtt   7140
ttcccagtca cgacgttgta aaacgacggc cagtgaattg taatacgact cactataggg   7200
cgaattgggt accgggcccc ccctcgaggt cgatggtgtc gataagcttg atatcgaatt   7260
catgtcacac aaaccgatct tcgcctcaag gaaacctaat tctacatccg agagactgcc   7320
gagatccagt ctacactgat taattttcgg gccaataatt taaaaaaatc gtgttatata   7380
atattatatg tattatatat atacatcatg atgatactga cagtcatgtc ccattgctaa   7440
atagacagac tccatctgcc gcctccaact gatgttctca atatttaagg ggtcatctcg   7500
cattgtttaa taataaacag actccatcta ccgcctccaa atgatgttct caaaatatat   7560
tgtatgaact tatttttatt acttagtatt attagacaac ttacttgctt tatgaaaaac   7620
acttcctatt taggaaacaa tttataatgg cagttcgttc atttaacaat ttatgtagaa   7680
taaatgttat aaatgcgtat gggaaatctt aaatatggat agcataaatg atatctgcat   7740
tgcctaattc gaaatcaaca gcaacgaaaa aaatcccttg tacaacataa atagtcatcg   7800
agaaatatca actatcaaag aacagctatt cacacgttac tattgagatt attattggac   7860
gagaatcaca cactcaactg tctttctctc ttctagaaat acaggtacaa gtatgtacta   7920
ttctcattgt tcatacttct agtcatttca tcccacatat tccttggatt tctctccaat   7980
gaatgacatt ctatcttgca aattcaacaa ttataataag atataccaaa gtagcggtat   8040
agtggcaatc aaaaagcttc tctggtgtgc ttctcgtatt tatttttatt ctaatgatcc   8100
attaaaggta tatatttatt tcttgttata taatcctttt gtttattaca tgggctggat   8160
acataaaggt attttgattt aatttttgc ttaaattcaa tccccccctcg ttcagtgtca   8220
actgtaatgg taggaaatta ccatactttt gaagaagcaa aaaaaatgaa agaaaaaaaa   8280
aatcgtattt ccaggttaga cgttccgcag aatctagaat gcggtatgcg gtacattgtt   8340
cttcgaacgt aaaagttgcg ctccctgaga tattgtacat ttttgctttt acaagtacaa   8400
gtacatcgta caactatgta ctactgttga tgcatccaca acagtttgtt ttgttttttt   8460
ttgttttttt tttttctaat gattcattac cgctatgtat acctacttgt acttgtagta   8520
agccgggtta ttggcgttca attaatcata gacttatgaa tctgcacggt gtgcgctgcg   8580
agttactttt agcttatgca tgctacttgg gtgtaatatt gggatctgtt cggaaatcaa   8640
cggatgctca atcgatttcg acagtaatta attaagtcat acacaagtca gctttcttcg   8700
agcctcatat aagtataagt agttcaacgt attagcactg tacccagcat ctccgtatcg   8760
```

-continued

```
agaaacacaa caacatgccc cattggacag atcatgcgga tacacaggtt gtgcagtatc   8820
atacatactc gatcagacag gtcgtctgac catcatacaa gctgaacaag cgctccatac   8880
ttgcacgctc tctatataca cagttaaatt acatatccat agtctaacct ctaacagtta   8940
atcttctggt aagcctccca gccagccttc tggtatcgct tggcctcctc aataggatct   9000
cggttctggc cgtacagacc tcggccgaca attatgatat ccgttccggt agacatgaca   9060
tcctcaacag ttcggtactg ctgtccgaga gcgtctccct tgtcgtcaag acccaccccg   9120
ggggtcagaa taagccagtc ctcagagtcg cccttaggtc ggttctgggc aatgaagcca   9180
accacaaact cggggtcgga tcgggcaagc tcaatggtct gcttggagta ctcgccagtg   9240
gccagagagc ccttgcaaga cagctcggcc agcatgagca gacctctggc cagcttctcg   9300
ttgggagagg ggactaggaa ctccttgtac tgggagttct cgtagtcaga gacgtcctcc   9360
ttcttctgtt cagagacagt ttcctcggca ccagctcgca ggccagcaat gattccggtt   9420
ccgggtacac cgtgggcgtt ggtgatatcg gaccactcgg cgattcggtg acaccggtac   9480
tggtgcttga cagtgttgcc aatatctgcg aactttctgt cctcgaacag gaagaaaccg   9540
tgcttaagag caagttcctt gagggggagc acagtgccgg cgtaggtgaa gtcgtcaatg   9600
atgtcgatat gggttttgat catgcacaca taaggtccga ccttatcggc aagctcaatg   9660
agctccttgg tggtggtaac atccagagaa gcacacaggt tggttttctt ggctgccacg   9720
agcttgagca ctcgagcggc aaaggcggac ttgtggacgt tagctcgagc ttcgtaggag   9780
ggcattttgg tggtgaagag gagactgaaa taaatttagt ctgcagaact ttttatcgga   9840
accttatctg gggcagtgaa gtatatgtta tggtaatagt tacgagttag ttgaacttat   9900
agatagactg gactatacgg ctatcggtcc aaattagaaa gaacgtcaat ggctctctgg   9960
gcgtcgcctt tgccgacaaa aatgtgatca tgatgaaagc cagcaatgac gttgcagctg  10020
atattgttgt cggccaaccg cgccgaaaac gcagctgtca gacccacagc ctccaacgaa  10080
gaatgtatcg tcaaagtgat ccaagcacac tcatagttgg agtcgtactc caaaggcggc  10140
aatgacgagt cagacagata ctcgtcgacg tttaaaccat catctaaggg cctcaaaact  10200
acctcggaac tgctgcgctg atctggacac cacagaggtt ccgagcactt taggttgcac  10260
caaatgtccc accaggtgca ggcagaaaac gctggaacag cgtgtacagt ttgtcttaac  10320
aaaaagtgag ggcgctgagg tcgagcaggg tggtgtgact tgttatagcc tttagagctg  10380
cgaaagcgcg tatggatttg gctcatcagg ccagattgag ggtctgtgga cacatgtcat  10440
gttagtgtac ttcaatcgcc ccctggatat agccccgaca ataggccgtg gcctcatttt  10500
tttgccttcc gcacatttcc attgctcggt acccacacct tgcttctcct gcacttgcca  10560
accttaatac tggtttacat tgaccaacat cttacaagcg gggggcttgt ctagggtata  10620
tataaacagt ggctctccca atcggttgcc agtctctttt ttcctttctt tccccacaga  10680
ttcgaaatct aaactacaca tcacac                                       10706
```

<210> SEQ ID NO 7
<211> LENGTH: 35
<212> TYPE: DNA
<213> ORGANISM: artificial sequence
<220> FEATURE:
<223> OTHER INFORMATION: Cas9-NLS forward PCR primer

<400> SEQUENCE: 7

```
gggggaattc gacaagaaat actccatcgg cctgg                             35
```

<210> SEQ ID NO 8
<211> LENGTH: 31
<212> TYPE: DNA
<213> ORGANISM: artificial sequence
<220> FEATURE:
<223> OTHER INFORMATION: Cas9-NLS reverse PCR primer

<400> SEQUENCE: 8
ccccaagctt agcggccgct tagacctttc g 31

<210> SEQ ID NO 9
<211> LENGTH: 4166
<212> TYPE: DNA
<213> ORGANISM: artificial sequence
<220> FEATURE:
<223> OTHER INFORMATION: EcoRI-Cas9-NLS-HinDIII PCR product

<400> SEQUENCE: 9
gggggaattc gacaagaaat actccatcgg cctggacatt ggaaccaact ctgtcggctg 60
ggctgtcatc accgacgagt acaaggtgcc ctccaagaaa ttcaaggtcc tcggaaacac 120
cgatcgacac tccatcaaga aaaacctcat tggtgccctg ttgttcgatt ctggcgagac 180
tgccgaagct accagactca agcgaactgc tcggcgacgt tacacccgac ggaagaaccg 240
aatctgctac ctgcaggaga tcttttccaa cgagatggcc aaggtggacg attcgttctt 300
tcatcgactg gaggaatcct tcctcgtcga ggaagacaag aaacacgagc gtcatcccat 360
ctttggcaac attgtggacg aggttgctta ccacgagaag tatcctacca tctaccacct 420
gcgaaagaaa ctcgtcgatt ccaccgacaa ggcggatctc agacttatct acctcgctct 480
ggcacacatg atcaagtttc gaggtcattt cctcatcgag ggcgatctca atcccgacaa 540
cagcgatgtg gacaagctgt tcattcagct cgttcagacc tacaaccagc tgttcgagga 600
aaaccccatc aatgcctccg gagtcgatgc aaaggccatc ttgtctgctc gactctcgaa 660
gagcagacga ctggagaacc tcattgccca acttcctggc gagaaaaaga acggactgtt 720
tggcaacctc attgcccttt ctcttggtct cacacccaac ttcaagtcca acttcgatct 780
ggcggaggac gccaagctcc agctgtccaa ggacacctac gacgatgacc tcgacaacct 840
gcttgcacag attggcgatc agtacgccga cctgtttctc gctgccaaga acctttcgga 900
tgctattctc ttgtctgaca ttctgcgagt caacaccgag atcacaaagg ctcccctttc 960
tgcctccatg atcaagcgat acgacgagca ccatcaggat ctcacactgc tcaaggctct 1020
tgtccgacag caactgcccg agaagtacaa ggagatcttt ttcgatcagt cgaagaacgg 1080
ctacgctgga tacatcgacg gcggagcctc tcaggaagag ttctacaagt tcatcaagcc 1140
aattctcgag aagatggacg gaaccgagga actgcttgtc aagctcaatc gagaggatct 1200
gcttcggaag caacgaacct tcgacaacgg cagcattcct catcagatcc acctcggtga 1260
gctgcacgcc attcttcgac gtcaggaaga cttctacccc tttctcaagg acaaccgaga 1320
gaagatcgag aagattctta cctttcgaat cccctactat gttggtcctc ttgccagagg 1380
aaactctcga tttgcttgga tgactcgaaa gtccgaggaa accatcactc cctggaactt 1440
cgaggaagtc gtggacaagg gtgcctctgc acagtccttc atcgagcgaa tgaccaactt 1500
cgacaagaat ctgcccaacg agaaggttct tcccaagcat tcgctgctct acgagtactt 1560
tacagtctac aacgaactca ccaaagtcaa gtacgttacc gagggaatgc gaaagcctgc 1620
cttcttgtct ggcgaacaga agaaagccat tgtcgatctc ctgttcaaga ccaaccgaaa 1680
ggtcactgtt aagcagctca aggaggacta cttcaagaaa atcgagtgtt tcgacagcgt 1740

-continued

```
cgagatttcc ggagttgagg accgattcaa cgcctctttg ggcacctatc acgatctgct   1800
caagattatc aaggacaagg attttctcga caacgaggaa aacgaggaca ttctggagga   1860
catcgtgctc actcttaccc tgttcgaaga tcgggagatg atcgaggaac gactcaagac   1920
atacgctcac ctgttcgacg acaaggtcat gaaacaactc aagcgacgta gatacaccgg   1980
ctggggaaga ctttcgcgaa agctcatcaa cggcatcaga gacaagcagt ccggaaagac   2040
cattctggac tttctcaagt ccgatggctt tgccaaccga aacttcatgc agctcattca   2100
cgacgattct cttaccttca aggaggacat ccagaaggca caagtgtccg gtcagggcga   2160
cagcttgcac gaacatattg ccaacctggc tggttcgcca gccatcaaga aaggcattct   2220
ccagactgtc aaggttgtcg acgagctggt gaaggtcatg ggacgtcaca agcccgagaa   2280
cattgtgatc gagatggcca gagagaacca gacaactcaa aagggtcaga aaaactcgcg   2340
agagcggatg aagcgaatcg aggaaggcat caaggagctg ggatcccaga ttctcaagga   2400
gcatcccgtc gagaacactc aactgcagaa cgagaagctg tatctctact atctgcagaa   2460
tggtcgagac atgtacgtgg atcaggaact ggacatcaat cgtctcagcg actacgatgt   2520
ggaccacatt gtccctcaat cctttctcaa ggacgattct atcgacaaca aggtccttac   2580
acgatccgac aagaacagag gcaagtcgga caacgttccc agcgaagagg tggtcaaaaa   2640
gatgaagaac tactggcgac agctgctcaa cgccaagctc attacccagc gaaagttcga   2700
caatcttacc aaggccgagc gaggcggtct gtccgagctc gacaaggctg gcttcatcaa   2760
gcgtcaactc gtcgagacca gacagatcac aaagcacgtc gcacagattc tcgattctcg   2820
gatgaacacc aagtacgacg agaacgacaa gctcatccga gaggtcaagg tgattactct   2880
caagtccaaa ctggtctccg atttccgaaa ggactttcag ttctacaagg tgcgagagat   2940
caacaattac caccatgccc acgatgctta cctcaacgcc gtcgttggca ctgcgctcat   3000
caagaaatac cccaagctcg aaagcgagtt cgtttacggc gattacaagg tctacgacgt   3060
tcgaaagatg attgccaagt ccgaacagga gattggcaag gctactgcca agtacttctt   3120
ttactccaac atcatgaact tttcaagac cgagatcacc ttggccaacg gagagattcg   3180
aaagagacca cttatcgaga ccaacggcga aactggagag atcgtgtggg acaagggtcg   3240
agactttgca accgtgcgaa aggttctgtc gatgcctcag gtcaacatcg tcaagaaaac   3300
cgaggttcag actggcggat tctccaagga gtcgattctg cccaagcgaa actccgacaa   3360
gctcatcgct cgaaagaaag actgggatcc caagaaatac ggtggcttcg attctcctac   3420
cgtcgcctat tccgtgcttg tcgttgcgaa ggtcgagaag ggcaagtcca aaaagctcaa   3480
gtccgtcaag gagctgctcg gaattaccat catggagcga tcgagcttcg agaagaatcc   3540
catcgacttc ttggaagcca agggttacaa ggaggtcaag aaagacctca ttatcaagct   3600
gcccaagtac tctctgttcg aactggagaa cggtcgaaag cgtatgctcg cctccgctgg   3660
cgagctgcag aagggaaacg agcttgcctt gccttcgaag tacgtcaact ttctctatct   3720
ggcttctcac tacgagaagc tcaagggttc tcccgaggac aacgaacaga agcaactctt   3780
cgttgagcag cacaaacatt acctcgacga gattatcgag cagatttccg agttttcgaa   3840
gcgagtcatc ctggctgatg ccaacttgga caaggtgctc tctgcctaca acaagcatcg   3900
ggacaaaccc attcgagaac aggcggagaa catcattcac ctgtttactc ttaccaacct   3960
gggtgctcct gcagctttca agtacttcga taccactatc gaccgaaagc ggtacacatc   4020
caccaaggag gttctcgatg ccaccctgat tcaccagtcc atcactggcc tgtacgagac   4080
ccgaatcgac ctgtctcagc ttggtggcga ctccagagcc gatcccaaga aaaagcgaaa   4140
```

ggtctaagcg gccgctaagc ttgggg 4166

<210> SEQ ID NO 10
<211> LENGTH: 4092
<212> TYPE: DNA
<213> ORGANISM: artificial sequence
<220> FEATURE:
<223> OTHER INFORMATION: pBAD/HisB plasmid

<400> SEQUENCE: 10
aagaaaccaa ttgtccatat tgcatcagac attgccgtca ctgcgtcttt tactggctct 60
tctcgctaac caaaccggta accccgctta ttaaaagcat tctgtaacaa agcgggacca 120
aagccatgac aaaaacgcgt aacaaaagtg tctataatca cggcagaaaa gtccacattg 180
attatttgca cggcgtcaca ctttgctatg ccatagcatt tttatccata agattagcgg 240
atcctacctg acgcttttta tcgcaactct ctactgtttc tccatacccg tttttgggc 300 taacaggagg aattaaccat ggggggttct catcatcatc atcatcatgg tatggctagc 360
atgactggtg gacagcaaat gggtcgggat ctgtacgacg atgacgataa ggatccgagc 420
tcgagatctg cagctggtac catatgggaa ttcgaagctt ggctgttttg gcggatgaga 480
gaagattttc agcctgatac agattaaatc agaacgcaga agcggtctga taaaacagaa 540
tttgcctggc ggcagtagcg cggtggtccc acctgacccc atgccgaact cagaagtgaa 600
acgccgtagc gccgatggta gtgtggggtc tccccatgcg agagtaggga actgccaggc 660
atcaaataaa acgaaaggct cagtcgaaag actgggcctt tcgttttatc tgttgtttgt 720
cggtgaacgc tctcctgagt aggacaaatc cgccgggagc ggatttgaac gttgcgaagc 780
aacggcccgg agggtggcgg gcaggacgcc cgccataaac tgccaggcat caaattaagc 840
agaaggccat cctgacggat ggcctttttg cgtttctaca aactcttttg tttatttttc 900
taaatacatt caaatatgta tccgctcatg agacaataac cctgataaat gcttcaataa 960
tattgaaaaa ggaagagtat gagtattcaa catttccgtg tcgcccttat tccctttttt 1020
gcggcatttt gccttcctgt ttttgctcac ccagaaacgc tggtgaaagt aaaagatgct 1080
gaagatcagt tgggtgcacg agtgggttac atcgaactgg atctcaacag cggtaagatc 1140
cttgagagtt ttcgccccga agaacgtttt ccaatgatga gcacttttaa agttctgcta 1200
tgtggcgcgg tattatcccg tgttgacgcc gggcaagagc aactcggtcg ccgcatacac 1260
tattctcaga atgacttggt tgagtactca ccagtcacag aaaagcatct tacggatggc 1320
atgacagtaa gagaattatg cagtgctgcc ataaccatga gtgataacac tgcggccaac 1380
ttacttctga caacgatcgg aggaccgaag gagctaaccg cttttttgca caacatgggg 1440
gatcatgtaa ctcgccttga tcgttgggaa ccggagctga atgaagccat accaaacgac 1500
gagcgtgaca ccacgatgcc tgtagcaatg gcaacaacgt tgcgcaaact attaactggc 1560
gaactactta ctctagcttc ccggcaacaa ttaatagact ggatggaggc ggataaagtt 1620
gcaggaccac ttctgcgctc ggcccttccg gctggctggt ttattgctga taaatctgga 1680
gccggtgagc gtgggtctcg cggtatcatt gcagcactgg ggccagatgg taagccctcc 1740
cgtatcgtag ttatctacac gacggggagt caggcaacta tggatgaacg aaatagacag 1800
atcgctgaga taggtgcctc actgattaag cattggtaac tgtcagacca agtttactca 1860
tatatacttt agattgattt aaaacttcat ttttaattta aaaggatcta ggtgaagatc 1920
ctttttgata atctcatgac caaaatccct taacgtgagt tttcgttcca ctgagcgtca 1980

-continued

```
gaccccgtag aaaagatcaa aggatcttct tgagatcctt tttttctgcg cgtaatctgc   2040
tgcttgcaaa caaaaaaacc accgctacca gcggtggttt gtttgccgga tcaagagcta   2100
ccaactcttt ttccgaaggt aactggcttc agcagagcgc agataccaaa tactgtcctt   2160
ctagtgtagc cgtagttagg ccaccacttc aagaactctg tagcaccgcc tacatacctc   2220
gctctgctaa tcctgttacc agtggctgct gccagtggcg ataagtcgtg tcttaccggg   2280
ttggactcaa gacgatagtt accggataag gcgcagcggt cgggctgaac ggggggttcg   2340
tgcacacagc ccagcttgga gcgaacgacc tacaccgaac tgagatacct acagcgtgag   2400
ctatgagaaa gcgccacgct tcccgaaggg agaaaggcgg acaggtatcc ggtaagcggc   2460
agggtcggaa caggagagcg cacgagggag cttccagggg gaaacgcctg gtatctttat   2520
agtcctgtcg ggtttcgcca cctctgactt gagcgtcgat ttttgtgatg ctcgtcaggg   2580
gggcggagcc tatggaaaaa cgccagcaac gcggcctttt tacggttcct ggccttttgc   2640
tggccttttg ctcacatgtt ctttcctgcg ttatcccctg attctgtgga taaccgtatt   2700
accgcctttg agtgagctga taccgctcgc cgcagccgaa cgaccgagcg cagcgagtca   2760
gtgagcgagg aagcggaaga gcgcctgatg cggtattttc tccttacgca tctgtgcggt   2820
atttcacacc gcatatggtg cactctcagt acaatctgct ctgatgccgc atagttaagc   2880
cagtatacac tccgctatcg ctacgtgact gggtcatggc tgcgccccga cacccgccaa   2940
cacccgctga cgcgccctga cgggcttgtc tgctcccggc atccgcttac agacaagctg   3000
tgaccgtctc cgggagctgc atgtgtcaga ggttttcacc gtcatcaccg aaacgcgcga   3060
ggcagcagat caattcgcgc gcgaaggcga agcggcatgc ataatgtgcc tgtcaaatgg   3120
acgaagcagg gattctgcaa accctatgct actccgtcaa gccgtcaatt gtctgattcg   3180
ttaccaatta tgacaacttg acggctacat cattcacttt ttcttcacaa ccggcacgga   3240
actcgctcgg gctggccccg gtgcattttt taaatacccg cgagaaatag agttgatcgt   3300
caaaaccaac attgcgaccg acggtggcga taggcatccg ggtggtgctc aaaagcagct   3360
tcgcctggct gatacgttgg tcctcgcgcc agcttaagac gctaatccct aactgctggc   3420
ggaaaagatg tgacagacgc gacggcgaca agcaaacatg ctgtgcgacg ctggcgatat   3480
caaaattgct gtctgccagg tgatcgctga tgtactgaca agcctcgcgt acccgattat   3540
ccatcggtgg atggagcgac tcgttaatcg cttccatgcg ccgcagtaac aattgctcaa   3600
gcagatttat cgccagcagc tccgaatagc gcccttcccc ttgcccggcg ttaatgattt   3660
gcccaaacag gtcgctgaaa tgcggctggt gcgcttcatc cgggcgaaag aaccccgtat   3720
tggcaaatat tgacggccag ttaagccatt catgccagta ggcgcgcgga cgaaagtaaa   3780
cccactggtg ataccattcg cgagcctccg gatgacgacc gtagtgatga atctctcctg   3840
gcgggaacag caaaatatca cccggtcggc aaacaaattc tcgtccctga tttttcacca   3900
ccccctgacc gcgaatggtg agattgagaa tataaccttt cattcccagc ggtcggtcga   3960
taaaaaaatc gagataaccg ttggcctcaa tcggcgttaa acccgccacc agatgggcat   4020
taaacgagta tcccggcagc aggggatcat tttgcgcttc agccatactt ttcatactcc   4080
cgccattcag ag                                                       4092
```

<210> SEQ ID NO 11
<211> LENGTH: 8237
<212> TYPE: DNA
<213> ORGANISM: artificial sequence
<220> FEATURE:
<223> OTHER INFORMATION: pRF48 plasmid

<400> SEQUENCE: 11
aattcgacaa gaaatactcc atcggcctgg acattggaac caactctgtc ggctgggctg 60
tcatcaccga cgagtacaag gtgccctcca agaaattcaa ggtcctcgga aacaccgatc 120
gacactccat caagaaaaac ctcattggtg ccctgttgtt cgattctggc gagactgccg 180
aagctaccag actcaagcga actgctcggc gacgttacac ccgacggaag aaccgaatct 240
gctacctgca ggagatcttt tccaacgaga tggccaaggt ggacgattcg ttctttcatc 300
gactggagga atccttcctc gtcgaggaag acaagaaaca cgagcgtcat cccatctttg 360
gcaacattgt ggacgaggtt gcttaccacg agaagtatcc taccatctac cacctgcgaa 420
agaaactcgt cgattccacc gacaaggcgg atctcagact tatctacctc gctctggcac 480
acatgatcaa gtttcgaggt catttcctca tcgagggcga tctcaatccc gacaacagcg 540
atgtggacaa gctgttcatt cagctcgttc agacctacaa ccagctgttc gaggaaaacc 600
ccatcaatgc ctccggagtc gatgcaaagg ccatcttgtc tgctcgactc tcgaagagca 660
gacgactgga gaacctcatt gcccaacttc ctggcgagaa aaagaacgga ctgtttggca 720
acctcattgc cctttctctt ggtctcacac ccaacttcaa gtccaacttc gatctggcgg 780
aggacgccaa gctccagctg tccaaggaca cctacgacga tgacctcgac aacctgcttg 840
cacagattgg cgatcagtac gccgacctgt ttctcgctgc caagaacctt tcggatgcta 900
ttctcttgtc tgacattctg cgagtcaaca ccgagatcac aaaggctccc ctttctgcct 960
ccatgatcaa gcgatacgac gagcaccatc aggatctcac actgctcaag gctcttgtcc 1020
gacagcaact gcccgagaag tacaaggaga tctttttcga tcagtcgaag aacggctacg 1080
ctggatacat cgacggcgga gcctctcagg aagagttcta caagttcatc aagccaattc 1140
tcgagaagat ggacggaacc gaggaactgc ttgtcaagct caatcgagag gatctgcttc 1200
ggaagcaacg aaccttcgac aacggcagca ttcctcatca gatccacctc ggtgagctgc 1260
acgccattct tcgacgtcag gaagacttct accccttttct caaggacaac cgagagaaga 1320
tcgagaagat tcttaccttt cgaatcccct actatgttgg tcctcttgcc agaggaaact 1380
ctcgatttgc ttggatgact cgaaagtccg aggaaaccat cactccctgg aacttcgagg 1440
aagtcgtgga caagggtgcc tctgcacagt ccttcatcga gcgaatgacc aacttcgaca 1500
agaatctgcc caacgagaag gttcttccca agcattcgct gctctacgag tactttacag 1560
tctacaacga actcaccaaa gtcaagtacg ttaccgaggg aatgcgaaag cctgccttct 1620
tgtctggcga acagaagaaa gccattgtcg atctcctgtt caagaccaac cgaaaggtca 1680
ctgttaagca gctcaaggag gactacttca agaaaatcga gtgtttcgac agcgtcgaga 1740
tttccggagt tgaggaccga ttcaacgcct ctttgggcac ctatcacgat ctgctcaaga 1800
ttatcaagga caaggatttt ctcgacaacg aggaaaacga ggacattctg gaggacatcg 1860
tgctcactct taccctgttc gaagatcggg agatgatcga ggaacgactc aagacatacg 1920
ctcacctgtt cgacgacaag gtcatgaaac aactcaagcg acgtagatac accggctggg 1980
gaagactttc gcgaaagctc atcaacggca tcagagacaa gcagtccgga aagaccattc 2040
tggactttct caagtccgat ggctttgcca accgaaactt catgcagctc attcacgacg 2100
attctcttac cttcaaggag gacatccaga aggcacaagt gtccggtcag ggcgacagct 2160
tgcacgaaca tattgccaac ctggctggtt cgccagccat caagaaaggc attctccaga 2220
ctgtcaaggt tgtcgacgag ctggtgaagg tcatgggacg tcacaagccc gagaacattg 2280

-continued

```
tgatcgagat ggccagagag aaccagacaa ctcaaaaggg tcagaaaaac tcgcgagagc   2340
ggatgaagcg aatcgaggaa ggcatcaagg agctgggatc ccagattctc aaggagcatc   2400
ccgtcgagaa cactcaactg cagaacgaga agctgtatct ctactatctg cagaatggtc   2460
gagacatgta cgtggatcag gaactggaca tcaatcgtct cagcgactac gatgtggacc   2520
acattgtccc tcaatccttt ctcaaggacg attctatcga caacaaggtc cttacacgat   2580
ccgacaagaa cagaggcaag tcggacaacg ttcccagcga agaggtggtc aaaaagatga   2640
agaactactg gcgacagctg ctcaacgcca agctcattac ccagcgaaag ttcgacaatc   2700
ttaccaaggc cgagcgaggc ggtctgtccg agctcgacaa ggctggcttc atcaagcgtc   2760
aactcgtcga gaccagacag atcacaaagc acgtcgcaca gattctcgat tctcggatga   2820
acaccaagta cgacgagaac gacaagctca tccgagaggt caaggtgatt actctcaagt   2880
ccaaactggt ctccgatttc cgaaaggact ttcagttcta caaggtgcga gagatcaaca   2940
attaccacca tgcccacgat gcttacctca acgccgtcgt tggcactgcg ctcatcaaga   3000
aataccccaa gctcgaaagc gagttcgttt acggcgatta caaggtctac gacgttcgaa   3060
agatgattgc caagtccgaa caggagattg gcaaggctac tgccaagtac ttcttttact   3120
ccaacatcat gaactttttc aagaccgaga tcaccttggc caacggagag attcgaaaga   3180
gaccacttat cgagaccaac ggcgaaactg gagagatcgt gtgggacaag ggtcgagact   3240
ttgcaaccgt gcgaaaggtt ctgtcgatgc ctcaggtcaa catcgtcaag aaaaccgagg   3300
ttcagactgg cggattctcc aaggagtcga ttctgcccaa gcgaaactcc gacaagctca   3360
tcgctcgaaa gaaagactgg gatcccaaga aatacggtgg cttcgattct cctaccgtcg   3420
cctattccgt gcttgtcgtt gcgaaggtcg agaagggcaa gtccaaaaag ctcaagtccg   3480
tcaaggagct gctcggaatt accatcatgg agcgatcgag cttcgagaag aatcccatcg   3540
acttcttgga agccaagggt tacaaggagg tcaagaaaga cctcattatc aagctgccca   3600
agtactctct gttcgaactg gagaacggtc gaaagcgtat gctcgcctcc gctggcgagc   3660
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560
ctttttgcgt ttctacaaac tcttttgttt atttttctaa atacattcaa atatgtatcc   4620
gctcatgaga caataaccct gataaatgct tcaataatat tgaaaaagga agagtatgag   4680
```

```
tattcaacat ttccgtgtcg cccttattcc cttttttgcg gcattttgcc ttcctgtttt   4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt   4920
tgacgccggg caagagcaac tcggtcgccg catacactat tctcagaatg acttggttga   4980
gtactcacca gtcacagaaa agcatcttac ggatggcatg acagtaagag aattatgcag   5040
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg ggtctcgcgg   5400
tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580
acttcatttt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga gatccttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
ccacttcaag aactctgtag caccgcctac atacctcgct ctgctaatcc tgttaccagt   5940
ggctgctgcc agtggcgata agtcgtgtct taccgggttg gactcaagac gatagttacc   6000
ggataaggcg cagcggtcgg gctgaacggg gggttcgtgc acacagccca gcttggagcg   6060
aacgacctac accgaactga gatacctaca gcgtgagcta tgagaaagcg ccacgcttcc   6120
cgaagggaga aaggcggaca ggtatccggt aagcggcagg gtcggaacag gagagcgcac   6180
gagggagctt ccagggggaa acgcctggta tctttatagt cctgtcgggt ttcgccacct   6240
ctgacttgag cgtcgatttt tgtgatgctc gtcagggggg cggagcctat ggaaaaacgc   6300
cagcaacgcg gcctttttac ggttcctggc cttttgctgg ccttttgctc acatgttctt   6360
tcctgcgtta tcccctgatt ctgtggataa ccgtattacc gcctttgagt gagctgatac   6420
cgctcgccgc agccgaacga ccgagcgcag cgagtcagtg agcgaggaag cggaagagcg   6480
cctgatgcgg tattttctcc ttacgcatct gtgcggtatt tcacaccgca tatggtgcac   6540
tctcagtaca atctgctctg atgccgcata gttaagccag tatacactcc gctatcgcta   6600
cgtgactggg tcatggctgc gccccgacac ccgccaacac ccgctgacgc gccctgacgg   6660
gcttgtctgc tcccggcatc cgcttacaga caagctgtga ccgtctccgg gagctgcatg   6720
tgtcagaggt tttcaccgtc atcaccgaaa cgcgcgaggc agcagatcaa ttcgcgcgcg   6780
aaggcgaagc ggcatgcata atgtgcctgt caaatggacg aagcagggat tctgcaaacc   6840
ctatgctact ccgtcaagcc gtcaattgtc tgattcgtta ccaattatga caacttgacg   6900
gctacatcat tcactttttc ttcacaaccg gcacggaact cgctcgggct ggccccggtg   6960
catttttaa atacccgcga gaaatagagt tgatcgtcaa aaccaacatt gcgaccgacg   7020
```

-continued

```
gtggcgatag gcatccgggt ggtgctcaaa agcagcttcg cctggctgat acgttggtcc   7080

tcgcgccagc ttaagacgct aatccctaac tgctggcgga aaagatgtga cagacgcgac   7140

ggcgacaagc aaacatgctg tgcgacgctg gcgatatcaa aattgctgtc tgccaggtga   7200

tcgctgatgt actgacaagc ctcgcgtacc cgattatcca tcggtggatg gagcgactcg   7260

ttaatcgctt ccatgcgccg cagtaacaat tgctcaagca gatttatcgc cagcagctcc   7320

gaatagcgcc cttccccttg cccggcgtta atgatttgcc caaacaggtc gctgaaatgc   7380

ggctggtgcg cttcatccgg gcgaaagaac cccgtattgg caaatattga cggccagtta   7440

agccattcat gccagtaggc gcgcggacga aagtaaaccc actggtgata ccattcgcga   7500

gcctccggat gacgaccgta gtgatgaatc tctcctggcg ggaacagcaa aatatcaccc   7560

ggtcggcaaa caaattctcg tccctgattt ttcaccaccc cctgaccgcg aatggtgaga   7620

ttgagaatat aacctttcat tcccagcggt cggtcgataa aaaaatcgag ataaccgttg   7680

gcctcaatcg gcgttaaacc cgccaccaga tgggcattaa acgagtatcc cggcagcagg   7740

ggatcatttt gcgcttcagc catacttttc atactcccgc cattcagaga agaaaccaat   7800

tgtccatatt gcatcagaca ttgccgtcac tgcgtctttt actggctctt ctcgctaacc   7860

aaaccggtaa ccccgcttat taaaagcatt ctgtaacaaa gcgggaccaa agccatgaca   7920

aaaacgcgta acaaaagtgt ctataatcac ggcagaaaag tccacattga ttatttgcac   7980

ggcgtcacac tttgctatgc catagcattt ttatccataa gattagcgga tcctacctga   8040

cgctttttat cgcaactctc tactgtttct ccatacccgt ttttgggct aacaggagga   8100

attaaccatg gggggttctc atcatcatca tcatcatggt atggctagca tgactggtgg   8160

acagcaaatg ggtcgggatc tgtacgacga tgacgataag gatccgagct cgagatctgc   8220

agctggtacc atatggg                                                   8237
```

<210> SEQ ID NO 12
<211> LENGTH: 54
<212> TYPE: PRT
<213> ORGANISM: Epstein-Barr virus

<400> SEQUENCE: 12

```
Glu Cys Asp Ser Glu Leu Glu Ile Lys Arg Tyr Lys Arg Val Arg Val
1               5                   10                  15

Ala Ser Arg Lys Cys Arg Ala Lys Phe Lys Gln Leu Leu Gln His Tyr
            20                  25                  30

Arg Glu Val Ala Ala Ala Lys Ser Ser Glu Asn Asp Arg Leu Arg Leu
        35                  40                  45

Leu Leu Lys Gln Met Cys
    50
```

<210> SEQ ID NO 13
<211> LENGTH: 18
<212> TYPE: PRT
<213> ORGANISM: mus musculus

<400> SEQUENCE: 13

```
Leu Leu Ile Ile Leu Arg Arg Arg Ile Arg Lys Gln Ala His Ala His
1               5                   10                  15

Ser Lys
```

<210> SEQ ID NO 14
<211> LENGTH: 21
<212> TYPE: PRT

<213> ORGANISM: unknown
<220> FEATURE:
<223> OTHER INFORMATION: TP10 CPP

<400> SEQUENCE: 14

Ala Gly Tyr Leu Leu Gly Lys Ile Asn Leu Lys Ala Cys Ala Ala Cys
1 5 10 15

Ala Lys Lys Ile Leu
20

<210> SEQ ID NO 15
<211> LENGTH: 17
<212> TYPE: PRT
<213> ORGANISM: artificial sequence
<220> FEATURE:
<223> OTHER INFORMATION: PolyR CPP

<400> SEQUENCE: 15

Gly Gly Gly Gly Arg Arg Arg Arg Arg Arg Arg Arg Arg Leu Leu Leu
1 5 10 15

Leu

<210> SEQ ID NO 16
<211> LENGTH: 194
<212> TYPE: DNA
<213> ORGANISM: artificial sequence
<220> FEATURE:
<223> OTHER INFORMATION: NcoI-6xHis-ZEBRA CPP-EcoRI

<400> SEQUENCE: 16
ccatggggca tcaccaccat caccacgaat gcgactcaga actggaaatc aaacgctata 60
aacgtgtgcg tgtggcatcc cgtaaatgtc gcgcaaagtt taaacagctg ctgcaacatt 120
atcgtgaagt agcggctgcg aaaagctccg aaaacgaccg tttacgcctc ctcctgaagc 180
aaatgtgcga attc 194

<210> SEQ ID NO 17
<211> LENGTH: 86
<212> TYPE: DNA
<213> ORGANISM: artificial sequence
<220> FEATURE:
<223> OTHER INFORMATION: NcoI-6xHis-pVEC CPP-EcoRI

<400> SEQUENCE: 17
ccatggggca tcaccaccat caccacttat tgattatctt gcgtcgtcgc atccgcaaac 60
aggcgcacgc acatagcaag gaattc 86

<210> SEQ ID NO 18
<211> LENGTH: 95
<212> TYPE: DNA
<213> ORGANISM: artificial sequence
<220> FEATURE:
<223> OTHER INFORMATION: NcoI-6xHis-TP10 CPP-EcoRI

<400> SEQUENCE: 18
ccatggggca tcaccaccat caccacgcgg gttacctgct gggcaagatt aatcttaaag 60
cctgcgccgc gtgtgctaag aaaattttgg aattc 95

<210> SEQ ID NO 19
<211> LENGTH: 83
<212> TYPE: DNA
<213> ORGANISM: artificial sequence
<220> FEATURE:

-continued

<223> OTHER INFORMATION: NcoI-6xHis-PolyR CPP-EcoRI

<400> SEQUENCE: 19
ccatggggca tcaccaccat caccacggcg ggggtggtcg tcgtcgccgt cgccgccgtc 60
gtcgcctcct gctgctggaa ttc 83

<210> SEQ ID NO 20
<211> LENGTH: 8294
<212> TYPE: DNA
<213> ORGANISM: artificial sequence
<220> FEATURE:
<223> OTHER INFORMATION: pRF144 plasmid

<400> SEQUENCE: 20
ccatggggca tcaccaccat caccacgaat gcgactcaga actggaaatc aaacgctata 60
aacgtgtgcg tgtggcatcc cgtaaatgtc gcgcaaagtt taaacagctg ctgcaacatt 120
atcgtgaagt agcggctgcg aaaagctccg aaaacgaccg tttacgcctc ctcctgaagc 180
aaatgtgcga attcgacaag aaatactcca tcggcctgga cattggaacc aactctgtcg 240
gctgggctgt catcaccgac gagtacaagg tgccctccaa gaaattcaag gtcctcggaa 300
acaccgatcg acactccatc aagaaaaacc tcattggtgc cctgttgttc gattctggcg 360
agactgccga agctaccaga ctcaagcgaa ctgctcggcg acgttacacc cgacggaaga 420
accgaatctg ctacctgcag gagatctttt ccaacgagat ggccaaggtg gacgattcgt 480
tctttcatcg actggaggaa tccttcctcg tcgaggaaga caagaaacac gagcgtcatc 540
ccatctttgg caacattgtg gacgaggttg cttaccacga gaagtatcct accatctacc 600
acctgcgaaa gaaactcgtc gattccaccg acaaggcgga tctcagactt atctacctcg 660
ctctggcaca catgatcaag tttcgaggtc atttcctcat cgagggcgat ctcaatcccg 720
acaacagcga tgtggacaag ctgttcattc agctcgttca gacctacaac cagctgttcg 780
aggaaaaccc catcaatgcc tccggagtcg atgcaaaggc catcttgtct gctcgactct 840
cgaagagcag acgactggag aacctcattg cccaacttcc tggcgagaaa aagaacggac 900
tgtttggcaa cctcattgcc ctttctcttg gtctcacacc caacttcaag tccaacttcg 960
atctggcgga ggacgccaag ctccagctgt ccaaggacac ctacgacgat gacctcgaca 1020
acctgcttgc acagattggc gatcagtacg ccgacctgtt tctcgctgcc aagaaccttt 1080
cggatgctat tctcttgtct gacattctgc gagtcaacac cgagatcaca aaggctcccc 1140
tttctgcctc catgatcaag cgatacgacg agcaccatca ggatctcaca ctgctcaagg 1200
ctcttgtccg acagcaactg cccgagaagt acaaggagat ctttttcgat cagtcgaaga 1260
acggctacgc tggatacatc gacggcggag cctctcagga agagttctac aagttcatca 1320
agccaattct cgagaagatg gacggaaccg aggaactgct tgtcaagctc aatcgagagg 1380
atctgcttcg gaagcaacga accttcgaca acggcagcat tcctcatcag atccacctcg 1440
gtgagctgca cgccattctt cgacgtcagg aagacttcta cccctttctc aaggacaacc 1500
gagagaagat cgagaagatt cttacctttc gaatccccta ctatgttggt cctcttgcca 1560
gaggaaactc tcgatttgct tggatgactc gaaagtccga ggaaaccatc actccctgga 1620
acttcgagga agtcgtggac aagggtgcct ctgcacagtc cttcatcgag cgaatgacca 1680
acttcgacaa gaatctgccc aacgagaagg ttcttcccaa gcattcgctg ctctacgagt 1740
actttacagt ctacaacgaa ctcaccaaag tcaagtacgt taccgaggga atgcgaaagc 1800
ctgccttctt gtctggcgaa cagaagaaag ccattgtcga tctcctgttc aagaccaacc 1860

```
gaaaggtcac tgttaagcag ctcaaggagg actacttcaa gaaaatcgag tgtttcgaca   1920
gcgtcgagat ttccggagtt gaggaccgat tcaacgcctc tttgggcacc tatcacgatc   1980
tgctcaagat tatcaaggac aaggattttc tcgacaacga ggaaaacgag gacattctgg   2040
aggacatcgt gctcactctt accctgttcg aagatcggga gatgatcgag gaacgactca   2100
agacatacgc tcacctgttc gacgacaagg tcatgaaaca actcaagcga cgtagataca   2160
ccggctgggg aagactttcg cgaaagctca tcaacggcat cagagacaag cagtccggaa   2220
agaccattct ggactttctc aagtccgatg gctttgccaa ccgaaacttc atgcagctca   2280
ttcacgacga ttctcttacc ttcaaggagg acatccagaa ggcacaagtg tccggtcagg   2340
gcgacagctt gcacgaacat attgccaacc tggctggttc gccagccatc aagaaaggca   2400
ttctccagac tgtcaaggtt gtcgacgagc tggtgaaggt catgggacgt cacaagcccg   2460
agaacattgt gatcgagatg gccagagaga accagacaac tcaaaagggt cagaaaaact   2520
cgcgagagcg gatgaagcga atcgaggaag gcatcaagga gctgggatcc cagattctca   2580
aggagcatcc cgtcgagaac actcaactgc agaacgagaa gctgtatctc tactatctgc   2640
agaatggtcg agacatgtac gtggatcagg aactggacat caatcgtctc agcgactacg   2700
atgtggacca cattgtccct caatcctttc tcaaggacga ttctatcgac aacaaggtcc   2760
ttacacgatc cgacaagaac agaggcaagt cggacaacgt tcccagcgaa gaggtggtca   2820
aaaagatgaa gaactactgg cgacagctgc tcaacgccaa gctcattacc cagcgaaagt   2880
tcgacaatct taccaaggcc gagcgaggcg gtctgtccga gctcgacaag gctggcttca   2940
tcaagcgtca actcgtcgag accagacaga tcacaaagca cgtcgcacag attctcgatt   3000
ctcggatgaa caccaagtac gacgagaacg acaagctcat ccgagaggtc aaggtgatta   3060
ctctcaagtc caaactggtc tccgatttcc gaaaggactt tcagttctac aaggtgcgag   3120
agatcaacaa ttaccaccat gcccacgatg cttacctcaa cgccgtcgtt ggcactgcgc   3180
tcatcaagaa ataccccaag ctcgaaagcg agttcgttta cggcgattac aaggtctacg   3240
acgttcgaaa gatgattgcc aagtccgaac aggagattgg caaggctact gccaagtact   3300
tcttttactc caacatcatg aactttttca agaccgagat caccttggcc aacggagaga   3360
ttcgaaagag accacttatc gagaccaacg gcgaaactgg agagatcgtg tgggacaagg   3420
gtcgagactt tgcaaccgtg cgaaaggttc tgtcgatgcc tcaggtcaac atcgtcaaga   3480
aaaccgaggt tcagactggc ggattctcca aggagtcgat tctgcccaag cgaaactccg   3540
acaagctcat cgctcgaaag aaagactggg atcccaagaa atacggtggc ttcgattctc   3600
ctaccgtcgc ctattccgtg cttgtcgttg cgaaggtcga gaagggcaag tccaaaaagc   3660
tcaagtccgt caaggagctg ctcggaatta ccatcatgga gcgatcgagc ttcgagaaga   3720
atcccatcga cttcttggaa gccaagggtt acaaggaggt caagaaagac ctcattatca   3780
agctgcccaa gtactctctg ttcgaactgg agaacggtcg aaagcgtatg ctcgcctccg   3840
ctggcgagct gcagaaggga aacgagcttg ccttgccttc gaagtacgtc aactttctct   3900
atctggcttc tcactacgag aagctcaagg gttctcccga ggacaacgaa cagaagcaac   3960
tcttcgttga gcagcacaaa cattacctcg acgagattat cgagcagatt tccgagtttt   4020
cgaagcgagt catcctggct gatgccaact tggacaaggt gctctctgcc tacaacaagc   4080
atcgggacaa acccattcga gaacaggcgg agaacatcat tcacctgttt actcttacca   4140
acctgggtgc tcctgcagct ttcaagtact tcgataccac tatcgaccga aagcggtaca   4200
```

-continued

```
catccaccaa ggaggttctc gatgccaccc tgattcacca gtccatcact ggcctgtacg   4260
agacccgaat cgacctgtct cagcttggtg gcgactccag agccgatccc aagaaaaagc   4320
gaaaggtcta agcggccgct aagcttggct gttttggcgg atgagagaag attttcagcc   4380
tgatacagat taaatcagaa cgcagaagcg gtctgataaa acagaatttg cctggcggca   4440
gtagcgcggt ggtcccacct gaccccatgc cgaactcaga agtgaaacgc cgtagcgccg   4500
atggtagtgt ggggtctccc catgcgagag tagggaactg ccaggcatca aataaaacga   4560
aaggctcagt cgaaagactg ggcctttcgt tttatctgtt gtttgtcggt gaacgctctc   4620
ctgagtagga caaatccgcc gggagcggat ttgaacgttg cgaagcaacg gcccggaggg   4680
tggcgggcag gacgcccgcc ataaactgcc aggcatcaaa ttaagcagaa ggccatcctg   4740
acggatggcc tttttgcgtt tctacaaact cttttgttta tttttctaaa tacattcaaa   4800
tatgtatccg ctcatgagac aataaccctg ataaatgctt caataatatt gaaaaaggaa   4860
gagtatgagt attcaacatt tccgtgtcgc ccttattccc ttttttgcgg cattttgcct   4920
tcctgttttt gctcacccag aaacgctggt gaaagtaaaa gatgctgaag atcagttggg   4980
tgcacgagtg ggttacatcg aactggatct caacagcggt aagatccttg agagttttcg   5040
ccccgaagaa cgttttccaa tgatgagcac ttttaaagtt ctgctatgtg gcgcggtatt   5100
atcccgtgtt gacgccgggc aagagcaact cggtcgccgc atacactatt ctcagaatga   5160
cttggttgag tactcaccag tcacagaaaa gcatcttacg gatggcatga cagtaagaga   5220
attatgcagt gctgccataa ccatgagtga taacactgcg gccaacttac ttctgacaac   5280
gatcggagga ccgaaggagc taaccgcttt tttgcacaac atgggggatc atgtaactcg   5340
ccttgatcgt tgggaaccgg agctgaatga agccatacca aacgacgagc gtgacaccac   5400
gatgcctgta gcaatggcaa caacgttgcg caaactatta actggcgaac tacttactct   5460
agcttcccgg caacaattaa tagactggat ggaggcggat aaagttgcag gaccacttct   5520
gcgctcggcc cttccggctg gctggtttat tgctgataaa tctggagccg gtgagcgtgg   5580
gtctcgcggt atcattgcag cactggggcc agatggtaag ccctcccgta tcgtagttat   5640
ctacacgacg gggagtcagg caactatgga tgaacgaaat agacagatcg ctgagatagg   5700
tgcctcactg attaagcatt ggtaactgtc agaccaagtt tactcatata tactttagat   5760
tgatttaaaa cttcattttt aatttaaaag gatctaggtg aagatccttt ttgataatct   5820
catgaccaaa atcccttaac gtgagttttc gttccactga gcgtcagacc ccgtagaaaa   5880
gatcaaagga tcttcttgag atcctttttt tctgcgcgta atctgctgct tgcaaacaaa   5940
aaaaccaccg ctaccagcgg tggtttgttt gccggatcaa gagctaccaa ctctttttcc   6000
gaaggtaact ggcttcagca gagcgcagat accaaatact gtccttctag tgtagccgta   6060
gttaggccac cacttcaaga actctgtagc accgcctaca tacctcgctc tgctaatcct   6120
gttaccagtg gctgctgcca gtggcgataa gtcgtgtctt accgggttgg actcaagacg   6180
atagttaccg gataaggcgc agcggtcggg ctgaacgggg ggttcgtgca cacagcccag   6240
cttggagcga acgacctaca ccgaactgag atacctacag cgtgagctat gagaaagcgc   6300
cacgcttccc gaagggagaa aggcggacag gtatccggta agcggcaggg tcggaacagg   6360
agagcgcacg agggagcttc cagggggaaa cgcctggtat ctttatagtc ctgtcgggtt   6420
tcgccacctc tgacttgagc gtcgattttt gtgatgctcg tcaggggggc ggagcctatg   6480
gaaaaacgcc agcaacgcgg cctttttacg gttcctggcc ttttgctggc cttttgctca   6540
catgttcttt cctgcgttat cccctgattc tgtggataac cgtattaccg cctttgagtg   6600
```

```
agctgatacc gctcgccgca gccgaacgac cgagcgcagc gagtcagtga gcgaggaagc   6660

ggaagagcgc ctgatgcggt attttctcct tacgcatctg tgcggtattt cacaccgcat   6720

atggtgcact ctcagtacaa tctgctctga tgccgcatag ttaagccagt atacactccg   6780

ctatcgctac gtgactgggt catggctgcg ccccgacacc cgccaacacc cgctgacgcg   6840

ccctgacggg cttgtctgct cccggcatcc gcttacagac aagctgtgac cgtctccggg   6900

agctgcatgt gtcagaggtt ttcaccgtca tcaccgaaac gcgcgaggca gcagatcaat   6960

tcgcgcgcga aggcgaagcg gcatgcataa tgtgcctgtc aaatggacga agcagggatt   7020

ctgcaaaccc tatgctactc cgtcaagccg tcaattgtct gattcgttac caattatgac   7080

aacttgacgg ctacatcatt cactttttct tcacaaccgg cacggaactc gctcgggctg   7140

gccccggtgc attttttaaa tacccgcgag aaatagagtt gatcgtcaaa accaacattg   7200

cgaccgacgg tggcgatagg catccgggtg gtgctcaaaa gcagcttcgc ctggctgata   7260

cgttggtcct cgcgccagct taagacgcta atccctaact gctggcggaa aagatgtgac   7320

agacgcgacg gcgacaagca aacatgctgt gcgacgctgg cgatatcaaa attgctgtct   7380

gccaggtgat cgctgatgta ctgacaagcc tcgcgtaccc gattatccat cggtggatgg   7440

agcgactcgt taatcgcttc catgcgccgc agtaacaatt gctcaagcag atttatcgcc   7500

agcagctccg aatagcgccc ttccccttgc ccggcgttaa tgatttgccc aaacaggtcg   7560

ctgaaatgcg gctggtgcgc ttcatccggg cgaaagaacc ccgtattggc aaatattgac   7620

ggccagttaa gccattcatg ccagtaggcg cgcggacgaa agtaaaccca ctggtgatac   7680

cattcgcgag cctccggatg acgaccgtag tgatgaatct ctcctggcgg gaacagcaaa   7740

atatcacccg gtcggcaaac aaattctcgt ccctgatttt tcaccacccc ctgaccgcga   7800

atggtgagat tgagaatata acctttcatt cccagcggtc ggtcgataaa aaaatcgaga   7860

taaccgttgg cctcaatcgg cgttaaaccc gccaccagat gggcattaaa cgagtatccc   7920

ggcagcaggg gatcattttg cgcttcagcc atacttttca tactcccgcc attcagagaa   7980

gaaaccaatt gtccatattg catcagacat tgccgtcact gcgtctttta ctggctcttc   8040

tcgctaacca aaccggtaac cccgcttatt aaaagcattc tgtaacaaag cgggaccaaa   8100

gccatgacaa aaacgcgtaa caaaagtgtc tataatcacg gcagaaaagt ccacattgat   8160

tatttgcacg gcgtcacact ttgctatgcc atagcatttt tatccataag attagcggat   8220

cctacctgac gctttttatc gcaactctct actgtttctc catacccgtt ttttgggcta   8280

acaggaggaa ttaa                                                      8294
```

```
<210> SEQ ID NO 21
<211> LENGTH: 8183
<212> TYPE: DNA
<213> ORGANISM: artificial sequence
<220> FEATURE:
<223> OTHER INFORMATION: pRF145 plasmid

<400> SEQUENCE: 21
```

```
aattcgacaa gaaatactcc atcggcctgg acattggaac caactctgtc ggctgggctg     60

tcatcaccga cgagtacaag gtgccctcca agaaattcaa ggtcctcgga aacaccgatc    120

gacactccat caagaaaaac ctcattggtg ccctgttgtt cgattctggc gagactgccg    180

aagctaccag actcaagcga actgctcggc gacgttacac ccgacggaag aaccgaatct    240

gctacctgca ggagatcttt tccaacgaga tggccaaggt ggacgattcg ttctttcatc    300
```

-continued

```
gactggagga atccttcctc gtcgaggaag acaagaaaca cgagcgtcat cccatctttg    360
gcaacattgt ggacgaggtt gcttaccacg agaagtatcc taccatctac cacctgcgaa    420
agaaactcgt cgattccacc gacaaggcgg atctcagact tatctacctc gctctggcac    480
acatgatcaa gtttcgaggt catttcctca tcgagggcga tctcaatccc gacaacagcg    540
atgtggacaa gctgttcatt cagctcgttc agacctacaa ccagctgttc gaggaaaacc    600
ccatcaatgc ctccggagtc gatgcaaagg ccatcttgtc tgctcgactc tcgaagagca    660
gacgactgga gaacctcatt gcccaacttc ctggcgagaa aaagaacgga ctgtttggca    720
acctcattgc cctttctctt ggtctcacac ccaacttcaa gtccaacttc gatctggcgg    780
aggacgccaa gctccagctg tccaaggaca cctacgacga tgacctcgac aacctgcttg    840
cacagattgg cgatcagtac gccgacctgt ttctcgctgc caagaacctt tcggatgcta    900
ttctcttgtc tgacattctg cgagtcaaca ccgagatcac aaaggctccc ctttctgcct    960
ccatgatcaa gcgatacgac gagcaccatc aggatctcac actgctcaag gctcttgtcc   1020
gacagcaact gcccgagaag tacaaggaga tctttttcga tcagtcgaag aacggctacg   1080
ctggatacat cgacggcgga gcctctcagg aagagttcta caagttcatc aagccaattc   1140
tcgagaagat ggacggaacc gaggaactgc ttgtcaagct caatcgagag gatctgcttc   1200
ggaagcaacg aaccttcgac aacggcagca ttcctcatca gatccacctc ggtgagctgc   1260
acgccattct tcgacgtcag gaagacttct acccctttct caaggacaac cgagagaaga   1320
tcgagaagat tcttaccttt cgaatcccct actatgttgg tcctcttgcc agaggaaact   1380
ctcgatttgc ttggatgact cgaaagtccg aggaaaccat cactccctgg aacttcgagg   1440
aagtcgtgga caagggtgcc tctgcacagt ccttcatcga gcgaatgacc aacttcgaca   1500
agaatctgcc caacgagaag gttcttccca agcattcgct gctctacgag tactttacag   1560
tctacaacga actcaccaaa gtcaagtacg ttaccgaggg aatgcgaaag cctgccttct   1620
tgtctggcga acagaagaaa gccattgtcg atctcctgtt caagaccaac cgaaaggtca   1680
ctgttaagca gctcaaggag gactacttca agaaaatcga gtgtttcgac agcgtcgaga   1740
tttccggagt tgaggaccga ttcaacgcct ctttgggcac ctatcacgat ctgctcaaga   1800
ttatcaagga caaggatttt ctcgacaacg aggaaaacga ggacattctg gaggacatcg   1860
tgctcactct taccctgttc gaagatcggg agatgatcga ggaacgactc aagacatacg   1920
ctcacctgtt cgacgacaag gtcatgaaac aactcaagcg acgtagatac accggctggg   1980
gaagactttc gcgaaagctc atcaacggca tcagagacaa gcagtccgga aagaccattc   2040
tggactttct caagtccgat ggctttgcca accgaaactt catgcagctc attcacgacg   2100
attctcttac cttcaaggag gacatccaga aggcacaagt gtccggtcag ggcgacagct   2160
tgcacgaaca tattgccaac ctggctggtt cgccagccat caagaaaggc attctccaga   2220
ctgtcaaggt tgtcgacgag ctggtgaagg tcatgggacg tcacaagccc gagaacattg   2280
tgatcgagat ggccagagag aaccagacaa ctcaaaaggg tcagaaaaac tcgcgagagc   2340
ggatgaagcg aatcgaggaa ggcatcaagg agctgggatc ccagattctc aaggagcatc   2400
ccgtcgagaa cactcaactg cagaacgaga agctgtatct ctactatctg cagaatggtc   2460
gagacatgta cgtggatcag gaactggaca tcaatcgtct cagcgactac gatgtggacc   2520
acattgtccc tcaatccttt ctcaaggacg attctatcga caacaaggtc cttacacgat   2580
ccgacaagaa cagaggcaag tcggacaacg ttcccagcga agaggtggtc aaaaagatga   2640
agaactactg gcgacagctg ctcaacgcca agctcattac ccagcgaaag ttcgacaatc   2700
```

-continued

```
ttaccaaggc cgagcgaggc ggtctgtccg agctcgacaa ggctggcttc atcaagcgtc   2760
aactcgtcga gaccagacag atcacaaagc acgtcgcaca gattctcgat tctcggatga   2820
acaccaagta cgacgagaac gacaagctca tccgagaggt caaggtgatt actctcaagt   2880
ccaaactggt ctccgatttc cgaaaggact ttcagttcta caaggtgcga gagatcaaca   2940
attaccacca tgcccacgat gcttacctca acgccgtcgt tggcactgcg ctcatcaaga   3000
aataccccaa gctcgaaagc gagttcgttt acggcgatta caaggtctac gacgttcgaa   3060
agatgattgc caagtccgaa caggagattg gcaaggctac tgccaagtac ttcttttact   3120
ccaacatcat gaactttttc aagaccgaga tcaccttggc caacggagag attcgaaaga   3180
gaccacttat cgagaccaac ggcgaaactg gagagatcgt gtgggacaag ggtcgagact   3240
ttgcaaccgt gcgaaaggtt ctgtcgatgc ctcaggtcaa catcgtcaag aaaaccgagg   3300
ttcagactgg cggattctcc aaggagtcga ttctgcccaa gcgaaactcc gacaagctca   3360
tcgctcgaaa gaaagactgg gatcccaaga aatacggtgg cttcgattct cctaccgtcg   3420
cctattccgt gcttgtcgtt gcgaaggtcg agaagggcaa gtccaaaaag ctcaagtccg   3480
tcaaggagct gctcggaatt accatcatgg agcgatcgag cttcgagaag aatcccatcg   3540
acttcttgga agccaagggt tacaaggagg tcaagaaaga cctcattatc aagctgccca   3600
agtactctct gttcgaactg gagaacggtc gaaagcgtat gctcgcctcc gctggcgagc   3660
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560
ctttttgcgt ttctacaaac tcttttgttt atttttctaa atacattcaa atatgtatcc   4620
gctcatgaga caataaccct gataaatgct tcaataatat tgaaaaagga agagtatgag   4680
tattcaacat ttccgtgtcg cccttattcc cttttttgcg gcattttgcc ttcctgtttt   4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt   4920
tgacgccggg caagagcaac tcggtcgccg catacactat tctcagaatg acttggttga   4980
gtactcacca gtcacagaaa agcatcttac ggatggcatg acagtaagag aattatgcag   5040
```

-continued

```
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg ggtctcgcgg   5400
tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580
acttcatttt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga gatccttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
ccacttcaag aactctgtag caccgcctac atacctcgct ctgctaatcc tgttaccagt   5940
ggctgctgcc agtggcgata agtcgtgtct taccgggttg gactcaagac gatagttacc   6000
ggataaggcg cagcggtcgg gctgaacggg gggttcgtgc acacagccca gcttggagcg   6060
aacgacctac accgaactga gatacctaca gcgtgagcta tgagaaagcg ccacgcttcc   6120
cgaagggaga aaggcggaca ggtatccggt aagcggcagg gtcggaacag gagagcgcac   6180
gagggagctt ccagggggaa acgcctggta tctttatagt cctgtcgggt ttcgccacct   6240
ctgacttgag cgtcgatttt tgtgatgctc gtcagggggg cggagcctat ggaaaaacgc   6300
cagcaacgcg gcctttttac ggttcctggc cttttgctgg ccttttgctc acatgttctt   6360
tcctgcgtta tcccctgatt ctgtggataa ccgtattacc gcctttgagt gagctgatac   6420
cgctcgccgc agccgaacga ccgagcgcag cgagtcagtg agcgaggaag cggaagagcg   6480
cctgatgcgg tattttctcc ttacgcatct gtgcggtatt tcacaccgca tatggtgcac   6540
tctcagtaca atctgctctg atgccgcata gttaagccag tatacactcc gctatcgcta   6600
cgtgactggg tcatggctgc gccccgacac ccgccaacac ccgctgacgc gccctgacgg   6660
gcttgtctgc tcccggcatc cgcttacaga caagctgtga ccgtctccgg gagctgcatg   6720
tgtcagaggt tttcaccgtc atcaccgaaa cgcgcgaggc agcagatcaa ttcgcgcgcg   6780
aaggcgaagc ggcatgcata atgtgcctgt caaatggacg aagcagggat tctgcaaacc   6840
ctatgctact ccgtcaagcc gtcaattgtc tgattcgtta ccaattatga caacttgacg   6900
gctacatcat tcactttttc ttcacaaccg gcacggaact cgctcgggct ggccccggtg   6960
catttttaaa atacccgcga gaaatagagt tgatcgtcaa aaccaacatt gcgaccgacg   7020
gtggcgatag gcatccgggt ggtgctcaaa agcagcttcg cctggctgat acgttggtcc   7080
tcgcgccagc ttaagacgct aatccctaac tgctggcgga aaagatgtga cagacgcgac   7140
ggcgacaagc aaacatgctg tgcgacgctg gcgatatcaa aattgctgtc tgccaggtga   7200
tcgctgatgt actgacaagc ctcgcgtacc cgattatcca tcggtggatg gagcgactcg   7260
ttaatcgctt ccatgcgccg cagtaacaat tgctcaagca gatttatcgc cagcagctcc   7320
gaatagcgcc cttccccttg cccggcgtta atgatttgcc caaacaggtc gctgaaatgc   7380
ggctggtgcg cttcatccgg gcgaaagaac cccgtattgg caaatattga cggccagtta   7440
```

agccattcat gccagtaggc gcgcggacga aagtaaaccc actggtgata ccattcgcga 7500
gcctccggat gacgaccgta gtgatgaatc tctcctggcg ggaacagcaa aatatcaccc 7560
ggtcggcaaa caaattctcg tccctgattt ttcaccaccc cctgaccgcg aatggtgaga 7620
ttgagaatat aacctttcat tcccagcggt cggtcgataa aaaaatcgag ataaccgttg 7680
gcctcaatcg gcgttaaacc cgccaccaga tgggcattaa acgagtatcc cggcagcagg 7740
ggatcatttt gcgcttcagc catacttttc atactcccgc cattcagaga agaaaccaat 7800
tgtccatatt gcatcagaca ttgccgtcac tgcgtctttt actggctctt ctcgctaacc 7860
aaaccggtaa ccccgcttat taaaagcatt ctgtaacaaa gcgggaccaa agccatgaca 7920
aaaacgcgta acaaaagtgt ctataatcac ggcagaaaag tccacattga ttatttgcac 7980
ggcgtcacac tttgctatgc catagcattt ttatccataa gattagcgga tcctacctga 8040
cgctttttat cgcaactctc tactgtttct ccatacccgt tttttgggct aacaggagga 8100
attaaccatg ggcatcacc accatcacca cggcgggggt ggtcgtcgtc gccgtcgccg 8160
ccgtcgtcgc ctcctgctgc tgg 8183

<210> SEQ ID NO 22
<211> LENGTH: 8195
<212> TYPE: DNA
<213> ORGANISM: artificial sequence
<220> FEATURE:
<223> OTHER INFORMATION: pRF146 plasmid

<400> SEQUENCE: 22
aattcgacaa gaaatactcc atcggcctgg acattggaac caactctgtc ggctgggctg 60
tcatcaccga cgagtacaag gtgccctcca agaaattcaa ggtcctcgga aacaccgatc 120
gacactccat caagaaaaac ctcattggtg ccctgttgtt cgattctggc gagactgccg 180
aagctaccag actcaagcga actgctcggc gacgttacac ccgacggaag aaccgaatct 240
gctacctgca ggagatcttt tccaacgaga tggccaaggt ggacgattcg ttctttcatc 300
gactggagga atccttcctc gtcgaggaag acaagaaaca cgagcgtcat cccatctttg 360
gcaacattgt ggacgaggtt gcttaccacg agaagtatcc taccatctac cacctgcgaa 420
agaaactcgt cgattccacc gacaaggcgg atctcagact tatctacctc gctctggcac 480
acatgatcaa gtttcgaggt catttcctca tcgagggcga tctcaatccc gacaacagcg 540
atgtggacaa gctgttcatt cagctcgttc agacctacaa ccagctgttc gaggaaaacc 600
ccatcaatgc ctccggagtc gatgcaaagg ccatcttgtc tgctcgactc tcgaagagca 660
gacgactgga gaacctcatt gcccaacttc ctggcgagaa aaagaacgga ctgtttggca 720
acctcattgc cctttctctt ggtctcacac ccaacttcaa gtccaacttc gatctggcgg 780
aggacgccaa gctccagctg tccaaggaca cctacgacga tgacctcgac aacctgcttg 840
cacagattgg cgatcagtac gccgacctgt ttctcgctgc caagaacctt tcggatgcta 900
ttctcttgtc tgacattctg cgagtcaaca ccgagatcac aaaggctccc ctttctgcct 960
ccatgatcaa gcgatacgac gagcaccatc aggatctcac actgctcaag gctcttgtcc 1020
gacagcaact gcccgagaag tacaaggaga tctttttcga tcagtcgaag aacggctacg 1080
ctggatacat cgacggcgga gcctctcagg aagagttcta caagttcatc aagccaattc 1140
tcgagaagat ggacggaacc gaggaactgc ttgtcaagct caatcgagag gatctgcttc 1200
ggaagcaacg aaccttcgac aacggcagca ttcctcatca gatccacctc ggtgagctgc 1260

-continued acgccattct tcgacgtcag gaagacttct accccttct caaggacaac cgagagaaga 1320
tcgagaagat tcttaccttt cgaatcccct actatgttgg tcctcttgcc agaggaaact 1380
ctcgatttgc ttggatgact cgaaagtccg aggaaaccat cactccctgg aacttcgagg 1440
aagtcgtgga caagggtgcc tctgcacagt ccttcatcga gcgaatgacc aacttcgaca 1500
agaatctgcc caacgagaag gttcttccca agcattcgct gctctacgag tactttacag 1560
tctacaacga actcaccaaa gtcaagtacg ttaccgaggg aatgcgaaag cctgccttct 1620
tgtctggcga acagaagaaa gccattgtcg atctcctgtt caagaccaac cgaaaggtca 1680
ctgttaagca gctcaaggag gactacttca agaaaatcga gtgtttcgac agcgtcgaga 1740
tttccggagt tgaggaccga ttcaacgcct ctttgggcac ctatcacgat ctgctcaaga 1800
ttatcaagga caaggatttt ctcgacaacg aggaaaacga ggacattctg gaggacatcg 1860
tgctcactct taccctgttc gaagatcggg agatgatcga ggaacgactc aagacatacg 1920
ctcacctgtt cgacgacaag gtcatgaaac aactcaagcg acgtagatac accggctggg 1980
gaagactttc gcgaaagctc atcaacggca tcagagacaa gcagtccgga aagaccattc 2040
tggactttct caagtccgat ggctttgcca accgaaactt catgcagctc attcacgacg 2100
attctcttac cttcaaggag gacatccaga aggcacaagt gtccggtcag ggcgacagct 2160
tgcacgaaca tattgccaac ctggctggtt cgccagccat caagaaaggc attctccaga 2220
ctgtcaaggt tgtcgacgag ctggtgaagg tcatgggacg tcacaagccc gagaacattg 2280
tgatcgagat ggccagagag aaccagacaa ctcaaaaggg tcagaaaaac tcgcgagagc 2340
ggatgaagcg aatcgaggaa ggcatcaagg agctgggatc ccagattctc aaggagcatc 2400
ccgtcgagaa cactcaactg cagaacgaga agctgtatct ctactatctg cagaatggtc 2460
gagacatgta cgtggatcag gaactggaca tcaatcgtct cagcgactac gatgtggacc 2520
acattgtccc tcaatccttt ctcaaggacg attctatcga caacaaggtc cttacacgat 2580
ccgacaagaa cagaggcaag tcggacaacg ttcccagcga agaggtggtc aaaaagatga 2640
agaactactg gcgacagctg ctcaacgcca agctcattac ccagcgaaag ttcgacaatc 2700
ttaccaaggc cgagcgaggc ggtctgtccg agctcgacaa ggctggcttc atcaagcgtc 2760
aactcgtcga gaccagacag atcacaaagc acgtcgcaca gattctcgat tctcggatga 2820
acaccaagta cgacgagaac gacaagctca tccgagaggt caaggtgatt actctcaagt 2880
ccaaactggt ctccgatttc cgaaaggact ttcagttcta caaggtgcga gagatcaaca 2940
attaccacca tgcccacgat gcttacctca acgccgtcgt tggcactgcg ctcatcaaga 3000
aataccccaa gctcgaaagc gagttcgttt acggcgatta caaggtctac gacgttcgaa 3060
agatgattgc caagtccgaa caggagattg gcaaggctac tgccaagtac ttcttttact 3120
ccaacatcat gaactttttc aagaccgaga tcaccttggc caacggagag attcgaaaga 3180
gaccacttat cgagaccaac ggcgaaactg gagagatcgt gtgggacaag ggtcgagact 3240
ttgcaaccgt gcgaaaggtt ctgtcgatgc ctcaggtcaa catcgtcaag aaaaccgagg 3300
ttcagactgg cggattctcc aaggagtcga ttctgcccaa gcgaaactcc gacaagctca 3360
tcgctcgaaa gaaagactgg gatcccaaga aatacggtgg cttcgattct cctaccgtcg 3420
cctattccgt gcttgtcgtt gcgaaggtcg agaagggcaa gtccaaaaag ctcaagtccg 3480
tcaaggagct gctcggaatt accatcatgg agcgatcgag cttcgagaag aatcccatcg 3540
acttcttgga agccaagggt tacaaggagg tcaagaaaga cctcattatc aagctgccca 3600
agtactctct gttcgaactg gagaacggtc gaaagcgtat gctcgcctcc gctggcgagc 3660

```
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560
ctttttgcgt ttctacaaac tcttttgttt atttttctaa atacattcaa atatgtatcc   4620
gctcatgaga caataaccct gataaatgct tcaataatat tgaaaaagga agagtatgag   4680
tattcaacat ttccgtgtcg cccttattcc cttttttgcg gcattttgcc ttcctgtttt   4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt   4920
tgacgccggg caagagcaac tcggtcgccg catacactat tctcagaatg acttggttga   4980
gtactcacca gtcacagaaa agcatcttac ggatggcatg acagtaagag aattatgcag   5040
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg ggtctcgcgg   5400
tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580
acttcatttt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga gatccttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
ccacttcaag aactctgtag caccgcctac atacctcgct ctgctaatcc tgttaccagt   5940
ggctgctgcc agtggcgata agtcgtgtct taccgggttg gactcaagac gatagttacc   6000
```

-continued

```
ggataaggcg cagcggtcgg gctgaacggg gggttcgtgc acacagccca gcttggagcg   6060
aacgacctac accgaactga gatacctaca gcgtgagcta tgagaaagcg ccacgcttcc   6120
cgaagggaga aaggcggaca ggtatccggt aagcggcagg gtcggaacag gagagcgcac   6180
gagggagctt ccagggggaa acgcctggta tctttatagt cctgtcgggt ttcgccacct   6240
ctgacttgag cgtcgatttt tgtgatgctc gtcagggggg cggagcctat ggaaaaacgc   6300
cagcaacgcg gcctttttac ggttcctggc cttttgctgg ccttttgctc acatgttctt   6360
tcctgcgtta tcccctgatt ctgtggataa ccgtattacc gcctttgagt gagctgatac   6420
cgctcgccgc agccgaacga ccgagcgcag cgagtcagtg agcgaggaag cggaagagcg   6480
cctgatgcgg tattttctcc ttacgcatct gtgcggtatt tcacaccgca tatggtgcac   6540
tctcagtaca atctgctctg atgccgcata gttaagccag tatacactcc gctatcgcta   6600
cgtgactggg tcatggctgc gccccgacac ccgccaacac ccgctgacgc gccctgacgg   6660
gcttgtctgc tcccggcatc cgcttacaga caagctgtga ccgtctccgg gagctgcatg   6720
tgtcagaggt tttcaccgtc atcaccgaaa cgcgcgaggc agcagatcaa ttcgcgcgcg   6780
aaggcgaagc ggcatgcata atgtgcctgt caaatggacg aagcagggat tctgcaaacc   6840
ctatgctact ccgtcaagcc gtcaattgtc tgattcgtta ccaattatga caacttgacg   6900
gctacatcat tcactttttc ttcacaaccg gcacggaact cgctcgggct ggccccggtg   6960
catttttaa atacccgcga gaaatagagt tgatcgtcaa aaccaacatt gcgaccgacg   7020
gtggcgatag gcatccgggt ggtgctcaaa agcagcttcg cctggctgat acgttggtcc   7080
tcgcgccagc ttaagacgct aatccctaac tgctggcgga aaagatgtga cagacgcgac   7140
ggcgacaagc aaacatgctg tgcgacgctg gcgatatcaa aattgctgtc tgccaggtga   7200
tcgctgatgt actgacaagc ctcgcgtacc cgattatcca tcggtggatg gagcgactcg   7260
ttaatcgctt ccatgcgccg cagtaacaat tgctcaagca gatttatcgc cagcagctcc   7320
gaatagcgcc cttccccttg cccggcgtta atgatttgcc caaacaggtc gctgaaatgc   7380
ggctggtgcg cttcatccgg gcgaaagaac cccgtattgg caaatattga cggccagtta   7440
agccattcat gccagtaggc gcgcggacga aagtaaaccc actggtgata ccattcgcga   7500
gcctccggat gacgaccgta gtgatgaatc tctcctggcg ggaacagcaa aatatcaccc   7560
ggtcggcaaa caaattctcg tccctgattt ttcaccaccc cctgaccgcg aatggtgaga   7620
ttgagaatat aacctttcat tcccagcggt cggtcgataa aaaaatcgag ataaccgttg   7680
gcctcaatcg gcgttaaacc cgccaccaga tgggcattaa acgagtatcc cggcagcagg   7740
ggatcatttt gcgcttcagc catacttttc atactcccgc cattcagaga agaaaccaat   7800
tgtccatatt gcatcagaca ttgccgtcac tgcgtctttt actggctctt ctcgctaacc   7860
aaaccggtaa ccccgcttat taaaagcatt ctgtaacaaa gcgggaccaa agccatgaca   7920
aaaacgcgta acaaaagtgt ctataatcac ggcagaaaag tccacattga ttatttgcac   7980
ggcgtcacac tttgctatgc catagcattt ttatccataa gattagcgga tcctacctga   8040
cgctttttat cgcaactctc tactgtttct ccatacccgt ttttgggct aacaggagga   8100
attaaccatg ggcatcacc accatcacca cgcgggttac ctgctgggca agattaatct   8160
taaagcctgc gccgcgtgtg ctaagaaaat tttgg                             8195
```

<210> SEQ ID NO 23
<211> LENGTH: 8186
<212> TYPE: DNA
<213> ORGANISM: artificial sequence
<220> FEATURE:
<223> OTHER INFORMATION: pRF162 plasmid

<400> SEQUENCE: 23
aattcgacaa gaaatactcc atcggcctgg acattggaac caactctgtc ggctgggctg 60
tcatcaccga cgagtacaag gtgccctcca agaaattcaa ggtcctcgga aacaccgatc 120
gacactccat caagaaaaac ctcattggtg ccctgttgtt cgattctggc gagactgccg 180
aagctaccag actcaagcga actgctcggc gacgttacac ccgacggaag aaccgaatct 240
gctacctgca ggagatcttt tccaacgaga tggccaaggt ggacgattcg ttctttcatc 300
gactggagga atccttcctc gtcgaggaag acaagaaaca cgagcgtcat cccatctttg 360
gcaacattgt ggacgaggtt gcttaccacg agaagtatcc taccatctac cacctgcgaa 420
agaaactcgt cgattccacc gacaaggcgg atctcagact tatctacctc gctctggcac 480
acatgatcaa gtttcgaggt catttcctca tcgagggcga tctcaatccc gacaacagcg 540
atgtggacaa gctgttcatt cagctcgttc agacctacaa ccagctgttc gaggaaaacc 600
ccatcaatgc ctccggagtc gatgcaaagg ccatcttgtc tgctcgactc tcgaagagca 660
gacgactgga gaacctcatt gcccaacttc ctggcgagaa aaagaacgga ctgtttggca 720
acctcattgc cctttctctt ggtctcacac ccaacttcaa gtccaacttc gatctggcgg 780
aggacgccaa gctccagctg tccaaggaca cctacgacga tgacctcgac aacctgcttg 840
cacagattgg cgatcagtac gccgacctgt ttctcgctgc caagaacctt tcggatgcta 900
ttctcttgtc tgacattctg cgagtcaaca ccgagatcac aaaggctccc ctttctgcct 960
ccatgatcaa gcgatacgac gagcaccatc aggatctcac actgctcaag gctcttgtcc 1020
gacagcaact gcccgagaag tacaaggaga tctttttcga tcagtcgaag aacggctacg 1080
ctggatacat cgacggcgga gcctctcagg aagagttcta caagttcatc aagccaattc 1140
tcgagaagat ggacggaacc gaggaactgc ttgtcaagct caatcgagag gatctgcttc 1200
ggaagcaacg aaccttcgac aacggcagca ttcctcatca gatccacctc ggtgagctgc 1260
acgccattct tcgacgtcag gaagacttct accccctttct caaggacaac cgagagaaga 1320
tcgagaagat tcttaccttt cgaatcccct actatgttgg tcctcttgcc agaggaaact 1380
ctcgatttgc ttggatgact cgaaagtccg aggaaaccat cactccctgg aacttcgagg 1440
aagtcgtgga caagggtgcc tctgcacagt ccttcatcga gcgaatgacc aacttcgaca 1500
agaatctgcc caacgagaag gttcttccca agcattcgct gctctacgag tactttacag 1560
tctacaacga actcaccaaa gtcaagtacg ttaccgaggg aatgcgaaag cctgccttct 1620
tgtctggcga acagaagaaa gccattgtcg atctcctgtt caagaccaac cgaaaggtca 1680
ctgttaagca gctcaaggag gactacttca agaaaatcga gtgtttcgac agcgtcgaga 1740
tttccggagt tgaggaccga ttcaacgcct ctttgggcac ctatcacgat ctgctcaaga 1800
ttatcaagga caaggatttt ctcgacaacg aggaaaacga ggacattctg gaggacatcg 1860
tgctcactct taccctgttc gaagatcggg agatgatcga ggaacgactc aagacatacg 1920
ctcacctgtt cgacgacaag gtcatgaaac aactcaagcg acgtagatac accggctggg 1980
gaagactttc gcgaaagctc atcaacggca tcagagacaa gcagtccgga aagaccattc 2040
tggactttct caagtccgat ggctttgcca accgaaactt catgcagctc attcacgacg 2100
attctcttac cttcaaggag gacatccaga aggcacaagt gtccggtcag ggcgacagct 2160
tgcacgaaca tattgccaac ctggctggtt cgccagccat caagaaaggc attctccaga 2220

-continued

```
ctgtcaaggt tgtcgacgag ctggtgaagg tcatgggacg tcacaagccc gagaacattg   2280
tgatcgagat ggccagagag aaccagacaa ctcaaaaggg tcagaaaaac tcgcgagagc   2340
ggatgaagcg aatcgaggaa ggcatcaagg agctgggatc ccagattctc aaggagcatc   2400
ccgtcgagaa cactcaactg cagaacgaga agctgtatct ctactatctg cagaatggtc   2460
gagacatgta cgtggatcag gaactggaca tcaatcgtct cagcgactac gatgtggacc   2520
acattgtccc tcaatccttt ctcaaggacg attctatcga caacaaggtc cttacacgat   2580
ccgacaagaa cagaggcaag tcggacaacg ttcccagcga agaggtggtc aaaaagatga   2640
agaactactg gcgacagctg ctcaacgcca agctcattac ccagcgaaag ttcgacaatc   2700
ttaccaaggc cgagcgaggc ggtctgtccg agctcgacaa ggctggcttc atcaagcgtc   2760
aactcgtcga gaccagacag atcacaaagc acgtcgcaca gattctcgat tctcggatga   2820
acaccaagta cgacgagaac gacaagctca tccgagaggt caaggtgatt actctcaagt   2880
ccaaactggt ctccgatttc cgaaaggact ttcagttcta caaggtgcga gagatcaaca   2940
attaccacca tgcccacgat gcttacctca acgccgtcgt tggcactgcg ctcatcaaga   3000
aataccccaa gctcgaaagc gagttcgttt acggcgatta caaggtctac gacgttcgaa   3060
agatgattgc caagtccgaa caggagattg gcaaggctac tgccaagtac ttcttttact   3120
ccaacatcat gaactttttc aagaccgaga tcaccttggc caacggagag attcgaaaga   3180
gaccacttat cgagaccaac ggcgaaactg gagagatcgt gtgggacaag ggtcgagact   3240
ttgcaaccgt gcgaaaggtt ctgtcgatgc ctcaggtcaa catcgtcaag aaaaccgagg   3300
ttcagactgg cggattctcc aaggagtcga ttctgcccaa gcgaaactcc gacaagctca   3360
tcgctcgaaa gaaagactgg gatcccaaga aatacggtgg cttcgattct cctaccgtcg   3420
cctattccgt gcttgtcgtt gcgaaggtcg agaagggcaa gtccaaaaag ctcaagtccg   3480
tcaaggagct gctcggaatt accatcatgg agcgatcgag cttcgagaag aatcccatcg   3540
acttcttgga agccaagggt tacaaggagg tcaagaaaga cctcattatc aagctgccca   3600
agtactctct gttcgaactg gagaacggtc gaaagcgtat gctcgcctcc gctggcgagc   3660
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560
ctttttgcgt ttctacaaac tcttttgttt atttttctaa atacattcaa atatgtatcc   4620
```

-continued

```
gctcatgaga caataaccct gataaatgct tcaataatat tgaaaaagga agagtatgag   4680
tattcaacat ttccgtgtcg cccttattcc cttttttgcg gcattttgcc ttcctgtttt   4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt   4920
tgacgccggg caagagcaac tcggtcgccg catacactat tctcagaatg acttggttga   4980
gtactcacca gtcacagaaa agcatcttac ggatggcatg acagtaagag aattatgcag   5040
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg ggtctcgcgg   5400
tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580
acttcatttt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga gatccttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
ccacttcaag aactctgtag caccgcctac atacctcgct ctgctaatcc tgttaccagt   5940
ggctgctgcc agtggcgata agtcgtgtct taccgggttg gactcaagac gatagttacc   6000
ggataaggcg cagcggtcgg gctgaacggg gggttcgtgc acacagccca gcttggagcg   6060
aacgacctac accgaactga gatacctaca gcgtgagcta tgagaaagcg ccacgcttcc   6120
cgaagggaga aaggcggaca ggtatccggt aagcggcagg gtcggaacag gagagcgcac   6180
gagggagctt ccagggggaa acgcctggta tctttatagt cctgtcgggt ttcgccacct   6240
ctgacttgag cgtcgatttt tgtgatgctc gtcagggggg cggagcctat ggaaaaacgc   6300
cagcaacgcg gcctttttac ggttcctggc cttttgctgg ccttttgctc acatgttctt   6360
tcctgcgtta tcccctgatt ctgtggataa ccgtattacc gcctttgagt gagctgatac   6420
cgctcgccgc agccgaacga ccgagcgcag cgagtcagtg agcgaggaag cggaagagcg   6480
cctgatgcgg tattttctcc ttacgcatct gtgcggtatt tcacaccgca tatggtgcac   6540
tctcagtaca atctgctctg atgccgcata gttaagccag tatacactcc gctatcgcta   6600
cgtgactggg tcatggctgc gccccgacac ccgccaacac ccgctgacgc gccctgacgg   6660
gcttgtctgc tcccggcatc cgcttacaga caagctgtga ccgtctccgg gagctgcatg   6720
tgtcagaggt tttcaccgtc atcaccgaaa cgcgcgaggc agcagatcaa ttcgcgcgcg   6780
aaggcgaagc ggcatgcata atgtgcctgt caaatggacg aagcagggat tctgcaaacc   6840
ctatgctact ccgtcaagcc gtcaattgtc tgattcgtta ccaattatga caacttgacg   6900
gctacatcat tcactttttc ttcacaaccg gcacggaact cgctcgggct ggccccggtg   6960
```

```
catttttaa atacccgcga gaaatagagt tgatcgtcaa aaccaacatt gcgaccgacg   7020

gtggcgatag gcatccgggt ggtgctcaaa agcagcttcg cctggctgat acgttggtcc   7080

tcgcgccagc ttaagacgct aatccctaac tgctggcgga aaagatgtga cagacgcgac   7140

ggcgacaagc aaacatgctg tgcgacgctg gcgatatcaa aattgctgtc tgccaggtga   7200

tcgctgatgt actgacaagc ctcgcgtacc cgattatcca tcggtggatg gagcgactcg   7260

ttaatcgctt ccatgcgccg cagtaacaat tgctcaagca gatttatcgc cagcagctcc   7320

gaatagcgcc cttccccttg cccggcgtta atgatttgcc caaacaggtc gctgaaatgc   7380

ggctggtgcg cttcatccgg gcgaaagaac cccgtattgg caaatattga cggccagtta   7440

agccattcat gccagtaggc gcgcggacga aagtaaaccc actggtgata ccattcgcga   7500

gcctccggat gacgaccgta gtgatgaatc tctcctggcg ggaacagcaa aatatcaccc   7560

ggtcggcaaa caaattctcg tccctgattt ttcaccaccc cctgaccgcg aatggtgaga   7620

ttgagaatat aacctttcat tcccagcggt cggtcgataa aaaaatcgag ataaccgttg   7680

gcctcaatcg gcgttaaacc cgccaccaga tgggcattaa acgagtatcc cggcagcagg   7740

ggatcatttt gcgcttcagc catacttttc atactcccgc cattcagaga agaaaccaat   7800

tgtccatatt gcatcagaca ttgccgtcac tgcgtctttt actggctctt ctcgctaacc   7860

aaaccggtaa ccccgcttat taaaagcatt ctgtaacaaa gcgggaccaa agccatgaca   7920

aaaacgcgta acaaaagtgt ctataatcac ggcagaaaag tccacattga ttatttgcac   7980

ggcgtcacac tttgctatgc catagcattt ttatccataa gattagcgga tcctacctga   8040

cgctttttat cgcaactctc tactgtttct ccatacccgt tttttgggct aacaggagga   8100

attaaccatg ggcatcacc accatcacca cttattgatt atcttgcgtc gtcgcatccg   8160

caaacaggcg cacgcacata gcaagg                                       8186
```

<210> SEQ ID NO 24
<211> LENGTH: 80
<212> TYPE: RNA
<213> ORGANISM: artificial sequence
<220> FEATURE:
<223> OTHER INFORMATION: Cas9 endonuclease recognition (CER) domain

<400> SEQUENCE: 24

```
guuuuagagc uagaaauagc aaguuaaaau aaggcuaguc cguuaucaac uugaaaaagu     60

ggcaccgagu cggugcuuuu                                                 80
```

<210> SEQ ID NO 25
<211> LENGTH: 20
<212> TYPE: DNA
<213> ORGANISM: Yarrowia lipolytica

<400> SEQUENCE: 25

```
tcaaacgatt acccaccctc                                                 20
```

<210> SEQ ID NO 26
<211> LENGTH: 43
<212> TYPE: RNA
<213> ORGANISM: artificial sequence
<220> FEATURE:
<223> OTHER INFORMATION: Hammerhead (HH) ribozyme
<220> FEATURE:
<221> NAME/KEY: misc_feature
<222> LOCATION: (1)..(6)
<223> OTHER INFORMATION: n is a, c, g, or u

<400> SEQUENCE: 26
nnnnnncuga ugaguccgug aggacgaaac gaguaagcuc guc 43

<210> SEQ ID NO 27
<211> LENGTH: 68
<212> TYPE: RNA
<213> ORGANISM: hepatitis delta virus

<400> SEQUENCE: 27
ggccggcaug gucccagccu ccucgcuggc gccggcuggg caacaugcuu cggcauggcg 60
aaugggac 68

<210> SEQ ID NO 28
<211> LENGTH: 211
<212> TYPE: DNA
<213> ORGANISM: artificial sequence
<220> FEATURE:
<223> OTHER INFORMATION: HH-sgRNA-HDV (RGR) pre-sgRNA expression cassette

<400> SEQUENCE: 28
gtttgactga tgagtccgtg aggacgaaac gagtaagctc gtctcaaacg attacccacc 60
ctcgttttag agctagaaat agcaagttaa aataaggcta gtccgttatc aacttgaaaa 120
agtggcaccg agtcggtgct tttggccggc atggtcccag cctcctcgct ggcgccggct 180
gggcaacatg cttcggcatg gcgaatggga c 211

<210> SEQ ID NO 29
<211> LENGTH: 20
<212> TYPE: DNA
<213> ORGANISM: Bacteriophage T7

<400> SEQUENCE: 29
taatacgact cactataggg 20

<210> SEQ ID NO 30
<211> LENGTH: 2875
<212> TYPE: DNA
<213> ORGANISM: artificial sequence
<220> FEATURE:
<223> OTHER INFORMATION: pRF46 plasmid

<400> SEQUENCE: 30
agcttgtccc attcgccatg ccgaagcatg ttgcccagcc ggcgccagcg aggaggctgg 60
gaccatgccg gccaaaagca ccaccgactc ggtgccactt tttcaagttg ataacggact 120
agccttattt taacttgcta tttctagctc taaaacgagg gtgggtaatc gtttgagacg 180
agcttactcg tttcgtcctc acggactcat cagtcaaacc cctatagtga gtcgtattag 240
aattcgtaat catggtcata gctgtttcct gtgtgaaatt gttatccgct cacaattcca 300
cacaacatac gagccggaag cataaagtgt aaagcctggg gtgcctaatg agtgagctaa 360
ctcacattaa ttgcgttgcg ctcactgccc gctttccagt cgggaaacct gtcgtgccag 420
ctgcattaat gaatcggcca acgcgcgggg agaggcggtt tgcgtattgg gcgctcttcc 480
gcttcctcgc tcactgactc gctgcgctcg gtcgttcggc tgcggcgagc ggtatcagct 540
cactcaaagg cggtaatacg gttatccaca gaatcagggg ataacgcagg aaagaacatg 600
tgagcaaaag gccagcaaaa ggccaggaac cgtaaaaagg ccgcgttgct ggcgtttttc 660
cataggctcc gcccccctga cgagcatcac aaaaatcgac gctcaagtca gaggtggcga 720
aacccgacag gactataaag ataccaggcg tttccccctg gaagctccct cgtgcgctct 780

```
cctgttccga ccctgccgct taccggatac ctgtccgcct ttctcccttc gggaagcgtg    840

gcgctttctc atagctcacg ctgtaggtat ctcagttcgg tgtaggtcgt tcgctccaag    900

ctgggctgtg tgcacgaacc ccccgttcag cccgaccgct gcgccttatc cggtaactat    960

cgtcttgagt ccaacccggt aagacacgac ttatcgccac tggcagcagc cactggtaac   1020

aggattagca gagcgaggta tgtaggcggt gctacagagt tcttgaagtg gtggcctaac   1080

tacggctaca ctagaaggac agtatttggt atctgcgctc tgctgaagcc agttaccttc   1140

ggaaaaagag ttggtagctc ttgatccggc aaacaaacca ccgctggtag cggtggtttt   1200

tttgtttgca agcagcagat tacgcgcaga aaaaaaggat ctcaagaaga tcctttgatc   1260

ttttctacgg ggtctgacgc tcagtggaac gaaaactcac gttaagggat tttggtcatg   1320

agattatcaa aaaggatctt cacctagatc cttttaaatt aaaaatgaag ttttaaatca   1380

atctaaagta tatatgagta aacttggtct gacagttacc aatgcttaat cagtgaggca   1440

cctatctcag cgatctgtct atttcgttca tccatagttg cctgactccc cgtcgtgtag   1500

ataactacga tacgggaggg cttaccatct ggccccagtg ctgcaatgat accgcgagac   1560

ccacgctcac cggctccaga tttatcagca ataaaccagc cagccggaag ggccgagcgc   1620

agaagtggtc ctgcaacttt atccgcctcc atccagtcta ttaattgttg ccgggaagct   1680

agagtaagta gttcgccagt taatagtttg cgcaacgttg ttgccattgc tacaggcatc   1740

gtggtgtcac gctcgtcgtt tggtatggct tcattcagct ccggttccca acgatcaagg   1800

cgagttacat gatcccccat gttgtgcaaa aaagcggtta gctccttcgg tcctccgatc   1860

gttgtcagaa gtaagttggc cgcagtgtta tcactcatgg ttatggcagc actgcataat   1920

tctcttactg tcatgccatc cgtaagatgc ttttctgtga ctggtgagta ctcaaccaag   1980

tcattctgag aatagtgtat gcggcgaccg agttgctctt gcccggcgtc aatacgggat   2040

aataccgcgc cacatagcag aactttaaaa gtgctcatca ttggaaaacg ttcttcgggg   2100

cgaaaactct caaggatctt accgctgttg agatccagtt cgatgtaacc cactcgtgca   2160

cccaactgat cttcagcatc ttttactttc accagcgttt ctgggtgagc aaaaacagga   2220

aggcaaaatg ccgcaaaaaa gggaataagg gcgacacgga aatgttgaat actcatactc   2280

ttcctttttc aatattattg aagcatttat cagggttatt gtctcatgag cggatacata   2340

tttgaatgta tttagaaaaa taaacaaata ggggttccgc gcacatttcc ccgaaaagtg   2400

ccacctgacg tctaagaaac cattattatc atgacattaa cctataaaaa taggcgtatc   2460

acgaggccct ttcgtctcgc gcgtttcggt gatgacggtg aaaacctctg acacatgcag   2520

ctcccggaga cggtcacagc ttgtctgtaa gcggatgccg ggagcagaca agcccgtcag   2580

ggcgcgtcag cgggtgttgg cgggtgtcgg ggctggctta actatgcggc atcagagcag   2640

attgtactga gagtgcacca tatgcggtgt gaaataccgc acagatgcgt aaggagaaaa   2700

taccgcatca ggcgccattc gccattcagg ctgcgcaact gttgggaagg gcgatcggtg   2760

cgggcctctt cgctattacg ccagctggcg aaagggggat gtgctgcaag gcgattaagt   2820

tgggtaacgc cagggttttc ccagtcacga cgttgtaaaa cgacggccag tgcca        2875
```

<210> SEQ ID NO 31
<211> LENGTH: 20
<212> TYPE: DNA
<213> ORGANISM: artificial sequence
<220> FEATURE:
<223> OTHER INFORMATION: T7 forward PCR primer

<400> SEQUENCE: 31
ccggctcgta tgttgtgtgg 20

<210> SEQ ID NO 32
<211> LENGTH: 20
<212> TYPE: DNA
<213> ORGANISM: artificial sequence
<220> FEATURE:
<223> OTHER INFORMATION: gRNArev1 reverse primer

<400> SEQUENCE: 32
aaaagcaccg actcggtgcc 20

<210> SEQ ID NO 33
<211> LENGTH: 21
<212> TYPE: DNA
<213> ORGANISM: artificial sequence
<220> FEATURE:
<223> OTHER INFORMATION: IV-up forward primer

<400> SEQUENCE: 33
ccacgaaacg acgtttcgac c 21

<210> SEQ ID NO 34
<211> LENGTH: 20
<212> TYPE: DNA
<213> ORGANISM: artificial sequence
<220> FEATURE:
<223> OTHER INFORMATION: IV-down reverse primer

<400> SEQUENCE: 34
gcaaagactc ggttgatggc 20

<210> SEQ ID NO 35
<211> LENGTH: 982
<212> TYPE: DNA
<213> ORGANISM: Yarrowia lipolytica

<400> SEQUENCE: 35
ccacgaaacg acgtttcgac cttaacgacc ctgccgtctc catccatccg accacaatgg 60
aaaagacatt ttcaaacgat tacccaccct ccgggactga ggcccacatc cacatcaacc 120
acacggccca ctcggatgac tcagaggagg tgccctcgca caaggaaaat tacaacacca 180
gtggccacga cctggaggag tccgacccgg ataaccatgt cggtgagacc ctcgaggtca 240
agcgaggtct caagatgcga cacatctcca tgatctcgct tggaggaacc attggtaccg 300
gtctcttcat tggtaccgga ggagctctcc agcaggccgg tccctgtggc gccctcgtcg 360
cctacgtgtt catggccacc attgtctact ctgttgccga gtctcttgga gaactggcta 420
cgtacattcc catcaccggc tcctttgccg tctttactac ccgatatctg tcacagtcgt 480
ttggtgcctc catgggctgg ctatactggt tctcgtgggc gatcaccttc gccatcgagc 540
tcaacaccat tggtcccgtg attgagtact ggactgacgc cgttcctact gctgcctgga 600
ttgccatctt cttcgtcatc ctcactacca tcaacttctt ccccgtgggc ttctatggcg 660
aagtcgagtt ctgggtggcc tccgtgaagg tcattgccat cattggatgg ctcatctacg 720
cgctctgcat gacgtgtgga gcaggtgtaa caggtcctgt gggattcaga tactggaacc 780
accccggacc catgggagac ggaatctgga ccgacggcgt gcccattgtg cgaaacgcgc 840
ccggtcgacg attcatggga tggctcaatt cgctcgttaa cgccgccttc acctaccagg 900
gctgtgagct ggtcggagtc actgccggtg aggcccagaa ccccagaaag tccgtccctc 960
gagccatcaa ccgagtcttt gc 982

<210> SEQ ID NO 36
<211> LENGTH: 4
<212> TYPE: RNA
<213> ORGANISM: unknown
<220> FEATURE:
<223> OTHER INFORMATION: RNA loop-forming sequence (GAAA)

<400> SEQUENCE: 36 gaaa 4

<210> SEQ ID NO 37
<211> LENGTH: 4
<212> TYPE: RNA
<213> ORGANISM: unknown
<220> FEATURE:
<223> OTHER INFORMATION: RNA loop-forming sequence (CAAA)

<400> SEQUENCE: 37 caaa 4

<210> SEQ ID NO 38
<211> LENGTH: 4
<212> TYPE: RNA
<213> ORGANISM: unknown
<220> FEATURE:
<223> OTHER INFORMATION: RNA loop-forming sequence (AAAG)

<400> SEQUENCE: 38 aaag 4

<210> SEQ ID NO 39
<211> LENGTH: 1434
<212> TYPE: PRT
<213> ORGANISM: artificial sequence
<220> FEATURE:
<223> OTHER INFORMATION: Zebra CPP-Cas9-NLS fusion protein

<400> SEQUENCE: 39

Glu Cys Asp Ser Glu Leu Glu Ile Lys Arg Tyr Lys Arg Val Arg Val
1 5 10 15

Ala Ser Arg Lys Cys Arg Ala Lys Phe Lys Gln Leu Leu Gln His Tyr
20 25 30

Arg Glu Val Ala Ala Ala Lys Ser Ser Glu Asn Asp Arg Leu Arg Leu
35 40 45

Leu Leu Lys Gln Met Cys Glu Phe Asp Lys Lys Tyr Ser Ile Gly Leu
50 55 60

Asp Ile Gly Thr Asn Ser Val Gly Trp Ala Val Ile Thr Asp Glu Tyr
65 70 75 80

Lys Val Pro Ser Lys Lys Phe Lys Val Leu Gly Asn Thr Asp Arg His
85 90 95

Ser Ile Lys Lys Asn Leu Ile Gly Ala Leu Leu Phe Asp Ser Gly Glu
100 105 110

Thr Ala Glu Ala Thr Arg Leu Lys Arg Thr Ala Arg Arg Arg Tyr Thr
115 120 125

Arg Arg Lys Asn Arg Ile Cys Tyr Leu Gln Glu Ile Phe Ser Asn Glu
130 135 140

Met Ala Lys Val Asp Asp Ser Phe Phe His Arg Leu Glu Glu Ser Phe
145 150 155 160

-continued

```
Leu Val Glu Glu Asp Lys Lys His Glu Arg His Pro Ile Phe Gly Asn
                165                 170                 175

Ile Val Asp Glu Val Ala Tyr His Glu Lys Tyr Pro Thr Ile Tyr His
            180                 185                 190

Leu Arg Lys Lys Leu Val Asp Ser Thr Asp Lys Ala Asp Leu Arg Leu
        195                 200                 205

Ile Tyr Leu Ala Leu Ala His Met Ile Lys Phe Arg Gly His Phe Leu
    210                 215                 220

Ile Glu Gly Asp Leu Asn Pro Asp Asn Ser Asp Val Asp Lys Leu Phe
225                 230                 235                 240

Ile Gln Leu Val Gln Thr Tyr Asn Gln Leu Phe Glu Glu Asn Pro Ile
                245                 250                 255

Asn Ala Ser Gly Val Asp Ala Lys Ala Ile Leu Ser Ala Arg Leu Ser
            260                 265                 270

Lys Ser Arg Arg Leu Glu Asn Leu Ile Ala Gln Leu Pro Gly Glu Lys
        275                 280                 285

Lys Asn Gly Leu Phe Gly Asn Leu Ile Ala Leu Ser Leu Gly Leu Thr
    290                 295                 300

Pro Asn Phe Lys Ser Asn Phe Asp Leu Ala Glu Asp Ala Lys Leu Gln
305                 310                 315                 320

Leu Ser Lys Asp Thr Tyr Asp Asp Asp Leu Asp Asn Leu Leu Ala Gln
                325                 330                 335

Ile Gly Asp Gln Tyr Ala Asp Leu Phe Leu Ala Ala Lys Asn Leu Ser
            340                 345                 350

Asp Ala Ile Leu Leu Ser Asp Ile Leu Arg Val Asn Thr Glu Ile Thr
        355                 360                 365

Lys Ala Pro Leu Ser Ala Ser Met Ile Lys Arg Tyr Asp Glu His His
    370                 375                 380

Gln Asp Leu Thr Leu Leu Lys Ala Leu Val Arg Gln Gln Leu Pro Glu
385                 390                 395                 400

Lys Tyr Lys Glu Ile Phe Phe Asp Gln Ser Lys Asn Gly Tyr Ala Gly
                405                 410                 415

Tyr Ile Asp Gly Gly Ala Ser Gln Glu Glu Phe Tyr Lys Phe Ile Lys
            420                 425                 430

Pro Ile Leu Glu Lys Met Asp Gly Thr Glu Glu Leu Leu Val Lys Leu
        435                 440                 445

Asn Arg Glu Asp Leu Leu Arg Lys Gln Arg Thr Phe Asp Asn Gly Ser
    450                 455                 460

Ile Pro His Gln Ile His Leu Gly Glu Leu His Ala Ile Leu Arg Arg
465                 470                 475                 480

Gln Glu Asp Phe Tyr Pro Phe Leu Lys Asp Asn Arg Glu Lys Ile Glu
                485                 490                 495

Lys Ile Leu Thr Phe Arg Ile Pro Tyr Tyr Val Gly Pro Leu Ala Arg
            500                 505                 510

Gly Asn Ser Arg Phe Ala Trp Met Thr Arg Lys Ser Glu Glu Thr Ile
        515                 520                 525

Thr Pro Trp Asn Phe Glu Glu Val Val Asp Lys Gly Ala Ser Ala Gln
    530                 535                 540

Ser Phe Ile Glu Arg Met Thr Asn Phe Asp Lys Asn Leu Pro Asn Glu
545                 550                 555                 560

Lys Val Leu Pro Lys His Ser Leu Leu Tyr Glu Tyr Phe Thr Val Tyr
                565                 570                 575

Asn Glu Leu Thr Lys Val Lys Tyr Val Thr Glu Gly Met Arg Lys Pro
```

-continued

```
            580                 585                 590

Ala Phe Leu Ser Gly Glu Gln Lys Lys Ala Ile Val Asp Leu Leu Phe
        595                 600                 605

Lys Thr Asn Arg Lys Val Thr Val Lys Gln Leu Lys Glu Asp Tyr Phe
    610                 615                 620

Lys Lys Ile Glu Cys Phe Asp Ser Val Glu Ile Ser Gly Val Glu Asp
625                 630                 635                 640

Arg Phe Asn Ala Ser Leu Gly Thr Tyr His Asp Leu Leu Lys Ile Ile
                645                 650                 655

Lys Asp Lys Asp Phe Leu Asp Asn Glu Glu Asn Glu Asp Ile Leu Glu
            660                 665                 670

Asp Ile Val Leu Thr Leu Thr Leu Phe Glu Asp Arg Glu Met Ile Glu
        675                 680                 685

Glu Arg Leu Lys Thr Tyr Ala His Leu Phe Asp Asp Lys Val Met Lys
    690                 695                 700

Gln Leu Lys Arg Arg Arg Tyr Thr Gly Trp Gly Arg Leu Ser Arg Lys
705                 710                 715                 720

Leu Ile Asn Gly Ile Arg Asp Lys Gln Ser Gly Lys Thr Ile Leu Asp
                725                 730                 735

Phe Leu Lys Ser Asp Gly Phe Ala Asn Arg Asn Phe Met Gln Leu Ile
            740                 745                 750

His Asp Asp Ser Leu Thr Phe Lys Glu Asp Ile Gln Lys Ala Gln Val
        755                 760                 765

Ser Gly Gln Gly Asp Ser Leu His Glu His Ile Ala Asn Leu Ala Gly
    770                 775                 780

Ser Pro Ala Ile Lys Lys Gly Ile Leu Gln Thr Val Lys Val Val Asp
785                 790                 795                 800

Glu Leu Val Lys Val Met Gly Arg His Lys Pro Glu Asn Ile Val Ile
                805                 810                 815

Glu Met Ala Arg Glu Asn Gln Thr Thr Gln Lys Gly Gln Lys Asn Ser
            820                 825                 830

Arg Glu Arg Met Lys Arg Ile Glu Glu Gly Ile Lys Glu Leu Gly Ser
        835                 840                 845

Gln Ile Leu Lys Glu His Pro Val Glu Asn Thr Gln Leu Gln Asn Glu
    850                 855                 860

Lys Leu Tyr Leu Tyr Tyr Leu Gln Asn Gly Arg Asp Met Tyr Val Asp
865                 870                 875                 880

Gln Glu Leu Asp Ile Asn Arg Leu Ser Asp Tyr Asp Val Asp His Ile
                885                 890                 895

Val Pro Gln Ser Phe Leu Lys Asp Asp Ser Ile Asp Asn Lys Val Leu
            900                 905                 910

Thr Arg Ser Asp Lys Asn Arg Gly Lys Ser Asp Asn Val Pro Ser Glu
        915                 920                 925

Glu Val Val Lys Lys Met Lys Asn Tyr Trp Arg Gln Leu Leu Asn Ala
    930                 935                 940

Lys Leu Ile Thr Gln Arg Lys Phe Asp Asn Leu Thr Lys Ala Glu Arg
945                 950                 955                 960

Gly Gly Leu Ser Glu Leu Asp Lys Ala Gly Phe Ile Lys Arg Gln Leu
                965                 970                 975

Val Glu Thr Arg Gln Ile Thr Lys His Val Ala Gln Ile Leu Asp Ser
            980                 985                 990

Arg Met Asn Thr Lys Tyr Asp Glu  Asn Asp Lys Leu Ile  Arg Glu Val
        995                 1000                 1005
```

```
Lys Val  Ile Thr Leu Lys Ser  Lys Leu Val Ser Asp  Phe Arg Lys
    1010                 1015                 1020

Asp Phe  Gln Phe Tyr Lys Val  Arg Glu Ile Asn Asn  Tyr His His
    1025                 1030                 1035

Ala His  Asp Ala Tyr Leu Asn  Ala Val Val Gly Thr  Ala Leu Ile
    1040                 1045                 1050

Lys Lys  Tyr Pro Lys Leu Glu  Ser Glu Phe Val Tyr  Gly Asp Tyr
    1055                 1060                 1065

Lys Val  Tyr Asp Val Arg Lys  Met Ile Ala Lys Ser  Glu Gln Glu
    1070                 1075                 1080

Ile Gly  Lys Ala Thr Ala Lys  Tyr Phe Phe Tyr Ser  Asn Ile Met
    1085                 1090                 1095

Asn Phe  Phe Lys Thr Glu Ile  Thr Leu Ala Asn Gly  Glu Ile Arg
    1100                 1105                 1110

Lys Arg  Pro Leu Ile Glu Thr  Asn Gly Glu Thr Gly  Glu Ile Val
    1115                 1120                 1125

Trp Asp  Lys Gly Arg Asp Phe  Ala Thr Val Arg Lys  Val Leu Ser
    1130                 1135                 1140

Met Pro  Gln Val Asn Ile Val  Lys Lys Thr Glu Val  Gln Thr Gly
    1145                 1150                 1155

Gly Phe  Ser Lys Glu Ser Ile  Leu Pro Lys Arg Asn  Ser Asp Lys
    1160                 1165                 1170

Leu Ile  Ala Arg Lys Lys Asp  Trp Asp Pro Lys Lys  Tyr Gly Gly
    1175                 1180                 1185

Phe Asp  Ser Pro Thr Val Ala  Tyr Ser Val Leu Val  Val Ala Lys
    1190                 1195                 1200

Val Glu  Lys Gly Lys Ser Lys  Lys Leu Lys Ser Val  Lys Glu Leu
    1205                 1210                 1215

Leu Gly  Ile Thr Ile Met Glu  Arg Ser Ser Phe Glu  Lys Asn Pro
    1220                 1225                 1230

Ile Asp  Phe Leu Glu Ala Lys  Gly Tyr Lys Glu Val  Lys Lys Asp
    1235                 1240                 1245

Leu Ile  Ile Lys Leu Pro Lys  Tyr Ser Leu Phe Glu  Leu Glu Asn
    1250                 1255                 1260

Gly Arg  Lys Arg Met Leu Ala  Ser Ala Gly Glu Leu  Gln Lys Gly
    1265                 1270                 1275

Asn Glu  Leu Ala Leu Pro Ser  Lys Tyr Val Asn Phe  Leu Tyr Leu
    1280                 1285                 1290

Ala Ser  His Tyr Glu Lys Leu  Lys Gly Ser Pro Glu  Asp Asn Glu
    1295                 1300                 1305

Gln Lys  Gln Leu Phe Val Glu  Gln His Lys His Tyr  Leu Asp Glu
    1310                 1315                 1320

Ile Ile  Glu Gln Ile Ser Glu  Phe Ser Lys Arg Val  Ile Leu Ala
    1325                 1330                 1335

Asp Ala  Asn Leu Asp Lys Val  Leu Ser Ala Tyr Asn  Lys His Arg
    1340                 1345                 1350

Asp Lys  Pro Ile Arg Glu Gln  Ala Glu Asn Ile Ile  His Leu Phe
    1355                 1360                 1365

Thr Leu  Thr Asn Leu Gly Ala  Pro Ala Ala Phe Lys  Tyr Phe Asp
    1370                 1375                 1380

Thr Thr  Ile Asp Arg Lys Arg  Tyr Thr Ser Thr Lys  Glu Val Leu
    1385                 1390                 1395
```

Asp Ala Thr Leu Ile His Gln Ser Ile Thr Gly Leu Tyr Glu Thr
1400 1405 1410

Arg Ile Asp Leu Ser Gln Leu Gly Gly Asp Ser Arg Ala Asp Pro
1415 1420 1425

Lys Lys Lys Arg Lys Val
1430

<210> SEQ ID NO 40
<211> LENGTH: 1397
<212> TYPE: PRT
<213> ORGANISM: artificial sequence
<220> FEATURE:
<223> OTHER INFORMATION: PolyR CPP-Cas9-NLS fusion protein

<400> SEQUENCE: 40

Gly Gly Gly Gly Arg Arg Arg Arg Arg Arg Arg Arg Arg Leu Leu Leu
1 5 10 15

Leu Glu Phe Asp Lys Lys Tyr Ser Ile Gly Leu Asp Ile Gly Thr Asn
20 25 30

Ser Val Gly Trp Ala Val Ile Thr Asp Glu Tyr Lys Val Pro Ser Lys
35 40 45

Lys Phe Lys Val Leu Gly Asn Thr Asp Arg His Ser Ile Lys Lys Asn
50 55 60

Leu Ile Gly Ala Leu Leu Phe Asp Ser Gly Glu Thr Ala Glu Ala Thr
65 70 75 80

Arg Leu Lys Arg Thr Ala Arg Arg Arg Tyr Thr Arg Arg Lys Asn Arg
85 90 95

Ile Cys Tyr Leu Gln Glu Ile Phe Ser Asn Glu Met Ala Lys Val Asp
100 105 110

Asp Ser Phe Phe His Arg Leu Glu Glu Ser Phe Leu Val Glu Glu Asp
115 120 125

Lys Lys His Glu Arg His Pro Ile Phe Gly Asn Ile Val Asp Glu Val
130 135 140

Ala Tyr His Glu Lys Tyr Pro Thr Ile Tyr His Leu Arg Lys Lys Leu
145 150 155 160

Val Asp Ser Thr Asp Lys Ala Asp Leu Arg Leu Ile Tyr Leu Ala Leu
165 170 175

Ala His Met Ile Lys Phe Arg Gly His Phe Leu Ile Glu Gly Asp Leu
180 185 190

Asn Pro Asp Asn Ser Asp Val Asp Lys Leu Phe Ile Gln Leu Val Gln
195 200 205

Thr Tyr Asn Gln Leu Phe Glu Glu Asn Pro Ile Asn Ala Ser Gly Val
210 215 220

Asp Ala Lys Ala Ile Leu Ser Ala Arg Leu Ser Lys Ser Arg Arg Leu
225 230 235 240

Glu Asn Leu Ile Ala Gln Leu Pro Gly Glu Lys Lys Asn Gly Leu Phe
245 250 255

Gly Asn Leu Ile Ala Leu Ser Leu Gly Leu Thr Pro Asn Phe Lys Ser
260 265 270

Asn Phe Asp Leu Ala Glu Asp Ala Lys Leu Gln Leu Ser Lys Asp Thr
275 280 285

Tyr Asp Asp Asp Leu Asp Asn Leu Leu Ala Gln Ile Gly Asp Gln Tyr
290 295 300

Ala Asp Leu Phe Leu Ala Ala Lys Asn Leu Ser Asp Ala Ile Leu Leu
305 310 315 320

-continued

```
Ser Asp Ile Leu Arg Val Asn Thr Glu Ile Thr Lys Ala Pro Leu Ser
                325                 330                 335

Ala Ser Met Ile Lys Arg Tyr Asp Glu His His Gln Asp Leu Thr Leu
            340                 345                 350

Leu Lys Ala Leu Val Arg Gln Gln Leu Pro Glu Lys Tyr Lys Glu Ile
        355                 360                 365

Phe Phe Asp Gln Ser Lys Asn Gly Tyr Ala Gly Tyr Ile Asp Gly Gly
    370                 375                 380

Ala Ser Gln Glu Glu Phe Tyr Lys Phe Ile Lys Pro Ile Leu Glu Lys
385                 390                 395                 400

Met Asp Gly Thr Glu Glu Leu Leu Val Lys Leu Asn Arg Glu Asp Leu
                405                 410                 415

Leu Arg Lys Gln Arg Thr Phe Asp Asn Gly Ser Ile Pro His Gln Ile
            420                 425                 430

His Leu Gly Glu Leu His Ala Ile Leu Arg Arg Gln Glu Asp Phe Tyr
        435                 440                 445

Pro Phe Leu Lys Asp Asn Arg Glu Lys Ile Glu Lys Ile Leu Thr Phe
    450                 455                 460

Arg Ile Pro Tyr Tyr Val Gly Pro Leu Ala Arg Gly Asn Ser Arg Phe
465                 470                 475                 480

Ala Trp Met Thr Arg Lys Ser Glu Glu Thr Ile Thr Pro Trp Asn Phe
                485                 490                 495

Glu Glu Val Val Asp Lys Gly Ala Ser Ala Gln Ser Phe Ile Glu Arg
            500                 505                 510

Met Thr Asn Phe Asp Lys Asn Leu Pro Asn Glu Lys Val Leu Pro Lys
        515                 520                 525

His Ser Leu Leu Tyr Glu Tyr Phe Thr Val Tyr Asn Glu Leu Thr Lys
    530                 535                 540

Val Lys Tyr Val Thr Glu Gly Met Arg Lys Pro Ala Phe Leu Ser Gly
545                 550                 555                 560

Glu Gln Lys Lys Ala Ile Val Asp Leu Leu Phe Lys Thr Asn Arg Lys
                565                 570                 575

Val Thr Val Lys Gln Leu Lys Glu Asp Tyr Phe Lys Lys Ile Glu Cys
            580                 585                 590

Phe Asp Ser Val Glu Ile Ser Gly Val Glu Asp Arg Phe Asn Ala Ser
        595                 600                 605

Leu Gly Thr Tyr His Asp Leu Leu Lys Ile Ile Lys Asp Lys Asp Phe
    610                 615                 620

Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
                645                 650                 655

Tyr Ala His Leu Phe Asp Asp Lys Val Met Lys Gln Leu Lys Arg Arg
            660                 665                 670

Arg Tyr Thr Gly Trp Gly Arg Leu Ser Arg Lys Leu Ile Asn Gly Ile
        675                 680                 685

Arg Asp Lys Gln Ser Gly Lys Thr Ile Leu Asp Phe Leu Lys Ser Asp
    690                 695                 700

Gly Phe Ala Asn Arg Asn Phe Met Gln Leu Ile His Asp Asp Ser Leu
705                 710                 715                 720

Thr Phe Lys Glu Asp Ile Gln Lys Ala Gln Val Ser Gly Gln Gly Asp
                725                 730                 735

Ser Leu His Glu His Ile Ala Asn Leu Ala Gly Ser Pro Ala Ile Lys
```

-continued

```
            740                 745                 750

Lys Gly Ile Leu Gln Thr Val Lys Val Val Asp Glu Leu Val Lys Val
        755                 760                 765

Met Gly Arg His Lys Pro Glu Asn Ile Val Ile Glu Met Ala Arg Glu
    770                 775                 780

Asn Gln Thr Thr Gln Lys Gly Gln Lys Asn Ser Arg Glu Arg Met Lys
785                 790                 795                 800

Arg Ile Glu Glu Gly Ile Lys Glu Leu Gly Ser Gln Ile Leu Lys Glu
                805                 810                 815

His Pro Val Glu Asn Thr Gln Leu Gln Asn Glu Lys Leu Tyr Leu Tyr
            820                 825                 830

Tyr Leu Gln Asn Gly Arg Asp Met Tyr Val Asp Gln Glu Leu Asp Ile
        835                 840                 845

Asn Arg Leu Ser Asp Tyr Asp Val Asp His Ile Val Pro Gln Ser Phe
    850                 855                 860

Leu Lys Asp Asp Ser Ile Asp Asn Lys Val Leu Thr Arg Ser Asp Lys
865                 870                 875                 880

Asn Arg Gly Lys Ser Asp Asn Val Pro Ser Glu Glu Val Val Lys Lys
                885                 890                 895

Met Lys Asn Tyr Trp Arg Gln Leu Leu Asn Ala Lys Leu Ile Thr Gln
            900                 905                 910

Arg Lys Phe Asp Asn Leu Thr Lys Ala Glu Arg Gly Gly Leu Ser Glu
        915                 920                 925

Leu Asp Lys Ala Gly Phe Ile Lys Arg Gln Leu Val Glu Thr Arg Gln
    930                 935                 940

Ile Thr Lys His Val Ala Gln Ile Leu Asp Ser Arg Met Asn Thr Lys
945                 950                 955                 960

Tyr Asp Glu Asn Asp Lys Leu Ile Arg Glu Val Lys Val Ile Thr Leu
                965                 970                 975

Lys Ser Lys Leu Val Ser Asp Phe Arg Lys Asp Phe Gln Phe Tyr Lys
            980                 985                 990

Val Arg Glu Ile Asn Asn Tyr His  His Ala His Asp Ala  Tyr Leu Asn
        995                 1000                1005

Ala Val  Val Gly Thr Ala Leu  Ile Lys Lys Tyr Pro  Lys Leu Glu
    1010                 1015                 1020

Ser Glu  Phe Val Tyr Gly Asp  Tyr Lys Val Tyr Asp  Val Arg Lys
    1025                 1030                 1035

Met Ile  Ala Lys Ser Glu Gln  Glu Ile Gly Lys Ala  Thr Ala Lys
    1040                 1045                 1050

Tyr Phe  Phe Tyr Ser Asn Ile  Met Asn Phe Phe Lys  Thr Glu Ile
    1055                 1060                 1065

Thr Leu  Ala Asn Gly Glu Ile  Arg Lys Arg Pro Leu  Ile Glu Thr
    1070                 1075                 1080

Asn Gly  Glu Thr Gly Glu Ile  Val Trp Asp Lys Gly  Arg Asp Phe
    1085                 1090                 1095

Ala Thr  Val Arg Lys Val Leu  Ser Met Pro Gln Val  Asn Ile Val
    1100                 1105                 1110

Lys Lys  Thr Glu Val Gln Thr  Gly Gly Phe Ser Lys  Glu Ser Ile
    1115                 1120                 1125

Leu Pro  Lys Arg Asn Ser Asp  Lys Leu Ile Ala Arg  Lys Lys Asp
    1130                 1135                 1140

Trp Asp  Pro Lys Lys Tyr Gly  Gly Phe Asp Ser Pro  Thr Val Ala
    1145                 1150                 1155
```

```
Tyr Ser  Val Leu Val Val Ala  Lys Val Glu Lys Gly  Lys Ser Lys
    1160                 1165                 1170

Lys Leu  Lys Ser Val Lys Glu  Leu Leu Gly Ile Thr  Ile Met Glu
    1175                 1180                 1185

Arg Ser  Ser Phe Glu Lys Asn  Pro Ile Asp Phe Leu  Glu Ala Lys
    1190                 1195                 1200

Gly Tyr  Lys Glu Val Lys Lys  Asp Leu Ile Ile Lys  Leu Pro Lys
    1205                 1210                 1215

Tyr Ser  Leu Phe Glu Leu Glu  Asn Gly Arg Lys Arg  Met Leu Ala
    1220                 1225                 1230

Ser Ala  Gly Glu Leu Gln Lys  Gly Asn Glu Leu Ala  Leu Pro Ser
    1235                 1240                 1245

Lys Tyr  Val Asn Phe Leu Tyr  Leu Ala Ser His Tyr  Glu Lys Leu
    1250                 1255                 1260

Lys Gly  Ser Pro Glu Asp Asn  Glu Gln Lys Gln Leu  Phe Val Glu
    1265                 1270                 1275

Gln His  Lys His Tyr Leu Asp  Glu Ile Ile Glu Gln  Ile Ser Glu
    1280                 1285                 1290

Phe Ser  Lys Arg Val Ile Leu  Ala Asp Ala Asn Leu  Asp Lys Val
    1295                 1300                 1305

Leu Ser  Ala Tyr Asn Lys His  Arg Asp Lys Pro Ile  Arg Glu Gln
    1310                 1315                 1320

Ala Glu  Asn Ile Ile His Leu  Phe Thr Leu Thr Asn  Leu Gly Ala
    1325                 1330                 1335

Pro Ala  Ala Phe Lys Tyr Phe  Asp Thr Thr Ile Asp  Arg Lys Arg
    1340                 1345                 1350

Tyr Thr  Ser Thr Lys Glu Val  Leu Asp Ala Thr Leu  Ile His Gln
    1355                 1360                 1365

Ser Ile  Thr Gly Leu Tyr Glu  Thr Arg Ile Asp Leu  Ser Gln Leu
    1370                 1375                 1380

Gly Gly  Asp Ser Arg Ala Asp  Pro Lys Lys Lys Arg  Lys Val
    1385                 1390                 1395


<210> SEQ ID NO 41
<211> LENGTH: 1401
<212> TYPE: PRT
<213> ORGANISM: artificial sequence
<220> FEATURE:
<223> OTHER INFORMATION: TP10 CPP-Cas9-NLS fusion protein

<400> SEQUENCE: 41

Ala Gly Tyr Leu Leu Gly Lys Ile Asn Leu Lys Ala Cys Ala Ala Cys
1               5                   10                  15

Ala Lys Lys Ile Leu Glu Phe Asp Lys Lys Tyr Ser Ile Gly Leu Asp
            20                  25                  30

Ile Gly Thr Asn Ser Val Gly Trp Ala Val Ile Thr Asp Glu Tyr Lys
        35                  40                  45

Val Pro Ser Lys Lys Phe Lys Val Leu Gly Asn Thr Asp Arg His Ser
    50                  55                  60

Ile Lys Lys Asn Leu Ile Gly Ala Leu Leu Phe Asp Ser Gly Glu Thr
65                  70                  75                  80

Ala Glu Ala Thr Arg Leu Lys Arg Thr Ala Arg Arg Arg Tyr Thr Arg
                85                  90                  95

Arg Lys Asn Arg Ile Cys Tyr Leu Gln Glu Ile Phe Ser Asn Glu Met
            100                 105                 110
```

-continued

```
Ala Lys Val Asp Asp Ser Phe Phe His Arg Leu Glu Glu Ser Phe Leu
        115                 120                 125

Val Glu Glu Asp Lys Lys His Glu Arg His Pro Ile Phe Gly Asn Ile
    130                 135                 140

Val Asp Glu Val Ala Tyr His Glu Lys Tyr Pro Thr Ile Tyr His Leu
145                 150                 155                 160

Arg Lys Lys Leu Val Asp Ser Thr Asp Lys Ala Asp Leu Arg Leu Ile
                165                 170                 175

Tyr Leu Ala Leu Ala His Met Ile Lys Phe Arg Gly His Phe Leu Ile
            180                 185                 190

Glu Gly Asp Leu Asn Pro Asp Asn Ser Asp Val Asp Lys Leu Phe Ile
        195                 200                 205

Gln Leu Val Gln Thr Tyr Asn Gln Leu Phe Glu Glu Asn Pro Ile Asn
    210                 215                 220

Ala Ser Gly Val Asp Ala Lys Ala Ile Leu Ser Ala Arg Leu Ser Lys
225                 230                 235                 240

Ser Arg Arg Leu Glu Asn Leu Ile Ala Gln Leu Pro Gly Glu Lys Lys
                245                 250                 255

Asn Gly Leu Phe Gly Asn Leu Ile Ala Leu Ser Leu Gly Leu Thr Pro
            260                 265                 270

Asn Phe Lys Ser Asn Phe Asp Leu Ala Glu Asp Ala Lys Leu Gln Leu
        275                 280                 285

Ser Lys Asp Thr Tyr Asp Asp Asp Leu Asp Asn Leu Leu Ala Gln Ile
    290                 295                 300

Gly Asp Gln Tyr Ala Asp Leu Phe Leu Ala Ala Lys Asn Leu Ser Asp
305                 310                 315                 320

Ala Ile Leu Leu Ser Asp Ile Leu Arg Val Asn Thr Glu Ile Thr Lys
                325                 330                 335

Ala Pro Leu Ser Ala Ser Met Ile Lys Arg Tyr Asp Glu His His Gln
            340                 345                 350

Asp Leu Thr Leu Leu Lys Ala Leu Val Arg Gln Gln Leu Pro Glu Lys
        355                 360                 365

Tyr Lys Glu Ile Phe Phe Asp Gln Ser Lys Asn Gly Tyr Ala Gly Tyr
    370                 375                 380

Ile Asp Gly Gly Ala Ser Gln Glu Glu Phe Tyr Lys Phe Ile Lys Pro
385                 390                 395                 400

Ile Leu Glu Lys Met Asp Gly Thr Glu Glu Leu Leu Val Lys Leu Asn
                405                 410                 415

Arg Glu Asp Leu Leu Arg Lys Gln Arg Thr Phe Asp Asn Gly Ser Ile
            420                 425                 430

Pro His Gln Ile His Leu Gly Glu Leu His Ala Ile Leu Arg Arg Gln
        435                 440                 445

Glu Asp Phe Tyr Pro Phe Leu Lys Asp Asn Arg Glu Lys Ile Glu Lys
    450                 455                 460

Ile Leu Thr Phe Arg Ile Pro Tyr Tyr Val Gly Pro Leu Ala Arg Gly
465                 470                 475                 480

Asn Ser Arg Phe Ala Trp Met Thr Arg Lys Ser Glu Glu Thr Ile Thr
                485                 490                 495

Pro Trp Asn Phe Glu Glu Val Val Asp Lys Gly Ala Ser Ala Gln Ser
            500                 505                 510

Phe Ile Glu Arg Met Thr Asn Phe Asp Lys Asn Leu Pro Asn Glu Lys
        515                 520                 525
```

-continued

```
Val Leu Pro Lys His Ser Leu Leu Tyr Glu Tyr Phe Thr Val Tyr Asn
    530                 535                 540

Glu Leu Thr Lys Val Lys Tyr Val Thr Glu Gly Met Arg Lys Pro Ala
545                 550                 555                 560

Phe Leu Ser Gly Glu Gln Lys Lys Ala Ile Val Asp Leu Leu Phe Lys
                565                 570                 575

Thr Asn Arg Lys Val Thr Val Lys Gln Leu Lys Glu Asp Tyr Phe Lys
            580                 585                 590

Lys Ile Glu Cys Phe Asp Ser Val Glu Ile Ser Gly Val Glu Asp Arg
        595                 600                 605

Phe Asn Ala Ser Leu Gly Thr Tyr His Asp Leu Leu Lys Ile Ile Lys
    610                 615                 620

Asp Lys Asp Phe Leu Asp Asn Glu Glu Asn Glu Asp Ile Leu Glu Asp
625                 630                 635                 640

Ile Val Leu Thr Leu Thr Leu Phe Glu Asp Arg Glu Met Ile Glu Glu
                645                 650                 655

Arg Leu Lys Thr Tyr Ala His Leu Phe Asp Asp Lys Val Met Lys Gln
            660                 665                 670

Leu Lys Arg Arg Arg Tyr Thr Gly Trp Gly Arg Leu Ser Arg Lys Leu
        675                 680                 685

Ile Asn Gly Ile Arg Asp Lys Gln Ser Gly Lys Thr Ile Leu Asp Phe
    690                 695                 700

Leu Lys Ser Asp Gly Phe Ala Asn Arg Asn Phe Met Gln Leu Ile His
705                 710                 715                 720

Asp Asp Ser Leu Thr Phe Lys Glu Asp Ile Gln Lys Ala Gln Val Ser
                725                 730                 735

Gly Gln Gly Asp Ser Leu His Glu His Ile Ala Asn Leu Ala Gly Ser
            740                 745                 750

Pro Ala Ile Lys Lys Gly Ile Leu Gln Thr Val Lys Val Val Asp Glu
        755                 760                 765

Leu Val Lys Val Met Gly Arg His Lys Pro Glu Asn Ile Val Ile Glu
    770                 775                 780

Met Ala Arg Glu Asn Gln Thr Thr Gln Lys Gly Gln Lys Asn Ser Arg
785                 790                 795                 800

Glu Arg Met Lys Arg Ile Glu Glu Gly Ile Lys Glu Leu Gly Ser Gln
                805                 810                 815

Ile Leu Lys Glu His Pro Val Glu Asn Thr Gln Leu Gln Asn Glu Lys
            820                 825                 830

Leu Tyr Leu Tyr Tyr Leu Gln Asn Gly Arg Asp Met Tyr Val Asp Gln
        835                 840                 845

Glu Leu Asp Ile Asn Arg Leu Ser Asp Tyr Asp Val Asp His Ile Val
    850                 855                 860

Pro Gln Ser Phe Leu Lys Asp Asp Ser Ile Asp Asn Lys Val Leu Thr
865                 870                 875                 880

Arg Ser Asp Lys Asn Arg Gly Lys Ser Asp Asn Val Pro Ser Glu Glu
                885                 890                 895

Val Val Lys Lys Met Lys Asn Tyr Trp Arg Gln Leu Leu Asn Ala Lys
            900                 905                 910

Leu Ile Thr Gln Arg Lys Phe Asp Asn Leu Thr Lys Ala Glu Arg Gly
        915                 920                 925

Gly Leu Ser Glu Leu Asp Lys Ala Gly Phe Ile Lys Arg Gln Leu Val
    930                 935                 940

Glu Thr Arg Gln Ile Thr Lys His Val Ala Gln Ile Leu Asp Ser Arg
```

-continued

```
945                 950                 955                 960

Met Asn Thr Lys Tyr Asp Glu Asn Asp Lys Leu Ile Arg Glu Val Lys
                965                 970                 975

Val Ile Thr Leu Lys Ser Lys Leu Val Ser Asp Phe Arg Lys Asp Phe
            980                 985                 990

Gln Phe Tyr Lys Val Arg Glu Ile  Asn Asn Tyr His His  Ala His Asp
        995                 1000                1005

Ala Tyr  Leu Asn Ala Val Val  Gly Thr Ala Leu Ile  Lys Lys Tyr
    1010                 1015                 1020

Pro Lys  Leu Glu Ser Glu Phe  Val Tyr Gly Asp Tyr  Lys Val Tyr
    1025                 1030                 1035

Asp Val  Arg Lys Met Ile Ala  Lys Ser Glu Gln Glu  Ile Gly Lys
    1040                 1045                 1050

Ala Thr  Ala Lys Tyr Phe Phe  Tyr Ser Asn Ile Met  Asn Phe Phe
    1055                 1060                 1065

Lys Thr  Glu Ile Thr Leu Ala  Asn Gly Glu Ile Arg  Lys Arg Pro
    1070                 1075                 1080

Leu Ile  Glu Thr Asn Gly Glu  Thr Gly Glu Ile Val  Trp Asp Lys
    1085                 1090                 1095

Gly Arg  Asp Phe Ala Thr Val  Arg Lys Val Leu Ser  Met Pro Gln
    1100                 1105                 1110

Val Asn  Ile Val Lys Lys Thr  Glu Val Gln Thr Gly  Gly Phe Ser
    1115                 1120                 1125

Lys Glu  Ser Ile Leu Pro Lys  Arg Asn Ser Asp Lys  Leu Ile Ala
    1130                 1135                 1140

Arg Lys  Lys Asp Trp Asp Pro  Lys Lys Tyr Gly Gly  Phe Asp Ser
    1145                 1150                 1155

Pro Thr  Val Ala Tyr Ser Val  Leu Val Val Ala Lys  Val Glu Lys
    1160                 1165                 1170

Gly Lys  Ser Lys Lys Leu Lys  Ser Val Lys Glu Leu  Leu Gly Ile
    1175                 1180                 1185

Thr Ile  Met Glu Arg Ser Ser  Phe Glu Lys Asn Pro  Ile Asp Phe
    1190                 1195                 1200

Leu Glu  Ala Lys Gly Tyr Lys  Glu Val Lys Lys Asp  Leu Ile Ile
    1205                 1210                 1215

Lys Leu  Pro Lys Tyr Ser Leu  Phe Glu Leu Glu Asn  Gly Arg Lys
    1220                 1225                 1230

Arg Met  Leu Ala Ser Ala Gly  Glu Leu Gln Lys Gly  Asn Glu Leu
    1235                 1240                 1245

Ala Leu  Pro Ser Lys Tyr Val  Asn Phe Leu Tyr Leu  Ala Ser His
    1250                 1255                 1260

Tyr Glu  Lys Leu Lys Gly Ser  Pro Glu Asp Asn Glu  Gln Lys Gln
    1265                 1270                 1275

Leu Phe  Val Glu Gln His Lys  His Tyr Leu Asp Glu  Ile Ile Glu
    1280                 1285                 1290

Gln Ile  Ser Glu Phe Ser Lys  Arg Val Ile Leu Ala  Asp Ala Asn
    1295                 1300                 1305

Leu Asp  Lys Val Leu Ser Ala  Tyr Asn Lys His Arg  Asp Lys Pro
    1310                 1315                 1320

Ile Arg  Glu Gln Ala Glu Asn  Ile Ile His Leu Phe  Thr Leu Thr
    1325                 1330                 1335

Asn Leu  Gly Ala Pro Ala Ala  Phe Lys Tyr Phe Asp  Thr Thr Ile
    1340                 1345                 1350
```

```
Asp Arg  Lys Arg Tyr Thr Ser  Thr Lys Glu Val Leu  Asp Ala Thr
    1355                 1360                 1365

Leu Ile  His Gln Ser Ile Thr  Gly Leu Tyr Glu Thr  Arg Ile Asp
    1370                 1375                 1380

Leu Ser  Gln Leu Gly Gly Asp  Ser Arg Ala Asp Pro  Lys Lys Lys
    1385                 1390                 1395

Arg Lys  Val
    1400
```

<210> SEQ ID NO 42
<211> LENGTH: 1398
<212> TYPE: PRT
<213> ORGANISM: artificial sequence
<220> FEATURE:
<223> OTHER INFORMATION: pVEC CPP-Cas9-NLS fusion protein

<400> SEQUENCE: 42

```
Leu Leu Ile Ile Leu Arg Arg Arg Ile Arg Lys Gln Ala His Ala His
1               5                   10                  15

Ser Lys Glu Phe Asp Lys Lys Tyr Ser Ile Gly Leu Asp Ile Gly Thr
            20                  25                  30

Asn Ser Val Gly Trp Ala Val Ile Thr Asp Glu Tyr Lys Val Pro Ser
        35                  40                  45

Lys Lys Phe Lys Val Leu Gly Asn Thr Asp Arg His Ser Ile Lys Lys
    50                  55                  60

Asn Leu Ile Gly Ala Leu Leu Phe Asp Ser Gly Glu Thr Ala Glu Ala
65                  70                  75                  80

Thr Arg Leu Lys Arg Thr Ala Arg Arg Arg Tyr Thr Arg Arg Lys Asn
                85                  90                  95

Arg Ile Cys Tyr Leu Gln Glu Ile Phe Ser Asn Glu Met Ala Lys Val
            100                 105                 110

Asp Asp Ser Phe Phe His Arg Leu Glu Glu Ser Phe Leu Val Glu Glu
        115                 120                 125

Asp Lys Lys His Glu Arg His Pro Ile Phe Gly Asn Ile Val Asp Glu
    130                 135                 140

Val Ala Tyr His Glu Lys Tyr Pro Thr Ile Tyr His Leu Arg Lys Lys
145                 150                 155                 160

Leu Val Asp Ser Thr Asp Lys Ala Asp Leu Arg Leu Ile Tyr Leu Ala
                165                 170                 175

Leu Ala His Met Ile Lys Phe Arg Gly His Phe Leu Ile Glu Gly Asp
            180                 185                 190

Leu Asn Pro Asp Asn Ser Asp Val Asp Lys Leu Phe Ile Gln Leu Val
        195                 200                 205

Gln Thr Tyr Asn Gln Leu Phe Glu Glu Asn Pro Ile Asn Ala Ser Gly
    210                 215                 220

Val Asp Ala Lys Ala Ile Leu Ser Ala Arg Leu Ser Lys Ser Arg Arg
225                 230                 235                 240

Leu Glu Asn Leu Ile Ala Gln Leu Pro Gly Glu Lys Lys Asn Gly Leu
                245                 250                 255

Phe Gly Asn Leu Ile Ala Leu Ser Leu Gly Leu Thr Pro Asn Phe Lys
            260                 265                 270

Ser Asn Phe Asp Leu Ala Glu Asp Ala Lys Leu Gln Leu Ser Lys Asp
        275                 280                 285

Thr Tyr Asp Asp Asp Leu Asp Asn Leu Leu Ala Gln Ile Gly Asp Gln
    290                 295                 300
```

```
Tyr Ala Asp Leu Phe Leu Ala Ala Lys Asn Leu Ser Asp Ala Ile Leu
305                 310                 315                 320

Leu Ser Asp Ile Leu Arg Val Asn Thr Glu Ile Thr Lys Ala Pro Leu
                325                 330                 335

Ser Ala Ser Met Ile Lys Arg Tyr Asp Glu His His Gln Asp Leu Thr
            340                 345                 350

Leu Leu Lys Ala Leu Val Arg Gln Gln Leu Pro Glu Lys Tyr Lys Glu
        355                 360                 365

Ile Phe Phe Asp Gln Ser Lys Asn Gly Tyr Ala Gly Tyr Ile Asp Gly
    370                 375                 380

Gly Ala Ser Gln Glu Glu Phe Tyr Lys Phe Ile Lys Pro Ile Leu Glu
385                 390                 395                 400

Lys Met Asp Gly Thr Glu Glu Leu Leu Val Lys Leu Asn Arg Glu Asp
                405                 410                 415

Leu Leu Arg Lys Gln Arg Thr Phe Asp Asn Gly Ser Ile Pro His Gln
            420                 425                 430

Ile His Leu Gly Glu Leu His Ala Ile Leu Arg Arg Gln Glu Asp Phe
        435                 440                 445

Tyr Pro Phe Leu Lys Asp Asn Arg Glu Lys Ile Glu Lys Ile Leu Thr
    450                 455                 460

Phe Arg Ile Pro Tyr Tyr Val Gly Pro Leu Ala Arg Gly Asn Ser Arg
465                 470                 475                 480

Phe Ala Trp Met Thr Arg Lys Ser Glu Glu Thr Ile Thr Pro Trp Asn
                485                 490                 495

Phe Glu Glu Val Val Asp Lys Gly Ala Ser Ala Gln Ser Phe Ile Glu
            500                 505                 510

Arg Met Thr Asn Phe Asp Lys Asn Leu Pro Asn Glu Lys Val Leu Pro
        515                 520                 525

Lys His Ser Leu Leu Tyr Glu Tyr Phe Thr Val Tyr Asn Glu Leu Thr
    530                 535                 540

Lys Val Lys Tyr Val Thr Glu Gly Met Arg Lys Pro Ala Phe Leu Ser
545                 550                 555                 560

Gly Glu Gln Lys Lys Ala Ile Val Asp Leu Leu Phe Lys Thr Asn Arg
                565                 570                 575

Lys Val Thr Val Lys Gln Leu Lys Glu Asp Tyr Phe Lys Lys Ile Glu
            580                 585                 590

Cys Phe Asp Ser Val Glu Ile Ser Gly Val Glu Asp Arg Phe Asn Ala
        595                 600                 605

Ser Leu Gly Thr Tyr His Asp Leu Leu Lys Ile Ile Lys Asp Lys Asp
    610                 615                 620

Phe Leu Asp Asn Glu Glu Asn Glu Asp Ile Leu Glu Asp Ile Val Leu
625                 630                 635                 640

Thr Leu Thr Leu Phe Glu Asp Arg Glu Met Ile Glu Glu Arg Leu Lys
                645                 650                 655

Thr Tyr Ala His Leu Phe Asp Asp Lys Val Met Lys Gln Leu Lys Arg
            660                 665                 670

Arg Arg Tyr Thr Gly Trp Gly Arg Leu Ser Arg Lys Leu Ile Asn Gly
        675                 680                 685

Ile Arg Asp Lys Gln Ser Gly Lys Thr Ile Leu Asp Phe Leu Lys Ser
    690                 695                 700

Asp Gly Phe Ala Asn Arg Asn Phe Met Gln Leu Ile His Asp Asp Ser
705                 710                 715                 720
```

-continued

```
Leu Thr Phe Lys Glu Asp Ile Gln Lys Ala Gln Val Ser Gly Gln Gly
                725                 730                 735

Asp Ser Leu His Glu His Ile Ala Asn Leu Ala Gly Ser Pro Ala Ile
            740                 745                 750

Lys Lys Gly Ile Leu Gln Thr Val Lys Val Val Asp Glu Leu Val Lys
        755                 760                 765

Val Met Gly Arg His Lys Pro Glu Asn Ile Val Ile Glu Met Ala Arg
    770                 775                 780

Glu Asn Gln Thr Thr Gln Lys Gly Gln Lys Asn Ser Arg Glu Arg Met
785                 790                 795                 800

Lys Arg Ile Glu Glu Gly Ile Lys Glu Leu Gly Ser Gln Ile Leu Lys
                805                 810                 815

Glu His Pro Val Glu Asn Thr Gln Leu Gln Asn Glu Lys Leu Tyr Leu
            820                 825                 830

Tyr Tyr Leu Gln Asn Gly Arg Asp Met Tyr Val Asp Gln Glu Leu Asp
        835                 840                 845

Ile Asn Arg Leu Ser Asp Tyr Asp Val Asp His Ile Val Pro Gln Ser
    850                 855                 860

Phe Leu Lys Asp Asp Ser Ile Asp Asn Lys Val Leu Thr Arg Ser Asp
865                 870                 875                 880

Lys Asn Arg Gly Lys Ser Asp Asn Val Pro Ser Glu Glu Val Val Lys
                885                 890                 895

Lys Met Lys Asn Tyr Trp Arg Gln Leu Leu Asn Ala Lys Leu Ile Thr
            900                 905                 910

Gln Arg Lys Phe Asp Asn Leu Thr Lys Ala Glu Arg Gly Gly Leu Ser
        915                 920                 925

Glu Leu Asp Lys Ala Gly Phe Ile Lys Arg Gln Leu Val Glu Thr Arg
    930                 935                 940

Gln Ile Thr Lys His Val Ala Gln Ile Leu Asp Ser Arg Met Asn Thr
945                 950                 955                 960

Lys Tyr Asp Glu Asn Asp Lys Leu Ile Arg Glu Val Lys Val Ile Thr
                965                 970                 975

Leu Lys Ser Lys Leu Val Ser Asp Phe Arg Lys Asp Phe Gln Phe Tyr
            980                 985                 990

Lys Val Arg Glu Ile Asn Asn Tyr  His His Ala His Asp  Ala Tyr Leu
        995                 1000                1005

Asn Ala  Val Val Gly Thr Ala  Leu Ile Lys Lys Tyr  Pro Lys Leu
    1010                1015                1020

Glu Ser  Glu Phe Val Tyr Gly  Asp Tyr Lys Val Tyr  Asp Val Arg
    1025                1030                1035

Lys Met  Ile Ala Lys Ser Glu  Gln Glu Ile Gly Lys  Ala Thr Ala
    1040                1045                1050

Lys Tyr  Phe Phe Tyr Ser Asn  Ile Met Asn Phe Phe  Lys Thr Glu
    1055                1060                1065

Ile Thr  Leu Ala Asn Gly Glu  Ile Arg Lys Arg Pro  Leu Ile Glu
    1070                1075                1080

Thr Asn  Gly Glu Thr Gly Glu  Ile Val Trp Asp Lys  Gly Arg Asp
    1085                1090                1095

Phe Ala  Thr Val Arg Lys Val  Leu Ser Met Pro Gln  Val Asn Ile
    1100                1105                1110

Val Lys  Lys Thr Glu Val Gln  Thr Gly Gly Phe Ser  Lys Glu Ser
    1115                1120                1125

Ile Leu  Pro Lys Arg Asn Ser  Asp Lys Leu Ile Ala  Arg Lys Lys
```

1130 1135 1140

Asp Trp Asp Pro Lys Lys Tyr Gly Gly Phe Asp Ser Pro Thr Val
1145 1150 1155

Ala Tyr Ser Val Leu Val Val Ala Lys Val Glu Lys Gly Lys Ser
1160 1165 1170

Lys Lys Leu Lys Ser Val Lys Glu Leu Leu Gly Ile Thr Ile Met
1175 1180 1185

Glu Arg Ser Ser Phe Glu Lys Asn Pro Ile Asp Phe Leu Glu Ala
1190 1195 1200

Lys Gly Tyr Lys Glu Val Lys Lys Asp Leu Ile Ile Lys Leu Pro
1205 1210 1215

Lys Tyr Ser Leu Phe Glu Leu Glu Asn Gly Arg Lys Arg Met Leu
1220 1225 1230

Ala Ser Ala Gly Glu Leu Gln Lys Gly Asn Glu Leu Ala Leu Pro
1235 1240 1245

Ser Lys Tyr Val Asn Phe Leu Tyr Leu Ala Ser His Tyr Glu Lys
1250 1255 1260

Leu Lys Gly Ser Pro Glu Asp Asn Glu Gln Lys Gln Leu Phe Val
1265 1270 1275

Glu Gln His Lys His Tyr Leu Asp Glu Ile Ile Glu Gln Ile Ser
1280 1285 1290

Glu Phe Ser Lys Arg Val Ile Leu Ala Asp Ala Asn Leu Asp Lys
1295 1300 1305

Val Leu Ser Ala Tyr Asn Lys His Arg Asp Lys Pro Ile Arg Glu
1310 1315 1320

Gln Ala Glu Asn Ile Ile His Leu Phe Thr Leu Thr Asn Leu Gly
1325 1330 1335

Ala Pro Ala Ala Phe Lys Tyr Phe Asp Thr Thr Ile Asp Arg Lys
1340 1345 1350

Arg Tyr Thr Ser Thr Lys Glu Val Leu Asp Ala Thr Leu Ile His
1355 1360 1365

Gln Ser Ile Thr Gly Leu Tyr Glu Thr Arg Ile Asp Leu Ser Gln
1370 1375 1380

Leu Gly Gly Asp Ser Arg Ala Asp Pro Lys Lys Lys Arg Lys Val
1385 1390 1395

<210> SEQ ID NO 43
<211> LENGTH: 23
<212> TYPE: DNA
<213> ORGANISM: unknown
<220> FEATURE:
<223> OTHER INFORMATION: Example of a Cas9 target site:PAM sequence
<220> FEATURE:
<221> NAME/KEY: misc_feature
<222> LOCATION: (1)..(20)
<223> OTHER INFORMATION: n = A, C, T, or G
<220> FEATURE:
<221> NAME/KEY: misc_feature
<222> LOCATION: (21)..(21)
<223> OTHER INFORMATION: n = A, C, T, or G (indicated as an “X” in
Specification)

<400> SEQUENCE: 43
nnnnnnnnnn nnnnnnnnnn ngg 23

<210> SEQ ID NO 44
<211> LENGTH: 3
<212> TYPE: DNA
<213> ORGANISM: unknown

-continued

<220> FEATURE:
<223> OTHER INFORMATION: PAM sequence NGG
<220> FEATURE:
<221> NAME/KEY: misc_feature
<222> LOCATION: (1)..(1)
<223> OTHER INFORMATION: n = A, C, T, or G

<400> SEQUENCE: 44 ngg 3

<210> SEQ ID NO 45
<211> LENGTH: 6
<212> TYPE: DNA
<213> ORGANISM: unknown
<220> FEATURE:
<223> OTHER INFORMATION: PAM sequence NNAGAA
<220> FEATURE:
<221> NAME/KEY: misc_feature
<222> LOCATION: (1)..(2)
<223> OTHER INFORMATION: n = A, C, T, or G

<400> SEQUENCE: 45 nnagaa 6

<210> SEQ ID NO 46
<211> LENGTH: 7
<212> TYPE: DNA
<213> ORGANISM: unknown
<220> FEATURE:
<223> OTHER INFORMATION: PAM sequence NNAGAAW
<220> FEATURE:
<221> NAME/KEY: misc_feature
<222> LOCATION: (1)..(2)
<223> OTHER INFORMATION: n = A, C, T, or G
<220> FEATURE:
<221> NAME/KEY: misc_feature
<222> LOCATION: (7)..(7)
<223> OTHER INFORMATION: w = A or T

<400> SEQUENCE: 46 nnagaaw 7

<210> SEQ ID NO 47
<211> LENGTH: 5
<212> TYPE: DNA
<213> ORGANISM: unknown
<220> FEATURE:
<223> OTHER INFORMATION: PAM sequence NGGNG
<220> FEATURE:
<221> NAME/KEY: misc_feature
<222> LOCATION: (1)..(1)
<223> OTHER INFORMATION: n = A, C, T, or G
<220> FEATURE:
<221> NAME/KEY: misc_feature
<222> LOCATION: (4)..(4)
<223> OTHER INFORMATION: n = A, C, T, or G

<400> SEQUENCE: 47 nggng 5

<210> SEQ ID NO 48
<211> LENGTH: 8
<212> TYPE: DNA
<213> ORGANISM: unknown
<220> FEATURE:
<223> OTHER INFORMATION: PAM sequence NNNNGATT
<220> FEATURE:
<221> NAME/KEY: misc_feature
<222> LOCATION: (1)..(4)
<223> OTHER INFORMATION: n = A, C, T, or G

<400> SEQUENCE: 48 nnnngatt 8

<210> SEQ ID NO 49
<211> LENGTH: 6
<212> TYPE: DNA
<213> ORGANISM: unknown
<220> FEATURE:
<223> OTHER INFORMATION: PAM sequence NAAAAC
<220> FEATURE:
<221> NAME/KEY: misc_feature
<222> LOCATION: (1)..(1)
<223> OTHER INFORMATION: n = A, C, T, or G

<400> SEQUENCE: 49 naaaac 6

<210> SEQ ID NO 50
<211> LENGTH: 2
<212> TYPE: DNA
<213> ORGANISM: unknown
<220> FEATURE:
<223> OTHER INFORMATION: PAM sequence NG
<220> FEATURE:
<221> NAME/KEY: misc_feature
<222> LOCATION: (1)..(1)
<223> OTHER INFORMATION: n = A, C, T, or G

<400> SEQUENCE: 50 ng 2

<210> SEQ ID NO 51
<211> LENGTH: 22
<212> TYPE: RNA
<213> ORGANISM: unknown
<220> FEATURE:
<223> OTHER INFORMATION: TracrRNA mate sequence example 1

<400> SEQUENCE: 51
guuuuuguac ucucaagauu ua 22

<210> SEQ ID NO 52
<211> LENGTH: 15
<212> TYPE: RNA
<213> ORGANISM: unknown
<220> FEATURE:
<223> OTHER INFORMATION: TracrRNA mate sequence example 2

<400> SEQUENCE: 52
guuuuuguac ucuca 15

<210> SEQ ID NO 53
<211> LENGTH: 12
<212> TYPE: RNA
<213> ORGANISM: unknown
<220> FEATURE:
<223> OTHER INFORMATION: TracrRNA mate sequence example 3

<400> SEQUENCE: 53
guuuuagagc ua 12

<210> SEQ ID NO 54
<211> LENGTH: 13
<212> TYPE: RNA
<213> ORGANISM: unknown
<220> FEATURE:
<223> OTHER INFORMATION: TracrRNA mate sequence example 4

<400> SEQUENCE: 54
guuuuagagc uag 13

<210> SEQ ID NO 55
<211> LENGTH: 60
<212> TYPE: RNA
<213> ORGANISM: Streptococcus pyogenes

<400> SEQUENCE: 55
uagcaaguua aaauaaggcu aguccguuau caacuugaaa aaguggcacc gagucggugc 60

<210> SEQ ID NO 56
<211> LENGTH: 45
<212> TYPE: RNA
<213> ORGANISM: Streptococcus pyogenes

<400> SEQUENCE: 56
uagcaaguua aaauaaggcu aguccguuau caacuugaaa aagug 45

<210> SEQ ID NO 57
<211> LENGTH: 32
<212> TYPE: RNA
<213> ORGANISM: Streptococcus pyogenes

<400> SEQUENCE: 57
uagcaaguua aaauaaggcu aguccguuau ca 32

<210> SEQ ID NO 58
<211> LENGTH: 85
<212> TYPE: RNA
<213> ORGANISM: Streptococcus thermophilus

<400> SEQUENCE: 58
uaaaucuugc agaagcuaca aagauaaggc uucaugccga aaucaacacc cugucauuuu 60
auggcagggu guuuucguua uuuaa 85

<210> SEQ ID NO 59
<211> LENGTH: 77
<212> TYPE: RNA
<213> ORGANISM: Streptococcus thermophilus

<400> SEQUENCE: 59
ugcagaagcu acaaagauaa ggcuucaugc cgaaaucaac acccugucau uuuauggcag 60
gguguuuucg uuauuua 77

<210> SEQ ID NO 60
<211> LENGTH: 65
<212> TYPE: RNA
<213> ORGANISM: Streptococcus thermophilus

<400> SEQUENCE: 60
ugcagaagcu acaaagauaa ggcuucaugc cgaaaucaac acccugucau uuuauggcag 60
ggugu 65

<210> SEQ ID NO 61
<211> LENGTH: 131
<212> TYPE: RNA
<213> ORGANISM: artificial sequence
<220> FEATURE:
<223> OTHER INFORMATION: gRNA example 1
<220> FEATURE:

<221> NAME/KEY: misc_feature
<222> LOCATION: (1)..(20)
<223> OTHER INFORMATION: n = A, C, U, or G

<400> SEQUENCE: 61
nnnnnnnnnn nnnnnnnnnn guuuuuguac ucucaagauu uagaaauaaa ucuugcagaa 60
gcuacaaaga uaaggcuuca ugccgaaauc aacacccugu cauuuuaugg cagggguguuu 120 ucguuauuua a 131

<210> SEQ ID NO 62
<211> LENGTH: 117
<212> TYPE: RNA
<213> ORGANISM: artificial sequence
<220> FEATURE:
<223> OTHER INFORMATION: gRNA example 2
<220> FEATURE:
<221> NAME/KEY: misc_feature
<222> LOCATION: (1)..(20)
<223> OTHER INFORMATION: n = A, C, U, or G

<400> SEQUENCE: 62
nnnnnnnnnn nnnnnnnnnn guuuuuguac ucucagaaau gcagaagcua caaagauaag 60
gcuucaugcc gaaaucaaca cccugucauu uuauggcagg guguuuucgu uauuuaa 117

<210> SEQ ID NO 63
<211> LENGTH: 104
<212> TYPE: RNA
<213> ORGANISM: artificial sequence
<220> FEATURE:
<223> OTHER INFORMATION: gRNA example 3
<220> FEATURE:
<221> NAME/KEY: misc_feature
<222> LOCATION: (1)..(20)
<223> OTHER INFORMATION: n = A, C, U, or G

<400> SEQUENCE: 63
nnnnnnnnnn nnnnnnnnnn guuuuuguac ucucagaaau gcagaagcua caaagauaag 60
gcuucaugcc gaaaucaaca cccugucauu uuauggcagg gugu 104

<210> SEQ ID NO 64
<211> LENGTH: 99
<212> TYPE: RNA
<213> ORGANISM: artificial sequence
<220> FEATURE:
<223> OTHER INFORMATION: gRNA example 4
<220> FEATURE:
<221> NAME/KEY: misc_feature
<222> LOCATION: (1)..(20)
<223> OTHER INFORMATION: n = A, C, U, or G

<400> SEQUENCE: 64
nnnnnnnnnn nnnnnnnnnn guuuuuguac ucucagaaau agcaaguuaa aauaaggcua 60
guccguuauc aacuugaaaa aguggcaccg agucggugc 99

<210> SEQ ID NO 65
<211> LENGTH: 81
<212> TYPE: RNA
<213> ORGANISM: artificial sequence
<220> FEATURE:
<223> OTHER INFORMATION: gRNA example 5
<220> FEATURE:
<221> NAME/KEY: misc_feature
<222> LOCATION: (1)..(20)
<223> OTHER INFORMATION: n = A, C, U, or G

<400> SEQUENCE: 65
nnnnnnnnnn nnnnnnnnnn guuuuagagc uagaaauagc aaguuaaaau aaggcuaguc 60
cguuaucaac uugaaaaagu g 81

<210> SEQ ID NO 66
<211> LENGTH: 68
<212> TYPE: RNA
<213> ORGANISM: artificial sequence
<220> FEATURE:
<223> OTHER INFORMATION: gRNA example 6
<220> FEATURE:
<221> NAME/KEY: misc_feature
<222> LOCATION: (1)..(20)
<223> OTHER INFORMATION: n = A, C, U, or G

<400> SEQUENCE: 66
nnnnnnnnnn nnnnnnnnnn guuuuagagc uagaaauagc aaguuaaaau aaggcuaguc 60
cguuauca 68

<210> SEQ ID NO 67
<211> LENGTH: 100
<212> TYPE: RNA
<213> ORGANISM: artificial sequence
<220> FEATURE:
<223> OTHER INFORMATION: gRNA example 7
<220> FEATURE:
<221> NAME/KEY: misc_feature
<222> LOCATION: (1)..(20)
<223> OTHER INFORMATION: n = A, C, U, or G

<400> SEQUENCE: 67
nnnnnnnnnn nnnnnnnnnn guuuuagagc uagaaauagc aaguuaaaau aaggcuaguc 60
cguuaucaac uugaaaaagu ggcaccgagu cggugcuuuu 100

<210> SEQ ID NO 68
<211> LENGTH: 10
<212> TYPE: PRT
<213> ORGANISM: Human immunodeficiency virus

<400> SEQUENCE: 68

Gly Arg Lys Lys Arg Arg Gln Arg Arg Arg
1 5 10

<210> SEQ ID NO 69
<211> LENGTH: 9
<212> TYPE: PRT
<213> ORGANISM: Human immunodeficiency virus

<400> SEQUENCE: 69

Arg Lys Lys Arg Arg Gln Arg Arg Arg
1 5

<210> SEQ ID NO 70
<211> LENGTH: 8
<212> TYPE: PRT
<213> ORGANISM: Human immunodeficiency virus

<400> SEQUENCE: 70

Arg Lys Lys Arg Arg Gln Arg Arg
1 5

<210> SEQ ID NO 71
<211> LENGTH: 16
<212> TYPE: PRT
<213> ORGANISM: Drosophila melanogaster

<400> SEQUENCE: 71

Arg Gln Ile Lys Ile Trp Phe Gln Asn Arg Arg Met Lys Trp Lys Lys
1 5 10 15

<210> SEQ ID NO 72
<211> LENGTH: 11
<212> TYPE: PRT
<213> ORGANISM: artificial sequence
<220> FEATURE:
<223> OTHER INFORMATION: polyarginine CPP example 2

<400> SEQUENCE: 72

Thr His Arg Leu Pro Arg Arg Arg Arg Arg Arg
1 5 10

<210> SEQ ID NO 73
<211> LENGTH: 11
<212> TYPE: PRT
<213> ORGANISM: artificial sequence
<220> FEATURE:
<223> OTHER INFORMATION: polyarginine CPP example 3

<400> SEQUENCE: 73

Gly Gly Arg Arg Ala Arg Arg Arg Arg Arg Arg
1 5 10

<210> SEQ ID NO 74
<211> LENGTH: 17
<212> TYPE: PRT
<213> ORGANISM: mus musculus

<400> SEQUENCE: 74

Leu Ile Ile Leu Arg Arg Arg Ile Arg Lys Gln Ala His Ala His Ser
1 5 10 15

Lys

<210> SEQ ID NO 75
<211> LENGTH: 10
<212> TYPE: PRT
<213> ORGANISM: artificial sequence
<220> FEATURE:
<223> OTHER INFORMATION: (KFF)3K CPP

<400> SEQUENCE: 75

Lys Phe Phe Lys Phe Phe Lys Phe Phe Lys
1 5 10

<210> SEQ ID NO 76
<211> LENGTH: 18
<212> TYPE: PRT
<213> ORGANISM: artificial sequence
<220> FEATURE:
<223> OTHER INFORMATION: MAP peptide CPP

<400> SEQUENCE: 76

Lys Leu Ala Leu Lys Leu Ala Leu Lys Ala Leu Lys Ala Ala Leu Lys
1 5 10 15

Leu Ala

<210> SEQ ID NO 77
<211> LENGTH: 12
<212> TYPE: PRT
<213> ORGANISM: artificial sequence
<220> FEATURE:

<223> OTHER INFORMATION: CPP (RRQRRTSKLMKR)

<400> SEQUENCE: 77

```
Arg Arg Gln Arg Arg Thr Ser Lys Leu Met Lys Arg
1               5                   10
```

<210> SEQ ID NO 78
<211> LENGTH: 33
<212> TYPE: PRT
<213> ORGANISM: artificial sequence
<220> FEATURE:
<223> OTHER INFORMATION: CPP (KALAWEAKLAKALAKALAKHLAKALAKALKCEA)

<400> SEQUENCE: 78

```
Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala
```

<210> SEQ ID NO 79
<211> LENGTH: 6
<212> TYPE: PRT
<213> ORGANISM: artificial sequence
<220> FEATURE:
<223> OTHER INFORMATION: Proline-rich CPP repeat example 1

<400> SEQUENCE: 79

```
Val His Leu Pro Pro Pro
1               5
```

<210> SEQ ID NO 80
<211> LENGTH: 6
<212> TYPE: PRT
<213> ORGANISM: artificial sequence
<220> FEATURE:
<223> OTHER INFORMATION: Proline-rich CPP repeat example 2

<400> SEQUENCE: 80

```
Val His Arg Pro Pro Pro
1               5
```

<210> SEQ ID NO 81
<211> LENGTH: 27
<212> TYPE: PRT
<213> ORGANISM: artificial sequence
<220> FEATURE:
<223> OTHER INFORMATION: MPG peptide CPP

<400> SEQUENCE: 81

```
Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```

<210> SEQ ID NO 82
<211> LENGTH: 21
<212> TYPE: PRT
<213> ORGANISM: artificial sequence
<220> FEATURE:
<223> OTHER INFORMATION: Pep-1 peptide CPP

<400> SEQUENCE: 82

```
Lys Glu Thr Trp Trp Glu Thr Trp Trp Thr Glu Trp Ser Gln Pro Lys
1               5                   10                  15
```

```
Lys Lys Arg Lys Val
            20


<210> SEQ ID NO 83
<211> LENGTH: 24
<212> TYPE: PRT
<213> ORGANISM: Homo sapiens

<400> SEQUENCE: 83

Leu Gly Thr Tyr Thr Gln Asp Phe Asn Lys Phe His Thr Phe Pro Gln
1               5                   10                  15

Thr Ala Ile Gly Val Gly Ala Pro
            20


<210> SEQ ID NO 84
<211> LENGTH: 18
<212> TYPE: PRT
<213> ORGANISM: Homo sapiens

<400> SEQUENCE: 84

Cys Gly Asn Leu Ser Thr Cys Met Leu Gly Thr Tyr Thr Gln Asp Phe
1               5                   10                  15

Asn Lys


<210> SEQ ID NO 85
<211> LENGTH: 240
<212> TYPE: PRT
<213> ORGANISM: Artificial sequence
<220> FEATURE:
<223> OTHER INFORMATION: his tagged dsRED

<400> SEQUENCE: 85

Met Gly Ser Ser His His His His His His Glu Phe Gly Gly Gly Gly
1               5                   10                  15

Ala Ser Ser Glu Asp Val Ile Lys Glu Phe Met Arg Phe Lys Val Arg
            20                  25                  30

Met Glu Gly Ser Val Asn Gly His Glu Phe Glu Ile Glu Gly Glu Gly
        35                  40                  45

Glu Gly Arg Pro Tyr Glu Gly Thr Gln Thr Ala Lys Leu Lys Val Thr
    50                  55                  60

Lys Gly Gly Pro Leu Pro Phe Ala Trp Asp Ile Leu Ser Pro Gln Phe
65                  70                  75                  80

Gln Tyr Gly Ser Lys Val Tyr Val Lys His Pro Ala Asp Ile Pro Asp
                85                  90                  95

Tyr Lys Lys Leu Ser Phe Pro Glu Gly Phe Lys Trp Glu Arg Val Met
            100                 105                 110

Asn Phe Glu Asp Gly Gly Val Val Thr Val Thr Gln Asp Ser Ser Leu
        115                 120                 125

Gln Asp Gly Ser Phe Ile Tyr Lys Val Lys Phe Ile Gly Val Asn Phe
    130                 135                 140

Pro Ser Asp Gly Pro Val Met Gln Lys Lys Thr Met Gly Trp Glu Ala
145                 150                 155                 160

Ser Thr Glu Arg Leu Tyr Pro Arg Asp Gly Val Leu Lys Gly Glu Ile
                165                 170                 175

His Lys Ala Leu Lys Leu Lys Asp Gly Gly His Tyr Leu Val Glu Phe
            180                 185                 190

Lys Ser Ile Tyr Met Ala Lys Lys Pro Val Gln Leu Pro Gly Tyr Tyr
        195                 200                 205
```

```
Tyr Val Asp Ser Lys Leu Asp Ile Thr Ser His Asn Glu Asp Tyr Thr
    210                 215                 220

Ile Val Glu Gln Tyr Glu Arg Ala Glu Gly Arg His His Leu Phe Leu
225                 230                 235                 240
```

<210> SEQ ID NO 86
<211> LENGTH: 731
<212> TYPE: DNA
<213> ORGANISM: Artificial sequence
<220> FEATURE:
<223> OTHER INFORMATION: E. coli codon optimized dsRED

<400> SEQUENCE: 86

```
ccatgggctc cagccatcat catcaccatc atgaattcgg aggtggcggt gcatcctcgg     60

aggatgtgat taaagaattt atgcggttta aagtacgtat ggaaggatcg gtgaatggcc    120

atgaatttga gattgagggt gaaggcgaag gccgcccgta cgaaggaact caaacagcga    180

aattaaaagt tacaaaagga ggtcctctgc cgtttgcctg ggacatcttg agcccgcaat    240

tccagtacgg ttccaaagtg tatgtaaaac accctgcgga tattccggat tataaaaaac    300

tgagttttcc cgaggggttt aaatgggaac gggtgatgaa ttttgaggat ggtggagttg    360

tcaccgtgac ccaggactct agcttacaag acggtagttt catctacaaa gtaaaattta    420

tcggcgtaaa cttcccatcg gacggccccg tcatgcagaa aaagacgatg ggctgggaag    480

ccagcaccga acgtttgtac ccacgggacg gcgttttgaa aggggaaatc cataaggccc    540

ttaaactgaa agacggtggt cactatctcg tggagtttaa atcgatttat atggctaaaa    600

aaccagtaca gcttccgggt tattattacg ttgactccaa attggacatc acatcgcata    660

atgaagatta cacgattgtt gaacagtacg agcgcgccga gggccggcac catctgtttc    720

tgtaaaagct t                                                         731
```

<210> SEQ ID NO 87
<211> LENGTH: 4092
<212> TYPE: DNA
<213> ORGANISM: Artificial sequence
<220> FEATURE:
<223> OTHER INFORMATION: pBAD/HisB

<400> SEQUENCE: 87

```
aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttgggc    300

taacaggagg aattaaccat gggggttct catcatcatc atcatcatgg tatggctagc    360

atgactggtg gacagcaaat gggtcgggat ctgtacgacg atgacgataa ggatccgagc    420

tcgagatctg cagctggtac catatgggaa ttcgaagctt ggctgttttg gcggatgaga    480

gaagattttc agcctgatac agattaaatc agaacgcaga agcggtctga taaaacagaa    540

tttgcctggc ggcagtagcg cggtggtccc acctgacccc atgccgaact cagaagtgaa    600

acgccgtagc gccgatggta gtgtggggtc tccccatgcg agagtaggga actgccaggc    660

atcaaataaa acgaaaggct cagtcgaaag actgggcctt tcgttttatc tgttgtttgt    720

cggtgaacgc tctcctgagt aggacaaatc cgccgggagc ggatttgaac gttgcgaagc    780
```

```
aacggcccgg agggtggcgg gcaggacgcc cgccataaac tgccaggcat caaattaagc    840
agaaggccat cctgacggat ggcctttttg cgtttctaca aactcttttg tttatttttc    900
taaatacatt caaatatgta tccgctcatg agacaataac cctgataaat gcttcaataa    960
tattgaaaaa ggaagagtat gagtattcaa catttccgtg tcgcccttat tccctttttt   1020
gcggcatttt gccttcctgt ttttgctcac ccagaaacgc tggtgaaagt aaaagatgct   1080
gaagatcagt tgggtgcacg agtgggttac atcgaactgg atctcaacag cggtaagatc   1140
cttgagagtt ttcgccccga agaacgtttt ccaatgatga gcacttttaa agttctgcta   1200
tgtggcgcgg tattatcccg tgttgacgcc gggcaagagc aactcggtcg ccgcatacac   1260
tattctcaga atgacttggt tgagtactca ccagtcacag aaaagcatct tacggatggc   1320
atgacagtaa gagaattatg cagtgctgcc ataaccatga gtgataacac tgcggccaac   1380
ttacttctga caacgatcgg aggaccgaag gagctaaccg cttttttgca caacatgggg   1440
gatcatgtaa ctcgccttga tcgttgggaa ccggagctga atgaagccat accaaacgac   1500
gagcgtgaca ccacgatgcc tgtagcaatg gcaacaacgt tgcgcaaact attaactggc   1560
gaactactta ctctagcttc ccggcaacaa ttaatagact ggatggaggc ggataaagtt   1620
gcaggaccac ttctgcgctc ggcccttccg gctggctggt ttattgctga taaatctgga   1680
gccggtgagc gtgggtctcg cggtatcatt gcagcactgg ggccagatgg taagccctcc   1740
cgtatcgtag ttatctacac gacggggagt caggcaacta tggatgaacg aaatagacag   1800
atcgctgaga taggtgcctc actgattaag cattggtaac tgtcagacca agtttactca   1860
tatatacttt agattgattt aaaacttcat ttttaattta aaaggatcta ggtgaagatc   1920
ctttttgata atctcatgac caaaatccct taacgtgagt tttcgttcca ctgagcgtca   1980
gaccccgtag aaaagatcaa aggatcttct tgagatcctt tttttctgcg cgtaatctgc   2040
tgcttgcaaa caaaaaaacc accgctacca gcggtggttt gtttgccgga tcaagagcta   2100
ccaactcttt ttccgaaggt aactggcttc agcagagcgc agataccaaa tactgtcctt   2160
ctagtgtagc cgtagttagg ccaccacttc aagaactctg tagcaccgcc tacatacctc   2220
gctctgctaa tcctgttacc agtggctgct gccagtggcg ataagtcgtg tcttaccggg   2280
ttggactcaa gacgatagtt accggataag gcgcagcggt cgggctgaac ggggggttcg   2340
tgcacacagc ccagcttgga gcgaacgacc tacaccgaac tgagatacct acagcgtgag   2400
ctatgagaaa gcgccacgct tcccgaaggg agaaaggcgg acaggtatcc ggtaagcggc   2460
agggtcggaa caggagagcg cacgagggag cttccagggg gaaacgcctg gtatctttat   2520
agtcctgtcg ggtttcgcca cctctgactt gagcgtcgat ttttgtgatg ctcgtcaggg   2580
gggcggagcc tatggaaaaa cgccagcaac gcggcctttt tacggttcct ggccttttgc   2640
tggccttttg ctcacatgtt ctttcctgcg ttatcccctg attctgtgga taaccgtatt   2700
accgcctttg agtgagctga taccgctcgc cgcagccgaa cgaccgagcg cagcgagtca   2760
gtgagcgagg aagcggaaga gcgcctgatg cggtattttc tccttacgca tctgtgcggt   2820
atttcacacc gcatatggtg cactctcagt acaatctgct ctgatgccgc atagttaagc   2880
cagtatacac tccgctatcg ctacgtgact gggtcatggc tgcgccccga cacccgccaa   2940
cacccgctga cgcgccctga cgggcttgtc tgctcccggc atccgcttac agacaagctg   3000
tgaccgtctc cgggagctgc atgtgtcaga ggttttcacc gtcatcaccg aaacgcgcga   3060
ggcagcagat caattcgcgc gcgaaggcga agcggcatgc ataatgtgcc tgtcaaatgg   3120
acgaagcagg gattctgcaa accctatgct actccgtcaa gccgtcaatt gtctgattcg   3180
```

```
ttaccaatta tgacaacttg acggctacat cattcacttt ttcttcacaa ccggcacgga   3240
actcgctcgg gctggccccg gtgcattttt taaatacccg cgagaaatag agttgatcgt   3300
caaaaccaac attgcgaccg acggtggcga taggcatccg ggtggtgctc aaaagcagct   3360
tcgcctggct gatacgttgg tcctcgcgcc agcttaagac gctaatccct aactgctggc   3420
ggaaaagatg tgacagacgc gacggcgaca agcaaacatg ctgtgcgacg ctggcgatat   3480
caaaattgct gtctgccagg tgatcgctga tgtactgaca agcctcgcgt acccgattat   3540
ccatcggtgg atggagcgac tcgttaatcg cttccatgcg ccgcagtaac aattgctcaa   3600
gcagatttat cgccagcagc tccgaatagc gcccttcccc ttgcccggcg ttaatgattt   3660
gcccaaacag gtcgctgaaa tgcggctggt gcgcttcatc cgggcgaaag aaccccgtat   3720
tggcaaatat tgacggccag ttaagccatt catgccagta ggcgcgcgga cgaaagtaaa   3780
cccactggtg ataccattcg cgagcctccg gatgacgacc gtagtgatga atctctcctg   3840
gcgggaacag caaaatatca cccggtcggc aaacaaattc tcgtccctga tttttcacca   3900
ccccctgacc gcgaatggtg agattgagaa tataaccttt cattcccagc ggtcggtcga   3960
taaaaaaatc gagataaccg ttggcctcaa tcggcgttaa acccgccacc agatgggcat   4020
taaacgagta tcccggcagc aggggatcat tttgcgcttc agccatactt ttcatactcc   4080
cgccattcag ag                                                       4092
```

<210> SEQ ID NO 88
<211> LENGTH: 4679
<212> TYPE: DNA
<213> ORGANISM: Artificial sequence
<220> FEATURE:
<223> OTHER INFORMATION: pRF161

<400> SEQUENCE: 88

```
catgggctcc agccatcatc atcaccatca tgaattcgga ggtggcggtg catcctcgga     60
ggatgtgatt aaagaattta tgcggtttaa agtacgtatg gaaggatcgg tgaatggcca    120
tgaatttgag attgagggtg aaggcgaagg ccgcccgtac gaaggaactc aaacagcgaa    180
attaaaagtt acaaaaggag gtcctctgcc gtttgcctgg gacatcttga gcccgcaatt    240
ccagtacggt tccaaagtgt atgtaaaaca ccctgcggat attccggatt ataaaaaact    300
gagttttccc gaggggttta aatgggaacg ggtgatgaat tttgaggatg gtggagttgt    360
caccgtgacc caggactcta gcttacaaga cggtagtttc atctacaaag taaaatttat    420
cggcgtaaac ttcccatcgg acggccccgt catgcagaaa aagacgatgg gctgggaagc    480
cagcaccgaa cgtttgtacc cacgggacgg cgttttgaaa ggggaaatcc ataaggccct    540
taaactgaaa gacggtggtc actatctcgt ggagtttaaa tcgatttata tggctaaaaa    600
accagtacag cttccgggtt attattacgt tgactccaaa ttggacatca catcgcataa    660
tgaagattac acgattgttg aacagtacga gcgcgccgag ggccggcacc atctgtttct    720
gtaaaagctt ggctgttttg gcggatgaga gaagattttc agcctgatac agattaaatc    780
agaacgcaga agcggtctga taaaacagaa tttgcctggc ggcagtagcg cggtggtccc    840
acctgacccc atgccgaact cagaagtgaa acgccgtagc gccgatggta gtgtggggtc    900
tccccatgcg agagtaggga actgccaggc atcaaataaa acgaaaggct cagtcgaaag    960
actgggcctt tcgttttatc tgttgtttgt cggtgaacgc tctcctgagt aggacaaatc   1020
cgccgggagc ggatttgaac gttgcgaagc aacggcccgg agggtggcgg gcaggacgcc   1080
```

-continued

```
cgccataaac tgccaggcat caaattaagc agaaggccat cctgacggat ggcctttttg   1140
cgtttctaca aactcttttg tttatttttc taaatacatt caaatatgta tccgctcatg   1200
agacaataac cctgataaat gcttcaataa tattgaaaaa ggaagagtat gagtattcaa   1260
catttccgtg tcgcccttat tccctttttt gcggcatttt gccttcctgt ttttgctcac   1320
ccagaaacgc tggtgaaagt aaaagatgct gaagatcagt tgggtgcacg agtgggttac   1380
atcgaactgg atctcaacag cggtaagatc cttgagagtt ttcgccccga agaacgtttt   1440
ccaatgatga gcacttttaa agttctgcta tgtggcgcgg tattatcccg tgttgacgcc   1500
gggcaagagc aactcggtcg ccgcatacac tattctcaga atgacttggt tgagtactca   1560
ccagtcacag aaaagcatct tacggatggc atgacagtaa gagaattatg cagtgctgcc   1620
ataaccatga gtgataacac tgcggccaac ttacttctga caacgatcgg aggaccgaag   1680
gagctaaccg cttttttgca caacatgggg gatcatgtaa ctcgccttga tcgttgggaa   1740
ccggagctga atgaagccat accaaacgac gagcgtgaca ccacgatgcc tgtagcaatg   1800
gcaacaacgt tgcgcaaact attaactggc gaactactta ctctagcttc ccggcaacaa   1860
ttaatagact ggatggaggc ggataaagtt gcaggaccac ttctgcgctc ggcccttccg   1920
gctggctggt ttattgctga taaatctgga gccggtgagc gtgggtctcg cggtatcatt   1980
gcagcactgg ggccagatgg taagccctcc cgtatcgtag ttatctacac gacggggagt   2040
caggcaacta tggatgaacg aaatagacag atcgctgaga taggtgcctc actgattaag   2100
cattggtaac tgtcagacca agtttactca tatatacttt agattgattt aaaacttcat   2160
ttttaattta aaaggatcta ggtgaagatc ctttttgata atctcatgac caaaatccct   2220
taacgtgagt tttcgttcca ctgagcgtca gaccccgtag aaaagatcaa aggatcttct   2280
tgagatcctt tttttctgcg cgtaatctgc tgcttgcaaa caaaaaaacc accgctacca   2340
gcggtggttt gtttgccgga tcaagagcta ccaactcttt ttccgaaggt aactggcttc   2400
agcagagcgc agataccaaa tactgtcctt ctagtgtagc cgtagttagg ccaccacttc   2460
aagaactctg tagcaccgcc tacatacctc gctctgctaa tcctgttacc agtggctgct   2520
gccagtggcg ataagtcgtg tcttaccggg ttggactcaa gacgatagtt accggataag   2580
gcgcagcggt cgggctgaac ggggggttcg tgcacacagc ccagcttgga gcgaacgacc   2640
tacaccgaac tgagatacct acagcgtgag ctatgagaaa gcgccacgct tcccgaaggg   2700
agaaaggcgg acaggtatcc ggtaagcggc agggtcggaa caggagagcg cacgagggag   2760
cttccagggg gaaacgcctg gtatctttat agtcctgtcg ggtttcgcca cctctgactt   2820
gagcgtcgat ttttgtgatg ctcgtcaggg gggcggagcc tatggaaaaa cgccagcaac   2880
gcggcctttt tacggttcct ggccttttgc tggccttttg ctcacatgtt ctttcctgcg   2940
ttatcccctg attctgtgga taaccgtatt accgcctttg agtgagctga taccgctcgc   3000
cgcagccgaa cgaccgagcg cagcgagtca gtgagcgagg aagcggaaga gcgcctgatg   3060
cggtattttc tccttacgca tctgtgcggt atttcacacc gcatatggtg cactctcagt   3120
acaatctgct ctgatgccgc atagttaagc cagtatacac tccgctatcg ctacgtgact   3180
gggtcatggc tgcgccccga cacccgccaa cacccgctga cgcgccctga cgggcttgtc   3240
tgctcccggc atccgcttac agacaagctg tgaccgtctc cgggagctgc atgtgtcaga   3300
ggttttcacc gtcatcaccg aaacgcgcga ggcagcagat caattcgcgc gcgaaggcga   3360
agcggcatgc ataatgtgcc tgtcaaatgg acgaagcagg gattctgcaa accctatgct   3420
actccgtcaa gccgtcaatt gtctgattcg ttaccaatta tgacaacttg acggctacat   3480
```

-continued

```
cattcacttt ttcttcacaa ccggcacgga actcgctcgg gctggccccg gtgcattttt   3540

taaatacccg cgagaaatag agttgatcgt caaaaccaac attgcgaccg acggtggcga   3600

taggcatccg ggtggtgctc aaaagcagct tcgcctggct gatacgttgg tcctcgcgcc   3660

agcttaagac gctaatccct aactgctggc ggaaaagatg tgacagacgc gacggcgaca   3720

agcaaacatg ctgtgcgacg ctggcgatat caaaattgct gtctgccagg tgatcgctga   3780

tgtactgaca agcctcgcgt acccgattat ccatcggtgg atggagcgac tcgttaatcg   3840

cttccatgcg ccgcagtaac aattgctcaa gcagatttat cgccagcagc tccgaatagc   3900

gcccttcccc ttgcccggcg ttaatgattt gcccaaacag gtcgctgaaa tgcggctggt   3960

gcgcttcatc cgggcgaaag aaccccgtat tggcaaatat tgacggccag ttaagccatt   4020

catgccagta ggcgcgcgga cgaaagtaaa cccactggtg ataccattcg cgagcctccg   4080

gatgacgacc gtagtgatga atctctcctg gcgggaacag caaaatatca cccggtcggc   4140

aaacaaattc tcgtccctga tttttcacca ccccctgacc gcgaatggtg agattgagaa   4200

tataaccttt cattcccagc ggtcggtcga taaaaaaatc gagataaccg ttggcctcaa   4260

tcggcgttaa acccgccacc agatgggcat taaacgagta tcccggcagc aggggatcat   4320

tttgcgcttc agccatactt ttcatactcc cgccattcag agaagaaacc aattgtccat   4380

attgcatcag acattgccgt cactgcgtct tttactggct cttctcgcta accaaaccgg   4440

taaccccgct tattaaaagc attctgtaac aaagcgggac caaagccatg acaaaaacgc   4500

gtaacaaaag tgtctataat cacggcagaa aagtccacat tgattatttg cacggcgtca   4560

cactttgcta tgccatagca tttttatcca taagattagc ggatcctacc tgacgctttt   4620

tatcgcaact ctctactgtt tctccatacc cgtttttttgg gctaacagga ggaattaac   4679
```

<210> SEQ ID NO 89
<211> LENGTH: 20
<212> TYPE: PRT
<213> ORGANISM: Artificial sequence
<220> FEATURE:
<223> OTHER INFORMATION: TAT

<400> SEQUENCE: 89

```
Gly Arg Lys Lys Arg Arg Gln Arg Arg Arg Pro Pro Gln Pro Lys Lys
1               5                   10                  15

Lys Arg Lys Val
            20
```

<210> SEQ ID NO 90
<211> LENGTH: 18
<212> TYPE: PRT
<213> ORGANISM: Artificial sequence
<220> FEATURE:
<223> OTHER INFORMATION: TLM

<400> SEQUENCE: 90

```
Pro Leu Ser Ser Ile Phe Ser Arg Ile Gly Asp Pro Lys Lys Lys Arg
1               5                   10                  15

Lys Val
```

<210> SEQ ID NO 91
<211> LENGTH: 23
<212> TYPE: PRT
<213> ORGANISM: Artificial sequence
<220> FEATURE:
<223> OTHER INFORMATION: MPG1

<400> SEQUENCE: 91

Ala Leu Phe Leu Gly Gln Leu Gly Ala Ala Gly Ser Thr Met Gly Ala
1 5 10 15

Pro Lys Lys Lys Arg Lys Val
20

<210> SEQ ID NO 92
<211> LENGTH: 21
<212> TYPE: PRT
<213> ORGANISM: Artificial sequence
<220> FEATURE:
<223> OTHER INFORMATION: pep1

<400> SEQUENCE: 92

Lys Glu Thr Trp Trp Glu Thr Trp Trp Thr Glu Trp Ser Gln Pro Lys
1 5 10 15

Lys Lys Arg Lys Val
20

<210> SEQ ID NO 93
<211> LENGTH: 7
<212> TYPE: PRT
<213> ORGANISM: Artificial sequence
<220> FEATURE:
<223> OTHER INFORMATION: CFFKDEL

<400> SEQUENCE: 93

Cys Phe Phe Lys Asp Glu Leu
1 5

<210> SEQ ID NO 94
<211> LENGTH: 98
<212> TYPE: DNA
<213> ORGANISM: Artificial sequence
<220> FEATURE:
<223> OTHER INFORMATION: his-TAT E. coli optimized

<400> SEQUENCE: 94
ccatggggca tcaccatcat catcacggcc gcaaaaaacg tcgtcagcgc cggcgtccgc 60
cccagccgaa aaaacggaaa gtgggcggcg gcgaattc 98

<210> SEQ ID NO 95
<211> LENGTH: 89
<212> TYPE: DNA
<213> ORGANISM: Artificial sequence
<220> FEATURE:
<223> OTHER INFORMATION: his-TLM E. coli optimized

<400> SEQUENCE: 95
ccatggggca tcaccatcat catcatccgt taagctcgat cttttctcgt atcggtgatc 60
cgccaaaaaa gaaacgcaaa gtagaattc 89

<210> SEQ ID NO 96
<211> LENGTH: 104
<212> TYPE: DNA
<213> ORGANISM: Artificial sequence
<220> FEATURE:
<223> OTHER INFORMATION: his-MPG1 E. coli optimized

<400> SEQUENCE: 96
ccatggggca tcatcatcac catcacggcg ccctgttctt aggccagctg ggcgccgcgg 60
gatccacgat gggtgcgccg aagaaaaagc gcaaagttga attc 104

<210> SEQ ID NO 97
<211> LENGTH: 95
<212> TYPE: DNA
<213> ORGANISM: Artificial sequence
<220> FEATURE:
<223> OTHER INFORMATION: his-pep1 E. coli optimized

<400> SEQUENCE: 97
ccatggggca ccatcaccat caccataaag aaacttggtg ggagacttgg tggaccgaat 60
ggtcccagcc gaagaaaaaa cgcaaggttg aattc 95

<210> SEQ ID NO 98
<211> LENGTH: 51
<212> TYPE: DNA
<213> ORGANISM: Artificial sequence
<220> FEATURE:
<223> OTHER INFORMATION: his-CFFKDEL E. coli optimized

<400> SEQUENCE: 98
ccatggggca tcaccatcac caccattgtt ttttcaaaga cgaactggaa t 51

<210> SEQ ID NO 99
<211> LENGTH: 4739
<212> TYPE: DNA
<213> ORGANISM: Artificial sequence
<220> FEATURE:
<223> OTHER INFORMATION: pRF224;

<400> SEQUENCE: 99
catggggcat caccatcatc atcacggccg caaaaaacgt cgtcagcgcc ggcgtccgcc 60
ccagccgaaa aaacggaaag tgggcggcgg cgaattcgga ggtggcggtg catcctcgga 120
ggatgtgatt aaagaattta tgcggtttaa agtacgtatg gaaggatcgg tgaatggcca 180
tgaatttgag attgagggtg aaggcgaagg ccgcccgtac gaaggaactc aaacagcgaa 240
attaaaagtt acaaaaggag gtcctctgcc gtttgcctgg gacatcttga gcccgcaatt 300
ccagtacggt tccaaagtgt atgtaaaaca ccctgcggat attccggatt ataaaaaact 360
gagttttccc gaggggttta aatgggaacg ggtgatgaat tttgaggatg gtggagttgt 420
caccgtgacc caggactcta gcttacaaga cggtagtttc atctacaaag taaaatttat 480
cggcgtaaac ttcccatcgg acggccccgt catgcagaaa aagacgatgg gctgggaagc 540
cagcaccgaa cgtttgtacc cacgggacgg cgttttgaaa ggggaaatcc ataaggccct 600
taaactgaaa gacggtggtc actatctcgt ggagtttaaa tcgatttata tggctaaaaa 660
accagtacag cttccgggtt attattacgt tgactccaaa ttggacatca catcgcataa 720
tgaagattac acgattgttg aacagtacga gcgcgccgag ggccggcacc atctgtttct 780
gtaaaagctt ggctgttttg gcggatgaga gaagattttc agcctgatac agattaaatc 840
agaacgcaga agcggtctga taaaacagaa tttgcctggc ggcagtagcg cggtggtccc 900
acctgacccc atgccgaact cagaagtgaa acgccgtagc gccgatggta gtgtggggtc 960
tccccatgcg agagtaggga actgccaggc atcaaataaa acgaaaggct cagtcgaaag 1020
actgggcctt tcgttttatc tgttgtttgt cggtgaacgc tctcctgagt aggacaaatc 1080
cgccgggagc ggatttgaac gttgcgaagc aacggcccgg agggtggcgg gcaggacgcc 1140
cgccataaac tgccaggcat caaattaagc agaaggccat cctgacggat ggcctttttg 1200
cgtttctaca aactcttttg tttatttttc taaatacatt caaatatgta tccgctcatg 1260

-continued

```
agacaataac cctgataaat gcttcaataa tattgaaaaa ggaagagtat gagtattcaa   1320
catttccgtg tcgcccttat tccctttttt gcggcatttt gccttcctgt ttttgctcac   1380
ccagaaacgc tggtgaaagt aaaagatgct gaagatcagt tgggtgcacg agtgggttac   1440
atcgaactgg atctcaacag cggtaagatc cttgagagtt ttcgccccga agaacgtttt   1500
ccaatgatga gcacttttaa agttctgcta tgtggcgcgg tattatcccg tgttgacgcc   1560
gggcaagagc aactcggtcg ccgcatacac tattctcaga atgacttggt tgagtactca   1620
ccagtcacag aaaagcatct tacggatggc atgacagtaa gagaattatg cagtgctgcc   1680
ataaccatga gtgataacac tgcggccaac ttacttctga caacgatcgg aggaccgaag   1740
gagctaaccg cttttttgca caacatgggg gatcatgtaa ctcgccttga tcgttgggaa   1800
ccggagctga atgaagccat accaaacgac gagcgtgaca ccacgatgcc tgtagcaatg   1860
gcaacaacgt tgcgcaaact attaactggc gaactactta ctctagcttc ccggcaacaa   1920
ttaatagact ggatggaggc ggataaagtt gcaggaccac ttctgcgctc ggcccttccg   1980
gctggctggt ttattgctga taaatctgga gccggtgagc gtgggtctcg cggtatcatt   2040
gcagcactgg ggccagatgg taagccctcc cgtatcgtag ttatctacac gacggggagt   2100
caggcaacta tggatgaacg aaatagacag atcgctgaga taggtgcctc actgattaag   2160
cattggtaac tgtcagacca agtttactca tatatacttt agattgattt aaaacttcat   2220
ttttaattta aaaggatcta ggtgaagatc ctttttgata atctcatgac caaaatccct   2280
taacgtgagt tttcgttcca ctgagcgtca gaccccgtag aaaagatcaa aggatcttct   2340
tgagatcctt tttttctgcg cgtaatctgc tgcttgcaaa caaaaaaacc accgctacca   2400
gcggtggttt gtttgccgga tcaagagcta ccaactcttt ttccgaaggt aactggcttc   2460
agcagagcgc agataccaaa tactgtcctt ctagtgtagc cgtagttagg ccaccacttc   2520
aagaactctg tagcaccgcc tacatacctc gctctgctaa tcctgttacc agtggctgct   2580
gccagtggcg ataagtcgtg tcttaccggg ttggactcaa gacgatagtt accggataag   2640
gcgcagcggt cgggctgaac ggggggttcg tgcacacagc ccagcttgga gcgaacgacc   2700
tacaccgaac tgagatacct acagcgtgag ctatgagaaa gcgccacgct tcccgaaggg   2760
agaaaggcgg acaggtatcc ggtaagcggc agggtcggaa caggagagcg cacgagggag   2820
cttccagggg gaaacgcctg gtatctttat agtcctgtcg ggtttcgcca cctctgactt   2880
gagcgtcgat ttttgtgatg ctcgtcaggg gggcggagcc tatggaaaaa cgccagcaac   2940
gcggcctttt tacggttcct ggccttttgc tggccttttg ctcacatgtt ctttcctgcg   3000
ttatcccctg attctgtgga taaccgtatt accgcctttg agtgagctga taccgctcgc   3060
cgcagccgaa cgaccgagcg cagcgagtca gtgagcgagg aagcggaaga gcgcctgatg   3120
cggtattttc tccttacgca tctgtgcggt atttcacacc gcatatggtg cactctcagt   3180
acaatctgct ctgatgccgc atagttaagc cagtatacac tccgctatcg ctacgtgact   3240
gggtcatggc tgcgccccga cacccgccaa cacccgctga cgcgccctga cgggcttgtc   3300
tgctcccggc atccgcttac agacaagctg tgaccgtctc cgggagctgc atgtgtcaga   3360
ggttttcacc gtcatcaccg aaacgcgcga ggcagcagat caattcgcgc gcgaaggcga   3420
agcggcatgc ataatgtgcc tgtcaaatgg acgaagcagg gattctgcaa accctatgct   3480
actccgtcaa gccgtcaatt gtctgattcg ttaccaatta tgacaacttg acggctacat   3540
cattcacttt ttcttcacaa ccggcacgga actcgctcgg gctggccccg gtgcattttt   3600
taaatacccg cgagaaatag agttgatcgt caaaaccaac attgcgaccg acggtggcga   3660
```

taggcatccg ggtggtgctc aaaagcagct tcgcctggct gatacgttgg tcctcgcgcc 3720
agcttaagac gctaatccct aactgctggc ggaaaagatg tgacagacgc gacggcgaca 3780
agcaaacatg ctgtgcgacg ctggcgatat caaaattgct gtctgccagg tgatcgctga 3840
tgtactgaca agcctcgcgt acccgattat ccatcggtgg atggagcgac tcgttaatcg 3900
cttccatgcg ccgcagtaac aattgctcaa gcagatttat cgccagcagc tccgaatagc 3960
gcccttcccc ttgcccggcg ttaatgattt gcccaaacag gtcgctgaaa tgcggctggt 4020
gcgcttcatc cgggcgaaag aaccccgtat tggcaaatat tgacggccag ttaagccatt 4080
catgccagta ggcgcgcgga cgaaagtaaa cccactggtg ataccattcg cgagcctccg 4140
gatgacgacc gtagtgatga atctctcctg gcgggaacag caaaatatca cccggtcggc 4200
aaacaaattc tcgtccctga tttttcacca ccccctgacc gcgaatggtg agattgagaa 4260
tataaccttt cattcccagc ggtcggtcga taaaaaaatc gagataaccg ttggcctcaa 4320
tcggcgttaa acccgccacc agatgggcat taaacgagta tcccggcagc aggggatcat 4380
tttgcgcttc agccatactt ttcatactcc cgccattcag agaagaaacc aattgtccat 4440
attgcatcag acattgccgt cactgcgtct tttactggct cttctcgcta accaaaccgg 4500
taaccccgct tattaaaagc attctgtaac aaagcgggac caaagccatg acaaaaacgc 4560
gtaacaaaag tgtctataat cacggcagaa aagtccacat tgattatttg cacggcgtca 4620
cactttgcta tgccatagca tttttatcca taagattagc ggatcctacc tgacgctttt 4680
tatcgcaact ctctactgtt tctccatacc cgtttttttgg gctaacagga ggaattaac 4739

<210> SEQ ID NO 100
<211> LENGTH: 4730
<212> TYPE: DNA
<213> ORGANISM: Artificial sequence
<220> FEATURE:
<223> OTHER INFORMATION: pRF214

<400> SEQUENCE: 100
catggggcat caccatcatc atcatccgtt aagctcgatc ttttctcgta tcggtgatcc 60
gccaaaaaag aaacgcaaag tagaattcgg aggtggcggt gcatcctcgg aggatgtgat 120
taaagaattt atgcggttta aagtacgtat ggaaggatcg gtgaatggcc atgaatttga 180
gattgagggt gaaggcgaag gccgcccgta cgaaggaact caaacagcga aattaaaagt 240
tacaaaagga ggtcctctgc cgtttgcctg ggacatcttg agcccgcaat tccagtacgg 300
ttccaaagtg tatgtaaaac accctgcgga tattccggat tataaaaaac tgagttttcc 360
cgaggggttt aaatgggaac gggtgatgaa ttttgaggat ggtggagttg tcaccgtgac 420
ccaggactct agcttacaag acggtagttt catctacaaa gtaaaattta tcggcgtaaa 480
cttcccatcg gacggccccg tcatgcagaa aaagacgatg ggctgggaag ccagcaccga 540
acgtttgtac ccacgggacg gcgttttgaa aggggaaatc cataaggccc ttaaactgaa 600
agacggtggt cactatctcg tggagtttaa atcgatttat atggctaaaa aaccagtaca 660
gcttccgggt tattattacg ttgactccaa attggacatc acatcgcata atgaagatta 720
cacgattgtt gaacagtacg agcgcgccga gggccggcac catctgtttc tgtaaaagct 780
tggctgtttt ggcggatgag agaagatttt cagcctgata cagattaaat cagaacgcag 840
aagcggtctg ataaaacaga atttgcctgg cggcagtagc gcggtggtcc cacctgaccc 900
catgccgaac tcagaagtga aacgccgtag cgccgatggt agtgtggggt ctccccatgc 960

-continued

```
gagagtaggg aactgccagg catcaaataa aacgaaaggc tcagtcgaaa gactgggcct   1020
ttcgttttat ctgttgtttg tcggtgaacg ctctcctgag taggacaaat ccgccgggag   1080
cggatttgaa cgttgcgaag caacggcccg gagggtggcg ggcaggacgc ccgccataaa   1140
ctgccaggca tcaaattaag cagaaggcca tcctgacgga tggccttttt gcgtttctac   1200
aaactctttt gtttattttt ctaaatacat tcaaatatgt atccgctcat gagacaataa   1260
ccctgataaa tgcttcaata atattgaaaa aggaagagta tgagtattca acatttccgt   1320
gtcgccctta ttcccttttt tgcggcattt tgccttcctg tttttgctca cccagaaacg   1380
ctggtgaaag taaaagatgc tgaagatcag ttgggtgcac gagtgggtta catcgaactg   1440
gatctcaaca gcggtaagat ccttgagagt tttcgccccg aagaacgttt tccaatgatg   1500
agcactttta aagttctgct atgtggcgcg gtattatccc gtgttgacgc cgggcaagag   1560
caactcggtc gccgcataca ctattctcag aatgacttgg ttgagtactc accagtcaca   1620
gaaaagcatc ttacggatgg catgacagta agagaattat gcagtgctgc cataaccatg   1680
agtgataaca ctgcggccaa cttacttctg acaacgatcg gaggaccgaa ggagctaacc   1740
gcttttttgc acaacatggg ggatcatgta actcgccttg atcgttggga accggagctg   1800
aatgaagcca taccaaacga cgagcgtgac accacgatgc ctgtagcaat ggcaacaacg   1860
ttgcgcaaac tattaactgg cgaactactt actctagctt cccggcaaca attaatagac   1920
tggatggagg cggataaagt tgcaggacca cttctgcgct cggcccttcc ggctggctgg   1980
tttattgctg ataaatctgg agccggtgag cgtgggtctc gcggtatcat tgcagcactg   2040
gggccagatg gtaagccctc ccgtatcgta gttatctaca cgacggggag tcaggcaact   2100
atggatgaac gaaatagaca gatcgctgag ataggtgcct cactgattaa gcattggtaa   2160
ctgtcagacc aagtttactc atatatactt tagattgatt taaaacttca tttttaattt   2220
aaaaggatct aggtgaagat cctttttgat aatctcatga ccaaaatccc ttaacgtgag   2280
ttttcgttcc actgagcgtc agaccccgta gaaaagatca aaggatcttc ttgagatcct   2340
ttttttctgc gcgtaatctg ctgcttgcaa acaaaaaaac caccgctacc agcggtggtt   2400
tgtttgccgg atcaagagct accaactctt tttccgaagg taactggctt cagcagagcg   2460
cagataccaa atactgtcct tctagtgtag ccgtagttag gccaccactt caagaactct   2520
gtagcaccgc ctacatacct cgctctgcta atcctgttac cagtggctgc tgccagtggc   2580
gataagtcgt gtcttaccgg gttggactca agacgatagt taccggataa ggcgcagcgg   2640
tcgggctgaa cggggggttc gtgcacacag cccagcttgg agcgaacgac ctacaccgaa   2700
ctgagatacc tacagcgtga gctatgagaa agcgccacgc ttcccgaagg gagaaaggcg   2760
gacaggtatc cggtaagcgg cagggtcgga acaggagagc gcacgaggga gcttccaggg   2820
ggaaacgcct ggtatcttta tagtcctgtc gggtttcgcc acctctgact tgagcgtcga   2880
tttttgtgat gctcgtcagg ggggcggagc ctatggaaaa acgccagcaa cgcggccttt   2940
ttacggttcc tggccttttg ctggcctttt gctcacatgt tctttcctgc gttatcccct   3000
gattctgtgg ataaccgtat taccgccttt gagtgagctg ataccgctcg ccgcagccga   3060
acgaccgagc gcagcgagtc agtgagcgag gaagcggaag agcgcctgat gcggtatttt   3120
ctccttacgc atctgtgcgg tatttcacac cgcatatggt gcactctcag tacaatctgc   3180
tctgatgccg catagttaag ccagtataca ctccgctatc gctacgtgac tgggtcatgg   3240
ctgcgccccg acacccgcca acacccgctg acgcgccctg acgggcttgt ctgctcccgg   3300
catccgctta cagacaagct gtgaccgtct ccgggagctg catgtgtcag aggttttcac   3360
```

```
cgtcatcacc gaaacgcgcg aggcagcaga tcaattcgcg cgcgaaggcg aagcggcatg   3420
cataatgtgc ctgtcaaatg gacgaagcag ggattctgca aaccctatgc tactccgtca   3480
agccgtcaat tgtctgattc gttaccaatt atgacaactt gacggctaca tcattcactt   3540
tttcttcaca accggcacgg aactcgctcg ggctggcccc ggtgcatttt ttaaataccc   3600
gcgagaaata gagttgatcg tcaaaaccaa cattgcgacc gacggtggcg ataggcatcc   3660
gggtggtgct caaaagcagc ttcgcctggc tgatacgttg gtcctcgcgc cagcttaaga   3720
cgctaatccc taactgctgg cggaaaagat gtgacagacg cgacggcgac aagcaaacat   3780
gctgtgcgac gctggcgata tcaaaattgc tgtctgccag gtgatcgctg atgtactgac   3840
aagcctcgcg tacccgatta tccatcggtg gatggagcga ctcgttaatc gcttccatgc   3900
gccgcagtaa caattgctca agcagattta tcgccagcag ctccgaatag cgcccttccc   3960
cttgcccggc gttaatgatt tgcccaaaca ggtcgctgaa atgcggctgg tgcgcttcat   4020
ccgggcgaaa gaaccccgta ttggcaaata ttgacggcca gttaagccat tcatgccagt   4080
aggcgcgcgg acgaaagtaa acccactggt gataccattc gcgagcctcc ggatgacgac   4140
cgtagtgatg aatctctcct ggcgggaaca gcaaaatatc acccggtcgg caaacaaatt   4200
ctcgtccctg atttttcacc accccctgac cgcgaatggt gagattgaga atataacctt   4260
tcattcccag cggtcggtcg ataaaaaaat cgagataacc gttggcctca atcggcgtta   4320
aacccgccac cagatgggca ttaaacgagt atcccggcag caggggatca ttttgcgctt   4380
cagccatact tttcatactc ccgccattca gagaagaaac caattgtcca tattgcatca   4440
gacattgccg tcactgcgtc ttttactggc tcttctcgct aaccaaaccg gtaaccccgc   4500
ttattaaaag cattctgtaa caaagcggga ccaaagccat gacaaaaacg cgtaacaaaa   4560
gtgtctataa tcacggcaga aaagtccaca ttgattattt gcacggcgtc acactttgct   4620
atgccatagc atttttatcc ataagattag cggatcctac ctgacgcttt ttatcgcaac   4680
tctctactgt ttctccatac ccgttttttg ggctaacagg aggaattaac               4730
```

<210> SEQ ID NO 101
<211> LENGTH: 4745
<212> TYPE: DNA
<213> ORGANISM: Artificial sequence
<220> FEATURE:
<223> OTHER INFORMATION: pRF213

<400> SEQUENCE: 101

```
catggggcat catcatcacc atcacggcgc cctgttctta ggccagctgg gcgccgcggg     60
atccacgatg ggtgcgccga agaaaaagcg caaagttgaa ttcggaggtg gcggtgcatc    120
ctcggaggat gtgattaaag aatttatgcg gtttaaagta cgtatggaag gatcggtgaa    180
tggccatgaa tttgagattg agggtgaagg cgaaggccgc ccgtacgaag gaactcaaac    240
agcgaaatta aaagttacaa aaggaggtcc tctgccgttt gcctgggaca tcttgagccc    300
gcaattccag tacggttcca aagtgtatgt aaaacaccct gcggatattc cggattataa    360
aaaactgagt tttcccgagg ggtttaaatg ggaacgggtg atgaattttg aggatggtgg    420
agttgtcacc gtgacccagg actctagctt acaagacggt agtttcatct acaaagtaaa    480
atttatcggc gtaaacttcc catcggacgg ccccgtcatg cagaaaaaga cgatgggctg    540
ggaagccagc accgaacgtt tgtacccacg ggacggcgtt ttgaaagggg aaatccataa    600
ggcccttaaa ctgaaagacg gtggtcacta tctcgtggag tttaaatcga tttatatggc    660
```

-continued

```
taaaaaacca gtacagcttc cgggttatta ttacgttgac tccaaattgg acatcacatc    720
gcataatgaa gattacacga ttgttgaaca gtacgagcgc gccgagggcc ggcaccatct    780
gtttctgtaa aagcttggct gttttggcgg atgagagaag attttcagcc tgatacagat    840
taaatcagaa cgcagaagcg gtctgataaa acagaatttg cctggcggca gtagcgcggt    900
ggtcccacct gaccccatgc cgaactcaga agtgaaacgc cgtagcgccg atggtagtgt    960
ggggtctccc catgcgagag tagggaactg ccaggcatca aataaaacga aaggctcagt   1020
cgaaagactg ggcctttcgt tttatctgtt gtttgtcggt gaacgctctc ctgagtagga   1080
caaatccgcc gggagcggat ttgaacgttg cgaagcaacg gcccggaggg tggcgggcag   1140
gacgcccgcc ataaactgcc aggcatcaaa ttaagcagaa ggccatcctg acggatggcc   1200
tttttgcgtt tctacaaact cttttgttta tttttctaaa tacattcaaa tatgtatccg   1260
ctcatgagac aataaccctg ataaatgctt caataatatt gaaaaaggaa gagtatgagt   1320
attcaacatt tccgtgtcgc ccttattccc ttttttgcgg cattttgcct tcctgttttt   1380
gctcacccag aaacgctggt gaaagtaaaa gatgctgaag atcagttggg tgcacgagtg   1440
ggttacatcg aactggatct caacagcggt aagatccttg agagttttcg ccccgaagaa   1500
cgttttccaa tgatgagcac ttttaaagtt ctgctatgtg gcgcggtatt atcccgtgtt   1560
gacgccgggc aagagcaact cggtcgccgc atacactatt ctcagaatga cttggttgag   1620
tactcaccag tcacagaaaa gcatcttacg gatggcatga cagtaagaga attatgcagt   1680
gctgccataa ccatgagtga taacactgcg gccaacttac ttctgacaac gatcggagga   1740
ccgaaggagc taaccgcttt tttgcacaac atgggggatc atgtaactcg ccttgatcgt   1800
tgggaaccgg agctgaatga agccatacca aacgacgagc gtgacaccac gatgcctgta   1860
gcaatggcaa caacgttgcg caaactatta actggcgaac tacttactct agcttcccgg   1920
caacaattaa tagactggat ggaggcggat aaagttgcag gaccacttct gcgctcggcc   1980
cttccggctg gctggtttat tgctgataaa tctggagccg gtgagcgtgg gtctcgcggt   2040
atcattgcag cactggggcc agatggtaag ccctcccgta tcgtagttat ctacacgacg   2100
gggagtcagg caactatgga tgaacgaaat agacagatcg ctgagatagg tgcctcactg   2160
attaagcatt ggtaactgtc agaccaagtt tactcatata tactttagat tgatttaaaa   2220
cttcattttt aatttaaaag gatctaggtg aagatccttt ttgataatct catgaccaaa   2280
atcccttaac gtgagttttc gttccactga gcgtcagacc ccgtagaaaa gatcaaagga   2340
tcttcttgag atcctttttt tctgcgcgta atctgctgct tgcaaacaaa aaaaccaccg   2400
ctaccagcgg tggtttgttt gccggatcaa gagctaccaa ctctttttcc gaaggtaact   2460
ggcttcagca gagcgcagat accaaatact gtccttctag tgtagccgta gttaggccac   2520
cacttcaaga actctgtagc accgcctaca tacctcgctc tgctaatcct gttaccagtg   2580
gctgctgcca gtggcgataa gtcgtgtctt accgggttgg actcaagacg atagttaccg   2640
gataaggcgc agcggtcggg ctgaacgggg ggttcgtgca cacagcccag cttggagcga   2700
acgacctaca ccgaactgag atacctacag cgtgagctat gagaaagcgc cacgcttccc   2760
gaagggagaa aggcggacag gtatccggta agcggcaggg tcggaacagg agagcgcacg   2820
agggagcttc cagggggaaa cgcctggtat ctttatagtc ctgtcgggtt tcgccacctc   2880
tgacttgagc gtcgattttt gtgatgctcg tcaggggggc ggagcctatg gaaaaacgcc   2940
agcaacgcgg cctttttacg gttcctggcc ttttgctggc cttttgctca catgttcttt   3000
cctgcgttat cccctgattc tgtggataac cgtattaccg cctttgagtg agctgatacc   3060
```

```
gctcgccgca gccgaacgac cgagcgcagc gagtcagtga gcgaggaagc ggaagagcgc   3120
ctgatgcggt attttctcct tacgcatctg tgcggtattt cacaccgcat atggtgcact   3180
ctcagtacaa tctgctctga tgccgcatag ttaagccagt atacactccg ctatcgctac   3240
gtgactgggt catggctgcg ccccgacacc cgccaacacc cgctgacgcg ccctgacggg   3300
cttgtctgct cccggcatcc gcttacagac aagctgtgac cgtctccggg agctgcatgt   3360
gtcagaggtt ttcaccgtca tcaccgaaac gcgcgaggca gcagatcaat tcgcgcgcga   3420
aggcgaagcg gcatgcataa tgtgcctgtc aaatggacga agcagggatt ctgcaaaccc   3480
tatgctactc cgtcaagccg tcaattgtct gattcgttac caattatgac aacttgacgg   3540
ctacatcatt cactttttct tcacaaccgg cacggaactc gctcgggctg gccccggtgc   3600
atttttaaa tacccgcgag aaatagagtt gatcgtcaaa accaacattg cgaccgacgg    3660
tggcgatagg catccgggtg gtgctcaaaa gcagcttcgc ctggctgata cgttggtcct   3720
cgcgccagct taagacgcta atccctaact gctggcggaa aagatgtgac agacgcgacg   3780
gcgacaagca aacatgctgt gcgacgctgg cgatatcaaa attgctgtct gccaggtgat   3840
cgctgatgta ctgacaagcc tcgcgtaccc gattatccat cggtggatgg agcgactcgt   3900
taatcgcttc catgcgccgc agtaacaatt gctcaagcag atttatcgcc agcagctccg   3960
aatagcgccc ttccccttgc ccggcgttaa tgatttgccc aaacaggtcg ctgaaatgcg   4020
gctggtgcgc ttcatccggg cgaaagaacc ccgtattggc aaatattgac ggccagttaa   4080
gccattcatg ccagtaggcg cgcggacgaa agtaaaccca ctggtgatac cattcgcgag   4140
cctccggatg acgaccgtag tgatgaatct ctcctggcgg gaacagcaaa atatcacccg   4200
gtcggcaaac aaattctcgt ccctgatttt tcaccacccc ctgaccgcga atggtgagat   4260
tgagaatata acctttcatt cccagcggtc ggtcgataaa aaaatcgaga taaccgttgg   4320
cctcaatcgg cgttaaaccc gccaccagat gggcattaaa cgagtatccc ggcagcaggg   4380
gatcattttg cgcttcagcc atacttttca tactcccgcc attcagagaa gaaaccaatt   4440
gtccatattg catcagacat tgccgtcact gcgtctttta ctggctcttc tcgctaacca   4500
aaccggtaac cccgcttatt aaaagcattc tgtaacaaag cgggaccaaa gccatgacaa   4560
aaacgcgtaa caaaagtgtc tataatcacg gcagaaaagt ccacattgat tatttgcacg   4620
gcgtcacact ttgctatgcc atagcatttt tatccataag attagcggat cctacctgac   4680
gctttttatc gcaactctct actgtttctc catacccgtt ttttgggcta acaggaggaa   4740
ttaac                                                               4745
```

<210> SEQ ID NO 102
<211> LENGTH: 4736
<212> TYPE: DNA
<213> ORGANISM: Artificial sequence
<220> FEATURE:
<223> OTHER INFORMATION: pRF217

<400> SEQUENCE: 102

```
catggggcac catcaccatc accataaaga aacttggtgg gagacttggt ggaccgaatg     60
gtcccagccg aagaaaaaac gcaaggttga attcggaggt ggcggtgcat cctcggagga    120
tgtgattaaa gaatttatgc ggtttaaagt acgtatggaa ggatcggtga atggccatga    180
atttgagatt gagggtgaag gcgaaggccg cccgtacgaa ggaactcaaa cagcgaaatt    240
aaaagttaca aaaggaggtc ctctgccgtt tgcctgggac atcttgagcc cgcaattcca    300
```

-continued

```
gtacggttcc aaagtgtatg taaaacaccc tgcggatatt ccggattata aaaaactgag    360
ttttcccgag ggtttaaat gggaacgggt gatgaatttt gaggatggtg gagttgtcac    420
cgtgacccag gactctagct tacaagacgg tagtttcatc tacaaagtaa aatttatcgg    480
cgtaaacttc ccatcggacg gccccgtcat gcagaaaaag acgatgggct gggaagccag    540
caccgaacgt ttgtacccac gggacggcgt tttgaaaggg gaaatccata aggcccttaa    600
actgaaagac ggtggtcact atctcgtgga gtttaaatcg atttatatgg ctaaaaaacc    660
agtacagctt ccgggttatt attacgttga ctccaaattg gacatcacat cgcataatga    720
agattacacg attgttgaac agtacgagcg cgccgagggc cggcaccatc tgtttctgta    780
aaagcttggc tgttttggcg gatgagagaa gattttcagc ctgatacaga ttaaatcaga    840
acgcagaagc ggtctgataa aacagaattt gcctggcggc agtagcgcgg tggtcccacc    900
tgaccccatg ccgaactcag aagtgaaacg ccgtagcgcc gatggtagtg tggggtctcc    960
ccatgcgaga gtagggaact gccaggcatc aaataaaacg aaaggctcag tcgaaagact   1020
gggcctttcg ttttatctgt tgtttgtcgg tgaacgctct cctgagtagg acaaatccgc   1080
cgggagcgga tttgaacgtt gcgaagcaac ggcccggagg gtggcgggca ggacgcccgc   1140
cataaactgc caggcatcaa attaagcaga aggccatcct gacggatggc ctttttgcgt   1200
ttctacaaac tcttttgttt atttttctaa atacattcaa atatgtatcc gctcatgaga   1260
caataaccct gataaatgct tcaataatat tgaaaaagga agagtatgag tattcaacat   1320
ttccgtgtcg cccttattcc cttttttgcg gcattttgcc ttcctgtttt tgctcaccca   1380
gaaacgctgg tgaaagtaaa agatgctgaa gatcagttgg gtgcacgagt gggttacatc   1440
gaactggatc tcaacagcgg taagatcctt gagagttttc gccccgaaga acgttttcca   1500
atgatgagca cttttaaagt tctgctatgt ggcgcggtat tatcccgtgt tgacgccggg   1560
caagagcaac tcggtcgccg catacactat tctcagaatg acttggttga gtactcacca   1620
gtcacagaaa agcatcttac ggatggcatg acagtaagag aattatgcag tgctgccata   1680
accatgagtg ataacactgc ggccaactta cttctgacaa cgatcggagg accgaaggag   1740
ctaaccgctt ttttgcacaa catgggggat catgtaactc gccttgatcg ttgggaaccg   1800
gagctgaatg aagccatacc aaacgacgag cgtgacacca cgatgcctgt agcaatggca   1860
acaacgttgc gcaaactatt aactggcgaa ctacttactc tagcttcccg gcaacaatta   1920
atagactgga tggaggcgga taaagttgca ggaccacttc tgcgctcggc ccttccggct   1980
ggctggttta ttgctgataa atctggagcc ggtgagcgtg ggtctcgcgg tatcattgca   2040
gcactggggc cagatggtaa gccctcccgt atcgtagtta tctacacgac ggggagtcag   2100
gcaactatgg atgaacgaaa tagacagatc gctgagatag gtgcctcact gattaagcat   2160
tggtaactgt cagaccaagt ttactcatat atactttaga ttgatttaaa acttcatttt   2220
taatttaaaa ggatctaggt gaagatcctt tttgataatc tcatgaccaa aatcccttaa   2280
cgtgagtttt cgttccactg agcgtcagac cccgtagaaa agatcaaagg atcttcttga   2340
gatccttttt ttctgcgcgt aatctgctgc ttgcaaacaa aaaaaccacc gctaccagcg   2400
gtggtttgtt tgccggatca agagctacca actctttttc cgaaggtaac tggcttcagc   2460
agagcgcaga taccaaatac tgtccttcta gtgtagccgt agttaggcca ccacttcaag   2520
aactctgtag caccgcctac atacctcgct ctgctaatcc tgttaccagt ggctgctgcc   2580
agtggcgata agtcgtgtct taccgggttg gactcaagac gatagttacc ggataaggcg   2640
cagcggtcgg gctgaacggg gggttcgtgc acacagccca gcttggagcg aacgacctac   2700
```

-continued accgaactga gatacctaca gcgtgagcta tgagaaagcg ccacgcttcc cgaagggaga 2760
aaggcggaca ggtatccggt aagcggcagg gtcggaacag gagagcgcac gagggagctt 2820
ccagggggaa acgcctggta tctttatagt cctgtcgggt ttcgccacct ctgacttgag 2880
cgtcgatttt tgtgatgctc gtcagggggg cggagcctat ggaaaaacgc cagcaacgcg 2940
gcctttttac ggttcctggc cttttgctgg ccttttgctc acatgttctt tcctgcgtta 3000
tcccctgatt ctgtggataa ccgtattacc gcctttgagt gagctgatac cgctcgccgc 3060
agccgaacga ccgagcgcag cgagtcagtg agcgaggaag cggaagagcg cctgatgcgg 3120
tattttctcc ttacgcatct gtgcggtatt tcacaccgca tatggtgcac tctcagtaca 3180
atctgctctg atgccgcata gttaagccag tatacactcc gctatcgcta cgtgactggg 3240
tcatggctgc gccccgacac ccgccaacac ccgctgacgc gccctgacgg gcttgtctgc 3300
tcccggcatc cgcttacaga caagctgtga ccgtctccgg gagctgcatg tgtcagaggt 3360
tttcaccgtc atcaccgaaa cgcgcgaggc agcagatcaa ttcgcgcgcg aaggcgaagc 3420
ggcatgcata atgtgcctgt caaatggacg aagcagggat tctgcaaacc ctatgctact 3480
ccgtcaagcc gtcaattgtc tgattcgtta ccaattatga caacttgacg gctacatcat 3540
tcactttttc ttcacaaccg gcacggaact cgctcgggct ggccccggtg catttttaa 3600 atacccgcga gaaatagagt tgatcgtcaa aaccaacatt gcgaccgacg gtggcgatag 3660
gcatccgggt ggtgctcaaa agcagcttcg cctggctgat acgttggtcc tcgcgccagc 3720
ttaagacgct aatccctaac tgctggcgga aaagatgtga cagacgcgac ggcgacaagc 3780
aaacatgctg tgcgacgctg gcgatatcaa aattgctgtc tgccaggtga tcgctgatgt 3840
actgacaagc ctcgcgtacc cgattatcca tcggtggatg gagcgactcg ttaatcgctt 3900
ccatgcgccg cagtaacaat tgctcaagca gatttatcgc cagcagctcc gaatagcgcc 3960
cttccccttg cccggcgtta atgatttgcc caaacaggtc gctgaaatgc ggctggtgcg 4020
cttcatccgg gcgaaagaac cccgtattgg caaatattga cggccagtta agccattcat 4080
gccagtaggc gcgcggacga aagtaaaccc actggtgata ccattcgcga gcctccggat 4140
gacgaccgta gtgatgaatc tctcctggcg ggaacagcaa aatatcaccc ggtcggcaaa 4200
caaattctcg tccctgattt ttcaccaccc cctgaccgcg aatggtgaga ttgagaatat 4260
aacctttcat tcccagcggt cggtcgataa aaaaatcgag ataaccgttg gcctcaatcg 4320
gcgttaaacc cgccaccaga tgggcattaa acgagtatcc cggcagcagg ggatcatttt 4380
gcgcttcagc catacttttc atactcccgc cattcagaga agaaaccaat tgtccatatt 4440
gcatcagaca ttgccgtcac tgcgtctttt actggctctt ctcgctaacc aaaccggtaa 4500
ccccgcttat taaaagcatt ctgtaacaaa gcgggaccaa agccatgaca aaaacgcgta 4560
acaaaagtgt ctataatcac ggcagaaaag tccacattga ttatttgcac ggcgtcacac 4620
tttgctatgc catagcattt ttatccataa gattagcgga tcctacctga cgctttttat 4680
cgcaactctc tactgtttct ccatacccgt tttttgggct aacaggagga attaac 4736

<210> SEQ ID NO 103
<211> LENGTH: 4694
<212> TYPE: DNA
<213> ORGANISM: Artificial sequence
<220> FEATURE:
<223> OTHER INFORMATION: pRF216

<400> SEQUENCE: 103

```
catggggcat caccatcacc accattgttt tttcaaagac gaactggaat tcggaggtgg     60
cggtgcatcc tcggaggatg tgattaaaga atttatgcgg tttaaagtac gtatggaagg    120
atcggtgaat ggccatgaat ttgagattga gggtgaaggc gaaggccgcc cgtacgaagg    180
aactcaaaca gcgaaattaa aagttacaaa aggaggtcct ctgccgtttg cctgggacat    240
cttgagcccg caattccagt acggttccaa agtgtatgta aaacaccctg cggatattcc    300
ggattataaa aaactgagtt ttcccgaggg gtttaaatgg gaacgggtga tgaattttga    360
ggatggtgga gttgtcaccg tgacccagga ctctagctta caagacggta gtttcatcta    420
caaagtaaaa tttatcggcg taaacttccc atcggacggc cccgtcatgc agaaaaagac    480
gatgggctgg gaagccagca ccgaacgttt gtacccacgg gacggcgttt tgaaagggga    540
aatccataag gcccttaaac tgaaagacgg tggtcactat ctcgtggagt ttaaatcgat    600
ttatatggct aaaaaaccag tacagcttcc gggttattat tacgttgact ccaaattgga    660
catcacatcg cataatgaag attacacgat tgttgaacag tacgagcgcg ccgagggccg    720
gcaccatctg tttctgtaaa agcttggctg ttttggcgga tgagagaaga ttttcagcct    780
gatacagatt aaatcagaac gcagaagcgg tctgataaaa cagaatttgc ctggcggcag    840
tagcgcggtg gtcccacctg accccatgcc gaactcagaa gtgaaacgcc gtagcgccga    900
tggtagtgtg gggtctcccc atgcgagagt agggaactgc caggcatcaa ataaaacgaa    960
aggctcagtc gaaagactgg gcctttcgtt ttatctgttg tttgtcggtg aacgctctcc   1020
tgagtaggac aaatccgccg ggagcggatt tgaacgttgc gaagcaacgg cccggagggt   1080
ggcgggcagg acgcccgcca taaactgcca ggcatcaaat taagcagaag gccatcctga   1140
cggatggcct ttttgcgttt ctacaaactc ttttgtttat ttttctaaat acattcaaat   1200
atgtatccgc tcatgagaca ataaccctga taaatgcttc aataatattg aaaaaggaag   1260
agtatgagta ttcaacattt ccgtgtcgcc cttattccct tttttgcggc attttgcctt   1320
cctgtttttg ctcacccaga aacgctggtg aaagtaaaag atgctgaaga tcagttgggt   1380
gcacgagtgg gttacatcga actggatctc aacagcggta agatccttga gagttttcgc   1440
cccgaagaac gttttccaat gatgagcact tttaaagttc tgctatgtgg cgcggtatta   1500
tcccgtgttg acgccgggca agagcaactc ggtcgccgca tacactattc tcagaatgac   1560
ttggttgagt actcaccagt cacagaaaag catcttacgg atggcatgac agtaagagaa   1620
ttatgcagtg ctgccataac catgagtgat aacactgcgg ccaacttact tctgacaacg   1680
atcggaggac cgaaggagct aaccgctttt ttgcacaaca tgggggatca tgtaactcgc   1740
cttgatcgtt gggaaccgga gctgaatgaa gccataccaa acgacgagcg tgacaccacg   1800
atgcctgtag caatggcaac aacgttgcgc aaactattaa ctggcgaact acttactcta   1860
gcttcccggc aacaattaat agactggatg gaggcggata aagttgcagg accacttctg   1920
cgctcggccc ttccggctgg ctggtttatt gctgataaat ctggagccgg tgagcgtggg   1980
tctcgcggta tcattgcagc actggggcca gatggtaagc cctcccgtat cgtagttatc   2040
tacacgacgg ggagtcaggc aactatggat gaacgaaata gacagatcgc tgagataggt   2100
gcctcactga ttaagcattg gtaactgtca gaccaagttt actcatatat actttagatt   2160
gatttaaaac ttcattttta atttaaaagg atctaggtga agatcctttt tgataatctc   2220
atgaccaaaa tcccttaacg tgagttttcg ttccactgag cgtcagaccc cgtagaaaag   2280
atcaaaggat cttcttgaga tccttttttt ctgcgcgtaa tctgctgctt gcaaacaaaa   2340
aaaccaccgc taccagcggt ggtttgtttg ccggatcaag agctaccaac tctttttccg   2400
```

```
aaggtaactg gcttcagcag agcgcagata ccaaatactg tccttctagt gtagccgtag   2460
ttaggccacc acttcaagaa ctctgtagca ccgcctacat acctcgctct gctaatcctg   2520
ttaccagtgg ctgctgccag tggcgataag tcgtgtctta ccgggttgga ctcaagacga   2580
tagttaccgg ataaggcgca gcggtcgggc tgaacggggg gttcgtgcac acagcccagc   2640
ttggagcgaa cgacctacac cgaactgaga tacctacagc gtgagctatg agaaagcgcc   2700
acgcttcccg aagggagaaa ggcggacagg tatccggtaa gcggcagggt cggaacagga   2760
gagcgcacga gggagcttcc agggggaaac gcctggtatc tttatagtcc tgtcgggttt   2820
cgccacctct gacttgagcg tcgatttttg tgatgctcgt caggggggcg gagcctatgg   2880
aaaaacgcca gcaacgcggc ctttttacgg ttcctggcct tttgctggcc ttttgctcac   2940
atgttctttc ctgcgttatc ccctgattct gtggataacc gtattaccgc ctttgagtga   3000
gctgataccg ctcgccgcag ccgaacgacc gagcgcagcg agtcagtgag cgaggaagcg   3060
gaagagcgcc tgatgcggta ttttctcctt acgcatctgt gcggtatttc acaccgcata   3120
tggtgcactc tcagtacaat ctgctctgat gccgcatagt taagccagta tacactccgc   3180
tatcgctacg tgactgggtc atggctgcgc cccgacaccc gccaacaccc gctgacgcgc   3240
cctgacgggc ttgtctgctc ccggcatccg cttacagaca agctgtgacc gtctccggga   3300
gctgcatgtg tcagaggttt tcaccgtcat caccgaaacg cgcgaggcag cagatcaatt   3360
cgcgcgcgaa ggcgaagcgg catgcataat gtgcctgtca aatggacgaa gcagggattc   3420
tgcaaaccct atgctactcc gtcaagccgt caattgtctg attcgttacc aattatgaca   3480
acttgacggc tacatcattc actttttctt cacaaccggc acggaactcg ctcgggctgg   3540
ccccggtgca tttttttaaat acccgcgaga aatagagttg atcgtcaaaa ccaacattgc   3600
gaccgacggt ggcgataggc atccgggtgg tgctcaaaag cagcttcgcc tggctgatac   3660
gttggtcctc gcgccagctt aagacgctaa tccctaactg ctggcggaaa agatgtgaca   3720
gacgcgacgg cgacaagcaa acatgctgtg cgacgctggc gatatcaaaa ttgctgtctg   3780
ccaggtgatc gctgatgtac tgacaagcct cgcgtacccg attatccatc ggtggatgga   3840
gcgactcgtt aatcgcttcc atgcgccgca gtaacaattg ctcaagcaga tttatcgcca   3900
gcagctccga atagcgccct tccccttgcc cggcgttaat gatttgccca aacaggtcgc   3960
tgaaatgcgg ctggtgcgct tcatccgggc gaaagaaccc cgtattggca aatattgacg   4020
gccagttaag ccattcatgc cagtaggcgc gcggacgaaa gtaaacccac tggtgatacc   4080
attcgcgagc ctccggatga cgaccgtagt gatgaatctc tcctggcggg aacagcaaaa   4140
tatcacccgg tcggcaaaca aattctcgtc cctgattttt caccaccccc tgaccgcgaa   4200
tggtgagatt gagaatataa cctttcattc ccagcggtcg gtcgataaaa aaatcgagat   4260
aaccgttggc ctcaatcggc gttaaacccg ccaccagatg ggcattaaac gagtatcccg   4320
gcagcagggg atcattttgc gcttcagcca tacttttcat actcccgcca ttcagagaag   4380
aaaccaattg tccatattgc atcagacatt gccgtcactg cgtcttttac tggctcttct   4440
cgctaaccaa accggtaacc ccgcttatta aaagcattct gtaacaaagc gggaccaaag   4500
ccatgacaaa aacgcgtaac aaaagtgtct ataatcacgg cagaaaagtc cacattgatt   4560
atttgcacgg cgtcacactt tgctatgcca tagcattttt atccataaga ttagcggatc   4620
ctacctgacg ctttttatcg caactctcta ctgtttctcc atacccgttt tttgggctaa   4680
caggaggaat taac                                                     4694
```

<210> SEQ ID NO 104
<211> LENGTH: 23
<212> TYPE: DNA
<213> ORGANISM: Artificial sequence
<220> FEATURE:
<223> OTHER INFORMATION: oligo 36

<400> SEQUENCE: 104
ccataagatt agcggatcct acc 23

<210> SEQ ID NO 105
<211> LENGTH: 331
<212> TYPE: DNA
<213> ORGANISM: Artificial sequence
<220> FEATURE:
<223> OTHER INFORMATION: His-Zebra PCR

<400> SEQUENCE: 105
ccataagatt agcggatcct acctgacgct ttttatcgca actctctact gtttctccat 60
acccgttttt tgggctaaca ggaggaatta accatggggc atcaccacca tcaccacgaa 120
tgcgactcag aactggaaat caaacgctat aaacgtgtgc gtgtggcatc ccgtaaatgt 180
cgcgcaaagt ttaaacagct gctgcaacat tatcgtgaag tagcggctgc gaaaagctcc 240
gaaaacgacc gtttacgcct cctcctgaag caaatgtgcg aattcgacaa gaaatactcc 300
atcggcctgg acattggaac caactctgtc g 331

<210> SEQ ID NO 106
<211> LENGTH: 232
<212> TYPE: DNA
<213> ORGANISM: Artificial sequence
<220> FEATURE:
<223> OTHER INFORMATION: His-tp10 PCR

<400> SEQUENCE: 106
ccataagatt agcggatcct acctgacgct ttttatcgca actctctact gtttctccat 60
acccgttttt tgggctaaca ggaggaatta accatggggc atcaccacca tcaccacgcg 120
ggttacctgc tgggcaagat taatcttaaa gcctgcgccg cgtgtgctaa gaaaattttg 180
gaattcgaca agaaatactc catcggcctg gacattggaa ccaactctgt cg 232

<210> SEQ ID NO 107
<211> LENGTH: 223
<212> TYPE: DNA
<213> ORGANISM: artificial sequence
<220> FEATURE:
<223> OTHER INFORMATION: His-pVEC PCR

<400> SEQUENCE: 107
ccataagatt agcggatcct acctgacgct ttttatcgca actctctact gtttctccat 60
acccgttttt tgggctaaca ggaggaatta accatggggc atcaccacca tcaccactta 120
ttgattatct tgcgtcgtcg catccgcaaa caggcgcacg cacatagcaa ggaattcgac 180
aagaaatact ccatcggcct ggacattgga accaactctg tcg 223

<210> SEQ ID NO 108
<211> LENGTH: 8294
<212> TYPE: DNA
<213> ORGANISM: Artificial sequence
<220> FEATURE:
<223> OTHER INFORMATION: pRF144

<400> SEQUENCE: 108

-continued

```
ccatggggca tcaccaccat caccacgaat gcgactcaga actggaaatc aaacgctata      60
aacgtgtgcg tgtggcatcc cgtaaatgtc gcgcaaagtt taaacagctg ctgcaacatt     120
atcgtgaagt agcggctgcg aaaagctccg aaaacgaccg tttacgcctc ctcctgaagc     180
aaatgtgcga attcgacaag aaatactcca tcggcctgga cattggaacc aactctgtcg     240
gctgggctgt catcaccgac gagtacaagg tgccctccaa gaaattcaag gtcctcggaa     300
acaccgatcg acactccatc aagaaaaacc tcattggtgc cctgttgttc gattctggcg     360
agactgccga agctaccaga ctcaagcgaa ctgctcggcg acgttacacc cgacggaaga     420
accgaatctg ctacctgcag gagatctttt ccaacgagat ggccaaggtg gacgattcgt     480
tctttcatcg actggaggaa tccttcctcg tcgaggaaga caagaaacac gagcgtcatc     540
ccatctttgg caacattgtg gacgaggttg cttaccacga gaagtatcct accatctacc     600
acctgcgaaa gaaactcgtc gattccaccg acaaggcgga tctcagactt atctacctcg     660
ctctggcaca catgatcaag tttcgaggtc atttcctcat cgagggcgat ctcaatcccg     720
acaacagcga tgtggacaag ctgttcattc agctcgttca gacctacaac cagctgttcg     780
aggaaaaccc catcaatgcc tccggagtcg atgcaaaggc catcttgtct gctcgactct     840
cgaagagcag acgactggag aacctcattg cccaacttcc tggcgagaaa aagaacggac     900
tgtttggcaa cctcattgcc ctttctcttg gtctcacacc caacttcaag tccaacttcg     960
atctggcgga ggacgccaag ctccagctgt ccaaggacac ctacgacgat gacctcgaca    1020
acctgcttgc acagattggc gatcagtacg ccgacctgtt tctcgctgcc aagaaccttt    1080
cggatgctat tctcttgtct gacattctgc gagtcaacac cgagatcaca aaggctcccc    1140
tttctgcctc catgatcaag cgatacgacg agcaccatca ggatctcaca ctgctcaagg    1200
ctcttgtccg acagcaactg cccgagaagt acaaggagat ctttttcgat cagtcgaaga    1260
acggctacgc tggatacatc gacggcggag cctctcagga agagttctac aagttcatca    1320
agccaattct cgagaagatg gacggaaccg aggaactgct tgtcaagctc aatcgagagg    1380
atctgcttcg gaagcaacga accttcgaca acggcagcat tcctcatcag atccacctcg    1440
gtgagctgca cgccattctt cgacgtcagg aagacttcta cccctttctc aaggacaacc    1500
gagagaagat cgagaagatt cttacctttc gaatcccccta ctatgttggt cctcttgcca    1560
gaggaaactc tcgatttgct tggatgactc gaaagtccga ggaaaccatc actccctgga    1620
acttcgagga agtcgtggac aagggtgcct ctgcacagtc cttcatcgag cgaatgacca    1680
acttcgacaa gaatctgccc aacgagaagg ttcttcccaa gcattcgctg ctctacgagt    1740
actttacagt ctacaacgaa ctcaccaaag tcaagtacgt taccgaggga atgcgaaagc    1800
ctgccttctt gtctggcgaa cagaagaaag ccattgtcga tctcctgttc aagaccaacc    1860
gaaaggtcac tgttaagcag ctcaaggagg actacttcaa gaaaatcgag tgtttcgaca    1920
gcgtcgagat ttccggagtt gaggaccgat tcaacgcctc tttgggcacc tatcacgatc    1980
tgctcaagat tatcaaggac aaggattttc tcgacaacga ggaaaacgag gacattctgg    2040
aggacatcgt gctcactctt accctgttcg aagatcggga gatgatcgag gaacgactca    2100
agacatacgc tcacctgttc gacgacaagg tcatgaaaca actcaagcga cgtagataca    2160
ccggctgggg aagactttcg cgaaagctca tcaacggcat cagagacaag cagtccggaa    2220
agaccattct ggactttctc aagtccgatg gctttgccaa ccgaaacttc atgcagctca    2280
ttcacgacga ttctcttacc ttcaaggagg acatccagaa ggcacaagtg tccggtcagg    2340
```

```
gcgacagctt gcacgaacat attgccaacc tggctggttc gccagccatc aagaaaggca   2400
ttctccagac tgtcaaggtt gtcgacgagc tggtgaaggt catgggacgt cacaagcccg   2460
agaacattgt gatcgagatg gccagagaga accagacaac tcaaaagggt cagaaaaact   2520
cgcgagagcg gatgaagcga atcgaggaag gcatcaagga gctgggatcc cagattctca   2580
aggagcatcc cgtcgagaac actcaactgc agaacgagaa gctgtatctc tactatctgc   2640
agaatggtcg agacatgtac gtggatcagg aactggacat caatcgtctc agcgactacg   2700
atgtggacca cattgtccct caatcctttc tcaaggacga ttctatcgac aacaaggtcc   2760
ttacacgatc cgacaagaac agaggcaagt cggacaacgt tcccagcgaa gaggtggtca   2820
aaaagatgaa gaactactgg cgacagctgc tcaacgccaa gctcattacc cagcgaaagt   2880
tcgacaatct taccaaggcc gagcgaggcg gtctgtccga gctcgacaag gctggcttca   2940
tcaagcgtca actcgtcgag accagacaga tcacaaagca cgtcgcacag attctcgatt   3000
ctcggatgaa caccaagtac gacgagaacg acaagctcat ccgagaggtc aaggtgatta   3060
ctctcaagtc caaactggtc tccgatttcc gaaaggactt tcagttctac aaggtgcgag   3120
agatcaacaa ttaccaccat gcccacgatg cttacctcaa cgccgtcgtt ggcactgcgc   3180
tcatcaagaa ataccccaag ctcgaaagcg agttcgttta cggcgattac aaggtctacg   3240
acgttcgaaa gatgattgcc aagtccgaac aggagattgg caaggctact gccaagtact   3300
tcttttactc caacatcatg aactttttca agaccgagat caccttggcc aacggagaga   3360
ttcgaaagag accacttatc gagaccaacg gcgaaactgg agagatcgtg tgggacaagg   3420
gtcgagactt tgcaaccgtg cgaaaggttc tgtcgatgcc tcaggtcaac atcgtcaaga   3480
aaaccgaggt tcagactggc ggattctcca aggagtcgat tctgcccaag cgaaactccg   3540
acaagctcat cgctcgaaag aaagactggg atcccaagaa atacggtggc ttcgattctc   3600
ctaccgtcgc ctattccgtg cttgtcgttg cgaaggtcga gaagggcaag tccaaaaagc   3660
tcaagtccgt caaggagctg ctcggaatta ccatcatgga gcgatcgagc ttcgagaaga   3720
atcccatcga cttcttggaa gccaagggtt acaaggaggt caagaaagac ctcattatca   3780
agctgcccaa gtactctctg ttcgaactgg agaacggtcg aaagcgtatg ctcgcctccg   3840
ctggcgagct gcagaaggga aacgagcttg ccttgccttc gaagtacgtc aactttctct   3900
atctggcttc tcactacgag aagctcaagg gttctcccga ggacaacgaa cagaagcaac   3960
tcttcgttga gcagcacaaa cattacctcg acgagattat cgagcagatt tccgagtttt   4020
cgaagcgagt catcctggct gatgccaact tggacaaggt gctctctgcc tacaacaagc   4080
atcgggacaa acccattcga gaacaggcgg agaacatcat tcacctgttt actcttacca   4140
acctgggtgc tcctgcagct ttcaagtact tcgataccac tatcgaccga aagcggtaca   4200
catccaccaa ggaggttctc gatgccaccc tgattcacca gtccatcact ggcctgtacg   4260
agacccgaat cgacctgtct cagcttggtg gcgactccag agccgatccc aagaaaaagc   4320
gaaaggtcta agcggccgct aagcttggct gttttggcgg atgagagaag attttcagcc   4380
tgatacagat taaatcagaa cgcagaagcg gtctgataaa acagaatttg cctggcggca   4440
gtagcgcggt ggtcccacct gaccccatgc cgaactcaga agtgaaacgc cgtagcgccg   4500
atggtagtgt ggggtctccc catgcgagag tagggaactg ccaggcatca aataaaacga   4560
aaggctcagt cgaaagactg ggcctttcgt tttatctgtt gtttgtcggt gaacgctctc   4620
ctgagtagga caaatccgcc gggagcggat ttgaacgttg cgaagcaacg gcccggaggg   4680
tggcgggcag gacgcccgcc ataaactgcc aggcatcaaa ttaagcagaa ggccatcctg   4740
```

acggatggcc tttttgcgtt tctacaaact cttttgttta tttttctaaa tacattcaaa 4800
tatgtatccg ctcatgagac aataaccctg ataaatgctt caataatatt gaaaaaggaa 4860
gagtatgagt attcaacatt tccgtgtcgc ccttattccc ttttttgcgg cattttgcct 4920
tcctgttttt gctcacccag aaacgctggt gaaagtaaaa gatgctgaag atcagttggg 4980
tgcacgagtg ggttacatcg aactggatct caacagcggt aagatccttg agagttttcg 5040
ccccgaagaa cgttttccaa tgatgagcac ttttaaagtt ctgctatgtg gcgcggtatt 5100
atcccgtgtt gacgccgggc aagagcaact cggtcgccgc atacactatt ctcagaatga 5160
cttggttgag tactcaccag tcacagaaaa gcatcttacg gatggcatga cagtaagaga 5220
attatgcagt gctgccataa ccatgagtga taacactgcg gccaacttac ttctgacaac 5280
gatcggagga ccgaaggagc taaccgcttt tttgcacaac atgggggatc atgtaactcg 5340
ccttgatcgt tgggaaccgg agctgaatga agccatacca aacgacgagc gtgacaccac 5400
gatgcctgta gcaatggcaa caacgttgcg caaactatta actggcgaac tacttactct 5460
agcttcccgg caacaattaa tagactggat ggaggcggat aaagttgcag gaccacttct 5520
gcgctcggcc cttccggctg gctggtttat tgctgataaa tctggagccg gtgagcgtgg 5580
gtctcgcggt atcattgcag cactggggcc agatggtaag ccctcccgta tcgtagttat 5640
ctacacgacg gggagtcagg caactatgga tgaacgaaat agacagatcg ctgagatagg 5700
tgcctcactg attaagcatt ggtaactgtc agaccaagtt tactcatata tactttagat 5760
tgatttaaaa cttcattttt aatttaaaag gatctaggtg aagatccttt ttgataatct 5820
catgaccaaa atcccttaac gtgagttttc gttccactga gcgtcagacc ccgtagaaaa 5880
gatcaaagga tcttcttgag atcctttttt tctgcgcgta atctgctgct tgcaaacaaa 5940
aaaaccaccg ctaccagcgg tggtttgttt gccggatcaa gagctaccaa ctctttttcc 6000
gaaggtaact ggcttcagca gagcgcagat accaaatact gtccttctag tgtagccgta 6060
gttaggccac cacttcaaga actctgtagc accgcctaca tacctcgctc tgctaatcct 6120
gttaccagtg gctgctgcca gtggcgataa gtcgtgtctt accgggttgg actcaagacg 6180
atagttaccg gataaggcgc agcggtcggg ctgaacgggg ggttcgtgca cacagcccag 6240
cttggagcga acgacctaca ccgaactgag atacctacag cgtgagctat gagaaagcgc 6300
cacgcttccc gaagggagaa aggcggacag gtatccggta agcggcaggg tcggaacagg 6360
agagcgcacg agggagcttc cagggggaaa cgcctggtat ctttatagtc ctgtcgggtt 6420
tcgccacctc tgacttgagc gtcgattttt gtgatgctcg tcaggggggc ggagcctatg 6480
gaaaaacgcc agcaacgcgg cctttttacg gttcctggcc ttttgctggc cttttgctca 6540
catgttcttt cctgcgttat cccctgattc tgtggataac cgtattaccg cctttgagtg 6600
agctgatacc gctcgccgca gccgaacgac cgagcgcagc gagtcagtga gcgaggaagc 6660
ggaagagcgc ctgatgcggt attttctcct tacgcatctg tgcggtattt cacaccgcat 6720
atggtgcact ctcagtacaa tctgctctga tgccgcatag ttaagccagt atacactccg 6780
ctatcgctac gtgactgggt catggctgcg ccccgacacc cgccaacacc cgctgacgcg 6840
ccctgacggg cttgtctgct cccggcatcc gcttacagac aagctgtgac cgtctccggg 6900
agctgcatgt gtcagaggtt ttcaccgtca tcaccgaaac gcgcgaggca gcagatcaat 6960
tcgcgcgcga aggcgaagcg gcatgcataa tgtgcctgtc aaatggacga agcagggatt 7020
ctgcaaaccc tatgctactc cgtcaagccg tcaattgtct gattcgttac caattatgac 7080
aacttgacgg ctacatcatt cacttttttct tcacaaccgg cacggaactc gctcgggctg 7140
gccccggtgc attttttaaa tacccgcgag aaatagagtt gatcgtcaaa accaacattg 7200
cgaccgacgg tggcgatagg catccgggtg gtgctcaaaa gcagcttcgc ctggctgata 7260
cgttggtcct cgcgccagct taagacgcta atccctaact gctggcggaa aagatgtgac 7320
agacgcgacg gcgacaagca aacatgctgt gcgacgctgg cgatatcaaa attgctgtct 7380
gccaggtgat cgctgatgta ctgacaagcc tcgcgtaccc gattatccat cggtggatgg 7440
agcgactcgt taatcgcttc catgcgccgc agtaacaatt gctcaagcag atttatcgcc 7500
agcagctccg aatagcgccc ttccccttgc ccggcgttaa tgatttgccc aaacaggtcg 7560
ctgaaatgcg gctggtgcgc ttcatccggg cgaaagaacc ccgtattggc aaatattgac 7620
ggccagttaa gccattcatg ccagtaggcg cgcggacgaa agtaaaccca ctggtgatac 7680
cattcgcgag cctccggatg acgaccgtag tgatgaatct ctcctggcgg gaacagcaaa 7740
atatcacccg gtcggcaaac aaattctcgt ccctgatttt tcaccacccc ctgaccgcga 7800
atggtgagat tgagaatata acctttcatt cccagcggtc ggtcgataaa aaaatcgaga 7860
taaccgttgg cctcaatcgg cgttaaaccc gccaccagat gggcattaaa cgagtatccc 7920
ggcagcaggg gatcattttg cgcttcagcc atacttttca tactcccgcc attcagagaa 7980
gaaaccaatt gtccatattg catcagacat tgccgtcact gcgtctttta ctggctcttc 8040
tcgctaacca aaccggtaac cccgcttatt aaaagcattc tgtaacaaag cgggaccaaa 8100
gccatgacaa aaacgcgtaa caaaagtgtc tataatcacg gcagaaaagt ccacattgat 8160
tatttgcacg gcgtcacact ttgctatgcc atagcatttt tatccataag attagcggat 8220
cctacctgac gctttttatc gcaactctct actgtttctc catacccgtt ttttgggcta 8280
acaggaggaa ttaa 8294

<210> SEQ ID NO 109
<211> LENGTH: 8195
<212> TYPE: DNA
<213> ORGANISM: Artificial sequence
<220> FEATURE:
<223> OTHER INFORMATION: pRF162

<400> SEQUENCE: 109
aattcgacaa gaaatactcc atcggcctgg acattggaac caactctgtc ggctgggctg 60
tcatcaccga cgagtacaag gtgccctcca agaaattcaa ggtcctcgga aacaccgatc 120
gacactccat caagaaaaac ctcattggtg ccctgttgtt cgattctggc gagactgccg 180
aagctaccag actcaagcga actgctcggc gacgttacac ccgacggaag aaccgaatct 240
gctacctgca ggagatcttt tccaacgaga tggccaaggt ggacgattcg ttctttcatc 300
gactggagga atccttcctc gtcgaggaag acaagaaaca cgagcgtcat cccatctttg 360
gcaacattgt ggacgaggtt gcttaccacg agaagtatcc taccatctac cacctgcgaa 420
agaaactcgt cgattccacc gacaaggcgg atctcagact tatctacctc gctctggcac 480
acatgatcaa gtttcgaggt catttcctca tcgagggcga tctcaatccc gacaacagcg 540
atgtggacaa gctgttcatt cagctcgttc agacctacaa ccagctgttc gaggaaaacc 600
ccatcaatgc ctccggagtc gatgcaaagg ccatcttgtc tgctcgactc tcgaagagca 660
gacgactgga gaacctcatt gcccaacttc ctggcgagaa aaagaacgga ctgtttggca 720
acctcattgc cctttctctt ggtctcacac ccaacttcaa gtccaacttc gatctggcgg 780
aggacgccaa gctccagctg tccaaggaca cctacgacga tgacctcgac aacctgcttg 840

```
cacagattgg cgatcagtac gccgacctgt ttctcgctgc caagaacctt tcggatgcta    900
ttctcttgtc tgacattctg cgagtcaaca ccgagatcac aaaggctccc ctttctgcct    960
ccatgatcaa gcgatacgac gagcaccatc aggatctcac actgctcaag gctcttgtcc   1020
gacagcaact gcccgagaag tacaaggaga tctttttcga tcagtcgaag aacggctacg   1080
ctggatacat cgacggcgga gcctctcagg aagagttcta caagttcatc aagccaattc   1140
tcgagaagat ggacggaacc gaggaactgc ttgtcaagct caatcgagag gatctgcttc   1200
ggaagcaacg aaccttcgac aacggcagca ttcctcatca gatccacctc ggtgagctgc   1260
acgccattct tcgacgtcag gaagacttct accccttttct caaggacaac cgagagaaga   1320
tcgagaagat tcttaccttt cgaatcccct actatgttgg tcctcttgcc agaggaaact   1380
ctcgatttgc ttggatgact cgaaagtccg aggaaaccat cactccctgg aacttcgagg   1440
aagtcgtgga caagggtgcc tctgcacagt ccttcatcga gcgaatgacc aacttcgaca   1500
agaatctgcc caacgagaag gttcttccca agcattcgct gctctacgag tactttacag   1560
tctacaacga actcaccaaa gtcaagtacg ttaccgaggg aatgcgaaag cctgccttct   1620
tgtctggcga acagaagaaa gccattgtcg atctcctgtt caagaccaac cgaaaggtca   1680
ctgttaagca gctcaaggag gactacttca agaaaatcga gtgtttcgac agcgtcgaga   1740
tttccggagt tgaggaccga ttcaacgcct ctttgggcac ctatcacgat ctgctcaaga   1800
ttatcaagga caaggatttt ctcgacaacg aggaaaacga ggacattctg gaggacatcg   1860
tgctcactct taccctgttc gaagatcggg agatgatcga ggaacgactc aagacatacg   1920
ctcacctgtt cgacgacaag gtcatgaaac aactcaagcg acgtagatac accggctggg   1980
gaagactttc gcgaaagctc atcaacggca tcagagacaa gcagtccgga aagaccattc   2040
tggactttct caagtccgat ggctttgcca accgaaactt catgcagctc attcacgacg   2100
attctcttac cttcaaggag gacatccaga aggcacaagt gtccggtcag ggcgacagct   2160
tgcacgaaca tattgccaac ctggctggtt cgccagccat caagaaaggc attctccaga   2220
ctgtcaaggt tgtcgacgag ctggtgaagg tcatgggacg tcacaagccc gagaacattg   2280
tgatcgagat ggccagagag aaccagacaa ctcaaaaggg tcagaaaaac tcgcgagagc   2340
ggatgaagcg aatcgaggaa ggcatcaagg agctgggatc ccagattctc aaggagcatc   2400
ccgtcgagaa cactcaactg cagaacgaga agctgtatct ctactatctg cagaatggtc   2460
gagacatgta cgtggatcag gaactggaca tcaatcgtct cagcgactac gatgtggacc   2520
acattgtccc tcaatccttt ctcaaggacg attctatcga caacaaggtc cttacacgat   2580
ccgacaagaa cagaggcaag tcggacaacg ttcccagcga agaggtggtc aaaaagatga   2640
agaactactg gcgacagctg ctcaacgcca agctcattac ccagcgaaag ttcgacaatc   2700
ttaccaaggc cgagcgaggc ggtctgtccg agctcgacaa ggctggcttc atcaagcgtc   2760
aactcgtcga gaccagacag atcacaaagc acgtcgcaca gattctcgat tctcggatga   2820
acaccaagta cgacgagaac gacaagctca tccgagaggt caaggtgatt actctcaagt   2880
ccaaactggt ctccgatttc cgaaaggact ttcagttcta caaggtgcga gagatcaaca   2940
attaccacca tgcccacgat gcttacctca acgccgtcgt tggcactgcg ctcatcaaga   3000
aataccccaa gctcgaaagc gagttcgttt acggcgatta caaggtctac gacgttcgaa   3060
agatgattgc caagtccgaa caggagattg gcaaggctac tgccaagtac ttcttttact   3120
ccaacatcat gaactttttc aagaccgaga tcaccttggc caacggagag attcgaaaga   3180
```

gaccacttat cgagaccaac ggcgaaactg gagagatcgt gtgggacaag ggtcgagact 3240
ttgcaaccgt gcgaaaggtt ctgtcgatgc ctcaggtcaa catcgtcaag aaaaccgagg 3300
ttcagactgg cggattctcc aaggagtcga ttctgcccaa gcgaaactcc gacaagctca 3360
tcgctcgaaa gaaagactgg gatcccaaga aatacggtgg cttcgattct cctaccgtcg 3420
cctattccgt gcttgtcgtt gcgaaggtcg agaagggcaa gtccaaaaag ctcaagtccg 3480
tcaaggagct gctcggaatt accatcatgg agcgatcgag cttcgagaag aatcccatcg 3540
acttcttgga agccaagggt tacaaggagg tcaagaaaga cctcattatc aagctgccca 3600
agtactctct gttcgaactg gagaacggtc gaaagcgtat gctcgcctcc gctggcgagc 3660
tgcagaaggg aaacgagctt gccttgcctt cgaagtacgt caactttctc tatctggctt 3720
ctcactacga gaagctcaag ggttctcccg aggacaacga acagaagcaa ctcttcgttg 3780
agcagcacaa acattacctc gacgagatta tcgagcagat ttccgagttt tcgaagcgag 3840
tcatcctggc tgatgccaac ttggacaagg tgctctctgc ctacaacaag catcgggaca 3900
aacccattcg agaacaggcg gagaacatca ttcacctgtt tactcttacc aacctgggtg 3960
ctcctgcagc tttcaagtac ttcgatacca ctatcgaccg aaagcggtac acatccacca 4020
aggaggttct cgatgccacc ctgattcacc agtccatcac tggcctgtac gagacccgaa 4080
tcgacctgtc tcagcttggt ggcgactcca gagccgatcc caagaaaaag cgaaaggtct 4140
aagcggccgc taagcttggc tgttttggcg gatgagagaa gattttcagc ctgatacaga 4200
ttaaatcaga acgcagaagc ggtctgataa aacagaattt gcctggcggc agtagcgcgg 4260
tggtcccacc tgaccccatg ccgaactcag aagtgaaacg ccgtagcgcc gatggtagtg 4320
tggggtctcc ccatgcgaga gtagggaact gccaggcatc aaataaaacg aaaggctcag 4380
tcgaaagact gggcctttcg ttttatctgt tgtttgtcgg tgaacgctct cctgagtagg 4440
acaaatccgc cgggagcgga tttgaacgtt gcgaagcaac ggcccggagg gtggcgggca 4500
ggacgcccgc cataaactgc caggcatcaa attaagcaga aggccatcct gacggatggc 4560
ctttttgcgt ttctacaaac tcttttgttt atttttctaa atacattcaa atatgtatcc 4620
gctcatgaga caataaccct gataaatgct tcaataatat tgaaaaagga agagtatgag 4680
tattcaacat ttccgtgtcg cccttattcc cttttttgcg gcattttgcc ttcctgtttt 4740
tgctcaccca gaaacgctgg tgaaagtaaa agatgctgaa gatcagttgg gtgcacgagt 4800
gggttacatc gaactggatc tcaacagcgg taagatcctt gagagttttc gccccgaaga 4860
acgttttcca atgatgagca cttttaaagt tctgctatgt ggcgcggtat tatcccgtgt 4920
tgacgccggg caagagcaac tcggtcgccg catacactat tctcagaatg acttggttga 4980
gtactcacca gtcacagaaa agcatcttac ggatggcatg acagtaagag aattatgcag 5040
tgctgccata accatgagtg ataacactgc ggccaactta cttctgacaa cgatcggagg 5100
accgaaggag ctaaccgctt ttttgcacaa catgggggat catgtaactc gccttgatcg 5160
ttgggaaccg gagctgaatg aagccatacc aaacgacgag cgtgacacca cgatgcctgt 5220
agcaatggca acaacgttgc gcaaactatt aactggcgaa ctacttactc tagcttcccg 5280
gcaacaatta atagactgga tggaggcgga taaagttgca ggaccacttc tgcgctcggc 5340
ccttccggct ggctggttta ttgctgataa atctggagcc ggtgagcgtg ggtctcgcgg 5400
tatcattgca gcactggggc cagatggtaa gccctcccgt atcgtagtta tctacacgac 5460
ggggagtcag gcaactatgg atgaacgaaa tagacagatc gctgagatag gtgcctcact 5520
gattaagcat tggtaactgt cagaccaagt ttactcatat atactttaga ttgatttaaa 5580

-continued

```
acttcatttt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga gatccttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
ccacttcaag aactctgtag caccgcctac atacctcgct ctgctaatcc tgttaccagt   5940
ggctgctgcc agtggcgata agtcgtgtct taccgggttg gactcaagac gatagttacc   6000
ggataaggcg cagcggtcgg gctgaacggg gggttcgtgc acacagccca gcttggagcg   6060
aacgacctac accgaactga gatacctaca gcgtgagcta tgagaaagcg ccacgcttcc   6120
cgaagggaga aaggcggaca ggtatccggt aagcggcagg gtcggaacag gagagcgcac   6180
gagggagctt ccagggggaa acgcctggta tctttatagt cctgtcgggt ttcgccacct   6240
ctgacttgag cgtcgatttt tgtgatgctc gtcagggggg cggagcctat ggaaaaacgc   6300
cagcaacgcg gcctttttac ggttcctggc cttttgctgg ccttttgctc acatgttctt   6360
tcctgcgtta tcccctgatt ctgtggataa ccgtattacc gcctttgagt gagctgatac   6420
cgctcgccgc agccgaacga ccgagcgcag cgagtcagtg agcgaggaag cggaagagcg   6480
cctgatgcgg tattttctcc ttacgcatct gtgcggtatt tcacaccgca tatggtgcac   6540
tctcagtaca atctgctctg atgccgcata gttaagccag tatacactcc gctatcgcta   6600
cgtgactggg tcatggctgc gccccgacac ccgccaacac ccgctgacgc gccctgacgg   6660
gcttgtctgc tcccggcatc cgcttacaga caagctgtga ccgtctccgg gagctgcatg   6720
tgtcagaggt tttcaccgtc atcaccgaaa cgcgcgaggc agcagatcaa ttcgcgcgcg   6780
aaggcgaagc ggcatgcata atgtgcctgt caaatggacg aagcagggat tctgcaaacc   6840
ctatgctact ccgtcaagcc gtcaattgtc tgattcgtta ccaattatga caacttgacg   6900
gctacatcat tcactttttc ttcacaaccg gcacggaact cgctcgggct ggccccggtg   6960
catttttaa atacccgcga gaaatagagt tgatcgtcaa aaccaacatt gcgaccgacg   7020
gtggcgatag gcatccgggt ggtgctcaaa agcagcttcg cctggctgat acgttggtcc   7080
tcgcgccagc ttaagacgct aatccctaac tgctggcgga aaagatgtga cagacgcgac   7140
ggcgacaagc aaacatgctg tgcgacgctg gcgatatcaa aattgctgtc tgccaggtga   7200
tcgctgatgt actgacaagc ctcgcgtacc cgattatcca tcggtggatg gagcgactcg   7260
ttaatcgctt ccatgcgccg cagtaacaat tgctcaagca gatttatcgc cagcagctcc   7320
gaatagcgcc cttccccttg cccggcgtta atgatttgcc caaacaggtc gctgaaatgc   7380
ggctggtgcg cttcatccgg gcgaaagaac cccgtattgg caaatattga cggccagtta   7440
agccattcat gccagtaggc gcgcggacga aagtaaaccc actggtgata ccattcgcga   7500
gcctccggat gacgaccgta gtgatgaatc tctcctggcg ggaacagcaa aatatcaccc   7560
ggtcggcaaa caaattctcg tccctgattt ttcaccaccc cctgaccgcg aatggtgaga   7620
ttgagaatat aacctttcat tcccagcggt cggtcgataa aaaaatcgag ataaccgttg   7680
gcctcaatcg gcgttaaacc cgccaccaga tgggcattaa acgagtatcc cggcagcagg   7740
ggatcatttt gcgcttcagc catacttttc atactcccgc cattcagaga agaaaccaat   7800
tgtccatatt gcatcagaca ttgccgtcac tgcgtctttt actggctctt ctcgctaacc   7860
aaaccggtaa ccccgcttat taaaagcatt ctgtaacaaa gcgggaccaa agccatgaca   7920
```

aaaacgcgta acaaaagtgt ctataatcac ggcagaaaag tccacattga ttatttgcac 7980
ggcgtcacac tttgctatgc catagcattt ttatccataa gattagcgga tcctacctga 8040
cgctttttat cgcaactctc tactgtttct ccatacccgt tttttgggct aacaggagga 8100
attaaccatg ggcatcacc accatcacca cgcgggttac ctgctgggca agattaatct 8160
taaagcctgc gccgcgtgtg ctaagaaaat tttgg 8195

<210> SEQ ID NO 110
<211> LENGTH: 8186
<212> TYPE: DNA
<213> ORGANISM: Artificial Sequence
<220> FEATURE:
<223> OTHER INFORMATION: pRF146

<400> SEQUENCE: 110
aattcgacaa gaaatactcc atcggcctgg acattggaac caactctgtc ggctgggctg 60
tcatcaccga cgagtacaag gtgccctcca agaaattcaa ggtcctcgga aacaccgatc 120
gacactccat caagaaaaac ctcattggtg ccctgttgtt cgattctggc gagactgccg 180
aagctaccag actcaagcga actgctcggc gacgttacac ccgacggaag aaccgaatct 240
gctacctgca ggagatcttt tccaacgaga tggccaaggt ggacgattcg ttctttcatc 300
gactggagga atccttcctc gtcgaggaag acaagaaaca cgagcgtcat cccatctttg 360
gcaacattgt ggacgaggtt gcttaccacg agaagtatcc taccatctac cacctgcgaa 420
agaaactcgt cgattccacc gacaaggcgg atctcagact tatctacctc gctctggcac 480
acatgatcaa gtttcgaggt catttcctca tcgagggcga tctcaatccc gacaacagcg 540
atgtggacaa gctgttcatt cagctcgttc agacctacaa ccagctgttc gaggaaaacc 600
ccatcaatgc ctccggagtc gatgcaaagg ccatcttgtc tgctcgactc tcgaagagca 660
gacgactgga gaacctcatt gcccaacttc ctggcgagaa aaagaacgga ctgtttggca 720
acctcattgc cctttctctt ggtctcacac ccaacttcaa gtccaacttc gatctggcgg 780
aggacgccaa gctccagctg tccaaggaca cctacgacga tgacctcgac aacctgcttg 840
cacagattgg cgatcagtac gccgacctgt ttctcgctgc caagaacctt tcggatgcta 900
ttctcttgtc tgacattctg cgagtcaaca ccgagatcac aaaggctccc ctttctgcct 960
ccatgatcaa gcgatacgac gagcaccatc aggatctcac actgctcaag gctcttgtcc 1020
gacagcaact gcccgagaag tacaaggaga tctttttcga tcagtcgaag aacggctacg 1080
ctggatacat cgacggcgga gcctctcagg aagagttcta caagttcatc aagccaattc 1140
tcgagaagat ggacggaacc gaggaactgc ttgtcaagct caatcgagag gatctgcttc 1200
ggaagcaacg aaccttcgac aacggcagca ttcctcatca gatccacctc ggtgagctgc 1260
acgccattct tcgacgtcag gaagacttct acccctttct caaggacaac cgagagaaga 1320
tcgagaagat tcttaccttt cgaatcccct actatgttgg tcctcttgcc agaggaaact 1380
ctcgatttgc ttggatgact cgaaagtccg aggaaaccat cactccctgg aacttcgagg 1440
aagtcgtgga caagggtgcc tctgcacagt ccttcatcga gcgaatgacc aacttcgaca 1500
agaatctgcc caacgagaag gttcttccca agcattcgct gctctacgag tactttacag 1560
tctacaacga actcaccaaa gtcaagtacg ttaccgaggg aatgcgaaag cctgccttct 1620
tgtctggcga acagaagaaa gccattgtcg atctcctgtt caagaccaac cgaaaggtca 1680
ctgttaagca gctcaaggag gactacttca agaaaatcga gtgtttcgac agcgtcgaga 1740
tttccggagt tgaggaccga ttcaacgcct ctttgggcac ctatcacgat ctgctcaaga 1800

-continued

```
ttatcaagga caaggatttt ctcgacaacg aggaaaacga ggacattctg gaggacatcg   1860
tgctcactct taccctgttc gaagatcggg agatgatcga ggaacgactc aagacatacg   1920
ctcacctgtt cgacgacaag gtcatgaaac aactcaagcg acgtagatac accggctggg   1980
gaagactttc gcgaaagctc atcaacggca tcagagacaa gcagtccgga aagaccattc   2040
tggactttct caagtccgat ggctttgcca accgaaactt catgcagctc attcacgacg   2100
attctcttac cttcaaggag gacatccaga aggcacaagt gtccggtcag ggcgacagct   2160
tgcacgaaca tattgccaac ctggctggtt cgccagccat caagaaaggc attctccaga   2220
ctgtcaaggt tgtcgacgag ctggtgaagg tcatgggacg tcacaagccc gagaacattg   2280
tgatcgagat ggccagagag aaccagacaa ctcaaaaggg tcagaaaaac tcgcgagagc   2340
ggatgaagcg aatcgaggaa ggcatcaagg agctgggatc ccagattctc aaggagcatc   2400
ccgtcgagaa cactcaactg cagaacgaga agctgtatct ctactatctg cagaatggtc   2460
gagacatgta cgtggatcag gaactggaca tcaatcgtct cagcgactac gatgtggacc   2520
acattgtccc tcaatccttt ctcaaggacg attctatcga caacaaggtc cttacacgat   2580
ccgacaagaa cagaggcaag tcggacaacg ttcccagcga agaggtggtc aaaaagatga   2640
agaactactg gcgacagctg ctcaacgcca agctcattac ccagcgaaag ttcgacaatc   2700
ttaccaaggc cgagcgaggc ggtctgtccg agctcgacaa ggctggcttc atcaagcgtc   2760
aactcgtcga gaccagacag atcacaaagc acgtcgcaca gattctcgat tctcggatga   2820
acaccaagta cgacgagaac gacaagctca tccgagaggt caaggtgatt actctcaagt   2880
ccaaactggt ctccgatttc cgaaaggact ttcagttcta caaggtgcga gagatcaaca   2940
attaccacca tgcccacgat gcttacctca acgccgtcgt tggcactgcg ctcatcaaga   3000
aataccccaa gctcgaaagc gagttcgttt acggcgatta caaggtctac gacgttcgaa   3060
agatgattgc caagtccgaa caggagattg gcaaggctac tgccaagtac ttcttttact   3120
ccaacatcat gaactttttc aagaccgaga tcaccttggc caacggagag attcgaaaga   3180
gaccacttat cgagaccaac ggcgaaactg gagagatcgt gtgggacaag ggtcgagact   3240
ttgcaaccgt gcgaaaggtt ctgtcgatgc ctcaggtcaa catcgtcaag aaaaccgagg   3300
ttcagactgg cggattctcc aaggagtcga ttctgcccaa gcgaaactcc gacaagctca   3360
tcgctcgaaa gaaagactgg gatcccaaga aatacggtgg cttcgattct cctaccgtcg   3420
cctattccgt gcttgtcgtt gcgaaggtcg agaagggcaa gtccaaaaag ctcaagtccg   3480
tcaaggagct gctcggaatt accatcatgg agcgatcgag cttcgagaag aatcccatcg   3540
acttcttgga agccaagggt tacaaggagg tcaagaaaga cctcattatc aagctgccca   3600
agtactctct gttcgaactg gagaacggtc gaaagcgtat gctcgcctcc gctggcgagc   3660
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
```

-continued

```
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560
ctttttgcgt ttctacaaac tcttttgttt atttttctaa atacattcaa atatgtatcc   4620
gctcatgaga caataaccct gataaatgct tcaataatat tgaaaaagga agagtatgag   4680
tattcaacat ttccgtgtcg cccttattcc cttttttgcg gcattttgcc ttcctgtttt   4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt   4920
tgacgccggg caagagcaac tcggtcgccg catacactat tctcagaatg acttggttga   4980
gtactcacca gtcacagaaa agcatcttac ggatggcatg acagtaagag aattatgcag   5040
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg ggtctcgcgg   5400
tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580
acttcatttt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga gatccttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
ccacttcaag aactctgtag caccgcctac atacctcgct ctgctaatcc tgttaccagt   5940
ggctgctgcc agtggcgata agtcgtgtct taccgggttg gactcaagac gatagttacc   6000
ggataaggcg cagcggtcgg gctgaacggg gggttcgtgc acacagccca gcttggagcg   6060
aacgacctac accgaactga gatacctaca gcgtgagcta tgagaaagcg ccacgcttcc   6120
cgaagggaga aaggcggaca ggtatccggt aagcggcagg gtcggaacag gagagcgcac   6180
gagggagctt ccagggggaa acgcctggta tctttatagt cctgtcgggt ttcgccacct   6240
ctgacttgag cgtcgatttt tgtgatgctc gtcagggggg cggagcctat ggaaaaacgc   6300
cagcaacgcg gcctttttac ggttcctggc cttttgctgg ccttttgctc acatgttctt   6360
tcctgcgtta tcccctgatt ctgtggataa ccgtattacc gcctttgagt gagctgatac   6420
cgctcgccgc agccgaacga ccgagcgcag cgagtcagtg agcgaggaag cggaagagcg   6480
cctgatgcgg tattttctcc ttacgcatct gtgcggtatt tcacaccgca tatggtgcac   6540
```

```
tctcagtaca atctgctctg atgccgcata gttaagccag tatacactcc gctatcgcta   6600

cgtgactggg tcatggctgc gccccgacac ccgccaacac ccgctgacgc gccctgacgg   6660

gcttgtctgc tcccggcatc cgcttacaga caagctgtga ccgtctccgg gagctgcatg   6720

tgtcagaggt tttcaccgtc atcaccgaaa cgcgcgaggc agcagatcaa ttcgcgcgcg   6780

aaggcgaagc ggcatgcata atgtgcctgt caaatggacg aagcagggat tctgcaaacc   6840

ctatgctact ccgtcaagcc gtcaattgtc tgattcgtta ccaattatga caacttgacg   6900

gctacatcat tcactttttc ttcacaaccg gcacggaact cgctcgggct ggccccggtg   6960

catttttaa atacccgcga gaaatagagt tgatcgtcaa aaccaacatt gcgaccgacg   7020

gtggcgatag gcatccgggt ggtgctcaaa agcagcttcg cctggctgat acgttggtcc   7080

tcgcgccagc ttaagacgct aatccctaac tgctggcgga aaagatgtga cagacgcgac   7140

ggcgacaagc aaacatgctg tgcgacgctg gcgatatcaa aattgctgtc tgccaggtga   7200

tcgctgatgt actgacaagc ctcgcgtacc cgattatcca tcggtggatg gagcgactcg   7260

ttaatcgctt ccatgcgccg cagtaacaat tgctcaagca gatttatcgc cagcagctcc   7320

gaatagcgcc cttccccttg cccggcgtta atgatttgcc caaacaggtc gctgaaatgc   7380

ggctggtgcg cttcatccgg gcgaaagaac cccgtattgg caaatattga cggccagtta   7440

agccattcat gccagtaggc gcgcggacga aagtaaaccc actggtgata ccattcgcga   7500

gcctccggat gacgaccgta gtgatgaatc tctcctggcg ggaacagcaa aatatcaccc   7560

ggtcggcaaa caaattctcg tccctgattt ttcaccaccc cctgaccgcg aatggtgaga   7620

ttgagaatat aacctttcat tcccagcggt cggtcgataa aaaaatcgag ataaccgttg   7680

gcctcaatcg gcgttaaacc cgccaccaga tgggcattaa acgagtatcc cggcagcagg   7740

ggatcatttt gcgcttcagc catacttttc atactcccgc cattcagaga agaaaccaat   7800

tgtccatatt gcatcagaca ttgccgtcac tgcgtctttt actggctctt ctcgctaacc   7860

aaaccggtaa ccccgcttat taaaagcatt ctgtaacaaa gcgggaccaa agccatgaca   7920

aaaacgcgta acaaaagtgt ctataatcac ggcagaaaag tccacattga ttatttgcac   7980

ggcgtcacac tttgctatgc catagcattt ttatccataa gattagcgga tcctacctga   8040

cgctttttat cgcaactctc tactgtttct ccatacccgt tttttgggct aacaggagga   8100

attaaccatg ggcatcacc accatcacca cttattgatt atcttgcgtc gtcgcatccg   8160

caaacaggcg cacgcacata gcaagg                                         8186
```

<210> SEQ ID NO 111
<211> LENGTH: 20
<212> TYPE: DNA
<213> ORGANISM: Artificial sequencE
<220> FEATURE:
<223> OTHER INFORMATION: oligo 153

<400> SEQUENCE: 111

```
cgacagagtt ggttccaatg                                                  20
```

<210> SEQ ID NO 112
<211> LENGTH: 4835
<212> TYPE: DNA
<213> ORGANISM: Artificial sequence
<220> FEATURE:
<223> OTHER INFORMATION: pRF186

<400> SEQUENCE: 112

-continued

```
catggggcat caccaccatc accacgaatg cgactcagaa ctggaaatca aacgctataa     60
acgtgtgcgt gtggcatccc gtaaatgtcg cgcaaagttt aaacagctgc tgcaacatta    120
tcgtgaagta gcggctgcga aaagctccga aaacgaccgt ttacgcctcc tcctgaagca    180
aatgtgcgaa ttcggaggtg gcggtgcatc ctcggaggat gtgattaaag aatttatgcg    240
gtttaaagta cgtatggaag gatcggtgaa tggccatgaa tttgagattg agggtgaagg    300
cgaaggccgc ccgtacgaag gaactcaaac agcgaaatta aaagttacaa aaggaggtcc    360
tctgccgttt gcctgggaca tcttgagccc gcaattccag tacggttcca aagtgtatgt    420
aaaacaccct gcggatattc cggattataa aaaactgagt tttcccgagg ggtttaaatg    480
ggaacgggtg atgaattttg aggatggtgg agttgtcacc gtgacccagg actctagctt    540
acaagacggt agtttcatct acaaagtaaa atttatcggc gtaaacttcc catcggacgg    600
ccccgtcatg cagaaaaaga cgatgggctg ggaagccagc accgaacgtt tgtacccacg    660
ggacggcgtt ttgaaagggg aaatccataa ggcccttaaa ctgaaagacg gtggtcacta    720
tctcgtggag tttaaatcga tttatatggc taaaaaacca gtacagcttc cgggttatta    780
ttacgttgac tccaaattgg acatcacatc gcataatgaa gattacacga ttgttgaaca    840
gtacgagcgc gccgagggcc ggcaccatct gtttctgtaa aagcttggct gttttggcgg    900
atgagagaag attttcagcc tgatacagat taaatcagaa cgcagaagcg gtctgataaa    960
acagaatttg cctggcggca gtagcgcggt ggtcccacct gaccccatgc cgaactcaga   1020
agtgaaacgc cgtagcgccg atggtagtgt ggggtctccc catgcgagag tagggaactg   1080
ccaggcatca aataaaacga aaggctcagt cgaaagactg ggcctttcgt tttatctgtt   1140
gtttgtcggt gaacgctctc ctgagtagga caaatccgcc gggagcggat ttgaacgttg   1200
cgaagcaacg gcccggaggg tggcgggcag gacgcccgcc ataaactgcc aggcatcaaa   1260
ttaagcagaa ggccatcctg acggatggcc tttttgcgtt tctacaaact cttttgttta   1320
tttttctaaa tacattcaaa tatgtatccg ctcatgagac aataaccctg ataaatgctt   1380
caataatatt gaaaaaggaa gagtatgagt attcaacatt tccgtgtcgc ccttattccc   1440
ttttttgcgg cattttgcct tcctgttttt gctcacccag aaacgctggt gaaagtaaaa   1500
gatgctgaag atcagttggg tgcacgagtg ggttacatcg aactggatct caacagcggt   1560
aagatccttg agagttttcg ccccgaagaa cgttttccaa tgatgagcac ttttaaagtt   1620
ctgctatgtg gcgcggtatt atcccgtgtt gacgccgggc aagagcaact cggtcgccgc   1680
atacactatt ctcagaatga cttggttgag tactcaccag tcacagaaaa gcatcttacg   1740
gatggcatga cagtaagaga attatgcagt gctgccataa ccatgagtga taacactgcg   1800
gccaacttac ttctgacaac gatcggagga ccgaaggagc taaccgcttt tttgcacaac   1860
atgggggatc atgtaactcg ccttgatcgt tgggaaccgg agctgaatga agccatacca   1920
aacgacgagc gtgacaccac gatgcctgta gcaatggcaa caacgttgcg caaactatta   1980
actggcgaac tacttactct agcttcccgg caacaattaa tagactggat ggaggcggat   2040
aaagttgcag gaccacttct gcgctcggcc cttccggctg gctggtttat tgctgataaa   2100
tctggagccg gtgagcgtgg gtctcgcggt atcattgcag cactggggcc agatggtaag   2160
ccctcccgta tcgtagttat ctacacgacg gggagtcagg caactatgga tgaacgaaat   2220
agacagatcg ctgagatagg tgcctcactg attaagcatt ggtaactgtc agaccaagtt   2280
tactcatata tactttagat tgatttaaaa cttcattttt aatttaaaag gatctaggtg   2340
aagatccttt ttgataatct catgaccaaa atcccttaac gtgagttttc gttccactga   2400
```

```
gcgtcagacc ccgtagaaaa gatcaaagga tcttcttgag atcctttttt tctgcgcgta   2460
atctgctgct tgcaaacaaa aaaaccaccg ctaccagcgg tggtttgttt gccggatcaa   2520
gagctaccaa ctctttttcc gaaggtaact ggcttcagca gagcgcagat accaaatact   2580
gtccttctag tgtagccgta gttaggccac cacttcaaga actctgtagc accgcctaca   2640
tacctcgctc tgctaatcct gttaccagtg gctgctgcca gtggcgataa gtcgtgtctt   2700
accgggttgg actcaagacg atagttaccg gataaggcgc agcggtcggg ctgaacgggg   2760
ggttcgtgca cacagcccag cttggagcga acgacctaca ccgaactgag atacctacag   2820
cgtgagctat gagaaagcgc cacgcttccc gaagggagaa aggcggacag gtatccggta   2880
agcggcaggg tcggaacagg agagcgcacg agggagcttc cagggggaaa cgcctggtat   2940
ctttatagtc ctgtcgggtt tcgccacctc tgacttgagc gtcgattttt gtgatgctcg   3000
tcaggggggc ggagcctatg gaaaaacgcc agcaacgcgg cctttttacg gttcctggcc   3060
ttttgctggc cttttgctca catgttcttt cctgcgttat cccctgattc tgtggataac   3120
cgtattaccg cctttgagtg agctgatacc gctcgccgca gccgaacgac cgagcgcagc   3180
gagtcagtga gcgaggaagc ggaagagcgc ctgatgcggt attttctcct tacgcatctg   3240
tgcggtattt cacaccgcat atggtgcact ctcagtacaa tctgctctga tgccgcatag   3300
ttaagccagt atacactccg ctatcgctac gtgactgggt catggctgcg ccccgacacc   3360
cgccaacacc cgctgacgcg ccctgacggg cttgtctgct cccggcatcc gcttacagac   3420
aagctgtgac cgtctccggg agctgcatgt gtcagaggtt ttcaccgtca tcaccgaaac   3480
gcgcgaggca gcagatcaat tcgcgcgcga aggcgaagcg gcatgcataa tgtgcctgtc   3540
aaatggacga agcagggatt ctgcaaaccc tatgctactc cgtcaagccg tcaattgtct   3600
gattcgttac caattatgac aacttgacgg ctacatcatt cactttttct tcacaaccgg   3660
cacggaactc gctcgggctg gccccggtgc attttttaaa tacccgcgag aaatagagtt   3720
gatcgtcaaa accaacattg cgaccgacgg tggcgatagg catccgggtg gtgctcaaaa   3780
gcagcttcgc ctggctgata cgttggtcct cgcgccagct taagacgcta atccctaact   3840
gctggcggaa aagatgtgac agacgcgacg gcgacaagca aacatgctgt gcgacgctgg   3900
cgatatcaaa attgctgtct gccaggtgat cgctgatgta ctgacaagcc tcgcgtaccc   3960
gattatccat cggtggatgg agcgactcgt taatcgcttc catgcgccgc agtaacaatt   4020
gctcaagcag atttatcgcc agcagctccg aatagcgccc ttccccttgc ccggcgttaa   4080
tgatttgccc aaacaggtcg ctgaaatgcg gctggtgcgc ttcatccggg cgaaagaacc   4140
ccgtattggc aaatattgac ggccagttaa gccattcatg ccagtaggcg cgcggacgaa   4200
agtaaaccca ctggtgatac cattcgcgag cctccggatg acgaccgtag tgatgaatct   4260
ctcctggcgg gaacagcaaa atatcacccg gtcggcaaac aaattctcgt ccctgatttt   4320
tcaccacccc ctgaccgcga atggtgagat tgagaatata acctttcatt cccagcggtc   4380
ggtcgataaa aaaatcgaga taaccgttgg cctcaatcgg cgttaaaccc gccaccagat   4440
gggcattaaa cgagtatccc ggcagcaggg gatcattttg cgcttcagcc atacttttca   4500
tactcccgcc attcagagaa gaaaccaatt gtccatattg catcagacat tgccgtcact   4560
gcgtctttta ctggctcttc tcgctaacca aaccggtaac cccgcttatt aaaagcattc   4620
tgtaacaaag cgggaccaaa gccatgacaa aaacgcgtaa caaaagtgtc tataatcacg   4680
gcagaaaagt ccacattgat tatttgcacg gcgtcacact ttgctatgcc atagcatttt   4740
```

```
tatccataag attagcggat cctacctgac gctttttatc gcaactctct actgtttctc   4800

catacccgtt ttttgggcta acaggaggaa ttaac                               4835
```

<210> SEQ ID NO 113
<211> LENGTH: 4736
<212> TYPE: DNA
<213> ORGANISM: Artificial sequence
<220> FEATURE:
<223> OTHER INFORMATION: pRF192

<400> SEQUENCE: 113

```
aattcggagg tggcggtgca tcctcggagg atgtgattaa agaatttatg cggtttaaag     60

tacgtatgga aggatcggtg aatggccatg aatttgagat tgagggtgaa ggcgaaggcc    120

gcccgtacga aggaactcaa acagcgaaat taaaagttac aaaaggaggt cctctgccgt    180

ttgcctggga catcttgagc ccgcaattcc agtacggttc caaagtgtat gtaaaacacc    240

ctgcggatat tccggattat aaaaaactga gttttcccga ggggtttaaa tgggaacggg    300

tgatgaattt tgaggatggt ggagttgtca ccgtgaccca ggactctagc ttacaagacg    360

gtagtttcat ctacaaagta aaatttatcg gcgtaaactt cccatcggac ggccccgtca    420

tgcagaaaaa gacgatgggc tgggaagcca gcaccgaacg tttgtaccca cgggacggcg    480

ttttgaaagg ggaaatccat aaggccctta aactgaaaga cggtggtcac tatctcgtgg    540

agtttaaatc gatttatatg gctaaaaaac cagtacagct tccgggttat tattacgttg    600

actccaaatt ggacatcaca tcgcataatg aagattacac gattgttgaa cagtacgagc    660

gcgccgaggg ccggcaccat ctgtttctgt aaaagcttgg ctgttttggc ggatgagaga    720

agattttcag cctgatacag attaaatcag aacgcagaag cggtctgata aaacagaatt    780

tgcctggcgg cagtagcgcg gtggtcccac ctgaccccat gccgaactca gaagtgaaac    840

gccgtagcgc cgatggtagt gtggggtctc cccatgcgag agtagggaac tgccaggcat    900

caaataaaac gaaaggctca gtcgaaagac tgggcctttc gttttatctg ttgtttgtcg    960

gtgaacgctc tcctgagtag gacaaatccg ccgggagcgg atttgaacgt tgcgaagcaa   1020

cggcccggag ggtggcgggc aggacgcccg ccataaactg ccaggcatca aattaagcag   1080

aaggccatcc tgacggatgg cctttttgcg tttctacaaa ctcttttgtt tatttttcta   1140

aatacattca aatatgtatc cgctcatgag acaataaccc tgataaatgc ttcaataata   1200

ttgaaaaagg aagagtatga gtattcaaca tttccgtgtc gcccttattc ccttttttgc   1260

ggcattttgc cttcctgttt ttgctcaccc agaaacgctg gtgaaagtaa aagatgctga   1320

agatcagttg ggtgcacgag tgggttacat cgaactggat ctcaacagcg gtaagatcct   1380

tgagagtttt cgccccgaag aacgttttcc aatgatgagc acttttaaag ttctgctatg   1440

tggcgcggta ttatcccgtg ttgacgccgg gcaagagcaa ctcggtcgcc gcatacacta   1500

ttctcagaat gacttggttg agtactcacc agtcacagaa aagcatctta cggatggcat   1560

gacagtaaga gaattatgca gtgctgccat aaccatgagt gataacactg cggccaactt   1620

acttctgaca acgatcggag gaccgaagga gctaaccgct tttttgcaca acatggggga   1680

tcatgtaact cgccttgatc gttgggaacc ggagctgaat gaagccatac caaacgacga   1740

gcgtgacacc acgatgcctg tagcaatggc aacaacgttg cgcaaactat taactggcga   1800

actacttact ctagcttccc ggcaacaatt aatagactgg atggaggcgg ataaagttgc   1860

aggaccactt ctgcgctcgg cccttccggc tggctggttt attgctgata aatctggagc   1920

cggtgagcgt gggtctcgcg gtatcattgc agcactgggg ccagatggta agccctcccg   1980
```

tatcgtagtt atctacacga cggggagtca ggcaactatg gatgaacgaa atagacagat 2040
cgctgagata ggtgcctcac tgattaagca ttggtaactg tcagaccaag tttactcata 2100
tatactttag attgatttaa aacttcattt ttaatttaaa aggatctagg tgaagatcct 2160
ttttgataat ctcatgacca aaatccctta acgtgagttt tcgttccact gagcgtcaga 2220
ccccgtagaa aagatcaaag gatcttcttg agatcctttt tttctgcgcg taatctgctg 2280
cttgcaaaca aaaaaaccac cgctaccagc ggtggtttgt ttgccggatc aagagctacc 2340
aactcttttt ccgaaggtaa ctggcttcag cagagcgcag ataccaaata ctgtccttct 2400
agtgtagccg tagttaggcc accacttcaa gaactctgta gcaccgccta catacctcgc 2460
tctgctaatc ctgttaccag tggctgctgc cagtggcgat aagtcgtgtc ttaccgggtt 2520
ggactcaaga cgatagttac cggataaggc gcagcggtcg ggctgaacgg ggggttcgtg 2580
cacacagccc agcttggagc gaacgaccta caccgaactg agatacctac agcgtgagct 2640
atgagaaagc gccacgcttc ccgaagggag aaaggcggac aggtatccgg taagcggcag 2700
ggtcggaaca ggagagcgca cgagggagct tccaggggga aacgcctggt atctttatag 2760
tcctgtcggg tttcgccacc tctgacttga gcgtcgattt ttgtgatgct cgtcaggggg 2820
gcggagccta tggaaaaacg ccagcaacgc ggccttttta cggttcctgg ccttttgctg 2880
gccttttgct cacatgttct ttcctgcgtt atcccctgat tctgtggata accgtattac 2940
cgcctttgag tgagctgata ccgctcgccg cagccgaacg accgagcgca gcgagtcagt 3000
gagcgaggaa gcggaagagc gcctgatgcg gtattttctc cttacgcatc tgtgcggtat 3060
ttcacaccgc atatggtgca ctctcagtac aatctgctct gatgccgcat agttaagcca 3120
gtatacactc cgctatcgct acgtgactgg gtcatggctg cgccccgaca cccgccaaca 3180
cccgctgacg cgccctgacg ggcttgtctg ctcccggcat ccgcttacag acaagctgtg 3240
accgtctccg ggagctgcat gtgtcagagg ttttcaccgt catcaccgaa acgcgcgagg 3300
cagcagatca attcgcgcgc gaaggcgaag cggcatgcat aatgtgcctg tcaaatggac 3360
gaagcaggga ttctgcaaac cctatgctac tccgtcaagc cgtcaattgt ctgattcgtt 3420
accaattatg acaacttgac ggctacatca ttcacttttt cttcacaacc ggcacggaac 3480
tcgctcgggc tggccccggt gcatttttta aatacccgcg agaaatagag ttgatcgtca 3540
aaaccaacat tgcgaccgac ggtggcgata ggcatccggg tggtgctcaa aagcagcttc 3600
gcctggctga tacgttggtc ctcgcgccag cttaagacgc taatccctaa ctgctggcgg 3660
aaaagatgtg acagacgcga cggcgacaag caaacatgct gtgcgacgct ggcgatatca 3720
aaattgctgt ctgccaggtg atcgctgatg tactgacaag cctcgcgtac ccgattatcc 3780
atcggtggat ggagcgactc gttaatcgct tccatgcgcc gcagtaacaa ttgctcaagc 3840
agatttatcg ccagcagctc cgaatagcgc ccttcccctt gcccggcgtt aatgatttgc 3900
ccaaacaggt cgctgaaatg cggctggtgc gcttcatccg ggcgaaagaa ccccgtattg 3960
gcaaatattg acggccagtt aagccattca tgccagtagg cgcgcggacg aaagtaaacc 4020
cactggtgat accattcgcg agcctccgga tgacgaccgt agtgatgaat ctctcctggc 4080
gggaacagca aaatatcacc cggtcggcaa acaaattctc gtccctgatt tttcaccacc 4140
ccctgaccgc gaatggtgag attgagaata taacctttca ttcccagcgg tcggtcgata 4200
aaaaaatcga gataaccgtt ggcctcaatc ggcgttaaac ccgccaccag atgggcatta 4260
aacgagtatc ccggcagcag gggatcattt tgcgcttcag ccatactttt catactcccg 4320

```
ccattcagag aagaaaccaa ttgtccatat tgcatcagac attgccgtca ctgcgtcttt   4380

tactggctct tctcgctaac caaaccggta accccgctta ttaaaagcat tctgtaacaa   4440

agcgggacca aagccatgac aaaaacgcgt aacaaaagtg tctataatca cggcagaaaa   4500

gtccacattg attatttgca cggcgtcaca ctttgctatg ccatagcatt tttatccata   4560

agattagcgg atcctacctg acgcttttta tcgcaactct ctactgtttc tccatacccg   4620

tttttgggc taacaggagg aattaaccat ggggcatcac caccatcacc acgcgggtta    4680

cctgctgggc aagattaatc ttaaagcctg cgccgcgtgt gctaagaaaa ttttgg       4736
```

<210> SEQ ID NO 114
<211> LENGTH: 4727
<212> TYPE: DNA
<213> ORGANISM: Artificial sequence
<220> FEATURE:
<223> OTHER INFORMATION: pRF190

<400> SEQUENCE: 114

```
aattcggagg tggcggtgca tcctcggagg atgtgattaa agaatttatg cggtttaaag     60

tacgtatgga aggatcggtg aatggccatg aatttgagat tgagggtgaa ggcgaaggcc    120

gcccgtacga aggaactcaa acagcgaaat taaaagttac aaaaggaggt cctctgccgt    180

ttgcctggga catcttgagc ccgcaattcc agtacggttc caaagtgtat gtaaaacacc    240

ctgcggatat tccggattat aaaaaactga gttttcccga ggggtttaaa tgggaacggg    300

tgatgaattt tgaggatggt ggagttgtca ccgtgaccca ggactctagc ttacaagacg    360

gtagtttcat ctacaaagta aaatttatcg gcgtaaactt cccatcggac ggccccgtca    420

tgcagaaaaa gacgatgggc tgggaagcca gcaccgaacg tttgtaccca cgggacggcg    480

ttttgaaagg ggaaatccat aaggccctta aactgaaaga cggtggtcac tatctcgtgg    540

agtttaaatc gatttatatg gctaaaaaac cagtacagct tccgggttat tattacgttg    600

actccaaatt ggacatcaca tcgcataatg aagattacac gattgttgaa cagtacgagc    660

gcgccgaggg ccggcaccat ctgtttctgt aaaagcttgg ctgttttggc ggatgagaga    720

agattttcag cctgatacag attaaatcag aacgcagaag cggtctgata aaacagaatt    780

tgcctggcgg cagtagcgcg gtggtcccac ctgaccccat gccgaactca gaagtgaaac    840

gccgtagcgc cgatggtagt gtggggtctc cccatgcgag agtagggaac tgccaggcat    900

caaataaaac gaaaggctca gtcgaaagac tgggcctttc gttttatctg ttgtttgtcg    960

gtgaacgctc tcctgagtag gacaaatccg ccgggagcgg atttgaacgt tgcgaagcaa   1020

cggcccggag ggtggcgggc aggacgcccg ccataaactg ccaggcatca aattaagcag   1080

aaggccatcc tgacggatgg cctttttgcg tttctacaaa ctcttttgtt tatttttcta   1140

aatacattca aatatgtatc cgctcatgag acaataaccc tgataaatgc ttcaataata   1200

ttgaaaaagg aagagtatga gtattcaaca tttccgtgtc gcccttattc ccttttttgc   1260

ggcattttgc cttcctgttt ttgctcaccc agaaacgctg gtgaaagtaa aagatgctga   1320

agatcagttg ggtgcacgag tgggttacat cgaactggat ctcaacagcg gtaagatcct   1380

tgagagtttt cgccccgaag aacgttttcc aatgatgagc acttttaaag ttctgctatg   1440

tggcgcggta ttatcccgtg ttgacgccgg gcaagagcaa ctcggtcgcc gcatacacta   1500

ttctcagaat gacttggttg agtactcacc agtcacagaa aagcatctta cggatggcat   1560

gacagtaaga gaattatgca gtgctgccat aaccatgagt gataacactg cggccaactt   1620

acttctgaca acgatcggag gaccgaagga gctaaccgct tttttgcaca acatggggga   1680
```

-continued tcatgtaact cgccttgatc gttgggaacc ggagctgaat gaagccatac caaacgacga 1740
gcgtgacacc acgatgcctg tagcaatggc aacaacgttg cgcaaactat taactggcga 1800
actacttact ctagcttccc ggcaacaatt aatagactgg atggaggcgg ataaagttgc 1860
aggaccactt ctgcgctcgg cccttccggc tggctggttt attgctgata aatctggagc 1920
cggtgagcgt gggtctcgcg gtatcattgc agcactgggg ccagatggta agccctcccg 1980
tatcgtagtt atctacacga cggggagtca ggcaactatg gatgaacgaa atagacagat 2040
cgctgagata ggtgcctcac tgattaagca ttggtaactg tcagaccaag tttactcata 2100
tatactttag attgatttaa aacttcattt ttaatttaaa aggatctagg tgaagatcct 2160
ttttgataat ctcatgacca aaatccctta acgtgagttt tcgttccact gagcgtcaga 2220
ccccgtagaa aagatcaaag gatcttcttg agatcctttt tttctgcgcg taatctgctg 2280
cttgcaaaca aaaaaaccac cgctaccagc ggtggtttgt ttgccggatc aagagctacc 2340
aactcttttt ccgaaggtaa ctggcttcag cagagcgcag ataccaaata ctgtccttct 2400
agtgtagccg tagttaggcc accacttcaa gaactctgta gcaccgccta catacctcgc 2460
tctgctaatc ctgttaccag tggctgctgc cagtggcgat aagtcgtgtc ttaccgggtt 2520
ggactcaaga cgatagttac cggataaggc gcagcggtcg ggctgaacgg ggggttcgtg 2580
cacacagccc agcttggagc gaacgaccta caccgaactg agatacctac agcgtgagct 2640
atgagaaagc gccacgcttc ccgaagggag aaaggcggac aggtatccgg taagcggcag 2700
ggtcggaaca ggagagcgca cgagggagct tccaggggga aacgcctggt atctttatag 2760
tcctgtcggg tttcgccacc tctgacttga gcgtcgattt ttgtgatgct cgtcaggggg 2820
gcggagccta tggaaaaacg ccagcaacgc ggccttttta cggttcctgg ccttttgctg 2880
gccttttgct cacatgttct ttcctgcgtt atcccctgat tctgtggata accgtattac 2940
cgcctttgag tgagctgata ccgctcgccg cagccgaacg accgagcgca gcgagtcagt 3000
gagcgaggaa gcggaagagc gcctgatgcg gtattttctc cttacgcatc tgtgcggtat 3060
ttcacaccgc atatggtgca ctctcagtac aatctgctct gatgccgcat agttaagcca 3120
gtatacactc cgctatcgct acgtgactgg gtcatggctg cgccccgaca cccgccaaca 3180
cccgctgacg cgccctgacg ggcttgtctg ctcccggcat ccgcttacag acaagctgtg 3240
accgtctccg ggagctgcat gtgtcagagg ttttcaccgt catcaccgaa acgcgcgagg 3300
cagcagatca attcgcgcgc gaaggcgaag cggcatgcat aatgtgcctg tcaaatggac 3360
gaagcaggga ttctgcaaac cctatgctac tccgtcaagc cgtcaattgt ctgattcgtt 3420
accaattatg acaacttgac ggctacatca ttcacttttt cttcacaacc ggcacggaac 3480
tcgctcgggc tggccccggt gcattttttta aatacccgcg agaaatagag ttgatcgtca 3540
aaaccaacat tgcgaccgac ggtggcgata ggcatccggg tggtgctcaa aagcagcttc 3600
gcctggctga tacgttggtc ctcgcgccag cttaagacgc taatccctaa ctgctggcgg 3660
aaaagatgtg acagacgcga cggcgacaag caaacatgct gtgcgacgct ggcgatatca 3720
aaattgctgt ctgccaggtg atcgctgatg tactgacaag cctcgcgtac ccgattatcc 3780
atcggtggat ggagcgactc gttaatcgct tccatgcgcc gcagtaacaa ttgctcaagc 3840
agatttatcg ccagcagctc cgaatagcgc ccttcccctt gcccggcgtt aatgatttgc 3900
ccaaacaggt cgctgaaatg cggctggtgc gcttcatccg ggcgaaagaa ccccgtattg 3960
gcaaatattg acggccagtt aagccattca tgccagtagg cgcgcggacg aaagtaaacc 4020

-continued

```
cactggtgat accattcgcg agcctccgga tgacgaccgt agtgatgaat ctctcctggc   4080

gggaacagca aaatatcacc cggtcggcaa acaaattctc gtccctgatt tttcaccacc   4140

ccctgaccgc gaatggtgag attgagaata taacctttca ttcccagcgg tcggtcgata   4200

aaaaaatcga gataaccgtt ggcctcaatc ggcgttaaac ccgccaccag atgggcatta   4260

aacgagtatc ccggcagcag gggatcattt tgcgcttcag ccatactttt catactcccg   4320

ccattcagag aagaaaccaa ttgtccatat tgcatcagac attgccgtca ctgcgtcttt   4380

tactggctct tctcgctaac caaaccggta accccgctta ttaaaagcat tctgtaacaa   4440

agcgggacca aagccatgac aaaaacgcgt aacaaaagtg tctataatca cggcagaaaa   4500

gtccacattg attatttgca cggcgtcaca ctttgctatg ccatagcatt tttatccata   4560

agattagcgg atcctacctg acgcttttta tcgcaactct ctactgtttc tccatacccg   4620

tttttgggc taacaggagg aattaaccat ggggcatcac caccatcacc acttattgat    4680

tatcttgcgt cgtcgcatcc gcaaacaggc gcacgcacat agcaagg                 4727
```

<210> SEQ ID NO 115
<211> LENGTH: 1395
<212> TYPE: PRT
<213> ORGANISM: artificial sequence
<220> FEATURE:
<223> OTHER INFORMATION: his-CFFKDEL-Cas9

<400> SEQUENCE: 115

```
Met Gly His His His His His His Cys Phe Phe Lys Asp Glu Leu Glu
1               5                   10                  15

Phe Asp Lys Lys Tyr Ser Ile Gly Leu Asp Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240
```

-continued

```
Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445

Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
```

660 665 670

Thr Gly Trp Gly Arg Leu Ser Arg Lys Leu Ile Asn Gly Ile Arg Asp
675 680 685

Lys Gln Ser Gly Lys Thr Ile Leu Asp Phe Leu Lys Ser Asp Gly Phe
690 695 700

Ala Asn Arg Asn Phe Met Gln Leu Ile His Asp Asp Ser Leu Thr Phe
705 710 715 720

Lys Glu Asp Ile Gln Lys Ala Gln Val Ser Gly Gln Gly Asp Ser Leu
725 730 735

His Glu His Ile Ala Asn Leu Ala Gly Ser Pro Ala Ile Lys Lys Gly
740 745 750

Ile Leu Gln Thr Val Lys Val Val Asp Glu Leu Val Lys Val Met Gly
755 760 765

Arg His Lys Pro Glu Asn Ile Val Ile Glu Met Ala Arg Glu Asn Gln
770 775 780

Thr Thr Gln Lys Gly Gln Lys Asn Ser Arg Glu Arg Met Lys Arg Ile
785 790 795 800

Glu Glu Gly Ile Lys Glu Leu Gly Ser Gln Ile Leu Lys Glu His Pro
805 810 815

Val Glu Asn Thr Gln Leu Gln Asn Glu Lys Leu Tyr Leu Tyr Tyr Leu
820 825 830

Gln Asn Gly Arg Asp Met Tyr Val Asp Gln Glu Leu Asp Ile Asn Arg
835 840 845

Leu Ser Asp Tyr Asp Val Asp His Ile Val Pro Gln Ser Phe Leu Lys
850 855 860

Asp Asp Ser Ile Asp Asn Lys Val Leu Thr Arg Ser Asp Lys Asn Arg
865 870 875 880

Gly Lys Ser Asp Asn Val Pro Ser Glu Glu Val Val Lys Lys Met Lys
885 890 895

Asn Tyr Trp Arg Gln Leu Leu Asn Ala Lys Leu Ile Thr Gln Arg Lys
900 905 910

Phe Asp Asn Leu Thr Lys Ala Glu Arg Gly Gly Leu Ser Glu Leu Asp
915 920 925

Lys Ala Gly Phe Ile Lys Arg Gln Leu Val Glu Thr Arg Gln Ile Thr
930 935 940

Lys His Val Ala Gln Ile Leu Asp Ser Arg Met Asn Thr Lys Tyr Asp
945 950 955 960

Glu Asn Asp Lys Leu Ile Arg Glu Val Lys Val Ile Thr Leu Lys Ser
965 970 975

Lys Leu Val Ser Asp Phe Arg Lys Asp Phe Gln Phe Tyr Lys Val Arg
980 985 990

Glu Ile Asn Asn Tyr His His Ala His Asp Ala Tyr Leu Asn Ala Val
995 1000 1005

Val Gly Thr Ala Leu Ile Lys Lys Tyr Pro Lys Leu Glu Ser Glu
1010 1015 1020

Phe Val Tyr Gly Asp Tyr Lys Val Tyr Asp Val Arg Lys Met Ile
1025 1030 1035

Ala Lys Ser Glu Gln Glu Ile Gly Lys Ala Thr Ala Lys Tyr Phe
1040 1045 1050

Phe Tyr Ser Asn Ile Met Asn Phe Phe Lys Thr Glu Ile Thr Leu
1055 1060 1065

Ala Asn Gly Glu Ile Arg Lys Arg Pro Leu Ile Glu Thr Asn Gly
1070 1075 1080

Glu Thr Gly Glu Ile Val Trp Asp Lys Gly Arg Asp Phe Ala Thr
1085 1090 1095

Val Arg Lys Val Leu Ser Met Pro Gln Val Asn Ile Val Lys Lys
1100 1105 1110

Thr Glu Val Gln Thr Gly Gly Phe Ser Lys Glu Ser Ile Leu Pro
1115 1120 1125

Lys Arg Asn Ser Asp Lys Leu Ile Ala Arg Lys Lys Asp Trp Asp
1130 1135 1140

Pro Lys Lys Tyr Gly Gly Phe Asp Ser Pro Thr Val Ala Tyr Ser
1145 1150 1155

Val Leu Val Val Ala Lys Val Glu Lys Gly Lys Ser Lys Lys Leu
1160 1165 1170

Lys Ser Val Lys Glu Leu Leu Gly Ile Thr Ile Met Glu Arg Ser
1175 1180 1185

Ser Phe Glu Lys Asn Pro Ile Asp Phe Leu Glu Ala Lys Gly Tyr
1190 1195 1200

Lys Glu Val Lys Lys Asp Leu Ile Ile Lys Leu Pro Lys Tyr Ser
1205 1210 1215

Leu Phe Glu Leu Glu Asn Gly Arg Lys Arg Met Leu Ala Ser Ala
1220 1225 1230

Gly Glu Leu Gln Lys Gly Asn Glu Leu Ala Leu Pro Ser Lys Tyr
1235 1240 1245

Val Asn Phe Leu Tyr Leu Ala Ser His Tyr Glu Lys Leu Lys Gly
1250 1255 1260

Ser Pro Glu Asp Asn Glu Gln Lys Gln Leu Phe Val Glu Gln His
1265 1270 1275

Lys His Tyr Leu Asp Glu Ile Ile Glu Gln Ile Ser Glu Phe Ser
1280 1285 1290

Lys Arg Val Ile Leu Ala Asp Ala Asn Leu Asp Lys Val Leu Ser
1295 1300 1305

Ala Tyr Asn Lys His Arg Asp Lys Pro Ile Arg Glu Gln Ala Glu
1310 1315 1320

Asn Ile Ile His Leu Phe Thr Leu Thr Asn Leu Gly Ala Pro Ala
1325 1330 1335

Ala Phe Lys Tyr Phe Asp Thr Thr Ile Asp Arg Lys Arg Tyr Thr
1340 1345 1350

Ser Thr Lys Glu Val Leu Asp Ala Thr Leu Ile His Gln Ser Ile
1355 1360 1365

Thr Gly Leu Tyr Glu Thr Arg Ile Asp Leu Ser Gln Leu Gly Gly
1370 1375 1380

Asp Ser Arg Ala Asp Pro Lys Lys Lys Arg Lys Val
1385 1390 1395

<210> SEQ ID NO 116
<211> LENGTH: 1412
<212> TYPE: PRT
<213> ORGANISM: Artificial sequence
<220> FEATURE:
<223> OTHER INFORMATION: his-MPG1-Cas9

<400> SEQUENCE: 116

Met Gly His His His His His His Gly Ala Leu Phe Leu Gly Gln Leu
1 5 10 15

Gly Ala Ala Gly Ser Thr Met Gly Ala Pro Lys Lys Lys Arg Lys Val
20 25 30

```
Glu Phe Asp Lys Lys Tyr Ser Ile Gly Leu Asp Ile Gly Thr Asn Ser
        35                  40                  45

Val Gly Trp Ala Val Ile Thr Asp Glu Tyr Lys Val Pro Ser Lys Lys
    50                  55                  60

Phe Lys Val Leu Gly Asn Thr Asp Arg His Ser Ile Lys Lys Asn Leu
65                  70                  75                  80

Ile Gly Ala Leu Leu Phe Asp Ser Gly Glu Thr Ala Glu Ala Thr Arg
                85                  90                  95

Leu Lys Arg Thr Ala Arg Arg Arg Tyr Thr Arg Arg Lys Asn Arg Ile
            100                 105                 110

Cys Tyr Leu Gln Glu Ile Phe Ser Asn Glu Met Ala Lys Val Asp Asp
        115                 120                 125

Ser Phe Phe His Arg Leu Glu Glu Ser Phe Leu Val Glu Glu Asp Lys
    130                 135                 140

Lys His Glu Arg His Pro Ile Phe Gly Asn Ile Val Asp Glu Val Ala
145                 150                 155                 160

Tyr His Glu Lys Tyr Pro Thr Ile Tyr His Leu Arg Lys Lys Leu Val
                165                 170                 175

Asp Ser Thr Asp Lys Ala Asp Leu Arg Leu Ile Tyr Leu Ala Leu Ala
            180                 185                 190

His Met Ile Lys Phe Arg Gly His Phe Leu Ile Glu Gly Asp Leu Asn
        195                 200                 205

Pro Asp Asn Ser Asp Val Asp Lys Leu Phe Ile Gln Leu Val Gln Thr
    210                 215                 220

Tyr Asn Gln Leu Phe Glu Glu Asn Pro Ile Asn Ala Ser Gly Val Asp
225                 230                 235                 240

Ala Lys Ala Ile Leu Ser Ala Arg Leu Ser Lys Ser Arg Arg Leu Glu
                245                 250                 255

Asn Leu Ile Ala Gln Leu Pro Gly Glu Lys Lys Asn Gly Leu Phe Gly
            260                 265                 270

Asn Leu Ile Ala Leu Ser Leu Gly Leu Thr Pro Asn Phe Lys Ser Asn
        275                 280                 285

Phe Asp Leu Ala Glu Asp Ala Lys Leu Gln Leu Ser Lys Asp Thr Tyr
    290                 295                 300

Asp Asp Asp Leu Asp Asn Leu Leu Ala Gln Ile Gly Asp Gln Tyr Ala
305                 310                 315                 320

Asp Leu Phe Leu Ala Ala Lys Asn Leu Ser Asp Ala Ile Leu Leu Ser
                325                 330                 335

Asp Ile Leu Arg Val Asn Thr Glu Ile Thr Lys Ala Pro Leu Ser Ala
            340                 345                 350

Ser Met Ile Lys Arg Tyr Asp Glu His His Gln Asp Leu Thr Leu Leu
        355                 360                 365

Lys Ala Leu Val Arg Gln Gln Leu Pro Glu Lys Tyr Lys Glu Ile Phe
    370                 375                 380

Phe Asp Gln Ser Lys Asn Gly Tyr Ala Gly Tyr Ile Asp Gly Gly Ala
385                 390                 395                 400

Ser Gln Glu Glu Phe Tyr Lys Phe Ile Lys Pro Ile Leu Glu Lys Met
                405                 410                 415

Asp Gly Thr Glu Glu Leu Leu Val Lys Leu Asn Arg Glu Asp Leu Leu
            420                 425                 430

Arg Lys Gln Arg Thr Phe Asp Asn Gly Ser Ile Pro His Gln Ile His
        435                 440                 445
```

-continued

```
Leu Gly Glu Leu His Ala Ile Leu Arg Arg Gln Glu Asp Phe Tyr Pro
    450                 455                 460

Phe Leu Lys Asp Asn Arg Glu Lys Ile Glu Lys Ile Leu Thr Phe Arg
465                 470                 475                 480

Ile Pro Tyr Tyr Val Gly Pro Leu Ala Arg Gly Asn Ser Arg Phe Ala
                485                 490                 495

Trp Met Thr Arg Lys Ser Glu Glu Thr Ile Thr Pro Trp Asn Phe Glu
            500                 505                 510

Glu Val Val Asp Lys Gly Ala Ser Ala Gln Ser Phe Ile Glu Arg Met
        515                 520                 525

Thr Asn Phe Asp Lys Asn Leu Pro Asn Glu Lys Val Leu Pro Lys His
    530                 535                 540

Ser Leu Leu Tyr Glu Tyr Phe Thr Val Tyr Asn Glu Leu Thr Lys Val
545                 550                 555                 560

Lys Tyr Val Thr Glu Gly Met Arg Lys Pro Ala Phe Leu Ser Gly Glu
                565                 570                 575

Gln Lys Lys Ala Ile Val Asp Leu Leu Phe Lys Thr Asn Arg Lys Val
            580                 585                 590

Thr Val Lys Gln Leu Lys Glu Asp Tyr Phe Lys Lys Ile Glu Cys Phe
        595                 600                 605

Asp Ser Val Glu Ile Ser Gly Val Glu Asp Arg Phe Asn Ala Ser Leu
    610                 615                 620

Gly Thr Tyr His Asp Leu Leu Lys Ile Ile Lys Asp Lys Asp Phe Leu
625                 630                 635                 640

Asp Asn Glu Glu Asn Glu Asp Ile Leu Glu Asp Ile Val Leu Thr Leu
                645                 650                 655

Thr Leu Phe Glu Asp Arg Glu Met Ile Glu Glu Arg Leu Lys Thr Tyr
            660                 665                 670

Ala His Leu Phe Asp Asp Lys Val Met Lys Gln Leu Lys Arg Arg Arg
        675                 680                 685

Tyr Thr Gly Trp Gly Arg Leu Ser Arg Lys Leu Ile Asn Gly Ile Arg
    690                 695                 700

Asp Lys Gln Ser Gly Lys Thr Ile Leu Asp Phe Leu Lys Ser Asp Gly
705                 710                 715                 720

Phe Ala Asn Arg Asn Phe Met Gln Leu Ile His Asp Asp Ser Leu Thr
                725                 730                 735

Phe Lys Glu Asp Ile Gln Lys Ala Gln Val Ser Gly Gln Gly Asp Ser
            740                 745                 750

Leu His Glu His Ile Ala Asn Leu Ala Gly Ser Pro Ala Ile Lys Lys
        755                 760                 765

Gly Ile Leu Gln Thr Val Lys Val Val Asp Glu Leu Val Lys Val Met
    770                 775                 780

Gly Arg His Lys Pro Glu Asn Ile Val Ile Glu Met Ala Arg Glu Asn
785                 790                 795                 800

Gln Thr Thr Gln Lys Gly Gln Lys Asn Ser Arg Glu Arg Met Lys Arg
                805                 810                 815

Ile Glu Glu Gly Ile Lys Glu Leu Gly Ser Gln Ile Leu Lys Glu His
            820                 825                 830

Pro Val Glu Asn Thr Gln Leu Gln Asn Glu Lys Leu Tyr Leu Tyr Tyr
        835                 840                 845

Leu Gln Asn Gly Arg Asp Met Tyr Val Asp Gln Glu Leu Asp Ile Asn
    850                 855                 860

Arg Leu Ser Asp Tyr Asp Val Asp His Ile Val Pro Gln Ser Phe Leu
```

-continued

```
865                 870                 875                 880

Lys Asp Asp Ser Ile Asp Asn Lys Val Leu Thr Arg Ser Asp Lys Asn
                885                 890                 895

Arg Gly Lys Ser Asp Asn Val Pro Ser Glu Glu Val Val Lys Lys Met
            900                 905                 910

Lys Asn Tyr Trp Arg Gln Leu Leu Asn Ala Lys Leu Ile Thr Gln Arg
        915                 920                 925

Lys Phe Asp Asn Leu Thr Lys Ala Glu Arg Gly Gly Leu Ser Glu Leu
    930                 935                 940

Asp Lys Ala Gly Phe Ile Lys Arg Gln Leu Val Glu Thr Arg Gln Ile
945                 950                 955                 960

Thr Lys His Val Ala Gln Ile Leu Asp Ser Arg Met Asn Thr Lys Tyr
                965                 970                 975

Asp Glu Asn Asp Lys Leu Ile Arg Glu Val Lys Val Ile Thr Leu Lys
            980                 985                 990

Ser Lys Leu Val Ser Asp Phe Arg  Lys Asp Phe Gln Phe  Tyr Lys Val
        995                 1000                1005

Arg Glu  Ile Asn Asn Tyr His  His Ala His Asp Ala  Tyr Leu Asn
    1010                1015                1020

Ala Val  Val Gly Thr Ala Leu  Ile Lys Lys Tyr Pro  Lys Leu Glu
    1025                1030                1035

Ser Glu  Phe Val Tyr Gly Asp  Tyr Lys Val Tyr Asp  Val Arg Lys
    1040                1045                1050

Met Ile  Ala Lys Ser Glu Gln  Glu Ile Gly Lys Ala  Thr Ala Lys
    1055                1060                1065

Tyr Phe  Phe Tyr Ser Asn Ile  Met Asn Phe Phe Lys  Thr Glu Ile
    1070                1075                1080

Thr Leu  Ala Asn Gly Glu Ile  Arg Lys Arg Pro Leu  Ile Glu Thr
    1085                1090                1095

Asn Gly  Glu Thr Gly Glu Ile  Val Trp Asp Lys Gly  Arg Asp Phe
    1100                1105                1110

Ala Thr  Val Arg Lys Val Leu  Ser Met Pro Gln Val  Asn Ile Val
    1115                1120                1125

Lys Lys  Thr Glu Val Gln Thr  Gly Gly Phe Ser Lys  Glu Ser Ile
    1130                1135                1140

Leu Pro  Lys Arg Asn Ser Asp  Lys Leu Ile Ala Arg  Lys Lys Asp
    1145                1150                1155

Trp Asp  Pro Lys Lys Tyr Gly  Gly Phe Asp Ser Pro  Thr Val Ala
    1160                1165                1170

Tyr Ser  Val Leu Val Val Ala  Lys Val Glu Lys Gly  Lys Ser Lys
    1175                1180                1185

Lys Leu  Lys Ser Val Lys Glu  Leu Leu Gly Ile Thr  Ile Met Glu
    1190                1195                1200

Arg Ser  Ser Phe Glu Lys Asn  Pro Ile Asp Phe Leu  Glu Ala Lys
    1205                1210                1215

Gly Tyr  Lys Glu Val Lys Lys  Asp Leu Ile Ile Lys  Leu Pro Lys
    1220                1225                1230

Tyr Ser  Leu Phe Glu Leu Glu  Asn Gly Arg Lys Arg  Met Leu Ala
    1235                1240                1245

Ser Ala  Gly Glu Leu Gln Lys  Gly Asn Glu Leu Ala  Leu Pro Ser
    1250                1255                1260

Lys Tyr  Val Asn Phe Leu Tyr  Leu Ala Ser His Tyr  Glu Lys Leu
    1265                1270                1275
```

```
Lys Gly  Ser Pro Glu Asp Asn  Glu Gln Lys Gln Leu  Phe Val Glu
    1280                 1285                 1290

Gln His  Lys His Tyr Leu Asp  Glu Ile Ile Glu Gln  Ile Ser Glu
    1295                 1300                 1305

Phe Ser  Lys Arg Val Ile Leu  Ala Asp Ala Asn Leu  Asp Lys Val
    1310                 1315                 1320

Leu Ser  Ala Tyr Asn Lys His  Arg Asp Lys Pro Ile  Arg Glu Gln
    1325                 1330                 1335

Ala Glu  Asn Ile Ile His Leu  Phe Thr Leu Thr Asn  Leu Gly Ala
    1340                 1345                 1350

Pro Ala  Ala Phe Lys Tyr Phe  Asp Thr Thr Ile Asp  Arg Lys Arg
    1355                 1360                 1365

Tyr Thr  Ser Thr Lys Glu Val  Leu Asp Ala Thr Leu  Ile His Gln
    1370                 1375                 1380

Ser Ile  Thr Gly Leu Tyr Glu  Thr Arg Ile Asp Leu  Ser Gln Leu
    1385                 1390                 1395

Gly Gly  Asp Ser Arg Ala Asp  Pro Lys Lys Lys Arg  Lys Val
    1400                 1405                 1410


<210> SEQ ID NO 117
<211> LENGTH: 8237
<212> TYPE: DNA
<213> ORGANISM: Artificial sequence
<220> FEATURE:
<223> OTHER INFORMATION: pRF48

<400> SEQUENCE: 117

aattcgacaa gaaatactcc atcggcctgg acattggaac caactctgtc ggctgggctg     60

tcatcaccga cgagtacaag gtgccctcca agaaattcaa ggtcctcgga aacaccgatc    120

gacactccat caagaaaaac ctcattggtg ccctgttgtt cgattctggc gagactgccg    180

aagctaccag actcaagcga actgctcggc gacgttacac ccgacggaag aaccgaatct    240

gctacctgca ggagatcttt tccaacgaga tggccaaggt ggacgattcg ttctttcatc    300

gactggagga atccttcctc gtcgaggaag acaagaaaca cgagcgtcat cccatctttg    360

gcaacattgt ggacgaggtt gcttaccacg agaagtatcc taccatctac cacctgcgaa    420

agaaactcgt cgattccacc gacaaggcgg atctcagact tatctacctc gctctggcac    480

acatgatcaa gtttcgaggt catttcctca tcgagggcga tctcaatccc gacaacagcg    540

atgtggacaa gctgttcatt cagctcgttc agacctacaa ccagctgttc gaggaaaacc    600

ccatcaatgc ctccggagtc gatgcaaagg ccatcttgtc tgctcgactc tcgaagagca    660

gacgactgga gaacctcatt gcccaacttc ctggcgagaa aaagaacgga ctgtttggca    720

acctcattgc cctttctctt ggtctcacac ccaacttcaa gtccaacttc gatctggcgg    780

aggacgccaa gctccagctg tccaaggaca cctacgacga tgacctcgac aacctgcttg    840

cacagattgg cgatcagtac gccgacctgt ttctcgctgc caagaacctt tcggatgcta    900

ttctcttgtc tgacattctg cgagtcaaca ccgagatcac aaaggctccc ctttctgcct    960

ccatgatcaa gcgatacgac gagcaccatc aggatctcac actgctcaag gctcttgtcc   1020

gacagcaact gcccgagaag tacaaggaga tctttttcga tcagtcgaag aacggctacg   1080

ctggatacat cgacggcgga gcctctcagg aagagttcta caagttcatc aagccaattc   1140

tcgagaagat ggacggaacc gaggaactgc ttgtcaagct caatcgagag gatctgcttc   1200

ggaagcaacg aaccttcgac aacggcagca ttcctcatca gatccacctc ggtgagctgc   1260
```

```
acgccattct tcgacgtcag gaagacttct accccttttct caaggacaac cgagagaaga   1320
tcgagaagat tcttaccttt cgaatcccct actatgttgg tcctcttgcc agaggaaact   1380
ctcgatttgc ttggatgact cgaaagtccg aggaaaccat cactccctgg aacttcgagg   1440
aagtcgtgga caagggtgcc tctgcacagt ccttcatcga gcgaatgacc aacttcgaca   1500
agaatctgcc caacgagaag gttcttccca agcattcgct gctctacgag tactttacag   1560
tctacaacga actcaccaaa gtcaagtacg ttaccgaggg aatgcgaaag cctgccttct   1620
tgtctggcga acagaagaaa gccattgtcg atctcctgtt caagaccaac cgaaaggtca   1680
ctgttaagca gctcaaggag gactacttca agaaaatcga gtgtttcgac agcgtcgaga   1740
tttccggagt tgaggaccga ttcaacgcct ctttgggcac ctatcacgat ctgctcaaga   1800
ttatcaagga caaggatttt ctcgacaacg aggaaaacga ggacattctg gaggacatcg   1860
tgctcactct taccctgttc gaagatcggg agatgatcga ggaacgactc aagacatacg   1920
ctcacctgtt cgacgacaag gtcatgaaac aactcaagcg acgtagatac accggctggg   1980
gaagactttc gcgaaagctc atcaacggca tcagagacaa gcagtccgga aagaccattc   2040
tggactttct caagtccgat ggctttgcca accgaaactt catgcagctc attcacgacg   2100
attctcttac cttcaaggag gacatccaga aggcacaagt gtccggtcag ggcgacagct   2160
tgcacgaaca tattgccaac ctggctggtt cgccagccat caagaaaggc attctccaga   2220
ctgtcaaggt tgtcgacgag ctggtgaagg tcatgggacg tcacaagccc gagaacattg   2280
tgatcgagat ggccagagag aaccagacaa ctcaaaaggg tcagaaaaac tcgcgagagc   2340
ggatgaagcg aatcgaggaa ggcatcaagg agctgggatc ccagattctc aaggagcatc   2400
ccgtcgagaa cactcaactg cagaacgaga agctgtatct ctactatctg cagaatggtc   2460
gagacatgta cgtggatcag gaactggaca tcaatcgtct cagcgactac gatgtggacc   2520
acattgtccc tcaatccttt ctcaaggacg attctatcga caacaaggtc cttacacgat   2580
ccgacaagaa cagaggcaag tcggacaacg ttcccagcga agaggtggtc aaaaagatga   2640
agaactactg gcgacagctg ctcaacgcca agctcattac ccagcgaaag ttcgacaatc   2700
ttaccaaggc cgagcgaggc ggtctgtccg agctcgacaa ggctggcttc atcaagcgtc   2760
aactcgtcga gaccagacag atcacaaagc acgtcgcaca gattctcgat tctcggatga   2820
acaccaagta cgacgagaac gacaagctca tccgagaggt caaggtgatt actctcaagt   2880
ccaaactggt ctccgatttc cgaaaggact ttcagttcta caaggtgcga gagatcaaca   2940
attaccacca tgcccacgat gcttacctca acgccgtcgt tggcactgcg ctcatcaaga   3000
aataccccaa gctcgaaagc gagttcgttt acggcgatta caaggtctac gacgttcgaa   3060
agatgattgc caagtccgaa caggagattg gcaaggctac tgccaagtac ttcttttact   3120
ccaacatcat gaactttttc aagaccgaga tcaccttggc caacggagag attcgaaaga   3180
gaccacttat cgagaccaac ggcgaaactg gagagatcgt gtgggacaag ggtcgagact   3240
ttgcaaccgt gcgaaaggtt ctgtcgatgc ctcaggtcaa catcgtcaag aaaaccgagg   3300
ttcagactgg cggattctcc aaggagtcga ttctgcccaa gcgaaactcc gacaagctca   3360
tcgctcgaaa gaaagactgg gatcccaaga aatacggtgg cttcgattct cctaccgtcg   3420
cctattccgt gcttgtcgtt gcgaaggtcg agaagggcaa gtccaaaaag ctcaagtccg   3480
tcaaggagct gctcggaatt accatcatgg agcgatcgag cttcgagaag aatcccatcg   3540
acttcttgga agccaagggt tacaaggagg tcaagaaaga cctcattatc aagctgccca   3600
```

-continued

```
agtactctct gttcgaactg gagaacggtc gaaagcgtat gctcgcctcc gctggcgagc   3660
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560
ctttttgcgt ttctacaaac tcttttgttt atttttctaa atacattcaa atatgtatcc   4620
gctcatgaga caataaccct gataaatgct tcaataatat tgaaaaagga agagtatgag   4680
tattcaacat ttccgtgtcg cccttattcc cttttttgcg gcattttgcc ttcctgtttt   4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt   4920
tgacgccggg caagagcaac tcggtcgccg catacactat tctcagaatg acttggttga   4980
gtactcacca gtcacagaaa agcatcttac ggatggcatg acagtaagag aattatgcag   5040
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg ggtctcgcgg   5400
tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580
acttcatttt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga gatccttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
ccacttcaag aactctgtag caccgcctac atacctcgct ctgctaatcc tgttaccagt   5940
ggctgctgcc agtggcgata agtcgtgtct taccgggttg gactcaagac gatagttacc   6000
```

```
ggataaggcg cagcggtcgg gctgaacggg gggttcgtgc acacagccca gcttggagcg   6060

aacgacctac accgaactga gatacctaca gcgtgagcta tgagaaagcg ccacgcttcc   6120

cgaagggaga aaggcggaca ggtatccggt aagcggcagg gtcggaacag gagagcgcac   6180

gagggagctt ccagggggaa acgcctggta tctttatagt cctgtcgggt ttcgccacct   6240

ctgacttgag cgtcgatttt tgtgatgctc gtcagggggg cggagcctat ggaaaaacgc   6300

cagcaacgcg gcctttttac ggttcctggc cttttgctgg ccttttgctc acatgttctt   6360

tcctgcgtta tcccctgatt ctgtggataa ccgtattacc gcctttgagt gagctgatac   6420

cgctcgccgc agccgaacga ccgagcgcag cgagtcagtg agcgaggaag cggaagagcg   6480

cctgatgcgg tattttctcc ttacgcatct gtgcggtatt tcacaccgca tatggtgcac   6540

tctcagtaca atctgctctg atgccgcata gttaagccag tatacactcc gctatcgcta   6600

cgtgactggg tcatggctgc gccccgacac ccgccaacac ccgctgacgc gccctgacgg   6660

gcttgtctgc tcccggcatc cgcttacaga caagctgtga ccgtctccgg gagctgcatg   6720

tgtcagaggt tttcaccgtc atcaccgaaa cgcgcgaggc agcagatcaa ttcgcgcgcg   6780

aaggcgaagc ggcatgcata atgtgcctgt caaatggacg aagcagggat tctgcaaacc   6840

ctatgctact ccgtcaagcc gtcaattgtc tgattcgtta ccaattatga caacttgacg   6900

gctacatcat tcactttttc ttcacaaccg gcacggaact cgctcgggct ggccccggtg   6960

cattttttaa atacccgcga gaaatagagt tgatcgtcaa aaccaacatt gcgaccgacg   7020

gtggcgatag gcatccgggt ggtgctcaaa agcagcttcg cctggctgat acgttggtcc   7080

tcgcgccagc ttaagacgct aatccctaac tgctggcgga aaagatgtga cagacgcgac   7140

ggcgacaagc aaacatgctg tgcgacgctg gcgatatcaa aattgctgtc tgccaggtga   7200

tcgctgatgt actgacaagc ctcgcgtacc cgattatcca tcggtggatg gagcgactcg   7260

ttaatcgctt ccatgcgccg cagtaacaat tgctcaagca gatttatcgc cagcagctcc   7320

gaatagcgcc cttccccttg cccggcgtta atgatttgcc caaacaggtc gctgaaatgc   7380

ggctggtgcg cttcatccgg gcgaaagaac cccgtattgg caaatattga cggccagtta   7440

agccattcat gccagtaggc gcgcggacga aagtaaaccc actggtgata ccattcgcga   7500

gcctccggat gacgaccgta gtgatgaatc tctcctggcg ggaacagcaa aatatcaccc   7560

ggtcggcaaa caaattctcg tccctgattt ttcaccaccc cctgaccgcg aatggtgaga   7620

ttgagaatat aacctttcat tcccagcggt cggtcgataa aaaaatcgag ataaccgttg   7680

gcctcaatcg gcgttaaacc cgccaccaga tgggcattaa acgagtatcc cggcagcagg   7740

ggatcatttt gcgcttcagc catacttttc atactcccgc cattcagaga agaaaccaat   7800

tgtccatatt gcatcagaca ttgccgtcac tgcgtctttt actggctctt ctcgctaacc   7860

aaaccggtaa ccccgcttat taaaagcatt ctgtaacaaa gcgggaccaa agccatgaca   7920

aaaacgcgta acaaaagtgt ctataatcac ggcagaaaag tccacattga ttatttgcac   7980

ggcgtcacac tttgctatgc catagcattt ttatccataa gattagcgga tcctacctga   8040

cgctttttat cgcaactctc tactgtttct ccatacccgt ttttgggct aacaggagga   8100

attaaccatg gggggttctc atcatcatca tcatcatggt atggctagca tgactggtgg   8160

acagcaaatg ggtcgggatc tgtacgacga tgacgataag gatccgagct cgagatctgc   8220

agctggtacc atatggg                                                  8237
```

<210> SEQ ID NO 118

<211> LENGTH: 8153
<212> TYPE: DNA
<213> ORGANISM: Artificial sequence
<220> FEATURE:
<223> OTHER INFORMATION: pRF243

<400> SEQUENCE: 118

```
catggggcat caccatcacc accattgttt tttcaaagac gaactggaat tcgacaagaa     60
atactccatc ggcctggaca ttggaaccaa ctctgtcggc tgggctgtca tcaccgacga    120
gtacaaggtg ccctccaaga aattcaaggt cctcggaaac accgatcgac actccatcaa    180
gaaaaacctc attggtgccc tgttgttcga ttctggcgag actgccgaag ctaccagact    240
caagcgaact gctcggcgac gttacacccg acggaagaac cgaatctgct acctgcagga    300
gatcttttcc aacgagatgg ccaaggtgga cgattcgttc tttcatcgac tggaggaatc    360
cttcctcgtc gaggaagaca agaaacacga gcgtcatccc atctttggca acattgtgga    420
cgaggttgct taccacgaga agtatcctac catctaccac ctgcgaaaga aactcgtcga    480
ttccaccgac aaggcggatc tcagacttat ctacctcgct ctggcacaca tgatcaagtt    540
tcgaggtcat ttcctcatcg agggcgatct caatcccgac aacagcgatg tggacaagct    600
gttcattcag ctcgttcaga cctacaacca gctgttcgag gaaaacccca tcaatgcctc    660
cggagtcgat gcaaaggcca tcttgtctgc tcgactctcg aagagcagac gactggagaa    720
cctcattgcc caacttcctg gcgagaaaaa gaacggactg tttggcaacc tcattgccct    780
ttctcttggt ctcacaccca acttcaagtc caacttcgat ctggcggagg acgccaagct    840
ccagctgtcc aaggacacct acgacgatga cctcgacaac ctgcttgcac agattggcga    900
tcagtacgcc gacctgtttc tcgctgccaa gaacctttcg gatgctattc tcttgtctga    960
cattctgcga gtcaacaccg agatcacaaa ggctcccctt tctgcctcca tgatcaagcg   1020
atacgacgag caccatcagg atctcacact gctcaaggct cttgtccgac agcaactgcc   1080
cgagaagtac aaggagatct tttcgatca gtcgaagaac ggctacgctg gatacatcga   1140
cggcggagcc tctcaggaag agttctacaa gttcatcaag ccaattctcg agaagatgga   1200
cggaaccgag gaactgcttg tcaagctcaa tcgagaggat ctgcttcgga agcaacgaac   1260
cttcgacaac ggcagcattc ctcatcagat ccacctcggt gagctgcacg ccattcttcg   1320
acgtcaggaa gacttctacc cctttctcaa ggacaaccga gagaagatcg agaagattct   1380
tacctttcga atcccctact atgttggtcc tcttgccaga ggaaactctc gatttgcttg   1440
gatgactcga aagtccgagg aaaccatcac tccctggaac ttcgaggaag tcgtggacaa   1500
gggtgcctct gcacagtcct tcatcgagcg aatgaccaac ttcgacaaga atctgcccaa   1560
cgagaaggtt cttcccaagc attcgctgct ctacgagtac tttacagtct acaacgaact   1620
caccaaagtc aagtacgtta ccgagggaat gcgaaagcct gccttcttgt ctggcgaaca   1680
gaagaaagcc attgtcgatc tcctgttcaa gaccaaccga aaggtcactg ttaagcagct   1740
caaggaggac tacttcaaga aaatcgagtg tttcgacagc gtcgagattt ccggagttga   1800
ggaccgattc aacgcctctt tgggcaccta tcacgatctg ctcaagatta tcaaggacaa   1860
ggattttctc gacaacgagg aaaacgagga cattctggag gacatcgtgc tcactcttac   1920
cctgttcgaa gatcgggaga tgatcgagga acgactcaag acatacgctc acctgttcga   1980
cgacaaggtc atgaaacaac tcaagcgacg tagatacacc ggctggggaa gactttcgcg   2040
aaagctcatc aacggcatca gagacaagca gtccggaaag accattctgg actttctcaa   2100
gtccgatggc tttgccaacc gaaacttcat gcagctcatt cacgacgatt ctcttacctt   2160
```

-continued

```
caaggaggac atccagaagg cacaagtgtc cggtcagggc gacagcttgc acgaacatat   2220
tgccaacctg gctggttcgc cagccatcaa gaaaggcatt ctccagactg tcaaggttgt   2280
cgacgagctg gtgaaggtca tgggacgtca caagcccgag aacattgtga tcgagatggc   2340
cagagagaac cagacaactc aaaagggtca gaaaaactcg cgagagcgga tgaagcgaat   2400
cgaggaaggc atcaaggagc tgggatccca gattctcaag gagcatcccg tcgagaacac   2460
tcaactgcag aacgagaagc tgtatctcta ctatctgcag aatggtcgag acatgtacgt   2520
ggatcaggaa ctggacatca atcgtctcag cgactacgat gtggaccaca ttgtccctca   2580
atcctttctc aaggacgatt ctatcgacaa caaggtcctt acacgatccg acaagaacag   2640
aggcaagtcg gacaacgttc ccagcgaaga ggtggtcaaa aagatgaaga actactggcg   2700
acagctgctc aacgccaagc tcattaccca gcgaaagttc gacaatctta ccaaggccga   2760
gcgaggcggt ctgtccgagc tcgacaaggc tggcttcatc aagcgtcaac tcgtcgagac   2820
cagacagatc acaaagcacg tcgcacagat tctcgattct cggatgaaca ccaagtacga   2880
cgagaacgac aagctcatcc gagaggtcaa ggtgattact ctcaagtcca aactggtctc   2940
cgatttccga aaggactttc agttctacaa ggtgcgagag atcaacaatt accaccatgc   3000
ccacgatgct tacctcaacg ccgtcgttgg cactgcgctc atcaagaaat accccaagct   3060
cgaaagcgag ttcgtttacg gcgattacaa ggtctacgac gttcgaaaga tgattgccaa   3120
gtccgaacag gagattggca aggctactgc caagtacttc ttttactcca acatcatgaa   3180
ctttttcaag accgagatca ccttggccaa cggagagatt cgaaagagac cacttatcga   3240
gaccaacggc gaaactggag agatcgtgtg ggacaagggt cgagactttg caaccgtgcg   3300
aaaggttctg tcgatgcctc aggtcaacat cgtcaagaaa accgaggttc agactggcgg   3360
attctccaag gagtcgattc tgcccaagcg aaactccgac aagctcatcg ctcgaaagaa   3420
agactgggat cccaagaaat acggtggctt cgattctcct accgtcgcct attccgtgct   3480
tgtcgttgcg aaggtcgaga agggcaagtc caaaaagctc aagtccgtca aggagctgct   3540
cggaattacc atcatggagc gatcgagctt cgagaagaat cccatcgact tcttggaagc   3600
caagggttac aaggaggtca agaaagacct cattatcaag ctgcccaagt actctctgtt   3660
cgaactggag aacggtcgaa agcgtatgct cgcctccgct ggcgagctgc agaagggaaa   3720
cgagcttgcc ttgccttcga agtacgtcaa ctttctctat ctggcttctc actacgagaa   3780
gctcaagggt tctcccgagg acaacgaaca gaagcaactc ttcgttgagc agcacaaaca   3840
ttacctcgac gagattatcg agcagatttc cgagttttcg aagcgagtca tcctggctga   3900
tgccaacttg gacaaggtgc tctctgccta caacaagcat cgggacaaac ccattcgaga   3960
acaggcggag aacatcattc acctgtttac tcttaccaac ctgggtgctc ctgcagcttt   4020
caagtacttc gataccacta tcgaccgaaa gcggtacaca tccaccaagg aggttctcga   4080
tgccaccctg attcaccagt ccatcactgg cctgtacgag acccgaatcg acctgtctca   4140
gcttggtggc gactccagag ccgatcccaa gaaaaagcga aaggtctaag cggccgctaa   4200
gcttggctgt tttggcggat gagagaagat tttcagcctg atacagatta aatcagaacg   4260
cagaagcggt ctgataaaac agaatttgcc tggcggcagt agcgcggtgg tcccacctga   4320
ccccatgccg aactcagaag tgaaacgccg tagcgccgat ggtagtgtgg ggtctcccca   4380
tgcgagagta gggaactgcc aggcatcaaa taaaacgaaa ggctcagtcg aaagactggg   4440
cctttcgttt tatctgttgt ttgtcggtga acgctctcct gagtaggaca aatccgccgg   4500
```

-continued

```
gagcggattt gaacgttgcg aagcaacggc ccggagggtg gcgggcagga cgcccgccat   4560
aaactgccag gcatcaaatt aagcagaagg ccatcctgac ggatggcctt tttgcgtttc   4620
tacaaactct tttgtttatt tttctaaata cattcaaata tgtatccgct catgagacaa   4680
taaccctgat aaatgcttca ataatattga aaaaggaaga gtatgagtat tcaacatttc   4740
cgtgtcgccc ttattccctt ttttgcggca ttttgccttc ctgtttttgc tcacccagaa   4800
acgctggtga aagtaaaaga tgctgaagat cagttgggtg cacgagtggg ttacatcgaa   4860
ctggatctca acagcggtaa gatccttgag agttttcgcc ccgaagaacg ttttccaatg   4920
atgagcactt ttaaagttct gctatgtggc gcggtattat cccgtgttga cgccgggcaa   4980
gagcaactcg gtcgccgcat acactattct cagaatgact tggttgagta ctcaccagtc   5040
acagaaaagc atcttacgga tggcatgaca gtaagagaat tatgcagtgc tgccataacc   5100
atgagtgata acactgcggc caacttactt ctgacaacga tcggaggacc gaaggagcta   5160
accgcttttt tgcacaacat gggggatcat gtaactcgcc ttgatcgttg ggaaccggag   5220
ctgaatgaag ccataccaaa cgacgagcgt gacaccacga tgcctgtagc aatggcaaca   5280
acgttgcgca aactattaac tggcgaacta cttactctag cttcccggca acaattaata   5340
gactggatgg aggcggataa agttgcagga ccacttctgc gctcggccct tccggctggc   5400
tggtttattg ctgataaatc tggagccggt gagcgtgggt ctcgcggtat cattgcagca   5460
ctggggccag atggtaagcc ctcccgtatc gtagttatct acacgacggg gagtcaggca   5520
actatggatg aacgaaatag acagatcgct gagataggtg cctcactgat taagcattgg   5580
taactgtcag accaagttta ctcatatata ctttagattg atttaaaact tcatttttaa   5640
tttaaaagga tctaggtgaa gatccttttt gataatctca tgaccaaaat cccttaacgt   5700
gagttttcgt tccactgagc gtcagacccc gtagaaaaga tcaaaggatc ttcttgagat   5760
cctttttttc tgcgcgtaat ctgctgcttg caaacaaaaa aaccaccgct accagcggtg   5820
gtttgtttgc cggatcaaga gctaccaact ctttttccga aggtaactgg cttcagcaga   5880
gcgcagatac caaatactgt ccttctagtg tagccgtagt taggccacca cttcaagaac   5940
tctgtagcac cgcctacata cctcgctctg ctaatcctgt taccagtggc tgctgccagt   6000
ggcgataagt cgtgtcttac cgggttggac tcaagacgat agttaccgga taaggcgcag   6060
cggtcgggct gaacgggggg ttcgtgcaca cagcccagct tggagcgaac gacctacacc   6120
gaactgagat acctacagcg tgagctatga gaaagcgcca cgcttcccga agggagaaag   6180
gcggacaggt atccggtaag cggcagggtc ggaacaggag agcgcacgag ggagcttcca   6240
gggggaaacg cctggtatct ttatagtcct gtcgggtttc gccacctctg acttgagcgt   6300
cgatttttgt gatgctcgtc aggggggcgg agcctatgga aaaacgccag caacgcggcc   6360
tttttacggt tcctggcctt ttgctggcct tttgctcaca tgttctttcc tgcgttatcc   6420
cctgattctg tggataaccg tattaccgcc tttgagtgag ctgataccgc tcgccgcagc   6480
cgaacgaccg agcgcagcga gtcagtgagc gaggaagcgg aagagcgcct gatgcggtat   6540
tttctcctta cgcatctgtg cggtatttca caccgcatat ggtgcactct cagtacaatc   6600
tgctctgatg ccgcatagtt aagccagtat acactccgct atcgctacgt gactgggtca   6660
tggctgcgcc ccgacacccg ccaacacccg ctgacgcgcc ctgacgggct tgtctgctcc   6720
cggcatccgc ttacagacaa gctgtgaccg tctccgggag ctgcatgtgt cagaggtttt   6780
caccgtcatc accgaaacgc gcgaggcagc agatcaattc gcgcgcgaag gcgaagcggc   6840
atgcataatg tgcctgtcaa atggacgaag cagggattct gcaaacccta tgctactccg   6900
```

```
tcaagccgtc aattgtctga ttcgttacca attatgacaa cttgacggct acatcattca   6960
ctttttcttc acaaccggca cggaactcgc tcgggctggc cccggtgcat tttttaaata   7020
cccgcgagaa atagagttga tcgtcaaaac caacattgcg accgacggtg gcgataggca   7080
tccgggtggt gctcaaaagc agcttcgcct ggctgatacg ttggtcctcg cgccagctta   7140
agacgctaat ccctaactgc tggcggaaaa gatgtgacag acgcgacggc gacaagcaaa   7200
catgctgtgc gacgctggcg atatcaaaat tgctgtctgc caggtgatcg ctgatgtact   7260
gacaagcctc gcgtacccga ttatccatcg gtggatggag cgactcgtta atcgcttcca   7320
tgcgccgcag taacaattgc tcaagcagat ttatcgccag cagctccgaa tagcgccctt   7380
ccccttgccc ggcgttaatg atttgcccaa acaggtcgct gaaatgcggc tggtgcgctt   7440
catccgggcg aaagaacccc gtattggcaa atattgacgg ccagttaagc cattcatgcc   7500
agtaggcgcg cggacgaaag taaacccact ggtgatacca ttcgcgagcc tccggatgac   7560
gaccgtagtg atgaatctct cctggcggga acagcaaaat atcacccggt cggcaaacaa   7620
attctcgtcc ctgatttttc accacccccct gaccgcgaat ggtgagattg agaatataac   7680
ctttcattcc cagcggtcgg tcgataaaaa aatcgagata accgttggcc tcaatcggcg   7740
ttaaacccgc caccagatgg gcattaaacg agtatcccgg cagcagggga tcattttgcg   7800
cttcagccat acttttcata ctcccgccat tcagagaaga aaccaattgt ccatattgca   7860
tcagacattg ccgtcactgc gtcttttact ggctcttctc gctaaccaaa ccggtaaccc   7920
cgcttattaa aagcattctg taacaaagcg ggaccaaagc catgacaaaa acgcgtaaca   7980
aaagtgtcta taatcacggc agaaaagtcc acattgatta tttgcacggc gtcacacttt   8040
gctatgccat agcattttta tccataagat tagcggatcc tacctgacgc tttttatcgc   8100
aactctctac tgtttctcca tacccgtttt ttgggctaac aggaggaatt aac          8153
```

<210> SEQ ID NO 119
<211> LENGTH: 8204
<212> TYPE: DNA
<213> ORGANISM: Artificial sequence
<220> FEATURE:
<223> OTHER INFORMATION: pRF238

<400> SEQUENCE: 119

```
catggggcat catcatcacc atcacggcgc cctgttctta ggccagctgg gcgccgcggg     60
atccacgatg ggtgcgccga agaaaaagcg caaagttgaa ttcgacaaga aatactccat    120
cggcctggac attggaacca actctgtcgg ctgggctgtc atcaccgacg agtacaaggt    180
gccctccaag aaattcaagg tcctcggaaa caccgatcga cactccatca agaaaaacct    240
cattggtgcc ctgttgttcg attctggcga gactgccgaa gctaccagac tcaagcgaac    300
tgctcggcga cgttacaccc gacggaagaa ccgaatctgc tacctgcagg agatcttttc    360
caacgagatg gccaaggtgg acgattcgtt ctttcatcga ctggaggaat ccttcctcgt    420
cgaggaagac aagaaacacg agcgtcatcc catctttggc aacattgtgg acgaggttgc    480
ttaccacgag aagtatccta ccatctacca cctgcgaaag aaactcgtcg attccaccga    540
caaggcggat ctcagactta tctacctcgc tctggcacac atgatcaagt ttcgaggtca    600
tttcctcatc gagggcgatc tcaatcccga caacagcgat gtggacaagc tgttcattca    660
gctcgttcag acctacaacc agctgttcga ggaaaacccc atcaatgcct ccggagtcga    720
tgcaaaggcc atcttgtctg ctcgactctc gaagagcaga cgactggaga acctcattgc    780
```

-continued

```
ccaacttcct ggcgagaaaa agaacggact gtttggcaac ctcattgccc tttctcttgg    840
tctcacaccc aacttcaagt ccaacttcga tctggcggag gacgccaagc tccagctgtc    900
caaggacacc tacgacgatg acctcgacaa cctgcttgca cagattggcg atcagtacgc    960
cgacctgttt ctcgctgcca agaacctttc ggatgctatt ctcttgtctg acattctgcg   1020
agtcaacacc gagatcacaa aggctcccct ttctgcctcc atgatcaagc gatacgacga   1080
gcaccatcag gatctcacac tgctcaaggc tcttgtccga cagcaactgc ccgagaagta   1140
caaggagatc tttttcgatc agtcgaagaa cggctacgct ggatacatcg acggcggagc   1200
ctctcaggaa gagttctaca agttcatcaa gccaattctc gagaagatgg acggaaccga   1260
ggaactgctt gtcaagctca atcgagagga tctgcttcgg aagcaacgaa ccttcgacaa   1320
cggcagcatt cctcatcaga tccacctcgg tgagctgcac gccattcttc gacgtcagga   1380
agacttctac ccctttctca aggacaaccg agagaagatc gagaagattc ttacctttcg   1440
aatcccctac tatgttggtc ctcttgccag aggaaactct cgatttgctt ggatgactcg   1500
aaagtccgag gaaaccatca ctccctggaa cttcgaggaa gtcgtggaca agggtgcctc   1560
tgcacagtcc ttcatcgagc gaatgaccaa cttcgacaag aatctgccca acgagaaggt   1620
tcttcccaag cattcgctgc tctacgagta ctttacagtc tacaacgaac tcaccaaagt   1680
caagtacgtt accgagggaa tgcgaaagcc tgccttcttg tctggcgaac agaagaaagc   1740
cattgtcgat ctcctgttca agaccaaccg aaaggtcact gttaagcagc tcaaggagga   1800
ctacttcaag aaaatcgagt gtttcgacag cgtcgagatt tccggagttg aggaccgatt   1860
caacgcctct ttgggcacct atcacgatct gctcaagatt atcaaggaca aggattttct   1920
cgacaacgag gaaaacgagg acattctgga ggacatcgtg ctcactctta ccctgttcga   1980
agatcgggag atgatcgagg aacgactcaa gacatacgct cacctgttcg acgacaaggt   2040
catgaaacaa ctcaagcgac gtagatacac cggctgggga agactttcgc gaaagctcat   2100
caacggcatc agagacaagc agtccggaaa gaccattctg gactttctca agtccgatgg   2160
ctttgccaac cgaaacttca tgcagctcat tcacgacgat tctcttacct tcaaggagga   2220
catccagaag gcacaagtgt ccggtcaggg cgacagcttg cacgaacata ttgccaacct   2280
ggctggttcg ccagccatca agaaaggcat tctccagact gtcaaggttg tcgacgagct   2340
ggtgaaggtc atgggacgtc acaagcccga gaacattgtg atcgagatgg ccagagagaa   2400
ccagacaact caaaagggtc agaaaaactc gcgagagcgg atgaagcgaa tcgaggaagg   2460
catcaaggag ctgggatccc agattctcaa ggagcatccc gtcgagaaca ctcaactgca   2520
gaacgagaag ctgtatctct actatctgca gaatggtcga gacatgtacg tggatcagga   2580
actggacatc aatcgtctca gcgactacga tgtggaccac attgtccctc aatcctttct   2640
caaggacgat tctatcgaca acaaggtcct tacacgatcc gacaagaaca gaggcaagtc   2700
ggacaacgtt cccagcgaag aggtggtcaa aaagatgaag aactactggc gacagctgct   2760
caacgccaag ctcattaccc agcgaaagtt cgacaatctt accaaggccg agcgaggcgg   2820
tctgtccgag ctcgacaagg ctggcttcat caagcgtcaa ctcgtcgaga ccagacagat   2880
cacaaagcac gtcgcacaga ttctcgattc tcggatgaac accaagtacg acgagaacga   2940
caagctcatc cgagaggtca aggtgattac tctcaagtcc aaactggtct ccgatttccg   3000
aaaggacttt cagttctaca aggtgcgaga gatcaacaat taccaccatg cccacgatgc   3060
ttacctcaac gccgtcgttg gcactgcgct catcaagaaa taccccaagc tcgaaagcga   3120
gttcgtttac ggcgattaca aggtctacga cgttcgaaag atgattgcca agtccgaaca   3180
```

```
ggagattggc aaggctactg ccaagtactt cttttactcc aacatcatga actttttcaa   3240
gaccgagatc accttggcca acggagagat tcgaaagaga ccacttatcg agaccaacgg   3300
cgaaactgga gagatcgtgt gggacaaggg tcgagacttt gcaaccgtgc gaaaggttct   3360
gtcgatgcct caggtcaaca tcgtcaagaa aaccgaggtt cagactggcg gattctccaa   3420
ggagtcgatt ctgcccaagc gaaactccga caagctcatc gctcgaaaga aagactggga   3480
tcccaagaaa tacggtggct tcgattctcc taccgtcgcc tattccgtgc ttgtcgttgc   3540
gaaggtcgag aagggcaagt ccaaaaagct caagtccgtc aaggagctgc tcggaattac   3600
catcatggag cgatcgagct tcgagaagaa tcccatcgac ttcttggaag ccaagggtta   3660
caaggaggtc aagaaagacc tcattatcaa gctgcccaag tactctctgt tcgaactgga   3720
gaacggtcga aagcgtatgc tcgcctccgc tggcgagctg cagaagggaa acgagcttgc   3780
cttgccttcg aagtacgtca actttctcta tctggcttct cactacgaga agctcaaggg   3840
ttctcccgag gacaacgaac agaagcaact cttcgttgag cagcacaaac attacctcga   3900
cgagattatc gagcagattt ccgagttttc gaagcgagtc atcctggctg atgccaactt   3960
ggacaaggtg ctctctgcct acaacaagca tcgggacaaa cccattcgag aacaggcgga   4020
gaacatcatt cacctgttta ctcttaccaa cctgggtgct cctgcagctt tcaagtactt   4080
cgataccact atcgaccgaa agcggtacac atccaccaag gaggttctcg atgccaccct   4140
gattcaccag tccatcactg gcctgtacga gacccgaatc gacctgtctc agcttggtgg   4200
cgactccaga gccgatccca agaaaaagcg aaaggtctaa gcggccgcta agcttggctg   4260
ttttggcgga tgagagaaga ttttcagcct gatacagatt aaatcagaac gcagaagcgg   4320
tctgataaaa cagaatttgc ctggcggcag tagcgcggtg gtcccacctg accccatgcc   4380
gaactcagaa gtgaaacgcc gtagcgccga tggtagtgtg gggtctcccc atgcgagagt   4440
agggaactgc caggcatcaa ataaaacgaa aggctcagtc gaaagactgg gcctttcgtt   4500
ttatctgttg tttgtcggtg aacgctctcc tgagtaggac aaatccgccg ggagcggatt   4560
tgaacgttgc gaagcaacgg cccggagggt ggcgggcagg acgcccgcca taaactgcca   4620
ggcatcaaat taagcagaag gccatcctga cggatggcct ttttgcgttt ctacaaactc   4680
ttttgtttat ttttctaaat acattcaaat atgtatccgc tcatgagaca ataaccctga   4740
taaatgcttc aataatattg aaaaaggaag agtatgagta ttcaacattt ccgtgtcgcc   4800
cttattccct tttttgcggc attttgcctt cctgtttttg ctcacccaga aacgctggtg   4860
aaagtaaaag atgctgaaga tcagttgggt gcacgagtgg gttacatcga actggatctc   4920
aacagcggta agatccttga gagttttcgc cccgaagaac gttttccaat gatgagcact   4980
tttaaagttc tgctatgtgg cgcggtatta tcccgtgttg acgccgggca agagcaactc   5040
ggtcgccgca tacactattc tcagaatgac ttggttgagt actcaccagt cacagaaaag   5100
catcttacgg atggcatgac agtaagagaa ttatgcagtg ctgccataac catgagtgat   5160
aacactgcgg ccaacttact tctgacaacg atcggaggac cgaaggagct aaccgctttt   5220
ttgcacaaca tgggggatca tgtaactcgc cttgatcgtt gggaaccgga gctgaatgaa   5280
gccataccaa acgacgagcg tgacaccacg atgcctgtag caatggcaac aacgttgcgc   5340
aaactattaa ctggcgaact acttactcta gcttcccggc aacaattaat agactggatg   5400
gaggcggata aagttgcagg accacttctg cgctcggccc ttccggctgg ctggtttatt   5460
gctgataaat ctggagccgg tgagcgtggg tctcgcggta tcattgcagc actggggcca   5520
```

```
gatggtaagc cctcccgtat cgtagttatc tacacgacgg ggagtcaggc aactatggat   5580
gaacgaaata gacagatcgc tgagataggt gcctcactga ttaagcattg gtaactgtca   5640
gaccaagttt actcatatat actttagatt gatttaaaac ttcattttta atttaaaagg   5700
atctaggtga agatcctttt tgataatctc atgaccaaaa tcccttaacg tgagttttcg   5760
ttccactgag cgtcagaccc cgtagaaaag atcaaaggat cttcttgaga tccttttttt   5820
ctgcgcgtaa tctgctgctt gcaaacaaaa aaaccaccgc taccagcggt ggtttgtttg   5880
ccggatcaag agctaccaac tctttttccg aaggtaactg gcttcagcag agcgcagata   5940
ccaaatactg tccttctagt gtagccgtag ttaggccacc acttcaagaa ctctgtagca   6000
ccgcctacat acctcgctct gctaatcctg ttaccagtgg ctgctgccag tggcgataag   6060
tcgtgtctta ccgggttgga ctcaagacga tagttaccgg ataaggcgca gcggtcgggc   6120
tgaacggggg gttcgtgcac acagcccagc ttggagcgaa cgacctacac cgaactgaga   6180
tacctacagc gtgagctatg agaaagcgcc acgcttcccg aagggagaaa ggcggacagg   6240
tatccggtaa gcggcagggt cggaacagga gagcgcacga gggagcttcc agggggaaac   6300
gcctggtatc tttatagtcc tgtcgggttt cgccacctct gacttgagcg tcgatttttg   6360
tgatgctcgt caggggggcg gagcctatgg aaaaacgcca gcaacgcggc ctttttacgg   6420
ttcctggcct tttgctggcc ttttgctcac atgttctttc ctgcgttatc ccctgattct   6480
gtggataacc gtattaccgc ctttgagtga gctgataccg ctcgccgcag ccgaacgacc   6540
gagcgcagcg agtcagtgag cgaggaagcg gaagagcgcc tgatgcggta ttttctcctt   6600
acgcatctgt gcggtatttc acaccgcata tggtgcactc tcagtacaat ctgctctgat   6660
gccgcatagt taagccagta tacactccgc tatcgctacg tgactgggtc atggctgcgc   6720
cccgacaccc gccaacaccc gctgacgcgc cctgacgggc ttgtctgctc ccggcatccg   6780
cttacagaca agctgtgacc gtctccggga gctgcatgtg tcagaggttt tcaccgtcat   6840
caccgaaacg cgcgaggcag cagatcaatt cgcgcgcgaa ggcgaagcgg catgcataat   6900
gtgcctgtca aatggacgaa gcagggattc tgcaaaccct atgctactcc gtcaagccgt   6960
caattgtctg attcgttacc aattatgaca acttgacggc tacatcattc actttttctt   7020
cacaaccggc acggaactcg ctcgggctgg ccccggtgca tttttaaat acccgcgaga   7080
aatagagttg atcgtcaaaa ccaacattgc gaccgacggt ggcgataggc atccgggtgg   7140
tgctcaaaag cagcttcgcc tggctgatac gttggtcctc gcgccagctt aagacgctaa   7200
tccctaactg ctggcggaaa agatgtgaca gacgcgacgg cgacaagcaa acatgctgtg   7260
cgacgctggc gatatcaaaa ttgctgtctg ccaggtgatc gctgatgtac tgacaagcct   7320
cgcgtacccg attatccatc ggtggatgga gcgactcgtt aatcgcttcc atgcgccgca   7380
gtaacaattg ctcaagcaga tttatcgcca gcagctccga atagcgccct tccccttgcc   7440
cggcgttaat gatttgccca aacaggtcgc tgaaatgcgg ctggtgcgct tcatccgggc   7500
gaaagaaccc cgtattggca aatattgacg gccagttaag ccattcatgc cagtaggcgc   7560
gcggacgaaa gtaaacccac tggtgatacc attcgcgagc ctccggatga cgaccgtagt   7620
gatgaatctc tcctggcggg aacagcaaaa tatcacccgg tcggcaaaca aattctcgtc   7680
cctgattttt caccaccccc tgaccgcgaa tggtgagatt gagaatataa cctttcattc   7740
ccagcggtcg gtcgataaaa aaatcgagat aaccgttggc ctcaatcggc gttaaacccg   7800
ccaccagatg ggcattaaac gagtatcccg gcagcagggg atcattttgc gcttcagcca   7860
tacttttcat actcccgcca ttcagagaag aaaccaattg tccatattgc atcagacatt   7920
```

gccgtcactg cgtcttttac tggctcttct cgctaaccaa accggtaacc ccgcttatta 7980
aaagcattct gtaacaaagc gggaccaaag ccatgacaaa aacgcgtaac aaaagtgtct 8040
ataatcacgg cagaaaagtc cacattgatt atttgcacgg cgtcacactt tgctatgcca 8100
tagcattttt atccataaga ttagcggatc ctacctgacg ctttttatcg caactctcta 8160
ctgtttctcc atacccgttt tttgggctaa caggaggaat taac 8204

<210> SEQ ID NO 120
<211> LENGTH: 1149
<212> TYPE: DNA
<213> ORGANISM: Escherichia coli
<220> FEATURE:
<221> NAME/KEY: misc_feature
<222> LOCATION: (1)..(1149)
<223> OTHER INFORMATION: galK gene

<400> SEQUENCE: 120
atgagtctga aagaaaaaac acaatctctg tttgccaacg catttggcta ccctgccact 60
cacaccattc aggcgcctgg ccgcgtgaat ttgattggtg aacacaccga ctacaacgac 120
ggtttcgttc tgccctgcgc gattgattat caaaccgtga tcagttgtgc accacgcgat 180
gaccgtaaag ttcgcgtgat ggcagccgat tatgaaaatc agctcgacga gttttccctc 240
gatgcgccca ttgtcgcaca tgaaaactat caatgggcta actacgttcg tggcgtggtg 300
aaacatctgc aactgcgtaa caacagcttc ggcggcgtgg acatggtgat cagcggcaat 360
gtgccgcagg gtgccgggtt aagttcttcc gcttcactgg aagtcgcggt cggaaccgta 420
ttgcagcagc tttatcatct gccgctggac ggcgcacaaa tcgcgcttaa cggtcaggaa 480
gcagaaaacc agtttgtagg ctgtaactgc gggatcatgg atcagctaat ttccgcgctc 540
ggcaagaaag atcatgcctt gctgatcgat tgccgctcac tggggaccaa agcagtttcc 600
atgcccaaag gtgtggctgt cgtcatcatc aacagtaact tcaaacgtac cctggttggc 660
agcgaataca acacccgtcg tgaacagtgc gaaaccggtg cgcgtttctt ccagcagcca 720
gccctgcgtg atgtcaccat tgaagagttc aacgctgttg cgcatgaact ggacccgatc 780
gtggcaaaac gcgtgcgtca tatactgact gaaaacgccc gcaccgttga agctgccagc 840
gcgctggagc aaggcgacct gaaacgtatg ggcgagttga tggcggagtc tcatgcctct 900
atgcgcgatg atttcgaaat caccgtgccg caaattgaca ctctggtaga aatcgtcaaa 960
gctgtgattg gcgacaaagg tggcgtacgc atgaccggcg gcggatttgg cggctgtatc 1020
gtcgcgctga tcccggaaga gctggtgcct gccgtacagc aagctgtcgc tgaacaatat 1080
gaagcaaaaa caggtattaa agagactttt tacgtttgta aaccatcaca aggagcagga 1140
cagtgctga 1149

<210> SEQ ID NO 121
<211> LENGTH: 1017
<212> TYPE: DNA
<213> ORGANISM: Escherichia coli

<400> SEQUENCE: 121
atgagagttc tggttaccgg tggtagcggt tacattggaa gtcatacctg tgtgcaatta 60
ctgcaaaacg gtcatgatgt catcattctt gataacctct gtaacagtaa gcgcagcgta 120
ctgcctgtta tcgagcgttt aggcggcaaa catccaacgt ttgttgaagg cgatattcgt 180
aacgaagcgt tgatgaccga gatcctgcac gatcacgcta tcgacaccgt gatccacttc 240

-continued

```
gccgggctga aagccgtggg cgaatcggta caaaaaccgc tggaatatta cgacaacaat    300

gtcaacggca ctctgcgcct gattagcgcc atgcgcgccg ctaacgtcaa aaactttatt    360

tttagctcct ccgccaccgt ttatggcgat cagcccaaaa ttccatacgt tgaaagcttc    420

ccgaccggca caccgcaaag cccttacggc aaaagcaagc tgatggtgga acagatcctc    480

accgatctgc aaaaagccca gccggactgg agcattgccc tgctgcgcta cttcaacccg    540

gttggcgcgc atccgtcggg cgatatgggc gaagatccgc aaggcattcc gaataacctg    600

atgccataca tcgcccaggt tgctgtaggc cgtcgcgact cgctggcgat ttttggtaac    660

gattatccga ccgaagatgg tactggcgta cgcgattaca tccacgtaat ggatctggcg    720

gacggtcacg tcgtggcgat ggaaaaactg gcgaacaagc caggcgtaca catctacaac    780

ctcggcgctg gcgtaggcaa cagcgtgctg gacgtggtta atgccttcag caaagcctgc    840

ggcaaaccgg ttaattatca ttttgcaccg cgtcgcgagg gcgaccttcc ggcctactgg    900

gcggacgcca gcaaagccga ccgtgaactg aactggcgcg taacgcgcac actcgatgaa    960

atggcgcagg acacctggca ctggcagtca cgccatccac agggatatcc cgattaa      1017
```

<210> SEQ ID NO 122
<211> LENGTH: 1047
<212> TYPE: DNA
<213> ORGANISM: Escherichia coli

<400> SEQUENCE: 122

```
atgacgcaat ttaatcccgt tgatcatcca catcgccgct acaacccgct caccgggcaa     60

tggattctgg tttcaccgca ccgcgctaag cgcccctggc aggggcgca ggaaacgcca    120

gccaaacagg tgttacctgc gcacgatcca gattgcttcc tctgcgcagg taatgtgcgg    180

gtgacaggcg ataaaaaccc cgattacacc gggacttacg ttttcactaa tgactttgcg    240

gctttgatgt ctgacacgcc agatgcgcca gaaagtcacg atccgctgat gcgttgccag    300

agcgcgcgcg gcaccagccg ggtgatctgc ttttcaccgg atcacagtaa aacgctgcca    360

gagctcagcg ttgcagcatt gacggaaatc gtcaaaacct ggcaggagca aaccgcagaa    420

ctggggaaaa cgtacccatg ggtgcaggtt tttgaaaaca aaggcgcggc gatgggctgc    480

tctaacccgc atccgcacgg tcagatttgg gcaaatagct tcctgcctaa cgaagctgag    540

cgcgaagacc gcctgcaaaa agaatatttt gccgaacaga aatcaccaat gctggtggat    600

tatgttcagc gcgagctggc agacggtagc cgtaccgttg tcgaaaccga acactggtta    660

gccgtcgtgc cttactgggc tgcctggccg ttcgaaacgc tactgctgcc caaagcccac    720

gttttacgga tcaccgattt gaccgacgcc cagcgcagcg atctggcgct ggcgttgaaa    780

aagctgacca gtcgttatga caacctcttc cagtgctcct tcccctactc tatgggctgg    840

cacggcgcgc catttaatgg cgaagagaat caacactggc agctgcacgc gcacttttat    900

ccgcctctgc tgcgctccgc caccgtacgt aaatttatgg ttggttatga aatgctggca    960

gagacccagc gagacctgac cgcagaacag gcagcagagc gtttgcgcgc agtcagcgat   1020

atccattttc gcgaatccgg agtgtaa                                       1047
```

<210> SEQ ID NO 123
<211> LENGTH: 76
<212> TYPE: RNA
<213> ORGANISM: Artificial sequence
<220> FEATURE:
<223> OTHER INFORMATION: CER domainl

<400> SEQUENCE: 123
guuuuagagc uagaaauagc aaguuaaaau aaggcuaguc cguuaucaac uugaaaaagu 60
ggcaccgagu cggugc 76

<210> SEQ ID NO 124
<211> LENGTH: 76
<212> TYPE: DNA
<213> ORGANISM: Artificial sequence
<220> FEATURE:
<223> OTHER INFORMATION: CER encoding DNA PCR

<400> SEQUENCE: 124
gttttagagc tagaaatagc aagttaaaat aaggctagtc cgttatcaac ttgaaaaagt 60
ggcaccgagt cggtgc 76

<210> SEQ ID NO 125
<211> LENGTH: 11714
<212> TYPE: DNA
<213> ORGANISM: Artificial sequence
<220> FEATURE:
<223> OTHER INFORMATION: pRF291

<400> SEQUENCE: 125
cgataaaaaa caaaaaaaaa agcaccgact cggtgccact ttttcaagtt gataacggac 60
tagccttatt ttaacttgct atttctagct ctaaaacgca ggtgtaaaaa taaaaaggcc 120
tgcgattacc agcaggcctg ttattaacct aagccttagg acgcttcacg ccatacttgg 180
aacgagcctg cttacggtct ttaacgccgg agcagtcaag cgcaccacgt acggtgtggt 240
aacgaacacc cgggaggtct ttaacacgac cgccacggat caggatcacg gagtgctcct 300
gcaggttgtg accttcacca ccgatgtagg aagtcacttc gaaaccgtta gtcagacgaa 360
cacggcatac tttacgcagc gcggagttcg gttttttagg agtggtagta tatacacgag 420
tacatacgcc acgtttttgc gggcatgctt ccagcgcagg cacgttgctt ttcgcaactt 480
tgcgagcacg tggtttgcgt accagctggt taactgttgc cattaaatag ctcctggttt 540
tagcttttgc ttcgtaaaca cgtaataaaa cgtcctcaca caatatgagg acgccgaatt 600
tagggcgatg ccgaaaaggt gtcaagaaat atacaacgat cccgccatca cctgcgtccc 660
attcgccatg ccgaagcatg ttgcccagcc ggcgccagcg aggaggctgg gaccatgccg 720
gccattattt tgcgttaagt ttctaatcat cacgaaatta tctatcaaaa ataactaggt 780
cccaccgaga ttcgaactcg ggaccttaag atttgcaatc tcacgcgcta ccgctgtgcc 840
ataggaccga agttaaaatt tggccaaaga aggacctggg caccctggac tgtgggttag 900
ggtaatattc cttatggaga caatgggcta gggtaaatta cctaaaatgg gtcgataaag 960
aggggtgttc ccagttggga agtgtaattg aagacggggt caaaaaagaa aatcaaaaaa 1020
aatttaatta agtcatacac aagtcagctt tcttcgagcc tcatataagt ataagtagtt 1080
caacgtatta gcactgtacc cagcatctcc gtatcgagaa acacaacaac atgccccatt 1140
ggacagatca tgcggataca caggttgtgc agtatcatac atactcgatc agacaggtcg 1200
tctgaccatc atacaagctg aacaagcgct ccatacttgc acgctctcta tatacacagt 1260
taaattacat atccatagtc taacctctaa cagttaatct tctggtaagc ctcccagcca 1320
gccttctggt atcgcttggc ctcctcaata ggatctcggt tctggccgta cagacctcgg 1380
ccgacaatta tgatatccgt tccggtagac atgacatcct caacagttcg gtactgctgt 1440
ccgagagcgt ctcccttgtc gtcaagaccc accccggggg tcagaataag ccagtcctca 1500

-continued

```
gagtcgccct taggtcggtt ctgggcaatg aagccaacca caaactcggg gtcggatcgg   1560
gcaagctcaa tggtctgctt ggagtactcg ccagtggcca gagagccctt gcaagacagc   1620
tcggccagca tgagcagacc tctggccagc ttctcgttgg gagaggggac taggaactcc   1680
ttgtactggg agttctcgta gtcagagacg tcctccttct tctgttcaga gacagtttcc   1740
tcggcaccag ctcgcaggcc agcaatgatt ccggttccgg gtacaccgtg ggcgttggtg   1800
atatcggacc actcggcgat tcggtgacac cggtactggt gcttgacagt gttgccaata   1860
tctgcgaact ttctgtcctc gaacaggaag aaaccgtgct taagagcaag ttccttgagg   1920
gggagcacag tgccggcgta ggtgaagtcg tcaatgatgt cgatatgggt tttgatcatg   1980
cacacataag gtccgacctt atcggcaagc tcaatgagct ccttggtggt ggtaacatcc   2040
agagaagcac acaggttggt tttcttggct gccacgagct tgagcactcg agcggcaaag   2100
gcggacttgt ggacgttagc tcgagcttcg taggagggca ttttggtggt gaagaggaga   2160
ctgaaataaa tttagtctgc agaacttttt atcggaacct tatctggggc agtgaagtat   2220
atgttatggt aatagttacg agttagttga acttatagat agactggact atacggctat   2280
cggtccaaat tagaaagaac gtcaatggct ctctgggcgt cgcctttgcc gacaaaaatg   2340
tgatcatgat gaaagccagc aatgacgttg cagctgatat tgttgtcggc caaccgcgcc   2400
gaaaacgcag ctgtcagacc cacagcctcc aacgaagaat gtatcgtcaa agtgatccaa   2460
gcacactcat agttggagtc gtactccaaa ggcggcaatg acgagtcaga cagatactcg   2520
tcgacgttta aaccatcatc taagggcctc aaaactacct cggaactgct gcgctgatct   2580
ggacaccaca gaggttccga gcactttagg ttgcaccaaa tgtcccacca ggtgcaggca   2640
gaaaacgctg gaacagcgtg tacagtttgt cttaacaaaa agtgagggcg ctgaggtcga   2700
gcagggtggt gtgacttgtt atagccttta gagctgcgaa agcgcgtatg gatttggctc   2760
atcaggccag attgagggtc tgtggacaca tgtcatgtta gtgtacttca atcgcccccct  2820
ggatatagcc ccgacaatag gccgtggcct catttttttg ccttccgcac atttccattg   2880
ctcggtaccc acaccttgct tctcctgcac ttgccaacct taatactggt ttacattgac   2940
caacatctta caagcggggg gcttgtctag ggtatatata aacagtggct ctcccaatcg   3000
gttgccagtc tctttttttcc tttctttccc cacagattcg aaatctaaac tacacatcac  3060
accatggaca agaaatactc catcggcctg gacattggaa ccaactctgt cggctgggct   3120
gtcatcaccg acgagtacaa ggtgccctcc aagaaattca aggtcctcgg aaacaccgat   3180
cgacactcca tcaagaaaaa cctcattggt gccctgttgt tcgattctgg cgagactgcc   3240
gaagctacca gactcaagcg aactgctcgg cgacgttaca cccgacggaa gaaccgaatc   3300
tgctacctgc aggagatctt ttccaacgag atggccaagg tggacgattc gttctttcat   3360
cgactggagg aatccttcct cgtcgaggaa gacaagaaac acgagcgtca tcccatcttt   3420
ggcaacattg tggacgaggt tgcttaccac gagaagtatc ctaccatcta ccatctccga   3480
aagaaactcg tcgattccac cgacaaggcg gatctcagac ttatctacct cgctctggca   3540
cacatgatca agtttcgagg tcatttcctc atcgagggcg atctcaatcc cgacaacagc   3600
gatgtggaca agctgttcat tcagctcgtt cagacctaca accagctgtt cgaggaaaac   3660
cccatcaatg cctccggagt cgatgcaaag gccatcttgt ctgctcgact ctcgaagagc   3720
agacgactgg agaacctcat tgcccaactt cctggcgaga aaaagaacgg actgtttggc   3780
aacctcattg ccctttctct tggtctcaca cccaacttca agtccaactt cgatctggcg   3840
gaggacgcca agctccagct gtccaaggac acctacgacg atgacctcga caacctgctt   3900
```

```
gcacagattg gcgatcagta cgccgacctg tttctcgctg ccaagaacct ttcggatgct   3960

attctcttgt ctgacattct gcgagtcaac accgagatca caaaggctcc cctttctgcc   4020

tccatgatca agcgatacga cgagcaccat caggatctca cactgctcaa ggctcttgtc   4080

cgacagcaac tgcccgagaa gtacaaggag atctttttcg atcagtcgaa gaacggctac   4140

gctggataca tcgacggcgg agcctctcag gaagagttct acaagttcat caagccaatt   4200

ctcgagaaga tggacggaac cgaggaactg cttgtcaagc tcaatcgaga ggatctgctt   4260

cggaagcaac gaaccttcga caacggcagc attcctcatc agatccacct cggtgagctg   4320

cacgccattc ttcgacgtca ggaagacttc tacccctttc tcaaggacaa ccgagagaag   4380

atcgagaaga ttcttacctt tcgaatcccc tactatgttg gtcctcttgc cagaggaaac   4440

tctcgatttg cttggatgac tcgaaagtcc gaggaaacca tcactccctg gaacttcgag   4500

gaagtcgtgg acaagggtgc ctctgcacag tccttcatcg agcgaatgac caacttcgac   4560

aagaatctgc ccaacgagaa ggttcttccc aagcattcgc tgctctacga gtactttaca   4620

gtctacaacg aactcaccaa agtcaagtac gttaccgagg gaatgcgaaa gcctgccttc   4680

ttgtctggcg aacagaagaa agccattgtc gatctcctgt tcaagaccaa ccgaaaggtc   4740

actgttaagc agctcaagga ggactacttc aagaaaatcg agtgtttcga cagcgtcgag   4800

atttccggag ttgaggaccg attcaacgcc tctttgggca cctatcacga tctgctcaag   4860

attatcaagg acaaggattt tctcgacaac gaggaaaacg aggacattct ggaggacatc   4920

gtgctcactc ttaccctgtt cgaagatcgg gagatgatcg aggaacgact caagacatac   4980

gctcacctgt tcgacgacaa ggtcatgaaa caactcaagc gacgtagata caccggctgg   5040

ggaagacttt cgcgaaagct catcaacggc atcagagaca agcagtccgg aaagaccatt   5100

ctggactttc tcaagtccga tggctttgcc aaccgaaact tcatgcagct cattcacgac   5160

gattctctta ccttcaagga ggacatccag aaggcacaag tgtccggtca gggcgacagc   5220

ttgcacgaac atattgccaa cctggctggt tcgccagcca tcaagaaagg cattctccag   5280

actgtcaagg ttgtcgacga gctggtgaag gtcatgggac gtcacaagcc cgagaacatt   5340

gtgatcgaga tggccagaga gaaccagaca actcaaaagg gtcagaaaaa ctcgcgagag   5400

cggatgaagc gaatcgagga aggcatcaag gagctgggat cccagattct caaggagcat   5460

cccgtcgaga acactcaact gcagaacgag aagctgtatc tctactatct gcagaatggt   5520

cgagacatgt acgtggatca ggaactggac atcaatcgtc tcagcgacta cgatgtggac   5580

cacattgtcc ctcaatcctt tctcaaggac gattctatcg acaacaaggt ccttacacga   5640

tccgacaaga acagaggcaa gtcggacaac gttcccagcg aagaggtggt caaaaagatg   5700

aagaactact ggcgacagct gctcaacgcc aagctcatta cccagcgaaa gttcgacaat   5760

cttaccaagg ccgagcgagg cggtctgtcc gagctcgaca aggctggctt catcaagcgt   5820

caactcgtcg agaccagaca gatcacaaag cacgtcgcac agattctcga ttctcggatg   5880

aacaccaagt acgacgagaa cgacaagctc atccgagagg tcaaggtgat tactctcaag   5940

tccaaactgg tctccgattt ccgaaaggac tttcagttct acaaggtgcg agagatcaac   6000

aattaccacc atgcccacga tgcttacctc aacgccgtcg ttggcactgc gctcatcaag   6060

aaatacccca agctcgaaag cgagttcgtt tacggcgatt acaaggtcta cgacgttcga   6120

aagatgattg ccaagtccga acaggagatt ggcaaggcta ctgccaagta cttcttttac   6180

tccaacatca tgaacttttt caagaccgag atcaccttgg ccaacggaga gattcgaaag   6240
```

-continued

```
agaccactta tcgagaccaa cggcgaaact ggagagatcg tgtgggacaa gggtcgagac   6300
tttgcaaccg tgcgaaaggt tctgtcgatg cctcaggtca acatcgtcaa gaaaaccgag   6360
gttcagactg gcggattctc caaggagtcg attctgccca agcgaaactc cgacaagctc   6420
atcgctcgaa agaaagactg ggatcccaag aaatacggtg gcttcgattc tcctaccgtc   6480
gcctattccg tgcttgtcgt tgcgaaggtc gagaagggca agtccaaaaa gctcaagtcc   6540
gtcaaggagc tgctcggaat taccatcatg gagcgatcga gcttcgagaa gaatcccatc   6600
gacttcttgg aagccaaggg ttacaaggag gtcaagaaag acctcattat caagctgccc   6660
aagtactctc tgttcgaact ggagaacggt cgaaagcgta tgctcgcctc cgctggcgag   6720
ctgcagaagg gaaacgagct tgccttgcct tcgaagtacg tcaactttct ctatctggct   6780
tctcactacg agaagctcaa gggttctccc gaggacaacg aacagaagca actcttcgtt   6840
gagcagcaca aacattacct cgacgagatt atcgagcaga tttccgagtt ttcgaagcga   6900
gtcatcctgg ctgatgccaa cttggacaag gtgctctctg cctacaacaa gcatcgggac   6960
aaacccattc gagaacaggc ggagaacatc attcacctgt ttactcttac caacctgggt   7020
gctcctgcag ctttcaagta cttcgatacc actatcgacc gaaagcggta cacatccacc   7080
aaggaggttc tcgatgccac cctgattcac cagtccatca ctggcctgta cgagacccga   7140
atcgacctgt ctcagcttgg tggcgactcc agagccgatc ccaagaaaaa gcgaaaggtc   7200
taagcggccg caagtgtgga tggggaagtg agtgcccggt tctgtgtgca caattggcaa   7260
tccaagatgg atggattcaa cacagggata tagcgagcta cgtggtggtg cgaggatata   7320
gcaacggata tttatgtttg acacttgaga atgtacgata caagcactgt ccaagtacaa   7380
tactaaacat actgtacata ctcatactcg tacccgggca acggtttcac ttgagtgcag   7440
tggctagtgc tcttactcgt acagtgtgca atactgcgta tcatagtctt tgatgtatat   7500
cgtattcatt catgttagtt gcgtacgagc cggaagcata aagtgtaaag cctggggtgc   7560
ctaatgagtg agctaactca cattaattgc gttgcgctca ctgcccgctt tccagtcggg   7620
aaacctgtcg tgccagctgc attaatgaat cggccaacgc gcggggagag gcggtttgcg   7680
tattgggcgc tcttccgctt cctcgctcac tgactcgctg cgctcggtcg ttcggctgcg   7740
gcgagcggta tcagctcact caaaggcggt aatacggtta tccacagaat caggggataa   7800
cgcaggaaag aacatgtgag caaaaggcca gcaaaaggcc aggaaccgta aaaaggccgc   7860
gttgctggcg tttttccata ggctccgccc ccctgacgag catcacaaaa atcgacgctc   7920
aagtcagagg tggcgaaacc cgacaggact ataaagatac caggcgtttc cccctggaag   7980
ctccctcgtg cgctctcctg ttccgaccct gccgcttacc ggatacctgt ccgcctttct   8040
cccttcggga agcgtggcgc tttctcatag ctcacgctgt aggtatctca gttcggtgta   8100
ggtcgttcgc tccaagctgg gctgtgtgca cgaacccccc gttcagcccg accgctgcgc   8160
cttatccggt aactatcgtc ttgagtccaa cccggtaaga cacgacttat cgccactggc   8220
agcagccact ggtaacagga ttagcagagc gaggtatgta ggcggtgcta cagagttctt   8280
gaagtggtgg cctaactacg gctacactag aaggacagta tttggtatct gcgctctgct   8340
gaagccagtt accttcggaa aaagagttgg tagctcttga tccggcaaac aaaccaccgc   8400
tggtagcggt ggtttttttg tttgcaagca gcagattacg cgcagaaaaa aaggatctca   8460
agaagatcct ttgatctttt ctacggggtc tgacgctcag tggaacgaaa actcacgtta   8520
agggattttg gtcatgagat tatcaaaaag gatcttcacc tagatccttt taaattaaaa   8580
atgaagtttt aaatcaatct aaagtatata tgagtaaact tggtctgaca gttaccaatg   8640
```

```
cttaatcagt gaggcaccta tctcagcgat ctgtctattt cgttcatcca tagttgcctg   8700
actccccgtc gtgtagataa ctacgatacg ggagggctta ccatctggcc ccagtgctgc   8760
aatgataccg cgagacccac gctcaccggc tccagattta tcagcaataa accagccagc   8820
cggaagggcc gagcgcagaa gtggtcctgc aactttatcc gcctccatcc agtctattaa   8880
ttgttgccgg gaagctagag taagtagttc gccagttaat agtttgcgca acgttgttgc   8940
cattgctaca ggcatcgtgg tgtcacgctc gtcgtttggt atggcttcat tcagctccgg   9000
ttcccaacga tcaaggcgag ttacatgatc ccccatgttg tgcaaaaaag cggttagctc   9060
cttcggtcct ccgatcgttg tcagaagtaa gttggccgca gtgttatcac tcatggttat   9120
ggcagcactg cataattctc ttactgtcat gccatccgta agatgctttt ctgtgactgg   9180
tgagtactca accaagtcat tctgagaata gtgtatgcgg cgaccgagtt gctcttgccc   9240
ggcgtcaata cgggataata ccgcgccaca tagcagaact ttaaaagtgc tcatcattgg   9300
aaaacgttct tcggggcgaa aactctcaag gatcttaccg ctgttgagat ccagttcgat   9360
gtaacccact cgtgcaccca actgatcttc agcatctttt actttcacca gcgtttctgg   9420
gtgagcaaaa acaggaaggc aaaatgccgc aaaaaaggga ataagggcga cacggaaatg   9480
ttgaatactc atactcttcc tttttcaata ttattgaagc atttatcagg gttattgtct   9540
catgagcgga tacatatttg aatgtattta gaaaaataaa caaatagggg ttccgcgcac   9600
atttccccga aaagtgccac ctgacgcgcc ctgtagcggc gcattaagcg cggcgggtgt   9660
ggtggttacg cgcagcgtga ccgctacact tgccagcgcc ctagcgcccg ctcctttcgc   9720
tttcttccct tcctttctcg ccacgttcgc cggctttccc cgtcaagctc taaatcgggg   9780
gctcccttta gggttccgat ttagtgcttt acggcacctc gaccccaaaa aacttgatta   9840
gggtgatggt tcacgtagtg ggccatcgcc ctgatagacg gtttttcgcc ctttgacgtt   9900
ggagtccacg ttctttaata gtggactctt gttccaaact ggaacaacac tcaaccctat   9960
ctcggtctat tcttttgatt tataagggat tttgccgatt tcggcctatt ggttaaaaaa  10020
tgagctgatt taacaaaaat ttaacgcgaa ttttaacaaa atattaacgc ttacaatttc  10080
cattcgccat tcaggctgcg caactgttgg gaagggcgat cggtgcgggc ctcttcgcta  10140
ttacgccagc tggcgaaagg gggatgtgct gcaaggcgat taagttgggt aacgccaggg  10200
ttttcccagt cacgacgttg taaaacgacg gccagtgaat tgtaatacga ctcactatag  10260
ggcgaattgg gtaccgggcc ccccctcgag gtcgatggtg tcgataagct tgatatcgaa  10320
ttcatgtcac acaaaccgat cttcgcctca aggaaaccta attctacatc cgagagactg  10380
ccgagatcca gtctacactg attaattttc gggccaataa tttaaaaaaa tcgtgttata  10440
taatattata tgtattatat atatacatca tgatgatact gacagtcatg tcccattgct  10500
aaatagacag actccatctg ccgcctccaa ctgatgttct caatatttaa ggggtcatct  10560
cgcattgttt aataataaac agactccatc taccgcctcc aaatgatgtt ctcaaaatat  10620
attgtatgaa cttattttta ttacttagta ttattagaca acttacttgc tttatgaaaa  10680
acacttccta tttaggaaac aatttataat ggcagttcgt tcatttaaca atttatgtag  10740
aataaatgtt ataaatgcgt atgggaaatc ttaaatatgg atagcataaa tgatatctgc  10800
attgcctaat tcgaaatcaa cagcaacgaa aaaaatccct tgtacaacat aaatagtcat  10860
cgagaaatat caactatcaa agaacagcta ttcacacgtt actattgaga ttattattgg  10920
acgagaatca cacactcaac tgtctttctc tcttctagaa atacaggtac aagtatgtac  10980
```

```
tattctcatt gttcatactt ctagtcattt catcccacat attccttgga tttctctcca  11040

atgaatgaca ttctatcttg caaattcaac aattataata agatatacca aagtagcggt  11100

atagtggcaa tcaaaaagct tctctggtgt gcttctcgta tttattttta ttctaatgat  11160

ccattaaagg tatatattta tttcttgtta tataatcctt ttgtttatta catgggctgg  11220

atacataaag gtattttgat ttaatttttt gcttaaattc aatccccccct cgttcagtgt  11280

caactgtaat ggtaggaaat taccatactt ttgaagaagc aaaaaaaatg aaagaaaaaa  11340

aaaatcgtat ttccaggtta gacgttccgc agaatctaga atgcggtatg cggtacattg  11400

ttcttcgaac gtaaaagttg cgctccctga gatattgtac atttttgctt ttacaagtac  11460

aagtacatcg tacaactatg tactactgtt gatgcatcca caacagtttg ttttgttttt  11520

ttttgttttt tttttttcta atgattcatt accgctatgt atacctactt gtacttgtag  11580

taagccgggt tattggcgtt caattaatca tagacttatg aatctgcacg gtgtgcgctg  11640

cgagttactt ttagcttatg catgctactt gggtgtaata ttgggatctg ttcggaaatc  11700

aacggatgct caat                                                    11714

<210> SEQ ID NO 126
<211> LENGTH: 20
<212> TYPE: DNA
<213> ORGANISM: Artificial sequence
<220> FEATURE:
<223> OTHER INFORMATION: CER forward

<400> SEQUENCE: 126

gttttagagc tagaaatagc                                                 20

<210> SEQ ID NO 127
<211> LENGTH: 20
<212> TYPE: DNA
<213> ORGANISM: Artificial sequence
<220> FEATURE:
<223> OTHER INFORMATION: univeral reverse

<400> SEQUENCE: 127

gcaccgactc ggtgccactt                                                 20

<210> SEQ ID NO 128
<211> LENGTH: 18
<212> TYPE: DNA
<213> ORGANISM: Artificial sequence
<220> FEATURE:
<223> OTHER INFORMATION: universal forward T7 primer

<400> SEQUENCE: 128

taatacgact cactatag                                                   18

<210> SEQ ID NO 129
<211> LENGTH: 34
<212> TYPE: DNA
<213> ORGANISM: Artificial sequence
<220> FEATURE:
<223> OTHER INFORMATION: galK2-1 forward primer

<400> SEQUENCE: 129

taatacgact cactatagat cagcggcaat gtgc                                 34

<210> SEQ ID NO 130
<211> LENGTH: 34
<212> TYPE: DNA
<213> ORGANISM: Artificial sequence
```

<220> FEATURE:
<223> OTHER INFORMATION: galK2-1 reverse primer

<400> SEQUENCE: 130
ttctagctct aaaactgcgg cacattgccg ctga 34

<210> SEQ ID NO 131
<211> LENGTH: 114
<212> TYPE: DNA
<213> ORGANISM: Artificial Sequence
<220> FEATURE:
<223> OTHER INFORMATION: galK2-1 sgRNA in vitro transcription template

<400> SEQUENCE: 131
taatacgact cactatagat cagcggcaat gtgccgcagt tttagagcta gaaatagcaa 60
gttaaaataa ggctagtccg ttatcaactt gaaaaagtgg caccgagtcg gtgc 114

<210> SEQ ID NO 132
<211> LENGTH: 18
<212> TYPE: DNA
<213> ORGANISM: T7 phage

<400> SEQUENCE: 132
taatacgact cactatag 18

<210> SEQ ID NO 133
<211> LENGTH: 20
<212> TYPE: DNA
<213> ORGANISM: Escherichia coli

<400> SEQUENCE: 133
atcagcggca atgtgccgca 20

<210> SEQ ID NO 134
<211> LENGTH: 23
<212> TYPE: DNA
<213> ORGANISM: Escherichia coli

<400> SEQUENCE: 134
atcagcggca atgtgccgca ggg 23

<210> SEQ ID NO 135
<211> LENGTH: 96
<212> TYPE: RNA
<213> ORGANISM: Artificial sequence
<220> FEATURE:
<223> OTHER INFORMATION: galK2-1 sgRNA

<400> SEQUENCE: 135
aucagcggca augugccgca guuuuagagc uagaaauagc aaguuaaaau aaggcuaguc 60
cguuaucaac uugaaaaagu ggcaccgagu cggugc 96

<210> SEQ ID NO 136
<211> LENGTH: 262
<212> TYPE: PRT
<213> ORGANISM: Artificial sequence
<220> FEATURE:
<223> OTHER INFORMATION: his-MPG1-dsREDexpress

<400> SEQUENCE: 136

Met Gly His His His His His His Gly Ala Leu Phe Leu Gly Gln Leu
1 5 10 15

Gly Ala Ala Gly Ser Thr Met Gly Ala Pro Lys Lys Lys Arg Lys Val

```
            20                  25                  30

Glu Phe Gly Gly Gly Gly Ala Ser Ser Glu Asp Val Ile Lys Glu Phe
        35                  40                  45

Met Arg Phe Lys Val Arg Met Glu Gly Ser Val Asn Gly His Glu Phe
    50                  55                  60

Glu Ile Glu Gly Glu Gly Glu Gly Arg Pro Tyr Glu Gly Thr Gln Thr
65                  70                  75                  80

Ala Lys Leu Lys Val Thr Lys Gly Gly Pro Leu Pro Phe Ala Trp Asp
                85                  90                  95

Ile Leu Ser Pro Gln Phe Gln Tyr Gly Ser Lys Val Tyr Val Lys His
            100                 105                 110

Pro Ala Asp Ile Pro Asp Tyr Lys Lys Leu Ser Phe Pro Glu Gly Phe
        115                 120                 125

Lys Trp Glu Arg Val Met Asn Phe Glu Asp Gly Gly Val Val Thr Val
    130                 135                 140

Thr Gln Asp Ser Ser Leu Gln Asp Gly Ser Phe Ile Tyr Lys Val Lys
145                 150                 155                 160

Phe Ile Gly Val Asn Phe Pro Ser Asp Gly Pro Val Met Gln Lys Lys
                165                 170                 175

Thr Met Gly Trp Glu Ala Ser Thr Glu Arg Leu Tyr Pro Arg Asp Gly
            180                 185                 190

Val Leu Lys Gly Glu Ile His Lys Ala Leu Lys Leu Lys Asp Gly Gly
        195                 200                 205

His Tyr Leu Val Glu Phe Lys Ser Ile Tyr Met Ala Lys Lys Pro Val
    210                 215                 220

Gln Leu Pro Gly Tyr Tyr Tyr Val Asp Ser Lys Leu Asp Ile Thr Ser
225                 230                 235                 240

His Asn Glu Asp Tyr Thr Ile Val Glu Gln Tyr Glu Arg Ala Glu Gly
                245                 250                 255

Arg His His Leu Phe Leu
            260


<210> SEQ ID NO 137
<211> LENGTH: 256
<212> TYPE: PRT
<213> ORGANISM: Artificial sequence
<220> FEATURE:
<223> OTHER INFORMATION: pVEC-dsREDexpress

<400> SEQUENCE: 137

Met Gly His His His His His His Leu Leu Ile Ile Leu Arg Arg Arg
1               5                   10                  15

Ile Arg Lys Gln Ala His Ala His Ser Lys Glu Phe Gly Gly Gly Gly
            20                  25                  30

Ala Ser Ser Glu Asp Val Ile Lys Glu Phe Met Arg Phe Lys Val Arg
        35                  40                  45

Met Glu Gly Ser Val Asn Gly His Glu Phe Glu Ile Glu Gly Glu Gly
    50                  55                  60

Glu Gly Arg Pro Tyr Glu Gly Thr Gln Thr Ala Lys Leu Lys Val Thr
65                  70                  75                  80

Lys Gly Gly Pro Leu Pro Phe Ala Trp Asp Ile Leu Ser Pro Gln Phe
                85                  90                  95

Gln Tyr Gly Ser Lys Val Tyr Val Lys His Pro Ala Asp Ile Pro Asp
            100                 105                 110

Tyr Lys Lys Leu Ser Phe Pro Glu Gly Phe Lys Trp Glu Arg Val Met
```

```
        115                 120                 125

Asn Phe Glu Asp Gly Gly Val Val Thr Val Thr Gln Asp Ser Ser Leu
    130                 135                 140

Gln Asp Gly Ser Phe Ile Tyr Lys Val Lys Phe Ile Gly Val Asn Phe
145                 150                 155                 160

Pro Ser Asp Gly Pro Val Met Gln Lys Lys Thr Met Gly Trp Glu Ala
                165                 170                 175

Ser Thr Glu Arg Leu Tyr Pro Arg Asp Gly Val Leu Lys Gly Glu Ile
            180                 185                 190

His Lys Ala Leu Lys Leu Lys Asp Gly Gly His Tyr Leu Val Glu Phe
        195                 200                 205

Lys Ser Ile Tyr Met Ala Lys Lys Pro Val Gln Leu Pro Gly Tyr Tyr
    210                 215                 220

Tyr Val Asp Ser Lys Leu Asp Ile Thr Ser His Asn Glu Asp Tyr Thr
225                 230                 235                 240

Ile Val Glu Gln Tyr Glu Arg Ala Glu Gly Arg His His Leu Phe Leu
                245                 250                 255


<210> SEQ ID NO 138
<211> LENGTH: 245
<212> TYPE: PRT
<213> ORGANISM: Artificial sequence
<220> FEATURE:
<223> OTHER INFORMATION: CFFKDEL-dsREDexpress

<400> SEQUENCE: 138

Met Gly His His His His His His Cys Phe Phe Lys Asp Glu Leu Glu
1               5                   10                  15

Phe Gly Gly Gly Gly Ala Ser Ser Glu Asp Val Ile Lys Glu Phe Met
            20                  25                  30

Arg Phe Lys Val Arg Met Glu Gly Ser Val Asn Gly His Glu Phe Glu
        35                  40                  45

Ile Glu Gly Glu Gly Glu Gly Arg Pro Tyr Glu Gly Thr Gln Thr Ala
    50                  55                  60

Lys Leu Lys Val Thr Lys Gly Gly Pro Leu Pro Phe Ala Trp Asp Ile
65                  70                  75                  80

Leu Ser Pro Gln Phe Gln Tyr Gly Ser Lys Val Tyr Val Lys His Pro
                85                  90                  95

Ala Asp Ile Pro Asp Tyr Lys Lys Leu Ser Phe Pro Glu Gly Phe Lys
            100                 105                 110

Trp Glu Arg Val Met Asn Phe Glu Asp Gly Gly Val Val Thr Val Thr
        115                 120                 125

Gln Asp Ser Ser Leu Gln Asp Gly Ser Phe Ile Tyr Lys Val Lys Phe
    130                 135                 140

Ile Gly Val Asn Phe Pro Ser Asp Gly Pro Val Met Gln Lys Lys Thr
145                 150                 155                 160

Met Gly Trp Glu Ala Ser Thr Glu Arg Leu Tyr Pro Arg Asp Gly Val
                165                 170                 175

Leu Lys Gly Glu Ile His Lys Ala Leu Lys Leu Lys Asp Gly Gly His
            180                 185                 190

Tyr Leu Val Glu Phe Lys Ser Ile Tyr Met Ala Lys Lys Pro Val Gln
        195                 200                 205

Leu Pro Gly Tyr Tyr Tyr Val Asp Ser Lys Leu Asp Ile Thr Ser His
    210                 215                 220

Asn Glu Asp Tyr Thr Ile Val Glu Gln Tyr Glu Arg Ala Glu Gly Arg
```

```
225                 230                 235                 240

His His Leu Phe Leu
                245


<210> SEQ ID NO 139
<211> LENGTH: 257
<212> TYPE: PRT
<213> ORGANISM: Artificial Sequence
<220> FEATURE:
<223> OTHER INFORMATION: TLM-dsREDexpress

<400> SEQUENCE: 139

Met Gly His His His His His His Pro Leu Ser Ser Ile Phe Ser Arg
1               5                   10                  15

Ile Gly Asp Pro Pro Lys Lys Lys Arg Lys Val Glu Phe Gly Gly Gly
            20                  25                  30

Gly Ala Ser Ser Glu Asp Val Ile Lys Glu Phe Met Arg Phe Lys Val
        35                  40                  45

Arg Met Glu Gly Ser Val Asn Gly His Glu Phe Glu Ile Glu Gly Glu
    50                  55                  60

Gly Glu Gly Arg Pro Tyr Glu Gly Thr Gln Thr Ala Lys Leu Lys Val
65                  70                  75                  80

Thr Lys Gly Gly Pro Leu Pro Phe Ala Trp Asp Ile Leu Ser Pro Gln
                85                  90                  95

Phe Gln Tyr Gly Ser Lys Val Tyr Val Lys His Pro Ala Asp Ile Pro
            100                 105                 110

Asp Tyr Lys Lys Leu Ser Phe Pro Glu Gly Phe Lys Trp Glu Arg Val
        115                 120                 125

Met Asn Phe Glu Asp Gly Gly Val Val Thr Val Thr Gln Asp Ser Ser
    130                 135                 140

Leu Gln Asp Gly Ser Phe Ile Tyr Lys Val Lys Phe Ile Gly Val Asn
145                 150                 155                 160

Phe Pro Ser Asp Gly Pro Val Met Gln Lys Lys Thr Met Gly Trp Glu
                165                 170                 175

Ala Ser Thr Glu Arg Leu Tyr Pro Arg Asp Gly Val Leu Lys Gly Glu
            180                 185                 190

Ile His Lys Ala Leu Lys Leu Lys Asp Gly Gly His Tyr Leu Val Glu
        195                 200                 205

Phe Lys Ser Ile Tyr Met Ala Lys Lys Pro Val Gln Leu Pro Gly Tyr
    210                 215                 220

Tyr Tyr Val Asp Ser Lys Leu Asp Ile Thr Ser His Asn Glu Asp Tyr
225                 230                 235                 240

Thr Ile Val Glu Gln Tyr Glu Arg Ala Glu Gly Arg His His Leu Phe
                245                 250                 255

Leu


<210> SEQ ID NO 140
<211> LENGTH: 292
<212> TYPE: PRT
<213> ORGANISM: Artificial sequence
<220> FEATURE:
<223> OTHER INFORMATION: Zebra-dsREDexpress

<400> SEQUENCE: 140

Met Gly His His His His His His Glu Cys Asp Ser Glu Leu Glu Ile
1               5                   10                  15

Lys Arg Tyr Lys Arg Val Arg Val Ala Ser Arg Lys Cys Arg Ala Lys
```

```
            20                  25                  30

Phe Lys Gln Leu Leu Gln His Tyr Arg Glu Val Ala Ala Ala Lys Ser
        35                  40                  45

Ser Glu Asn Asp Arg Leu Arg Leu Leu Leu Lys Gln Met Cys Glu Phe
    50                  55                  60

Gly Gly Gly Gly Ala Ser Ser Glu Asp Val Ile Lys Glu Phe Met Arg
65                  70                  75                  80

Phe Lys Val Arg Met Glu Gly Ser Val Asn Gly His Glu Phe Glu Ile
                85                  90                  95

Glu Gly Glu Gly Glu Gly Arg Pro Tyr Glu Gly Thr Gln Thr Ala Lys
            100                 105                 110

Leu Lys Val Thr Lys Gly Gly Pro Leu Pro Phe Ala Trp Asp Ile Leu
        115                 120                 125

Ser Pro Gln Phe Gln Tyr Gly Ser Lys Val Tyr Val Lys His Pro Ala
    130                 135                 140

Asp Ile Pro Asp Tyr Lys Lys Leu Ser Phe Pro Glu Gly Phe Lys Trp
145                 150                 155                 160

Glu Arg Val Met Asn Phe Glu Asp Gly Gly Val Val Thr Val Thr Gln
                165                 170                 175

Asp Ser Ser Leu Gln Asp Gly Ser Phe Ile Tyr Lys Val Lys Phe Ile
            180                 185                 190

Gly Val Asn Phe Pro Ser Asp Gly Pro Val Met Gln Lys Lys Thr Met
        195                 200                 205

Gly Trp Glu Ala Ser Thr Glu Arg Leu Tyr Pro Arg Asp Gly Val Leu
    210                 215                 220

Lys Gly Glu Ile His Lys Ala Leu Lys Leu Lys Asp Gly Gly His Tyr
225                 230                 235                 240

Leu Val Glu Phe Lys Ser Ile Tyr Met Ala Lys Lys Pro Val Gln Leu
                245                 250                 255

Pro Gly Tyr Tyr Tyr Val Asp Ser Lys Leu Asp Ile Thr Ser His Asn
            260                 265                 270

Glu Asp Tyr Thr Ile Val Glu Gln Tyr Glu Arg Ala Glu Gly Arg His
        275                 280                 285

His Leu Phe Leu
    290


<210> SEQ ID NO 141
<211> LENGTH: 259
<212> TYPE: PRT
<213> ORGANISM: Artificial sequence
<220> FEATURE:
<223> OTHER INFORMATION: pep1-dsREDexpress

<400> SEQUENCE: 141

Met Gly His His His His His His Lys Glu Thr Trp Trp Glu Thr Trp
1               5                   10                  15

Trp Thr Glu Trp Ser Gln Pro Lys Lys Lys Arg Lys Val Glu Phe Gly
            20                  25                  30

Gly Gly Gly Ala Ser Ser Glu Asp Val Ile Lys Glu Phe Met Arg Phe
        35                  40                  45

Lys Val Arg Met Glu Gly Ser Val Asn Gly His Glu Phe Glu Ile Glu
    50                  55                  60

Gly Glu Gly Glu Gly Arg Pro Tyr Glu Gly Thr Gln Thr Ala Lys Leu
65                  70                  75                  80

Lys Val Thr Lys Gly Gly Pro Leu Pro Phe Ala Trp Asp Ile Leu Ser
```

```
                85                  90                  95

Pro Gln Phe Gln Tyr Gly Ser Lys Val Tyr Val Lys His Pro Ala Asp
            100                 105                 110

Ile Pro Asp Tyr Lys Lys Leu Ser Phe Pro Glu Gly Phe Lys Trp Glu
        115                 120                 125

Arg Val Met Asn Phe Glu Asp Gly Gly Val Val Thr Val Thr Gln Asp
    130                 135                 140

Ser Ser Leu Gln Asp Gly Ser Phe Ile Tyr Lys Val Lys Phe Ile Gly
145                 150                 155                 160

Val Asn Phe Pro Ser Asp Gly Pro Val Met Gln Lys Lys Thr Met Gly
                165                 170                 175

Trp Glu Ala Ser Thr Glu Arg Leu Tyr Pro Arg Asp Gly Val Leu Lys
            180                 185                 190

Gly Glu Ile His Lys Ala Leu Lys Leu Lys Asp Gly Gly His Tyr Leu
        195                 200                 205

Val Glu Phe Lys Ser Ile Tyr Met Ala Lys Lys Pro Val Gln Leu Pro
    210                 215                 220

Gly Tyr Tyr Tyr Val Asp Ser Lys Leu Asp Ile Thr Ser His Asn Glu
225                 230                 235                 240

Asp Tyr Thr Ile Val Glu Gln Tyr Glu Arg Ala Glu Gly Arg His His
                245                 250                 255

Leu Phe Leu


<210> SEQ ID NO 142
<211> LENGTH: 259
<212> TYPE: PRT
<213> ORGANISM: Artificial sequence
<220> FEATURE:
<223> OTHER INFORMATION: tp10-dsREDexpress

<400> SEQUENCE: 142

Met Gly His His His His His His Ala Gly Tyr Leu Leu Gly Lys Ile
1               5                   10                  15

Asn Leu Lys Ala Cys Ala Ala Cys Ala Lys Lys Ile Leu Glu Phe Gly
            20                  25                  30

Gly Gly Gly Ala Ser Ser Glu Asp Val Ile Lys Glu Phe Met Arg Phe
        35                  40                  45

Lys Val Arg Met Glu Gly Ser Val Asn Gly His Glu Phe Glu Ile Glu
    50                  55                  60

Gly Glu Gly Glu Gly Arg Pro Tyr Glu Gly Thr Gln Thr Ala Lys Leu
65                  70                  75                  80

Lys Val Thr Lys Gly Gly Pro Leu Pro Phe Ala Trp Asp Ile Leu Ser
                85                  90                  95

Pro Gln Phe Gln Tyr Gly Ser Lys Val Tyr Val Lys His Pro Ala Asp
            100                 105                 110

Ile Pro Asp Tyr Lys Lys Leu Ser Phe Pro Glu Gly Phe Lys Trp Glu
        115                 120                 125

Arg Val Met Asn Phe Glu Asp Gly Gly Val Val Thr Val Thr Gln Asp
    130                 135                 140

Ser Ser Leu Gln Asp Gly Ser Phe Ile Tyr Lys Val Lys Phe Ile Gly
145                 150                 155                 160

Val Asn Phe Pro Ser Asp Gly Pro Val Met Gln Lys Lys Thr Met Gly
                165                 170                 175

Trp Glu Ala Ser Thr Glu Arg Leu Tyr Pro Arg Asp Gly Val Leu Lys
            180                 185                 190
```

```
Gly Glu Ile His Lys Ala Leu Lys Leu Lys Asp Gly Gly His Tyr Leu
        195                 200                 205

Val Glu Phe Lys Ser Ile Tyr Met Ala Lys Lys Pro Val Gln Leu Pro
    210                 215                 220

Gly Tyr Tyr Tyr Val Asp Ser Lys Leu Asp Ile Thr Ser His Asn Glu
225                 230                 235                 240

Asp Tyr Thr Ile Val Glu Gln Tyr Glu Arg Ala Glu Gly Arg His His
                245                 250                 255

Leu Phe Leu


<210> SEQ ID NO 143
<211> LENGTH: 1442
<212> TYPE: PRT
<213> ORGANISM: Artificial sequence
<220> FEATURE:
<223> OTHER INFORMATION: Zebra-Cas9

<400> SEQUENCE: 143

Met Gly His His His His His His Glu Cys Asp Ser Glu Leu Glu Ile
1               5                   10                  15

Lys Arg Tyr Lys Arg Val Arg Val Ala Ser Arg Lys Cys Arg Ala Lys
            20                  25                  30

Phe Lys Gln Leu Leu Gln His Tyr Arg Glu Val Ala Ala Ala Lys Ser
        35                  40                  45

Ser Glu Asn Asp Arg Leu Arg Leu Leu Leu Lys Gln Met Cys Glu Phe
    50                  55                  60

Asp Lys Lys Tyr Ser Ile Gly Leu Asp Ile Gly Thr Asn Ser Val Gly
65                  70                  75                  80

Trp Ala Val Ile Thr Asp Glu Tyr Lys Val Pro Ser Lys Lys Phe Lys
                85                  90                  95

Val Leu Gly Asn Thr Asp Arg His Ser Ile Lys Lys Asn Leu Ile Gly
            100                 105                 110

Ala Leu Leu Phe Asp Ser Gly Glu Thr Ala Glu Ala Thr Arg Leu Lys
        115                 120                 125

Arg Thr Ala Arg Arg Arg Tyr Thr Arg Arg Lys Asn Arg Ile Cys Tyr
    130                 135                 140

Leu Gln Glu Ile Phe Ser Asn Glu Met Ala Lys Val Asp Asp Ser Phe
145                 150                 155                 160

Phe His Arg Leu Glu Glu Ser Phe Leu Val Glu Glu Asp Lys Lys His
                165                 170                 175

Glu Arg His Pro Ile Phe Gly Asn Ile Val Asp Glu Val Ala Tyr His
            180                 185                 190

Glu Lys Tyr Pro Thr Ile Tyr His Leu Arg Lys Lys Leu Val Asp Ser
        195                 200                 205

Thr Asp Lys Ala Asp Leu Arg Leu Ile Tyr Leu Ala Leu Ala His Met
    210                 215                 220

Ile Lys Phe Arg Gly His Phe Leu Ile Glu Gly Asp Leu Asn Pro Asp
225                 230                 235                 240

Asn Ser Asp Val Asp Lys Leu Phe Ile Gln Leu Val Gln Thr Tyr Asn
                245                 250                 255

Gln Leu Phe Glu Glu Asn Pro Ile Asn Ala Ser Gly Val Asp Ala Lys
            260                 265                 270

Ala Ile Leu Ser Ala Arg Leu Ser Lys Ser Arg Arg Leu Glu Asn Leu
        275                 280                 285
```

-continued

```
Ile Ala Gln Leu Pro Gly Glu Lys Lys Asn Gly Leu Phe Gly Asn Leu
    290                 295                 300

Ile Ala Leu Ser Leu Gly Leu Thr Pro Asn Phe Lys Ser Asn Phe Asp
305                 310                 315                 320

Leu Ala Glu Asp Ala Lys Leu Gln Leu Ser Lys Asp Thr Tyr Asp Asp
                325                 330                 335

Asp Leu Asp Asn Leu Leu Ala Gln Ile Gly Asp Gln Tyr Ala Asp Leu
            340                 345                 350

Phe Leu Ala Ala Lys Asn Leu Ser Asp Ala Ile Leu Leu Ser Asp Ile
        355                 360                 365

Leu Arg Val Asn Thr Glu Ile Thr Lys Ala Pro Leu Ser Ala Ser Met
    370                 375                 380

Ile Lys Arg Tyr Asp Glu His His Gln Asp Leu Thr Leu Leu Lys Ala
385                 390                 395                 400

Leu Val Arg Gln Gln Leu Pro Glu Lys Tyr Lys Glu Ile Phe Phe Asp
                405                 410                 415

Gln Ser Lys Asn Gly Tyr Ala Gly Tyr Ile Asp Gly Gly Ala Ser Gln
            420                 425                 430

Glu Glu Phe Tyr Lys Phe Ile Lys Pro Ile Leu Glu Lys Met Asp Gly
        435                 440                 445

Thr Glu Glu Leu Leu Val Lys Leu Asn Arg Glu Asp Leu Leu Arg Lys
    450                 455                 460

Gln Arg Thr Phe Asp Asn Gly Ser Ile Pro His Gln Ile His Leu Gly
465                 470                 475                 480

Glu Leu His Ala Ile Leu Arg Arg Gln Glu Asp Phe Tyr Pro Phe Leu
                485                 490                 495

Lys Asp Asn Arg Glu Lys Ile Glu Lys Ile Leu Thr Phe Arg Ile Pro
            500                 505                 510

Tyr Tyr Val Gly Pro Leu Ala Arg Gly Asn Ser Arg Phe Ala Trp Met
        515                 520                 525

Thr Arg Lys Ser Glu Glu Thr Ile Thr Pro Trp Asn Phe Glu Glu Val
    530                 535                 540

Val Asp Lys Gly Ala Ser Ala Gln Ser Phe Ile Glu Arg Met Thr Asn
545                 550                 555                 560

Phe Asp Lys Asn Leu Pro Asn Glu Lys Val Leu Pro Lys His Ser Leu
                565                 570                 575

Leu Tyr Glu Tyr Phe Thr Val Tyr Asn Glu Leu Thr Lys Val Lys Tyr
            580                 585                 590

Val Thr Glu Gly Met Arg Lys Pro Ala Phe Leu Ser Gly Glu Gln Lys
        595                 600                 605

Lys Ala Ile Val Asp Leu Leu Phe Lys Thr Asn Arg Lys Val Thr Val
    610                 615                 620

Lys Gln Leu Lys Glu Asp Tyr Phe Lys Lys Ile Glu Cys Phe Asp Ser
625                 630                 635                 640

Val Glu Ile Ser Gly Val Glu Asp Arg Phe Asn Ala Ser Leu Gly Thr
                645                 650                 655

Tyr His Asp Leu Leu Lys Ile Ile Lys Asp Lys Asp Phe Leu Asp Asn
            660                 665                 670

Glu Glu Asn Glu Asp Ile Leu Glu Asp Ile Val Leu Thr Leu Thr Leu
        675                 680                 685

Phe Glu Asp Arg Glu Met Ile Glu Glu Arg Leu Lys Thr Tyr Ala His
    690                 695                 700

Leu Phe Asp Asp Lys Val Met Lys Gln Leu Lys Arg Arg Arg Tyr Thr
```

-continued

```
705                 710                 715                 720

Gly Trp Gly Arg Leu Ser Arg Lys Leu Ile Asn Gly Ile Arg Asp Lys
                725                 730                 735

Gln Ser Gly Lys Thr Ile Leu Asp Phe Leu Lys Ser Asp Gly Phe Ala
            740                 745                 750

Asn Arg Asn Phe Met Gln Leu Ile His Asp Asp Ser Leu Thr Phe Lys
        755                 760                 765

Glu Asp Ile Gln Lys Ala Gln Val Ser Gly Gln Gly Asp Ser Leu His
    770                 775                 780

Glu His Ile Ala Asn Leu Ala Gly Ser Pro Ala Ile Lys Lys Gly Ile
785                 790                 795                 800

Leu Gln Thr Val Lys Val Val Asp Glu Leu Val Lys Val Met Gly Arg
                805                 810                 815

His Lys Pro Glu Asn Ile Val Ile Glu Met Ala Arg Glu Asn Gln Thr
            820                 825                 830

Thr Gln Lys Gly Gln Lys Asn Ser Arg Glu Arg Met Lys Arg Ile Glu
        835                 840                 845

Glu Gly Ile Lys Glu Leu Gly Ser Gln Ile Leu Lys Glu His Pro Val
    850                 855                 860

Glu Asn Thr Gln Leu Gln Asn Glu Lys Leu Tyr Leu Tyr Tyr Leu Gln
865                 870                 875                 880

Asn Gly Arg Asp Met Tyr Val Asp Gln Glu Leu Asp Ile Asn Arg Leu
                885                 890                 895

Ser Asp Tyr Asp Val Asp His Ile Val Pro Gln Ser Phe Leu Lys Asp
            900                 905                 910

Asp Ser Ile Asp Asn Lys Val Leu Thr Arg Ser Asp Lys Asn Arg Gly
        915                 920                 925

Lys Ser Asp Asn Val Pro Ser Glu Glu Val Val Lys Lys Met Lys Asn
    930                 935                 940

Tyr Trp Arg Gln Leu Leu Asn Ala Lys Leu Ile Thr Gln Arg Lys Phe
945                 950                 955                 960

Asp Asn Leu Thr Lys Ala Glu Arg Gly Gly Leu Ser Glu Leu Asp Lys
                965                 970                 975

Ala Gly Phe Ile Lys Arg Gln Leu Val Glu Thr Arg Gln Ile Thr Lys
            980                 985                 990

His Val Ala Gln Ile Leu Asp Ser  Arg Met Asn Thr Lys  Tyr Asp Glu
        995                 1000                1005

Asn Asp  Lys Leu Ile Arg Glu  Val Lys Val Ile Thr  Leu Lys Ser
    1010                1015                1020

Lys Leu  Val Ser Asp Phe Arg  Lys Asp Phe Gln Phe  Tyr Lys Val
    1025                1030                1035

Arg Glu  Ile Asn Asn Tyr His  His Ala His Asp Ala  Tyr Leu Asn
    1040                1045                1050

Ala Val  Val Gly Thr Ala Leu  Ile Lys Lys Tyr Pro  Lys Leu Glu
    1055                1060                1065

Ser Glu  Phe Val Tyr Gly Asp  Tyr Lys Val Tyr Asp  Val Arg Lys
    1070                1075                1080

Met Ile  Ala Lys Ser Glu Gln  Glu Ile Gly Lys Ala  Thr Ala Lys
    1085                1090                1095

Tyr Phe  Phe Tyr Ser Asn Ile  Met Asn Phe Phe Lys  Thr Glu Ile
    1100                1105                1110

Thr Leu  Ala Asn Gly Glu Ile  Arg Lys Arg Pro Leu  Ile Glu Thr
    1115                1120                1125
```

```
Asn Gly  Glu Thr Gly Glu Ile  Val Trp Asp Lys Gly  Arg Asp Phe
    1130                 1135                 1140

Ala Thr  Val Arg Lys Val Leu  Ser Met Pro Gln Val  Asn Ile Val
    1145                 1150                 1155

Lys Lys  Thr Glu Val Gln Thr  Gly Gly Phe Ser Lys  Glu Ser Ile
    1160                 1165                 1170

Leu Pro  Lys Arg Asn Ser Asp  Lys Leu Ile Ala Arg  Lys Lys Asp
    1175                 1180                 1185

Trp Asp  Pro Lys Lys Tyr Gly  Gly Phe Asp Ser Pro  Thr Val Ala
    1190                 1195                 1200

Tyr Ser  Val Leu Val Val Ala  Lys Val Glu Lys Gly  Lys Ser Lys
    1205                 1210                 1215

Lys Leu  Lys Ser Val Lys Glu  Leu Leu Gly Ile Thr  Ile Met Glu
    1220                 1225                 1230

Arg Ser  Ser Phe Glu Lys Asn  Pro Ile Asp Phe Leu  Glu Ala Lys
    1235                 1240                 1245

Gly Tyr  Lys Glu Val Lys Lys  Asp Leu Ile Ile Lys  Leu Pro Lys
    1250                 1255                 1260

Tyr Ser  Leu Phe Glu Leu Glu  Asn Gly Arg Lys Arg  Met Leu Ala
    1265                 1270                 1275

Ser Ala  Gly Glu Leu Gln Lys  Gly Asn Glu Leu Ala  Leu Pro Ser
    1280                 1285                 1290

Lys Tyr  Val Asn Phe Leu Tyr  Leu Ala Ser His Tyr  Glu Lys Leu
    1295                 1300                 1305

Lys Gly  Ser Pro Glu Asp Asn  Glu Gln Lys Gln Leu  Phe Val Glu
    1310                 1315                 1320

Gln His  Lys His Tyr Leu Asp  Glu Ile Ile Glu Gln  Ile Ser Glu
    1325                 1330                 1335

Phe Ser  Lys Arg Val Ile Leu  Ala Asp Ala Asn Leu  Asp Lys Val
    1340                 1345                 1350

Leu Ser  Ala Tyr Asn Lys His  Arg Asp Lys Pro Ile  Arg Glu Gln
    1355                 1360                 1365

Ala Glu  Asn Ile Ile His Leu  Phe Thr Leu Thr Asn  Leu Gly Ala
    1370                 1375                 1380

Pro Ala  Ala Phe Lys Tyr Phe  Asp Thr Thr Ile Asp  Arg Lys Arg
    1385                 1390                 1395

Tyr Thr  Ser Thr Lys Glu Val  Leu Asp Ala Thr Leu  Ile His Gln
    1400                 1405                 1410

Ser Ile  Thr Gly Leu Tyr Glu  Thr Arg Ile Asp Leu  Ser Gln Leu
    1415                 1420                 1425

Gly Gly  Asp Ser Arg Ala Asp  Pro Lys Lys Lys Arg  Lys Val
    1430                 1435                 1440
```

<210> SEQ ID NO 144
<211> LENGTH: 1406
<212> TYPE: PRT
<213> ORGANISM: Artificial sequence
<220> FEATURE:
<223> OTHER INFORMATION: pVEC-Cas9

<400> SEQUENCE: 144

```
Met Gly His His His His His His Leu Leu Ile Ile Leu Arg Arg Arg
1               5                   10                  15

Ile Arg Lys Gln Ala His Ala His Ser Lys Glu Phe Asp Lys Lys Tyr
            20                  25                  30
```

-continued

```
Ser Ile Gly Leu Asp Ile Gly Thr Asn Ser Val Gly Trp Ala Val Ile
        35                  40                  45

Thr Asp Glu Tyr Lys Val Pro Ser Lys Lys Phe Lys Val Leu Gly Asn
    50                  55                  60

Thr Asp Arg His Ser Ile Lys Lys Asn Leu Ile Gly Ala Leu Leu Phe
65                  70                  75                  80

Asp Ser Gly Glu Thr Ala Glu Ala Thr Arg Leu Lys Arg Thr Ala Arg
                85                  90                  95

Arg Arg Tyr Thr Arg Arg Lys Asn Arg Ile Cys Tyr Leu Gln Glu Ile
            100                 105                 110

Phe Ser Asn Glu Met Ala Lys Val Asp Asp Ser Phe Phe His Arg Leu
        115                 120                 125

Glu Glu Ser Phe Leu Val Glu Glu Asp Lys Lys His Glu Arg His Pro
    130                 135                 140

Ile Phe Gly Asn Ile Val Asp Glu Val Ala Tyr His Glu Lys Tyr Pro
145                 150                 155                 160

Thr Ile Tyr His Leu Arg Lys Lys Leu Val Asp Ser Thr Asp Lys Ala
                165                 170                 175

Asp Leu Arg Leu Ile Tyr Leu Ala Leu Ala His Met Ile Lys Phe Arg
            180                 185                 190

Gly His Phe Leu Ile Glu Gly Asp Leu Asn Pro Asp Asn Ser Asp Val
        195                 200                 205

Asp Lys Leu Phe Ile Gln Leu Val Gln Thr Tyr Asn Gln Leu Phe Glu
    210                 215                 220

Glu Asn Pro Ile Asn Ala Ser Gly Val Asp Ala Lys Ala Ile Leu Ser
225                 230                 235                 240

Ala Arg Leu Ser Lys Ser Arg Arg Leu Glu Asn Leu Ile Ala Gln Leu
                245                 250                 255

Pro Gly Glu Lys Lys Asn Gly Leu Phe Gly Asn Leu Ile Ala Leu Ser
            260                 265                 270

Leu Gly Leu Thr Pro Asn Phe Lys Ser Asn Phe Asp Leu Ala Glu Asp
        275                 280                 285

Ala Lys Leu Gln Leu Ser Lys Asp Thr Tyr Asp Asp Asp Leu Asp Asn
    290                 295                 300

Leu Leu Ala Gln Ile Gly Asp Gln Tyr Ala Asp Leu Phe Leu Ala Ala
305                 310                 315                 320

Lys Asn Leu Ser Asp Ala Ile Leu Leu Ser Asp Ile Leu Arg Val Asn
                325                 330                 335

Thr Glu Ile Thr Lys Ala Pro Leu Ser Ala Ser Met Ile Lys Arg Tyr
            340                 345                 350

Asp Glu His His Gln Asp Leu Thr Leu Leu Lys Ala Leu Val Arg Gln
        355                 360                 365

Gln Leu Pro Glu Lys Tyr Lys Glu Ile Phe Phe Asp Gln Ser Lys Asn
    370                 375                 380

Gly Tyr Ala Gly Tyr Ile Asp Gly Gly Ala Ser Gln Glu Glu Phe Tyr
385                 390                 395                 400

Lys Phe Ile Lys Pro Ile Leu Glu Lys Met Asp Gly Thr Glu Glu Leu
                405                 410                 415

Leu Val Lys Leu Asn Arg Glu Asp Leu Leu Arg Lys Gln Arg Thr Phe
            420                 425                 430

Asp Asn Gly Ser Ile Pro His Gln Ile His Leu Gly Glu Leu His Ala
        435                 440                 445
```

-continued

```
Ile Leu Arg Arg Gln Glu Asp Phe Tyr Pro Phe Leu Lys Asp Asn Arg
    450                 455                 460

Glu Lys Ile Glu Lys Ile Leu Thr Phe Arg Ile Pro Tyr Tyr Val Gly
465                 470                 475                 480

Pro Leu Ala Arg Gly Asn Ser Arg Phe Ala Trp Met Thr Arg Lys Ser
                485                 490                 495

Glu Glu Thr Ile Thr Pro Trp Asn Phe Glu Glu Val Val Asp Lys Gly
            500                 505                 510

Ala Ser Ala Gln Ser Phe Ile Glu Arg Met Thr Asn Phe Asp Lys Asn
        515                 520                 525

Leu Pro Asn Glu Lys Val Leu Pro Lys His Ser Leu Leu Tyr Glu Tyr
    530                 535                 540

Phe Thr Val Tyr Asn Glu Leu Thr Lys Val Lys Tyr Val Thr Glu Gly
545                 550                 555                 560

Met Arg Lys Pro Ala Phe Leu Ser Gly Glu Gln Lys Lys Ala Ile Val
                565                 570                 575

Asp Leu Leu Phe Lys Thr Asn Arg Lys Val Thr Val Lys Gln Leu Lys
            580                 585                 590

Glu Asp Tyr Phe Lys Lys Ile Glu Cys Phe Asp Ser Val Glu Ile Ser
        595                 600                 605

Gly Val Glu Asp Arg Phe Asn Ala Ser Leu Gly Thr Tyr His Asp Leu
    610                 615                 620

Leu Lys Ile Ile Lys Asp Lys Asp Phe Leu Asp Asn Glu Glu Asn Glu
625                 630                 635                 640

Asp Ile Leu Glu Asp Ile Val Leu Thr Leu Thr Leu Phe Glu Asp Arg
                645                 650                 655

Glu Met Ile Glu Glu Arg Leu Lys Thr Tyr Ala His Leu Phe Asp Asp
            660                 665                 670

Lys Val Met Lys Gln Leu Lys Arg Arg Arg Tyr Thr Gly Trp Gly Arg
        675                 680                 685

Leu Ser Arg Lys Leu Ile Asn Gly Ile Arg Asp Lys Gln Ser Gly Lys
    690                 695                 700

Thr Ile Leu Asp Phe Leu Lys Ser Asp Gly Phe Ala Asn Arg Asn Phe
705                 710                 715                 720

Met Gln Leu Ile His Asp Asp Ser Leu Thr Phe Lys Glu Asp Ile Gln
                725                 730                 735

Lys Ala Gln Val Ser Gly Gln Gly Asp Ser Leu His Glu His Ile Ala
            740                 745                 750

Asn Leu Ala Gly Ser Pro Ala Ile Lys Lys Gly Ile Leu Gln Thr Val
        755                 760                 765

Lys Val Val Asp Glu Leu Val Lys Val Met Gly Arg His Lys Pro Glu
    770                 775                 780

Asn Ile Val Ile Glu Met Ala Arg Glu Asn Gln Thr Thr Gln Lys Gly
785                 790                 795                 800

Gln Lys Asn Ser Arg Glu Arg Met Lys Arg Ile Glu Glu Gly Ile Lys
                805                 810                 815

Glu Leu Gly Ser Gln Ile Leu Lys Glu His Pro Val Glu Asn Thr Gln
            820                 825                 830

Leu Gln Asn Glu Lys Leu Tyr Leu Tyr Tyr Leu Gln Asn Gly Arg Asp
        835                 840                 845

Met Tyr Val Asp Gln Glu Leu Asp Ile Asn Arg Leu Ser Asp Tyr Asp
    850                 855                 860

Val Asp His Ile Val Pro Gln Ser Phe Leu Lys Asp Asp Ser Ile Asp
```

```
865                 870                 875                 880

Asn Lys Val Leu Thr Arg Ser Asp Lys Asn Arg Gly Lys Ser Asp Asn
                885                 890                 895

Val Pro Ser Glu Glu Val Val Lys Lys Met Lys Asn Tyr Trp Arg Gln
            900                 905                 910

Leu Leu Asn Ala Lys Leu Ile Thr Gln Arg Lys Phe Asp Asn Leu Thr
        915                 920                 925

Lys Ala Glu Arg Gly Gly Leu Ser Glu Leu Asp Lys Ala Gly Phe Ile
    930                 935                 940

Lys Arg Gln Leu Val Glu Thr Arg Gln Ile Thr Lys His Val Ala Gln
945                 950                 955                 960

Ile Leu Asp Ser Arg Met Asn Thr Lys Tyr Asp Glu Asn Asp Lys Leu
                965                 970                 975

Ile Arg Glu Val Lys Val Ile Thr Leu Lys Ser Lys Leu Val Ser Asp
            980                 985                 990

Phe Arg Lys Asp Phe Gln Phe Tyr  Lys Val Arg Glu Ile  Asn Asn Tyr
        995                 1000                1005

His His  Ala His Asp Ala Tyr  Leu Asn Ala Val Val  Gly Thr Ala
    1010                 1015                1020

Leu Ile  Lys Lys Tyr Pro Lys  Leu Glu Ser Glu Phe  Val Tyr Gly
    1025                 1030                1035

Asp Tyr  Lys Val Tyr Asp Val  Arg Lys Met Ile Ala  Lys Ser Glu
    1040                 1045                1050

Gln Glu  Ile Gly Lys Ala Thr  Ala Lys Tyr Phe Phe  Tyr Ser Asn
    1055                 1060                1065

Ile Met  Asn Phe Phe Lys Thr  Glu Ile Thr Leu Ala  Asn Gly Glu
    1070                 1075                1080

Ile Arg  Lys Arg Pro Leu Ile  Glu Thr Asn Gly Glu  Thr Gly Glu
    1085                 1090                1095

Ile Val  Trp Asp Lys Gly Arg  Asp Phe Ala Thr Val  Arg Lys Val
    1100                 1105                1110

Leu Ser  Met Pro Gln Val Asn  Ile Val Lys Lys Thr  Glu Val Gln
    1115                 1120                1125

Thr Gly  Gly Phe Ser Lys Glu  Ser Ile Leu Pro Lys  Arg Asn Ser
    1130                 1135                1140

Asp Lys  Leu Ile Ala Arg Lys  Lys Asp Trp Asp Pro  Lys Lys Tyr
    1145                 1150                1155

Gly Gly  Phe Asp Ser Pro Thr  Val Ala Tyr Ser Val  Leu Val Val
    1160                 1165                1170

Ala Lys  Val Glu Lys Gly Lys  Ser Lys Lys Leu Lys  Ser Val Lys
    1175                 1180                1185

Glu Leu  Leu Gly Ile Thr Ile  Met Glu Arg Ser Ser  Phe Glu Lys
    1190                 1195                1200

Asn Pro  Ile Asp Phe Leu Glu  Ala Lys Gly Tyr Lys  Glu Val Lys
    1205                 1210                1215

Lys Asp  Leu Ile Ile Lys Leu  Pro Lys Tyr Ser Leu  Phe Glu Leu
    1220                 1225                1230

Glu Asn  Gly Arg Lys Arg Met  Leu Ala Ser Ala Gly  Glu Leu Gln
    1235                 1240                1245

Lys Gly  Asn Glu Leu Ala Leu  Pro Ser Lys Tyr Val  Asn Phe Leu
    1250                 1255                1260

Tyr Leu  Ala Ser His Tyr Glu  Lys Leu Lys Gly Ser  Pro Glu Asp
    1265                 1270                1275
```

-continued

| | | | | | | | | | | | | | |
|---|---|---|---|---|---|---|---|---|---|---|---|---|---|
| Asn | Glu | Gln | Lys | Gln | Leu | Phe | Val | Glu | Gln | His | Lys | His | Tyr | Leu |
| | 1280 | | | | | 1285 | | | | | 1290 | | | |
| Asp | Glu | Ile | Ile | Glu | Gln | Ile | Ser | Glu | Phe | Ser | Lys | Arg | Val | Ile |
| | 1295 | | | | | 1300 | | | | | 1305 | | | |
| Leu | Ala | Asp | Ala | Asn | Leu | Asp | Lys | Val | Leu | Ser | Ala | Tyr | Asn | Lys |
| | 1310 | | | | | 1315 | | | | | 1320 | | | |
| His | Arg | Asp | Lys | Pro | Ile | Arg | Glu | Gln | Ala | Glu | Asn | Ile | Ile | His |
| | 1325 | | | | | 1330 | | | | | 1335 | | | |
| Leu | Phe | Thr | Leu | Thr | Asn | Leu | Gly | Ala | Pro | Ala | Ala | Phe | Lys | Tyr |
| | 1340 | | | | | 1345 | | | | | 1350 | | | |
| Phe | Asp | Thr | Thr | Ile | Asp | Arg | Lys | Arg | Tyr | Thr | Ser | Thr | Lys | Glu |
| | 1355 | | | | | 1360 | | | | | 1365 | | | |
| Val | Leu | Asp | Ala | Thr | Leu | Ile | His | Gln | Ser | Ile | Thr | Gly | Leu | Tyr |
| | 1370 | | | | | 1375 | | | | | 1380 | | | |
| Glu | Thr | Arg | Ile | Asp | Leu | Ser | Gln | Leu | Gly | Gly | Asp | Ser | Arg | Ala |
| | 1385 | | | | | 1390 | | | | | 1395 | | | |
| Asp | Pro | Lys | Lys | Lys | Arg | Lys | Val | | | | | | | |
| | 1400 | | | | | 1405 | | | | | | | | |